(12) United States Patent
Ismagilov et al.

(10) Patent No.: US 12,173,361 B2
(45) Date of Patent: *Dec. 24, 2024

(54) RODENT MODEL AND RELATED DEVICE, COMPOSITIONS, METHODS AND SYSTEMS

(71) Applicant: CALIFORNIA INSTITUTE OF TECHNOLOGY, Pasadena, CA (US)

(72) Inventors: Rustem F Ismagilov, Altadena, CA (US); Jacob T Barlow, Pasadena, CA (US); Said R Bogatyrev, Pasadena, CA (US)

(73) Assignee: CALIFORNIA INSTITUTE OF TECHNOLOGY

( * ) Notice: Subject to any disclaimer, the term of this patent is extended or adjusted under 35 U.S.C. 154(b) by 759 days.

This patent is subject to a terminal disclaimer.

(21) Appl. No.: 17/148,543

(22) Filed: Jan. 13, 2021

(65) Prior Publication Data

US 2021/0147911 A1 May 20, 2021

Related U.S. Application Data

(63) Continuation-in-part of application No. 16/927,496, filed on Jul. 13, 2020, now Pat. No. 11,427,865.

(Continued)

(51) Int. Cl.
*C12Q 1/68* (2018.01)
*A01K 67/0278* (2024.01)
(Continued)

(52) U.S. Cl.
CPC .......... *C12Q 1/686* (2013.01); *A01K 67/0278* (2013.01); *C12Q 1/6883* (2013.01);
(Continued)

(58) Field of Classification Search
None
See application file for complete search history.

(56) References Cited

U.S. PATENT DOCUMENTS 8,889,358 B2    11/2014  Rudi et al.
11,427,865 B2    8/2022  Ismagilov et al.
(Continued)

FOREIGN PATENT DOCUMENTS

CN    107287293          10/2017
CN    107287293 A    *   10/2017  ........... C12Q 1/6851
(Continued)

OTHER PUBLICATIONS

Jian, C., et al., "Quantitative PCR provides a simple and accessible method for quantitative microbiota profiling," *PLoS One*, 2020. 15(1): p. e0227285. 11 Pages.

(Continued)

*Primary Examiner* — Aaron A Priest
(74) *Attorney, Agent, or Firm* — Steinfl + Bruno LLP

(57) ABSTRACT

Provided herein are methods and systems and related composition, to provide a rodent model having a target microbiome profile formed by a target presence, a target proportion and/or a target total load of a target prokaryote of a target taxon, based on absolute quantification of the target prokaryote. Further provided are rodents obtained by the methods herein described and related use in testing methods performed in connection with physiological or pathological conditions in an individual preferably a human individual. Also provided herein is a tailcup device and related use to prevent coprophagia in rodents.

25 Claims, 55 Drawing Sheets

Specification includes a Sequence Listing.

Related U.S. Application Data

(60) Provisional application No. 62/961,584, filed on Jan. 15, 2020, provisional application No. 62/960,527, filed on Jan. 13, 2020, provisional application No. 62/873,410, filed on Jul. 12, 2019, provisional application No. 62/873,838, filed on Jul. 12, 2019.

(51) Int. Cl.
    *C12Q 1/686*     (2018.01)
    *C12Q 1/6883*     (2018.01)

(52) U.S. Cl.
    CPC .... *A01K 2207/15* (2013.01); *A01K 2227/105* (2013.01); *A01K 2267/03* (2013.01); *C12Q 2561/113* (2013.01)

(56) References Cited

U.S. PATENT DOCUMENTS

| | | | | |
|---|---|---|---|---|
| 2014/0107092 | A1* | 4/2014 | Meyerson | C12Q 1/689 435/6.12 |
| 2016/0312275 | A1* | 10/2016 | Blainey | C12Q 1/6853 |
| 2017/0196921 | A1* | 7/2017 | Embree | A61K 9/0019 |
| 2019/0160095 | A1 | 5/2019 | Hart | |
| 2019/0169680 | A1* | 6/2019 | David | G01N 1/28 |
| 2019/0241943 | A1* | 8/2019 | Villa | C12Q 1/686 |
| 2021/0002718 | A1* | 1/2021 | Zwirko | C12Q 1/6813 |
| 2021/0079447 | A1 | 3/2021 | Ismagilov et al. | |
| 2023/0227885 | A1* | 7/2023 | De Wouters | C12N 1/20 435/39 |
| 2023/0272466 | A1 | 8/2023 | Ismagilov et al. | |

FOREIGN PATENT DOCUMENTS

| | | |
|---|---|---|
| WO | 2021/011460 A1 | 1/2021 |
| WO | 2021/146338 A1 | 7/2021 |

OTHER PUBLICATIONS

Johansson, M.E.V., et al., "The gastrointestinal mucus system in health and disease," *Nature Reviews Gastroenterology & Hepatology* vol. 10, pp. 352-361. Jun. 2013. 11 Pages.

Jonsson, H., et al., "Segmented filamentous bacteria in human ileostomy samples after high-fiber intake" *FEMS Microbiol. Lett.* 342, 24-29, 2013. 7 Pages.

Joyce, S.A., et al., "Bacterial bile salt hydrolase in host metabolism: Potential for influencing gastrointestinal microbe-host crosstalk," *Gut Microbes*, 2014. 5(5): p. 669-674. doi:10.4161/19490976.2014. 969986. 8 Pages.

Joyce, SA, et al., "Regulation of host weight gain and lipid metabolism by bacterial bile acid modification in the gut," *Proc Natl Acad Sci U S A*. May 20, 2014. 111:7421-6. doi:10.1073/pnas. 1323599111. 7 pages.

Karched, M., et al., "Coaggregation and biofilm growth of *Granulicatella* spp. with Fusobacterium nucleatum and Aggregatibacter actinomycetemcomitans," *BMC Microbiol*. 15, 114. 2015. 11 Pages.

Karlin, S., et al., "Applications and statistics for multiple high-scoring segments in molecular sequences," *Proc Natl Acad Sci USA*, 1993. 90(12): p. 5873-5877. 6 Pages.

Karlin, S., et al., "Methods for assessing the statistical significance of molecular sequence features by using general scoring schemes," *Proc Natl Acad Sci USA*, 1990. 87(6): p. 2264-2268. 6 Pages.

Kemis JH, et al., "Genetic determinants of gut microbiota composition and bile acid profiles in mice," *PLoS Genet*. 2019 ;15:e1008073. doi:10.1371/journal.pgen.1008073.

Kenagy GJ, et al. "Reingestion of feces in rodents and its daily rhythmicity," Oecologia. 1980; 44:403-9. doi:10.1007/BF00545245.

Kennedy, N.A., et al., "The impact of different DNA extraction kits and laboratories upon the assessment of human gut microbiota composition by 16S rRNA gene sequencing," *PLoS One*, 2014. 9(2): p. e88982. 10 Pages.

Khazaei, T. et al. "Metabolic multi-stability and hysteresis in a model aerobe-anaerobe microbiome community," Science Advances, (2020), 6, eaba0353. 11 pages.

Kim YS, et al., "The role of altered bile acid metabolism in the steatorrhea of experimental blind loop," *J Clin Invest*. 1966 ;45:956-62.doi:10.1172/JCI105411.

Klaasen, Hlbm, et al., "Effect of Preventing Coprophagy on Colonisation by Segmented Filamentous Bacteria in the Small Bowel of Mice," *Microb Ecol Health Dis*. 1990; 3:99-103. doi:10.3109/08910609009140123. 7 pages.

Klaassen, C.D., et al., "Review: Mechanisms of How the Intestinal Microbiota Alters the Effects of Drugs and bile Acids," *Drug Metab Dispos*, Oct. 2015. 43(10): p. 1505-1521. 18 Pages.

Klein, M.S. et al., "Metabolomic Modeling To Monitor Host Responsiveness to Gut Microbiota Manipulation in the BTBRT+tf/j Mouse," J. Proteome Res. 15,1143-1150, 2016. 9 Pages.

Kleyer, H., et al., "Resolving Species Level Changes in a Representative Soil Bacterial Community Using Microfluidic Quantitative PCR," *Front. Micro biol*. Oct. 8, 2017. 13 Pages.

Klindworth, A., et al., "Evaluation of general 16S ribosomal RNA gene PCR primers for classical and next-generation sequencing-based diversity studies," *Nucleic Acids Res*, 2013. 41(1): p. e1. 12 Pages.

Kluyver, T., et al. "Jupyter Notebooks—a publishing format for reproducible computational workflows," in *20th International Conference on Electronic Publishing*. 2016. pp. 87-90. 5 pages.

Knight, R. et al. "Best practices for analyzing microbiomes," *Nature Reviews Microbiology* 16, 410-422, Jul. 2018. 14 Pages.

Ko, H.-J. et al., "Regulation of intestinal immune system by dendritic cells," Immune Netw. 15, 1-8 (2015).

Korbie, D.J., et al., "Touchdown PCR for increased specificity and sensitivity in PCR amplification," *Nat Protoc*, 2008. 3(9): p. 1452-1456. 6 pages.

Koressaar, T., et al., "Enhancements and modifications of primer design program Primer3," *Bioinformatics*, 2007. 23(10): p. 1289-1291. 4 pages.

Koressaar, T., et al., "Primer3_masker: integrating masking of template sequence with primer design software," *Bioinformatics*, 2018. 34(11): p. 1937-1938. 3 Pages.

Kreutz, J.E., "Theoretical design and analysis of multivolume digital assays with wide dynamic range validated experimentally with microfluidic digital PCR," Anal Chem, 2011. 83(21): p. 8158-8168.

Kruskal, W.H., et al., "Use of Ranks in One-Criterion Variance Analysis," *Journal of the American Statistical Association*, 1952. 47(260): p. 583-621. 41 Pages.

Kuai, L., et al., "Rapid and simple method for the most-probable-number estimation of arsenic-reducing bacteria," *Appl Environ Microbiol*, 2001. 67(7): p. 3168-3173. 7 Pages.

Kuribayashi H, et al., "Enterobacteria-mediated deconjugation of taurocholic acid enhances ileal farnesoid X receptor signaling," *Eur J Pharmacol*. 2012 ;697:132-8. doi:10.1016/j.ejphar.2012.09.048.

Kurtz, Z.D., et al., "Sparse and Compositionally Robust Inference of Microbial Ecological Networks," *PLoS Comp. Biol*. 11, e1004226, May 7, 2015. 26 Pages.

Lagkouvardos, I., J. Overmann, and T. Clavel, "Cultured microbes represent a substantial fraction of the human and mouse gut microbiota" Gut Microbes, 2017. 8(5): p. 493-503.

Lambert JM, et al., "Improved annotation of conjugated bile acid hydrolase superfamily members in Gram-positive bacteria," Microbiology. 2008 ;154Pt 8:2492-500. doi:10.1099/mic.0.2008/016808-0.

Lane, D.J., "16S/23S rRNA sequencing, in Nucleic acid techniques in bacterial systematics," E. Stackebrandtand M. Goodfellow, Editors. 1991, *John Wiley and Sons*: New York, NY. p. 115-175. Excerpt: 1 Page.

Langille, M.G., et al., "Predictive functional profiling of microbial communities using 16S rRNA marker gene sequences," *Nat Biotechnol*, 2013. 31(9): p. 814-821. 11 Pages.

Langmead, B., et al., "Fast gapped-read alignment with Bowtie 2" Nat Methods vol. 9, No. 4,, Apr. 2012. pp. 357-359. 5 Pages.

(56) References Cited

OTHER PUBLICATIONS

Larsen GL., et al., "Deconjugation of Biliary Metabolites by Microfloral β-glucuronidases, Sulphatases and Cysteine Conjugate β- lyases and their Subsequent Enterohepatic Circulation," In: Role of the Gut Flora in Toxicity and Cancer. Elsevier; 1988. p. 79-107. doi:10.1016/B978-0-12-599920-5.50008-X.

Leite, G., et al., "The duodenal microbiome is altered in small intestinal bacterial overgrowth" PLOS ONE, 2020. 15(7): p. e0234906.

Leite, G.G.S., et al., "Mapping the Segmental Microbiomes in the Human Small Bowel in Comparison with Stool: A Reimagine Study" Digestive Diseases and Sciences, 2020. 65(9): p. 2595-2604.

Leite, G.G.S., et al., "Optimizing microbiome sequencing for small intestinal aspirates: validation of novel techniques through the REIMAGINE study," BMC Microbiology, 2019. 19(1): p. 239.

Lesker T.R. et al., "An Integrated Metagenome Catalog Reveals New Insights into the Murine Gut Microbiome", Cell Reports, 30 (9). Mar. 3, 2020. 2909-2922.e6. 40 pages.

Lev, M., et al., "Stability of the Lactobacillus population in feces and stomach contents of rats prevented from coprophagy," *J Bacteriol.* Jul. 1966; 92:13-6. 4 Pages.

Li C, et al., "Cholesterol-lowering effect of Lactobacillus plantarum NCU116 in a hyperlipidaemic rat model," *J Funct Foods.* 2014 ;8:340-347. doi:10.1016/j.jff.2014.03.031.

Liang X, et al., "Bidirectional interactions between indomethacin and the murine intestinal microbiota," Elife. 2015 ;4:e08973 doi:10.7554/eLife.08973.

Lievin-Le Moal, V., et al., "Anti-infective activities of lactobacillus strains in the human intestinal microbiota from probiotics to gastrointestinal anti-infectious biotherapeutic agents," Clin Microbiol Rev, 27(2). 2014. p. 167-199. 34 Pages.

Litvak, Y. et al. "Commensal Enterobacteriaceae Protect against *Salmonella* Colonization through Oxygen Competition" Cell Host Microbe 25, 128-139.e125 (2019).

Llopis M, et al., ". Intestinal microbiota contributes to individual susceptibility to alcoholic liver disease," Gut. 2016 ;65:830-9.doi:10.1136/gutjnl-2015-310585.

Llorente C, et al., "Gastric acid suppression promotes alcoholic liver disease by inducing overgrowth of intestinal Enterococcus," Nat Commun. 2017 ;8:837.doi:10.1038/s41467-017-00796.

LoGuidice A, et al., "Pharmacologic targeting of bacterialβ-glucuronidase alleviates nonsteroidal anti-inflammatory drug-induced enteropathyin mice," J Pharmacol Exp Ther. 2012; 341:447-54.

Lou, J., et al., "Assessing soil bacterial community and dynamics by integrated high throughput absolute abundance quantification," *Peer J* 6, e4514-e4514, 2018. 20 Pages.

Lovell, D., et al. "Proportionality: a valid alternative to correlation for relative data," *PLoS Comput Biol*, 2015. 11(3): p. e1004075. 13 Pages.

Lozupone CA, et al., "Diversity, stability and resilience of the human gut microbiota," *Nature.* 2012; 489:220-30. doi:10.1038/nature11550. 12 Pages.

Lundberg, D.S., et al., "Practical innovations for high-throughput amplicon sequencing," Nat Methods, 2013. 10(10): p. 999-1002.

Lupascu, A. et al. "Hydrogen glucose breath test to detect small intestinal bacterial overgrowth: a prevalence case-control study in irritable bowel syndrome. Aliment" *Pharmacol. Ther.* 22, 1157-1160. 2005. 5 Pages.

Lutz, T.A. and S.C. Woods, "Overview of animal models of obesity," Current protocols in pharmacology, 2012. Chapter 5: p. Unit5.61-Unit5.61.

Lutzoni Lab: 16S ribosomal DNA. [cited Jul. 9, 2020]; Available from internet lutzonilab.org/16s-ribosomal-dna/, downloaded on Nov. 18, 2020. 4 Pages.

Ma, R., et al., "Investigation of the effects of pH and bile on the growth of oral Campylobacte concisus strains isolated from patients with inflammatory bowel disease and controls" Journal of Medical Microbiology, 2015. 64(4): p. 438-445.

Madsen, D, et al., "Analysis of bile acids in conventional and germfree rats," J Lipid Res., 17. 1976. 107-11. 5 pages.

Mandal, S. et al. "Analysis of composition of microbiomes: a novel method for studying microbial composition.," *Microb. Ecol. Health Dis.* 26,27663, 2015. 8 Pages.

Marcotte, H. and M.C. Lavoie, "Oral microbial ecology and the role of salivary immunoglobulin A." Microbiology and molecular biology reviews: MMBR, 1998. 62(1): p. 71-109.

Marotz, C.A., et al, "Improving saliva shotgun metagenomics by chemical host DNA depletion," *Microbiome* 6, 42-42, 2018. 10 Pages.

Marshall, O.J., et al., "PerlPrimer: cross-platform, graphical primer design for standard, bisulphite and real-time PCR," Bioinformatics, 20(15). 2004. p. 2471-2472. 3 Pages.

Martinez-Guryn K, et al., "Small Intestine Microbiota Regulate Host Digestive and Absorptive Adaptive Responses to Dietary Lipids," *Cell Host Microbe.* 2018 ;23:458-469.e5. doi:10.1016/j.chom.2018.03.011.

Martino, C., et al., "A novel Sparse Compositional Technique Reveals Microbial Perturbations," *mSystems*, 2019. 4(1): p. e00016-19. 14 Pages.

Mayo SA, et al., "Indomethacin injury to the rat small intestine is dependent upon biliary secretion and is associated with overgrowth of enterococci.," *Physiol Rep.* 2016; vol. 4, issue 6, e12725. 10 pages. doi: 10.14814/phy2.12725.

McKinney, W., et al., "Data Structures for Statistical Computing in Python," in *Proc. of the 9th Python in Science Conference.* Scipy 2010, 56-61. 7 Pages.

McMurdie, P.J., et al., "Waste Not, Want Not: Why Rarefying Microbiome Data Is Inadmissible," *PLOS Computational Biology*, 2014. 10(4): p. e1003531. 13 Pages.

Metta, V.C., et al., "A Tubular Coprophagy-Preventing Cage for the Rat," *The Journal of Nutrition*, 1961. 74(4): p. 473-476. 8 Pages.

Metzker, M., et al., "Sequencing technologies—the next generation," Nature Reviews Genetics vol. 11, pp. 31-46 (2010).

Mizrahi-Man, Orna et al., "Taxonomic classification of bacterial 16S Rrna genes using short sequencing reads: evaluation of effective study designs," PLOS ONE, 2013, vol. 8, No. 1, Article No. e53608 internal pp. 3-8. 15 Pages.

Mondragon-Palomino, O., et al., "Tools for Quantitative Spatial Analysis of Mucosal Gut Microbiota in IBD," I-Poster printed on Jul. 10, 2019. Presentation at Kenneth Rainin Foundation conference (Hawaii)—Jul. 13, 2019.

Morton, J.T. et al. "Balance Trees Reveal Microbial Niche Differentiation," *mSystems*, vol. 2, Issue 1, e00162-016, Jan./Feb. 2017. 12 Pages.

Morton, J.T. et al. "Establishing microbial composition measurement standards with reference frames," Nature Communications 10:2719, 2019. 12 pages. doi.org/10.1038/s41467-019-10656-5.

Mu, Q., V.J. Tavella, and X.M. Luo, "Role of Lactobacillus reuteri in Human Health and Diseases" Frontiers in Microbiology, 2018. 9(757). 17 pages.

Muraki M, et al., "Role of small intestinal bacterial overgrowth in severe small intestinal damage in chronic non-steroidal anti-inflammatory drug users," *Scand J Gastroenterol.* 2014; 49:267-73. doi:10.3109/00365521.2014.880182. 9 Pages.

Myers, E.W., et al., "Optimal alignments in linear space," *Comput Appl Bio sci*, 1988. 4(1): p. 11-17. 8 Pages.

Narushima, S., et al., "Absence of cecal secondary bile acids in gnotobiotic mice associated with two human intestinal bacteria with the ability to dehydroxylate bile acids in vitro," *Microbiol Immunol*, 1999. 43(9): p. 893-897. 5 pages.

Narushima, S., et al., "Deoxycholic acid formation in gnotobiotic mice associated with human intestinal bacteria," *Lipids*, 2006. 41(9): p. 835-843. 10 pages.

Neale, R.J., "Coprophagy in iron-deficient rats: II. 2 novel methods of prevention" *Lab Anim*, 1984. 18(2): p. 119-124. 6 Pages.

Neale, R.J., "Coprophagy in iron-deficient rats" *Lab Anim*, 1982. 16(2):p. 204-207. 4 Pages.

Needleman, S.B., et al., "A general method applicable to the search for similarities in the amino acid sequence of two proteins," *J Mol Biol*, 1970. 48(3): p. 443-453. 12 Pages.

Newell, C. et al. "Ketogenic diet modifies the gut microbiota in a murine model of autism spectrum disorder". Mol Autism 7,37. 2016. 7 Pages.

(56) References Cited

OTHER PUBLICATIONS

Ng KM, et al., "Recovery of the gut microbiota after antibiotics depends on host diet and environmental reservoir," bioRxiv. 2019. doi:10.1101/717686.

Ng K.M., et al., "Recovery of the gut microbiota after antibiotics depends on host diet, community context, and environmental reservoir," *Cell Host & Microbe*, 26, 650-665, Nov. 13, 2019. 22 Pages.

Nguyen, T.L., et al., "How informative is the mouse for human gut microbiota research?" *Dis Model Mech*, 2015. 8(1): p. 1-16. 19 Pages.

Northfield, T.C. and I. McColl, "Postprandial concentrations of free and conjugated bile acids down the length of the normal human small intestine," *Gut*, 1973. 14(7): p. 513-518. 7 pages.

Northfield TC.,. "Intraluminal precipitation of bile acids in stagnant loop syndrome," *Br Med J*., Jun. 30, 1973 2:743-745. doi:10.1136/bmj.2.5869.743. 4 Pages.

Nubel, U., et al. "PCR primers to amplify 16S rRNA genes from cyanobacteria," Appl Environ Microbiol, 63(8).Aug. 1997. p. 3327-3332. 7 pages.

Nygaard, A.B., et al., "A preliminary study on the potential of Nanopore MinION and Illumina MiSeq 16S rRNA gene sequencing to characterize building-dust microbiomes," Sci Rep, 2020. 10(1): p. 3209. 11 pages.

Oblinger, J.L., et al., "Understanding and Teaching the Most Probable Number Technique," *Journal of Milk and Food Technology*, Sep. 1975. 38(9): p. 540-545. 7 Pages.

Ohta, A., et al., "Prevention of coprophagy modifies magnesium absorption in rats fed with fructo-oligosaccharides" *Br J Nutr*, 1996. 75(5):p. 775-784. 10 Pages.

Olson, C.A., et al., "the gut Microbiota Mediates the Anti-Seizure Effects of the Ketogenic Diet," + Supplemental Data. *Cell*, 2018. 173(7): p. 1728-1741.e13. 29 Pages.

O'Sullivan DM, et al. "Assessing the accuracy of quantitative molecular microbial profiling" Int J Mol Sci. 2014; 15:21476-91. doi:10.3390/ijms151121476.

Ozkanca, R., et al., "Resuscitation and quantification of stressed *Escherichia coli* K12 NCTC8797 in water samples," *Microbiol Res*, 2009. 164(2): p. 212-220. 10 pages.

Park, J.C. and S.-H. Im, "Of men in mice: the development and application of a humanized gnotobiotic mouse model fo microbiome therapeutics" Experimental & Molecular Medicine, 2020. 52(9): p. 1383-1396.

Park, S., et al., "Cholesterol-lowering effect of Lactobacillus rhamnosus BFE5264 and its influence on the gut microbiome and propionate level in a murine model," *PLoS ONE* 13(8): e0203150. 2018. doi.org/10.1371/journal.pone.0203150. 16 Pages.

Paulson, J.N., et al., "Differential abundance analysis for microbial marker-gene surveys," *Nat Methods*, vol. 10, No. 12, pp. 1200-1202. Dec. 2013. 7 Pages.

Pearson, J.A., F.S. Wong, and L. Wen, "The importance of the Non-Obese Diabetic (NOD) mouse model in autoimmune diabetes," Journal of autoimmunity, 2016. 66: p. 76-88.

Pearson, W.R. and D.J. Lipman, "Improved tools for biological sequence comparison," *Proc Natl Acad Sci USA*, 1988. 85(8): p. 2444-2448. 6 Pages.

Pedregosa, F., et al., "Scikit-learn: Machine Learning in Python," *Journal of machine learning research*, 2011. 12: p. 2825-2830. 6 Pages.

Perez, F., et al., "IPython: A System for interactive Scientific Computing," *Computing in Science & Engineering*, 2007. 9(3): p. 21-29. 10 Pages.

Phan, C.T., et al., "Intestinal lipid absorption and transport," *Front Biosci*, Mar. 1, 2001. 6: p. D299-319. 22 Pages.

Pimentel, M., et al., "ACG Clinical Guideline: Small Intestinal Bacterial Overgrowth" The American College of Gastroenterology. The American Journal of Gastroenterology | ACG, 2020. 115 (2), 165-178.

Pizarro, T.T., et al., "SAMP1/YitFc mouse strain: a spontaneous model of Crohn's disease-like ileitis," Inflammatory bowel diseases, 2011. 17(12):p. 2566-2584.

Polz, M.F., et al., "Bias in template-to-product ratios in multi template PCR," *Appl Environ Microbiol*, 1998. 64(10): p. 3724-3730. 8 Pages.

Props R,, et al. "Absolute quantification of microbial taxon abundances" *ISME J*. 2017; 11:584-7. doi:10.1038/ismej.2016.117. 5 Pages.

Pruesse, E., et al., "SILVA: a comprehensive online resource for quality checked and aligned ribosomal RNA sequence data compatible with ARB," *Nucleic Acids Res*, 2007. 35(21): p. 7188-7196. 10 Pages.

Quast, C., et al., "The SILVA ribosomal RNA gene database project: improved data processing and web-based tools," *Nucleic acids research*, 2013. 41 (Database issue): p. D590-D596. 8 Pages.

Restriction Requirement issued for U.S. Appl. No. 16/927,496, filed Jul. 13, 2020, on behalf of California Institute of Technology. Mail Date: Dec. 1, 2021. 10 Pages.

Rezaie, A. et al. "Hydrogen and Methane-Based Breath Testing in Gastrointestinal Disorders: The North American Consensus," The American journal of gastroenterology 112, 775-784 (2017).

Ridlon JM, et al., "Bile salt biotransformations by human intestinal bacteria," J Lipid Res. 2006; 47:241-59. doi:10.1194/jlr.R500013-JLR200.

Ridlon, J.M., et al., "The human gut sterolbiome: bile acid-microbiome endocrine aspects and therapeutics," *Acta Pharm Sin B*, 2015. 5(2): p. 99-105. 8 Pages.

Rigottier-Gois, L., "Dysbiosis in inflammatory bowel diseases: the oxygen hypothesis," *The ISME journal 7*, 1256-1261. 2013. 7 Pages.

Rinttilä, T., et al., "Development of an extensive set of 16S rDNA-targeted primers for quantification of pathogenic and indigenous bacteria in fecal samples by real-time PCR," *Journal of Applied Microbiology*, 2004. 97(6): p. 1166-1177. 13 Pages.

Rios, D. et al. "Antigen sampling by intestinal M cells is the principal pathway initiating mucosal IgA production to commensal enteric bacteria" Mucosal Immunol. vol. 9, No. 4, 907-916 (Jul. 2016).

Rolando, J.C., "Bioanalytical Tools to Develop Rapid Diagnostics and Study Physiology," Thesis In Partial Fulfillment of the Requirements for the degree of Doctor of Philosophy. California Institute of Technology. Defended May 10, 2019. 211 Pages.

Roscoe, M.H., "Spontaneous Cures in Rats reared upon a Diet devoid of Vitamin B and Antineuritic Vitamin," *J Hyg (Lond)*, 1927. 27(1): p. 103-107. 6 Pages.

Rosselli, R., et al., "Direct 16S rRNA-seq from bacterial communities: a PCR-independent approach to simultaneously assess microbial diversity and functional activity potential of each taxon," *Scientific Reports*, 2016, vol. 6, Article No. 32165 internal pp. 2-6. 13 Pages.

Rosshart SP, et al., "Wild Mouse Gut Microbiota Promotes Host Fitness and Improves Disease Resistance.," Cell. 2017; 171:1015-1028.e13.doi:10.1016/j.cell.2017.09.016.

Routy, B. et al. "Gut microbiome influences efficacy of PD-1-based immunotherapy against epithelial tumors," Science 359, 91-97. 2018. 10 Pages.

Rowe, R., et al., "Microtechnique for most-probable-number analysis," *Appl Environ Microbiol*, 1977. 33(3): p. 675-680. 6 Pages.

Rudi, K., et al., "Strain characterization and classification of oxyphotobacteria in clone cultures on the basis of 16S rRNA sequences from the variable regions V6, V7, and V8," *Appl Environ Microbiol*, 1997. 63(7): p. 2593-2599. 8 Pages.

Ruoff, K.L., "Miscellaneous Catalase-Negative, Gram-Positive Cocci: Emerging Opportunists" Journal of Clinical Microbiology, Apr. 2002. 40(4):p. 1129-1133.

Ryer F. H. et al., "An Anal Cup for Rats in Metabolic Studies involving Radioactive Materials" *Laboratory Animal Science* vol. 21, No. 6, Dec. 1971 pp. 942-943. 2 Pages.

S. Sukemori, S. Ikeda, Y. Kurihara, S. Ito, "Comparison of Three Types of Equipment for Preventing Coprophagy in Rats". Japanese Journal of Livestock Management, 2000. 36(2): p. 69-75.

Saffouri, G.B., et al., "Small intestinal microbial dysbiosis underlies symptoms associated with functional gastrointestinal disorders," *Nat Commun*, 2019. 10(1): p. 2012. 12 Pages.

Saitta, KS, et al., "Bacterial β-glucuronidase inhibition protects mice against enteropathy induced by indomethacin, ketoprofen or

(56) References Cited

OTHER PUBLICATIONS diclofenac: mode of action and pharmacokinetics," *Xenobiotica*. 2014 ;44(1):28-35. 17 Pages doi:10.3109/00498254.2013.811314.
Sambo, F., et al., "Optimizing PCR primers targeting the bacterial 16S ribosomal RNA gene," *BMC Bioinformatics*, 2018. 19(1): p. 343. 11 Pages.
Sanders, R. et al. "Evaluation of Digital PCR for Absolute DNA Quantification," *Anal. Chem.* 83,6474-6484, Mar. 30, 2011. 12 Pages.
Satoh H, et al., "Role of bacteria in gastric ulceration produced by indomethacin in the rat: cytoprotective action of antibiotics," *Gastroenterology*. 1983. 84:483-9. 8 pages.
Sayin SI, et al., "Gut microbiota regulates bile acid metabolism by reducing the levels of tauro-beta-muricholic acid, a naturally occurring FXR antagonist," Cell Metab. 2013 ;17:225-35. doi:10.1016/j.cmet.2013.01.003.
Scarpignato C., "NSAID-induced intestinal damage: are luminal bacteria the therapeutic target?" Gut. Feb. 2008; 57 (2):145-8. doi:10.1136/gut.2007.134502.
Schaarschmidt K. et al., "Improved model of a fecal collection cup for preventing coprophagy in rats" J. Exp. Anim. Sci. 1991; 34: pp. 67-71. 5 Pages. German with English Summary.
Schirmer, M. et al. "Compositional and Temporal Changes in the Gut Microbiome of Pediatric Ulcerative Colitis Patients Are Linked to Disease Course," Cell Host Microbe, 24, 600-610 + e1-e4. Oct. 2018. 17 Pages.
Schloss, P.D., et al., "Introducing mothur: open-source, platform-independent, community-supported software for describing and comparing microbial communities,". *Appl Environ Microbiol*, 2009. 75(23): p. 7537-7541. . 6 Pages.
Schmidt, T.S.B., et al., "Extensive transmission of microbes along the gastrointestinal tract". eLife, 2019. 8: p. e42693. 19 pages.
Schneider, K.M., et al., "Role of bile acids in the gut-liver axis," *J Hepatol*, 2018. 68(5): p. 1083-1085 3 Pages.
Seabold, S., et al., "Statsmodels: Econometric and statistical modeling with python," In 9th Python in Science Conference. 2010, 92-96. 6 Pages.
Seekatz, A.M., et al., "Spatial and Temporal Analysis of the Stomach and Small-Intestinal Microbiota in Fasted Healthy Humans," *mSphere*, Mar./Apr. 2019. 4(2). 13 Pages.
Seitz S, et al., "Diclofenac acyl glucuronide, a major biliary metabolite, is directly involved in small intestinal injury in Rats," *Gastroenterology*. 1998; 115:1476-82. 8 Pages.
Shah A, et al., "Gastroduodenal "Dysbiosis": a New Clinical Entity," Curr Treat Options Gastroenterol. 2018;16:591-604.doi:10.1007/s11938-018-0207-x.
Shah, A. et al. "Small Intestinal Bacterial Overgrowth in Irritable Bowel Syndrome: A Systematic Review and Meta-Analysis of Case-Control Studies". *Official Journal of the American College of Gastroenterology | ACG 115*. Feb. 2020. pp. 190-201.14 Pages.
Shah A, et al., "Systematic review with meta-analysis: the prevalence of small intestinal bacterial overgrowth in inflammatory bowel disease," Aliment Pharmacol Ther. 2019 ;49:624-35. doi:10.1111/apt.15133.
Sharara, S.L., et al., "HACEK endocarditis: a review," Expert Rev. Anti Infect. Ther. vol. 14, No. 6, 539-545 (2016).
Sharon, G. et al. "Human Gut Microbiota from autism Spectrum Disorder Promote Behavioral Symptoms in Mice," *Cell 177*, 1600-1618 + e1-e10 + Supplemental figures. e1617 (2019). 38 Pages.
Shen, F., et al., "Digital PCR on a SlipChip," Lab on a Chip, vol. 10, No. 20, 2666-2672, Oct. 2010. 9 Pages.
Shin, J., et al., "Analysis of the mouse gut microbiome using full-length 16S rRNA amplicon sequencing," *Sci Rep*, 2016. 6: p. 29681. 11 Pages.
Shindo K, et al., "Omeprazole induces altered bile acid metabolism," Gut. 1998; 42:266-71. doi:10.1136/gut.42.2.266.
Shinichi, K., et al., "Rapid bacterial identification by direct PCR amplification of 16S rRNA genes using the MinION nanopore sequencer," *FEBS Open Bio*, Mar. 2019, vol. 9, No. 3, pp. 548-557 abstract; pp. 549-553; and figures 1, 6. 11 Pages.

Silva rRNA database project. Available from: https://www.arbsilva.de/download/archive/qiime. Archive page retrieved Nov. 12, 2020 and home page retrieved Mar. 8, 2021. 4 Pages.
Smith, H.W., "Observations on the Flora of the Alimentary Tract of Animals and Factors Affecting Its Composition," *J Pathol Bacteriol*, 1965. 89: p. 95-122. 30 Pages.
Smith, J.L. & Fratamico, P.M. "*Escherichia coli* and Other Enterobacteriaceae: Food Poisoning and Health Effects," in Encyclopedia of Food and Health. (eds. B. Caballero, P.M. Finglas & F. Toldrá) 539-544. Academic Press, Oxford; 2016. 7 Pages.
Smith, T.F., et al., "Comparison of biosequences," *Advances in Applied Mathematics*, 1981. 2(4): p. 482-489.
Smyth R. E. "Fecal Cup for Collection of Feces in Male Rats" *Laboratory Animal Science* pp. 677-678. 1979. 2 Pages.
Snijders AM, et al., "Influence of early life exposure, host genetics and diet on the mouse gut microbiome and metabolome," *Nat Microbiol*. 2016; 2:16221, 9 pages. doi:10.1038/nmicrobiol.2016.221.
Soave O, et al., "Coprophagy in animals: a review," Cornell Vet. 1991; 81:357-64.
Spiess, A.N., et al., "Highly accurate sigmoidal fitting of real-time PCR data by introducing a parameter for asymmetry," *BMC Bioinformatics*, 2008. 9: p. 221. 13 pages.
Stämmler, F. et al. "Adjusting microbiome profiles for differences in microbial load by spike-in bacteria," *Microbiome*, 4, 28. 2016. 14 Pages.
Stoddard, S.F., et al., "rrnDB: improved tools for interpreting rRNA gene abundance in bacteria and archaea and a new foundation for future development,". *Nucleic Acids Res*, 2015. 43(Database issue): p. D593-D598. 7 Pages.
Supplementary Information for Barlow, J.T., et al., "A quantitative sequencing framework for absolute abundance measurements of mucosal and lumenal microbial communities," *Nature Communications, Supplement*, Barlow et al. 2020. doi.org/10.1038/s41467-020-16224-6. 13 pages.
Supplementary Information for Bogatyrev, S.R., et al., "Quantitative microbiome profiling in lumenal and tissue samples with broad coverage and dynamic range via a single-step 16S rRNA gene DNA copy quantification and ampliconbar coding," bioRxiv p. 2020 01.22.914705. 2020. 2 pages.
Supplementary Information for Bogatyrev, S.R., et al., "Self-reinoculation with fecal flora changes microbiota density and composition leading to an altered bile-acid profile in the mouse small intestine," *Microbiome*, 2020. 11 Pages.
Suzuki, M.T., et al., "Bias caused by template annealing in the amplification of mixtures of 16S rRNA genes by PCR," *Appl Environ Microbiol*, 1996. 62(2): p. 625-630. 7 Pages.
Suzuki, T.A., "Spatial Heterogeneity of Gut Microbial Compositionalong the Gastrointestinal Tract in Natural Populations of House Mice," PLoSOne, 2016. 11(9): p. e0163720.
Syed, S.A., et al., "Efficiency of various intestinal bacteria in assuming normal functions of enteric flora after association with germ-free mice," *Infect Immun*, 1970. 2(4): p. 376-386. 11 Pages.
Tabaqchali S, et al., "Influence of abnormal bacterial flora on small intestinal function," Proc R Soc Med. 1966; 59:1244-6. 3 Pages.
Tabaqchali S, et al., "Bile-salt deconjugation and steatorrhoea in patients with the stagnant-loop syndrome," Lancet (London, England). 1968; 2:12-6.doi:10.1016/s0140-6736(68)92888-2.
Taconic, Models for Life. "Prepare your Model: Germ-Free Mice" Downloaded from https://www.taconic.com/prepare-your-model/microbiome-solutions-and-germ-free-mice/germ-free-mice/# on Mar. 9, 2021. 4 Pages.
Takahashi, K.W., et al., "Strain Difference in Coprophagous Behavior in Laboratory Mice (Mus musculus)," *Zoological Science*, 1985. 2(2): p. p249-p255. 8 Pages.
Tannock GW, et al., "Lactobacilli and bile salt hydrolase in the murine intestinal tract," *Appl Environ Microbiol*. 1989; vol. 55, No. 7:1848-5. 4 Pages.
Tannock, G.W., "The Lactic Microflora of Pigs, Mice and Rats," in The Lactic Acid Bacteria vol. 1: The Lactic Acid Bacteria in Health and Disease, B.J.B. Wood, Editor. 1992, Springer US: Boston, MA. p. 21-48. 18 Pages.

(56) References Cited

OTHER PUBLICATIONS

Tanoue, T., et al., "A defined commensal consortium elicits CD8 T cells and anti-cancer immunity," Nature 565, 600-605, Jan. 31, 2019. 26 Pages.

Taxonomy classifiers for use with q2-feature-classifier. [Aug. 6, 2019]; Available from https://docs.qiime2.org/2019.1/data-resources/#taxonomy-classifiers-for-use-with-q2-featureclassifier. Downloaded Mar. 8, 2021. 3 Pages.

The advantage of long reads in 16S rDNA-based microbiome studies. [cited Jul. 9, 2020]; Available from: https://nanoporetech.com/resource-centre/advantage-long-reads-16s-rdnabased-microbiome-studies. Downloaded on Nov. 12, 2020. 4 Pages.

Theriot CM, et al., "Antibiotic-induced alterations of the gut microbiota alter secondary bile acid production and allow for clostridium difficile spore germination and outgrowth in the large intestine," mSphere, vol. 1, Issue 1. 2016. 17 Pages.

Thomas, R.L. and L.J. Roe, "Coprophagy in laboratory animals: a preliminary study to assess potential influences of excreta ingestion on radionuclide retention patterns" Am Ind Hyg Assoc J, 1974. 35(11):p. 741-747.

Tkacz, A., et al., "Absolute quantitation of microbiota abundance in environmental samples," Microbiome 6, 110, 2018. 14 Pages.

Tourlousse, D.M., et al., "Synthetic spike-in standards for high-throughput 16S rRNA gene amplicon sequencing," Nucleic Acids Research, 2016. 45(4): p. e23-e23. 15 Pages.

Tsilimigras, M.C., et al,. "Compositional data analysis of the microbiome: fundamentals, tools, and challenges," Ann. Epidemiol. 26,330-335. 2016. 7 Pages.

Tso, P., et al., "Acute inhibition of intestinal lipid transport by Pluronic L-81 in the rat," Am J Physiol, 1981. 241(6): p. G487-G497. 12 Pages.

Turner P V. "The role of the gut microbiota on animal model reproducibility," Anim Model Exp Med. 2018;1:109-15. doi:10.1002/ame2.12022.

Turner, S., et al., "Investigating deep phylogenetic relationships among cyanobacteria and plastids by small subunit rRNA sequence analysis," J Eukaryot Microbiol, 1999. 46(4): p. 327-338. 14 Pages.

Untergasser, A., et al., "Primer3—new capabilities and interfaces," Nucleic Acids Res, 2012. 40(15): p. e115. 13 pages.

Van den Berg, R.A., et al. "Centering, scaling, and transformations: improving the biological information content of metabolomics data," BMC Genomics, 2006. 7: p. 142. 16 Pages.

Vandeputte, D., et al., "Quantitative microbiome profiling links gut community variation to microbial load," Nature, 2017. 551(7681): p. 507-511. 22 pages.

Virtanen, P., et al., "SciPy 1.0: fundamental algorithms for scientific computing in Python," Nat Methods, 2020. 17(3): p. 261-272. 15 Pages.

Vuik, F., et al., "Composition of the mucosa-associated microbiota along the entire gastrointestinal tract of human individuals," United European Gastroenterol J, 2019. 7(7): p. 897-907. 11 Pages.

Wahlstrom, A., et al., "Intestinal Crosstalk between Bile Acids and Microbiota and Its Impact on Host Metabolism," Cell Metab, 2016. 24(1): p. 41-50. 10 Pages.

Waldner, M.J. and M.F. Neurath, "Chemically Induced Mouse Models of Colitis," Current Protocols in Pharmacology, 2009. 46(1): p. 5.55.1-5.55.15. 16 pages.

Wallace JL, et al,. "Proton pump inhibitors exacerbate NSAID-induced small intestinal injury by inducing dysbiosis" Gastroenterology. 2011; 141:1314-22, 1322.e1-5. doi:10.1053/j.gastro.2011.06.075.

Walt, S.v.d., et al., "The NumPy Array: A Structure for Efficient Numerical Computation," Computing in Science& Engineering, Mar./Apr. 2011. 13(2): p. 22-30.

Wang G, et al., "Cholesterol-lowering potentials of Lactobacillus strain overexpression of bile salt hydrolase on high cholesterol diet-induced hypercholesterolemic mice," Food Funct. 2019; 10:1684-95. doi:10.1039/c8fo02181c.

Wang, Z.K., et al., "Upper gastrointestinal microbiota and digestive diseases," World J Gastroenterol, Mar. 2013. 19(10): p. 1541-1550.

Weisburg, W.G., et al., "16S ribosomal DNA amplification for phylogenetic study," J. Bacteriol, Jan. 1991. 173(2): p. 697-703. 7 Pages.

Weiss, S., et al., "Normalization and microbial differential abundance strategies depend upon data characteristics," Microbiome, 2017. 5(1): p. 27. 18 Pages.

Wen, C. et al. "Evaluation of the reproducibility of amplicon sequencing with Illumina MiSeq platform," PLoSOne 12(4), e0176716. 2017. 20 Pages.

Wilson ID, et al. "Gut microbiome interactions with drug metabolism, efficacy, and toxicity," Transl Res. 2017; 179:204-22. doi:10.1016/j.trsl.2016.08.002.

Wirtz, S. and M.F. Neurath, "Mouse models of inflammatory bowel disease," Advanced Drug Delivery Reviews, 2007. 59(11): p. 1073-1083.

Wrzosek, L., et al., "Transplantation of human microbiota into conventional mice durably reshapes the gut microbiota," Scientific Reports, 2018. 8(1): p. 6854.

Xia, Y., et al., "Hypothesis testing and statistical analysis of microbiome," Genes & Diseases 4, 138-148. 2017. 11 Pages.

Xiao L, et al., "A catalog of the mouse gut metagenome," Nat Biotechnol. 2015; 33:1103-8. doi:10.1038/nbt.3353.

Xu, Z., et al., "Which is more important for classifying microbial communities: who's there or what they can do?" ISME J,. 8(12). 2014. pp. 2357-2359. 3 Pages.

Yahiro K, et al., "Effect of coprophagy on bile acid metabolism in the rabbit," Gastroenterol Jpn., 1979; vol. 14, No. 6:545-52.

Yamamoto Y, et al., "A Metabolomic-Based Evaluation of the Role of commensal Microbiota throughout the Gastrointestinal Tract in Mice," Microorganisms. 2018; 6. doi:10.3390/microorganisms6040101.

Yao L, et al., "A selective gut bacterial bile salt hydrolase alters host metabolism," Elife, 7. 2018. doi:10.7554/eLife.37182. 54 Pages.

Yasuda K, et al., "Biogeography of the intestinal mucosal and lumenal microbiome in the rhesus macaque," Cell Host Microbe. 2015;17:385-91. doi:10.1016/j.chom.2015.01.015.

Ye, J., et al., "Primer-BLAST: a tool to design target-specific primers for a polymerase chain reaction," BMC Bioinformatics, 2012. 13: p. 134. 11 Pages.

Yi, M., et al., "Gut microbiome modulates efficacy of immune checkpoint inhibitors," Journal of Hematology & Oncology, 11(1). 2018. p. 47. 10 Pages.

Yoshio Kurihara, S. Ikeda, Seizi Sukemori, Sumimaro Itoh, "Hydrous Feces Induced Coprophagy in Rat". Japanese Journal of Livestock Management, 1997. 32(3): p. 91-98. 9 Pages.

Zaiontz, C., Real Statistics ResourcePack (Release 6.2). 2019. Downloaded from www.real-statistics.com on Mar. 9, 2021. Home page + Resource pack download page. 39 Pages.

Zelenin, S., et al., "Microfluidic-based isolation of bacteria from whole blood for sepsis diagnostics," Biotechnol.Lett. 37, 825-830 (2015).

Zhang, D., et al, "Effect of coprophagy on bioavailability of iron from plant foods fed to anemic rats" Plant Foods Human Nutr, 1992. 42(2): p. 97-108.

Zhang, Z., et al., "Roles and applications of probiotic Lactobacillus strains" Applied Microbiology and Biotechnology, 2018. 102(19): p. 8135-8143.

Zhong Z-Y, et al., "Ciprofloxacin blocked enterohepatic circulation of diclofenac and alleviated NSAID-induced enteropathy in rats partly by inhibiting intestinal β-glucuronidase activity," Acta Pharmacol Sin. 2016; 37:1002-12. doi:10.1038/aps.2016.54.

Zhou, H.W., et al., "BIPES, a cost-effective high-throughput method for assessing microbial diversity," ISME J, 2011. 5(4): p. 741-749. 9 Pages.

Zmora, N., et al., "Personalized Gut Mucosal Colonization Resistance to Empiric Probiotics Is Associated with Unique Host and Microbiome Features," Cell, 2018. 174(6): p. 1388-1405 e21. 40 Pages.

Zoetendal, E.G. et al. "The human small intestinal microbiota is driven by rapid uptake and conversion of simple carbohydrates" The ISME Journal, 6, 1415-1426 . 2012. 12 pages.

(56) References Cited

OTHER PUBLICATIONS

Zymo Research: Quick-16S NGS Library Prep Kit. [cited Jul. 9, 2020];Available from: https://www.zymoresearch.com/products/quick-16s-ngs-library-prep-kit. Downloaded Nov. 12, 2020. 3 Pages.

Zymo Research: ZymoBIOMICS Microbial Community Standards. [cited Jul. 9, 2020]; Available from: https://www.zymoresearch.com/collections/zymobiomics-microbialcommunity-standards. Downloaded Nov. 12, 2020. 3 pages.

International Preliminary Report on Patentability for PCT App. No. PCT/US2021/013308 field on Jan. 13, 202, on behalf of California Institute of Technology. Mail Date: Jul. 28, 2022. 8 Pages.

Notice of Allowance issued for U.S. Appl. No. 16/927,496, filed Jul. 13, 2020, on behalf of California Institute of Technology. Mail Date: Apr. 13, 2022. 33 Pages.

Zymo Research, 16S/IT Amplicon Sequencing Service. From Jul. 1, 2022. Downloaded through the Wayback Machine. Website: www.zymoresearch.com/pages/16s-its-amplicon-sequencing. 7 pages.

16S Metagenomic sequencing library preparation: Preparing 16S ribosomal RNA gene amplicons for the Illumina MiSeq system (Illumina Technical Note 15044223 Rev. B) 2013, Illumina. 29 Pages.

Acinas, S.G., et al., "PCR-induced sequence artifacts and bias: insights from comparison of two 16S rRNA clone libraries constructed from the same sample," Applied and environmental microbiology, 2005. 71(12): p. 8966-8969.

Aßhauer—KP, et al., "Tax4Fun: predicting functional profiles from-metagenomic 16S rRNA data," Bioinformatics. 2015 ;31:2882-4. doi:10.1093/bioinformatics/btv287.

Aigrain, L., et al., " Quantitation of next-generation sequencing library preparation protocol efficiencies using droplet digital PCR assays—a systematic comparison of DNA library preparation kit for Illumina sequencing," BMC Genomics, 2016. 17: p. 458. 11 pages.

Aitchison, J., et al., "The Statistical Analysis of Compositional Data. Journal of the Royal Statistical Society: Series B (Methodological)," 1982. 44(2): p. 139-177.

Anaconda, Anaconda Software Distribution. Version 4.7.11. 2019. Home page downloaded from https://anaconda.com on Mar. 9, 2021. 9 Pages.

Angly, F.E., et al., "CopyRighter: a rapid tool for improving the accuracy of microbial community profiles through lineage-specific gene copy number correction," Microbiome, 2014. 2: p. 11. 13 pages.

Armstrong et al., "Prevention of coprophagy in the rat. A new method" Br J Ntr. V. 20, 1966. pp. 595-598. 5 pages.

Arrieta M-C, et al ., "Human Microbiota-Associated Mice: A Model with Challenges," Cell Host Microbe. 2016; 19:575-8. doi:10.1016/j.chom.2016.04.014.

Atarashi, K., et al., "Ectopic colonization of oral bacteria in the intestine drives TH1 cell induction and inflammation". Science, 2017. 358 (6361):pp. 359-365.

Barlow, J., et al., "Quantitative sequencing clarifies the role of disruptor taxa, the oral microbiome, and strict anaerobes in the human small-intestine microbiome," (Version 1.0) [Data set]. CaltechDATA. 2020. Downloaded from https://doi.org/10.22002/D1.1701 on Mar. 9, 2021. 2 Pages.

Barlow, J.T., et al., "A quantitative sequencing framework for absolute abundance measurements of mucosal and lumenal microbial communities,". Nat Commun, 2020. 11(1): p. 2590. 13 pages.

Barnes et al., "Prevention of Coprophagy in the rat" The Journal of Nutrition pp. 489-498 1957. 10 pages.

Barnes, R.H., et al., "Effects of the prevention of coprophagy in the rat. I. Growth studies," J Nutr, 1958. 64(4): p. 533-540. 5 Pages.

Barnes, R.H., "Nutritional implications of coprophagy," Nutrition Reviews, Oct. 1962. vol. 20, No. 10: p. 289-291.

Barthel, M. et al. "Pretreatment of Mice with Streptomycin Provides a Salmonella enterica Serovar Typhimurium Colitis Model That Allows Analysis of Both Pathogen and Host." Infect. Immun. 71, No. 5, 2003.pp. 2839-2858. 20 Pages.

Batta AK, et al., "Side chain conjugation prevents bacterial 7-dehydroxylation of bile acids," J Biol Chem. 1990; vol. 265, No. 19:10925-10928. 5 pages.

Begley M, et al., "Bile salt hydrolase activity in probiotics," Appl Environ Microbiol. Mar. 2006; vol. 72, No. 3:1729-1738.doi:10.1128/AEM.72.3.1729-1738.2006.

Benjamini, Y., et al., "Controlling the False Discovery Rate: A Practical and Powerful Approach to Multiple Testing," Journal of the Royal Statistical Society: Series B (Methodological), 1995. 57(1): p. 289-300.

Blackler RW, et al., "Hydrogen sulphide protects against NSAID-enteropathy through modulation of bile and the microbiota," Br J Pharmacol. 2015;172:992-1004. doi:10.1111/bph.12961.

Blodgett, R., et al., "BAM Appendix 2: Most Probable Number from Serial Dilutions," 2010; Available from: https://www.fda.gov/food/laboratory-methods-food/bam-appendix-2-most-probable-numberserial-dilutions. Downloaded Nov. 12, 2020. 27 pages.

Bo, T.B., et al., "Coprophagy prevention alters microbiome, metabolism, neurochemistry, and cognitive behavior in a small mammal," ISME Journal, 2020. 14(10): p. 2625-2645.

Bodilis, J., et al., "Variable copy number, intra-genomic heterogeneities and lateral transfers of the 16S rRNA gene in pseudomonas," PLoS One, 2012. 7(4): p. e35647. 14 pages.

Bogatyrev, Et al., "Making gut microbiome studies more human" Video Script published on Research Square. Downloaded from https://www.researchsquare.com/article/rs-25831/v1 on Mar. 15, 2021. 2 Pages.

Bogatyrev, S.R., et al., "Development of Analytical Tools and Animal Models for Studies of Small-Intestine Dysbiosis," Thesis Defense. Sep. 20, 2019 . 64 Pages.

Bogatyrev, S.R., "Development of Analytical Tools and Animal Models for Studies of Small-Intestine Dysbiosis," Thesis by Said R. Bogatyrev, California Institute of Technology. 2020. 96 pages.

Bogatyrev, S.R., et al., "Quantitative microbiome profiling in lumenal and tissue samples with broad coverage and dynamic range via a single-step 16S rRNA gene DNA copy quantification and amplicon barcoding," bioRxiv p. Jan. 22, 2020. 914705.2020. 16 Pages.

Bogatyrev, S.R., et al., "Self-reinoculation with fecal flora changes microbiota density and composition leading to an altered bile-acid profile in the mouse small intestine,". Microbiome, 2020. 8(19): p. 22 Pages.

Bokulich, N.A., et al., "Optimizing taxonomic classification of marker-gene amplicon sequences with QIIME 2's q2-feature classifier plugin," Microbiome, 2018. 6(1): p. 90. 18 Pages.

Bolyen, E., et al., "QIIME 2: Reproducible, interactive, scalable, and extensible microbiome data science," PeerJ Preprints 6, e27295v27292 (2018). 53 Pages.

Bolyen, E., et al., "Reproducible, interactive, scalable and extensible microbiome data science using QIIME 2," Nat Biotechnol, 2019. 37(8): p. 852-857. 7 Pages.

Bowman, J.S., et al., "Microbial Communities Can Be Described by Metabolic Structure: A General Framework and Application to a Seasonally Variable, Depth-Stratified Microbial Community from the Coastal West Antarctic Peninsula," PLoS One, 2015. 10(8): p. e0135868. 19 Pages.

Brown EM, et al., "Diet and specific microbial exposure trigger features of environmental enteropathy in a novel murine model," Nat Commun. Aug. 4, 2015; 6:7806. 16 pages. doi:10.1038/ncomms8806.

Buhnik-Rosenblau K, et al., "Predominant effect of host genetics on levels of Lactobacillus johnsonii bacteria in the mouse gut," Appl Environ Microbiol. 2011; vol. 77, No. 18:6531-6538. doi:10.1128/AEM.00324-11.

Calattini, S., et al., "Functional and Biochemical Characterization of Hepatitis C Virus (HCV) Particles Produced in a Humanized Liver Mouse Model" J Biol Chem, 2015. 290(38): p. 23173-23187. 15 Pages.

Callahan, B.J., et al., "DADA2:High-resolution sample inference from Illumina amplicon data," Nat Methods, 2016. 13(7): p. 581-583. 8 Pages.

Caporaso, J.G., et al., "Global patterns of 16S rRNA diversity at a depth of millions of sequences per sample," Proc Natl Acad Sci USA, 2011. 108 Suppl 1: p. 4516-4522. 8 Pages.

(56) References Cited

OTHER PUBLICATIONS

Caporaso, J.G., et al., "QIIME allows analysis of high-throughput community sequencing data," *Nat Methods*, 2010. 7(5): p. 335-336. 3 Pages.
Caporaso, J.G., et al., "Ultra-high-throughput microbial community analysis on the Illumina HiSeq and MiSeq platforms," *ISMEJ*, 2012. 6(8): p. 1621-1624. 5 pages.
Carmody, Rachel N. et al. "Diet Dominates Host Genotype in Shaping the Murine Gut Microbiota," *Cell Host Microbe* 17,72-84, Jan. 14, 2015. 14 pages.
Caruso, V., et al., "Performance of Microbiome Sequence Inference Methods in Environments with Varying Biomass," mSystems, vol. 4, Issue 1, e00163-18, Jan./Feb. 2019. 20 Pages.
Castillo, M., et al., "Quantification of total bacteria, enterobacteria and lactobacilli populations in pig digesta by real-time PCR," *Veterinary Microbiology*, 2006. 114(1): p. 165-170. 7 Pages.
Chakravorty, Soumitesh et al., "A detailed analysis of 16S ribosomal RNA gene segments for the diagnosis of pathogenic bacteria," *Journal of Microbiological Methods*, 2007, vol. 69, No. 2, pp. 330-339. 11 Pages.
Chen, C.Y., et al., "A 6 × 6 drop plate method for simultaneous colony counting and MPN enumeration of *Campylobacter jejuni*, *Listeria monocytogenes*, and *Escherichia coli*," *J Microbiol Methods*, 2003. 55(2): p. 475-479. 6 Pages.
Chen, R.Y. et al. "Duodenal Microbiota in Stunted Undernourished Children with Enteropathy" New Engl. J. Med. 383, 321-333 (2020).
Chen, Y. et al. "Dysbiosis of small intestinal microbiota in liver cirrhosis and its association with etiology" *Sci. Rep.* 6, 34055, 2016. 10 Pages.
Chikai, T., et al., "Deconjugation of bile acids by human intestinal bacteria implanted in germ-free rats," *Lipids*, 1987. 22(9): p. 669-671. 4 Pages.
Chung H, et al., "Gut immune maturation depends on colonization with a host-specific microbiota," Cell. 2012 ;149:1578-93.doi:10. 1016/j.cell.2012.04.037.
Claesson, M.J., et al., "Comparison of two next-generation sequencing technologies for resolving highly complex microbiota composition using tandem variable 16S rRNA gene regions," *Nucleic Acids Res*, Sep. 29, 2010. 38(22): p. e200. 14 Pages.
Claus SP, et al., "Systemic multicompartmental effects of the gut microbiome on mouse metabolic phenotypes," *Mol Syst Biol*. 2008; 4:219.doi:10.1038/msb.2008.56 14 pages.
Collado, M.C., et al., "Intestinal integrity and Akkermansia muciniphila, a mucin-degrading member of the intestinal microbiota present in infants, adults, and the elderly," *Applied and environmental microbiology*, 2007. 73(23): p. 7767-7770. 5 pages.
Contijoch, E.J., et al., "Gut microbiota density influences host physiology and is shaped by host and microbial factors," *eLIFE*, 2019, 8 e40553. 27 Pages.
Coyte KZ, et al., "The ecology of the microbiome: Networks, competition, and stability," Science, vol. 350, Issue 6261. Nov. 6, 2015. pp. 663-666 doi:10.1126/science.aad2602. 6 Pages.
Croy, B.A., et al., "Chapter 13—Mouse Models of Immunodeficiency," in The Mouse in Biomedical Research (Second Edition), J.G. Fox, et al., Editors. 2007, Academic Press: Burlington. p. 275-289.
Davis, N.M., et al., "Simple statistical identification and removal of contaminant sequences in marker-gene and metagenomics data," *Microbiome*, 2018. 6(1): p. 226. 14 Pages.
Dawson AM. "Bile salts and fat absorption," Gut. 1967;8:1-3. doi:10.1136/gut.8.1.1.
Dejea, C.M. et al. "Patients with familial adenomatous polyposis harbor colonic biofilms containing tumorigenic bacteria" Science 359, 592-597 (2018).
Dey N, et al., "Regulators of gut motility revealed by a gnotobiotic model of diet-microbiome interactions related to travel," Cell. 2015; 163:95-107. doi:10.1016/j.cell.2015.08.059.

Di Gioia, D., et al., "Bifidobacteria: their impact on gut microbiota composition and their applications as probiotics in infants," Applied Microbiology and Biotechnology, 2014. 98(2): p. 563-577.
Donaldson, G.P., et al., "Gut biogeography of the bacterial microbiota," *Nat Rev Microbiol*, 2016. 14(1): p. 20-32. 14 Pages.
Donaldson RM. Et al., "Studies on the pathogenesis of steatorrhea in the blind loop syndrome," J Clin Invest. 1965; 44:1815-25. doi:10.1172/JCI105289.
Dong, Z., et al., "Bile salt hydrolases: Structure and function, substrate preference, and inhibitor development.," *Protein Sci*, 2018. 27(10): p. 1742-1754. 14 Pages.
Donowitz JR, et al., "Pediatric small intestine bacterial overgrowth in low-income countries," *Trends in Molecular Med*. 2015; vol. 21, No. 1:6-15. doi: 10.1016/j.molmed.2014.11.001.
Douglas, G.M., et al., "PICRUSt2: An improved and customizable approach for metagenome inference," bioRxiv, 2020: p. 672295. 17 Pages.
Ebino, K.Y., et al., "A simple method for prevention of coprophagy in the mouse," *Lab Anim*, 1988. 22(1): p. 1-4. 4 Pages.
Ebino KY, et al., "Analyses of constituents of feces and the effect of a vitamin B12 fortified diet on coprophagy in the mouse, " *Jikken Dobutsu (Exp. Anim.)* 1986; 35:381-6. 7 Pages.
Ebino KY, et al., "Coprophagy in the germ-free mouse". *Exp. Anim.* 1987; 36:33-37. English Abstract Only.
Ebino, K.Y., "Studies on coprophagy in experimental animals," (Jikken Dobutsu) Exper. Anim., 1993. 42(1): p. 1-9.
El Aidy S, et al., "The small intestine microbiota, nutritional modulation and relevance for health," Curr Opin Biotechnol. 2015; 32:14-20.doi:10.1016/j.copbio.2014.09.005.
Elazhary, M.A., et al., "A simple procedure for the preliminary identification of aerobic gram negative intestinal bacteria with special reference to the Enterobacteriaceae". Canadian journal of comparative medicine : Revuecanadienne de medecine comparee, 1973. 37(1): p. 43-46.
Enright EF, et al., "Microbiome-mediated bile acid modification: Role in intestinal drug absorption and metabolism," *Pharmacol Res*. 2018 ;133:170-86. doi:10.1016/j.phrs.2018.04.009.
Ericsson, A.C., et al., "The influence of caging, bedding, and diet on the composition of the microbiota in different regions of the mouse gut" Sci Rep, 2018. 8(1): p. 4065. 14 pages.
Faith, J.J., et al., "Predicting a Human Gut Microbiota's Response to Diet in Gnotobiotic Mice," Science 333, 101, Jul. 1, 2011. 6 Pages.
Faith, J.J. et al. "The long-term stability of the human gut microbiota," Science, vol. 341, 1237439. Jul. 5, 2013. 11 pages.
Fajardo, G. and H. Hornicke, "Problems in estimating the extent of coprophagy in the rat" *Br J Nutr*, 1989. 62(3): p. 551-561. 11 Pages.
Feighner SD, et al., "Subtherapeutic levels of antibiotics in poultry feeds and their effects on weight gain, feed efficiency, and bacterial cholyltaurine hydrolase activity," *Appl Environ Microbiol*. 1987 ;53:331-6. 6 Pages.
Fernandes, A.D., et al., "ANOVA-Like Differential Expression (ALDEx) Analysis for Mixed Population RNA-Seq," *PLoSOne* vol. 8, Issue 6, e67019, Jun. 2013. 16 Pages.
Fiorucci S, et al., "Activation of the farnesoid-X receptor protects against gastrointestinal injury caused by non-steroidal anti-inflammatory drugs in mice," Br J Pharmacol. 2011; 164:1929-38. doi:10.1111/j.1476-5381.2011.01481.x.
Fitzgerald RJ, et al., "Effects of Coprophagy Prevention on Intestinal Microflora in Rats," J Nutr., Oct. 1964; vol. 84, No. 2:155-60. doi:10.1093/jn/84.2.155.
Foley, M.H., et al., "Bile salt hydrolases: Gatekeepers of bile acid metabolism and host-microbiome crosstalk in the gastrointestinal tract," *PLoS Pathog*, Mar. 2019. 15(3): p. e1007581. 7 pages.
Franklin, C.L., et al., "Microbiota and reproducibility of rodent models," *Lab Anim* (NY), Apr. 2017. 46(4): p. 114-122. 9 Pages.
Frape, D.L., et al., "A simplified metabolism cage and tail cup for young rats," Lab Anim, 1970. 4(1): p. 67-73. 8 Pages.
Friedman, J., et al., "Inferring Correlation Networks from Genomic Survey Data," *PLoS Comp. Biol*. 8, issue 9 e1002687, Sep. 2012. 12 Pages.

(56) References Cited

OTHER PUBLICATIONS

Geever, E.F., D. Kan, and S.M. Levenson, "Effect of coprophagy on experimental iron absorption in the rat" J Nutr, 1969. 98(1): p. 95-98.

Geng W, et al., " Bacterial bile salt hydrolase: an intestinal microbiome target for enhanced animal health," Anim Heal Res Rev. 2016; 17:148-58.doi:10.1017/S1466252316000153.

George SE, et al., "Acute colonization study of polychlorinated biphenyl-degrading pseudomonads in the mouse intestinal tract: Comparison of single and multiple exposures," Environ Toxicol Chem. 1989 ;8:123-31. doi:10.1002/etc.5620080203. 10 Pages.

Gevers, D., et al., "The Treatment-Naïve Microbiome in New-Onset Crohn's Disease," Cell Host & Microbe, 2014. 15(3): p. 382-392.

Geyer, R.P. et al., "Growth studies with rats kept under conditions that prevent coprophagy" J Nutr, 1947. 33(2): p. 129-142. 17 Pages.

Giamarellos-Bourboulis EJ., et al., "Small intestinal bacterial overgrowth is associated with irritable bowel syndrome and is independent of proton pump inhibitor usage," BMC Gastroenterol. 2016; 16:67. doi:10.1186/s12876-016-0484-6.

Glassing, A., et al., "Inherent bacterial DNA contamination of extraction and sequencing reagents may affect interpretation of microbiota in low bacterial biomass samples," Gut Pathog. 8,24, 2016. 13 Pages.

Gloor, G.B., et al., "Compositional analysis: a valid approach to analyze microbiome high-throughput sequencing data," Can.J. Microbiol. 62,692-703, Apr. 12, 2016. 13 Pages.

Gloor, G.B., et al., "It's all relative: analyzing microbiome data as composition," Ann Epidemiol, 2016. 26(5): p. 322-329. 9 Pages.

Gloor, G.B., et al., "Microbiome Datasets Are Compositional: And This Is Not Optional," Front Microbio. vol. 8, Article 2224, Nov. 2017. 6 Pages.

Gohl, D.M., et al., "Systematic improvement of amplicon marker gene methods for increased accuracy in microbiome studies," Nat Biotechnol, 2016. 34(9): p. 942-949. 12 Pages.

Goldberg, S., et al., "Isolation of Enterobacteriaceae from the Mouth and Potential Association with Malodor" J. Dent. Res. 76(11), 1770-1775 (1997).

Gonçalves, M.O. et al. "Periodontal disease as reservoir for multiresistant and hydrolytic enterobacterial species" Lett. Appl. Microbiol. 44,488-494 (2007).

Grompe, M. and Strom, S., "Mice With Human Livers" Gastroenterology, 2013. 145(6):p. 1209-1214. 6 Pages.

Gu, S., et al., "Bacterial community mapping of the mouse gastrointestinal tract," PLoS One, 2013. 8(10): p. e74957.

Guan X, et al., "Screening and characterization of lactic acid bacterial strains that produce fermented milk and reduce cholesterol levels," Braz J Microbiol. 2017 ;48:730-739. doi:10.1016/j.bjm. 2017.02.011.

Hardwick, S.A. et al. "Synthetic microbe communities provide internal reference standards for metagenome sequencing and analysis," Nature Communications 9, 3096, 2018. 11 Pages.

Hartman, A.L. et al. "Human gut microbiome adopts an alternative state following small bowel transplantation," Proc. Natl. Acad. Sci. U. S. A. 106, 17187-17192, Oct. 6, 2009. 7 Pages.

Hawinkel, S., et a., "A broken promise: microbiome differential abundance methods do not control the false discovery rate," Brief. Bioinform. 20, 210-221 (2017). 13 Pages.

Hayashi H, et al., "Molecular analysis of jejunal, ileal, caecal and recto-sigmoidal human colonic microbiota using 16S rRNA gene libraries and terminal restriction fragment length polymorphism.," J Med Microbiol. 2005; 54:1093-1101. doi:10.1099/jmm.0.45935-0.

Heeney, D.D., et al., "Intestinal Lactobacillus in health and disease, a driver or just along for the ride?" Current Opinion in Biotechnology, 2018. 49: p. 140-147.

Helander HF, et al., "Surface area of the digestive tract—revisited," Scand J Gastroenterol 2014; 49:681-9. doi:10.3109/00365521.2014. 898326.

Hellstrom K, et al., "Turnover of deoxycholic acid in the rabbit," J Lipid Res. 1962; 3:397-404. 8 Pages.

"HepatoRat: Hera Biolabs" Downloaded from https://www.herabiolabs.com/humanized-liver-mice/ on Mar. 9, 2021. 4 Pages.

Hindson, B.J. et al. "High-Throughput Droplet Digital PCR System for Absolute Quantitation of DNA Copy Number," Anal Chem. 83,8604-8610, 2011. 8 Pages.

Hodkinson, B.P., "A microbiotic survey of lichen-associated bacteria reveals a new lineage from the Rhizobiales," Symbiosis, 2009. 49(3): p. 163-180. 18 Pages.

Hoff, J., "Methods of blood collection in the mouse," Lab Animal, 2000. 29(10): p. 47-53. 8 Pages.

Hofmann AF. Et al., "Targeting drugs to the enterohepatic circulation: Lessons from bile acids and other endobiotics," J Control Release. 1985;2:3-11.doi:10.1016/0168-3659(85)90028-8.

Hoshino, T., et al., "Application of Stochastic Labeling with Random-Sequence Barcodes for Simultaneous Quantification and sequencing of Environmental 16S rRNA Genes," PLoSOne 12, e0169431, 2017. 16 Pages.

Hörnicke, H., et al., "Coprophagy and related strategies for digesta utilization," in Digestive Physiology and Metabolism in Ruminants: Proceedings of the 5th International Symposium on Ruminant Physiology, held at Clermont—Ferrand, on Sep. 3-7, 1979, Y. Ruckebusch and P. Thivend, Editors. 1980, Springer Netherlands: Dordrecht. p. 707-730. 25 Pages.

Hugenholtz, F., et al., "Mouse models for human intestinal microbiota research: a critical evaluation," Cell Mol Life Sci, 2018. 75(1): p. 149-160. 13 pages.

Hunter, J.D., "Matplotlib: A 2D graphics environment," Computing in Science & Engineering, 2007. 9(3): p. 90-95. 7 Pages.

Ierardi E, et al., "Macronutrient intakes in obese subjects with or without small intestinal bacterial overgrowth: an alimentary survey," Scand J Gastroenterol. 2015; vol. 51, No. 3:277-80. doi:10. 3109/00365521.2015.1086020.

International Preliminary Report on Patentability for International Application No. PCT/US2020/041787 filed on Jul. 13, 2020 on behalf of California Institute of Technology Mail Date: Jan. 18, 2022 8 pages.

International Search Report and Written Opinion for PCT App. No. PCT/US2021/013308 field on Jan. 13, 2021 on behalf of California Institute of Technology. Mail Date: May 12, 2021. 14 Pages.

International Search Report and Written Opinion for PCT App. No. PCT/US2020/041787 filed on Jul. 13, 2020 on behalf of California Institute of Technology. Mail Date: Nov. 6, 2020. 14 Pages.

Ivanov II, et al., "Induction of intestinal Th17 cells by segmented filamentous bacteria," Cell. 2009; 139:485-98. doi:10.1016/j.cell. 2009.09.033.

Iwai S, et al., "Piphillin: improved prediction of metagenomic content by direct inference from human microbiomes," PLoS One. 2016; 11:e0166104.doi:10.1371/journal.pone.0166104.

Jeun J, et al., "Hypocholesterolemic effects of Lactobacillus plantarum KCTC3928 by increased bile acid excretion in C57BL/6 mice," Nutrition, 2010; 26:321-30. doi:10.1016/j.nut.2009.04.011.

Ji, B.W., et al., "Quantifying spatiotemporal dynamics and noise in absolute microbiota abundances using replicate sampling," bioRxiv, 310649, 2018. 13 pages.

"Patient-Derived Xenografts"—PDX Models by Charles River Laboratories, Downloaded from www.criver.com/products-services/discovery-services/pharmacology-studies/oncology-immuno-oncology-studies/oncology-study-models/patient-derived-xenografts-pdx-models?region=3601 on Mar. 9, 2021. 10 Pages.

"Primary Cell Liver Humanized Animal Models: The relevance of data from human tissue generated from an in vivo rodent model," downloaded from Yecuris FRG: Liver-Humanized Mice & Preclinical Research Services found online at https://www.yecuris.com/frg-ko-mice/ on Mar. 12, 2019. 7 Pages.

"Quantitative Methods for Improved Accuracy and Insights in Microbiome Studies" BBE Retreat Poster by Ismagilov Lab. 2019. 1 Page.

Notice of Allowance for U.S. Appl. No. 17/863,183, filed Jul. 12, 2022 on behalf of California Institute of Technology. Mailed on May 23, 2024. 11 pages.

Certification Statement and list—37 CFR 1.98(d)(1) filed in U.S. Appl. No. 17/148,543, filed Jan. 13, 2021 on behalf of California Institute of Technology. 1 page.

(56) References Cited

OTHER PUBLICATIONS

Corrected Notice of Allowability for U.S. Appl. No. 17/863,183, filed Jul. 12, 2022 on behalf of California Institute of Technology. Mailed on Jun. 5, 2024. 5 pages.
Notice of Allowance for U.S. Appl. No. 17/863,183, filed Jul. 12, 2022 on behalf of California Institute of Technology. Mailed on Aug. 15, 2024. 8 pages.

* cited by examiner

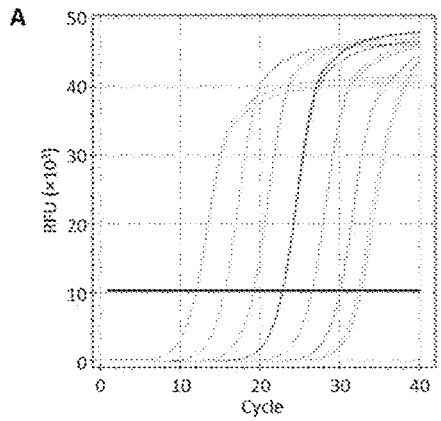

$$sample = standard \times (2 \times PCR\ efficiency)^{\Delta Cq} \quad (Eq.\ 1.1)$$

$$\Delta Cq = Cq_{standard} - Cq_{sample} \quad (Eq.\ 1.2)$$

$$PCR\ efficiency = 95.0\%$$

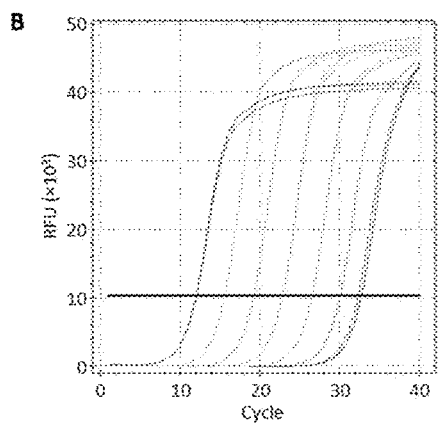

$$sample = standard \times (2 \times PCR\ efficiency)^{\Delta Cq} \quad (Eq.\ 2.1)$$

$$PCR\ efficiency = \frac{\sqrt[\Delta Cq_{standard}]{\frac{standard1}{standard2}}}{2} \quad (Eq.\ 2.2)$$

$$PCR\ efficiency = 10^{\frac{1}{slope}} - 1 \quad (Eq.\ 2.3)$$

$$slope = -\frac{\Delta Cq_{standard}}{\log_{10}\left(\frac{standard1}{standard2}\right)} \quad (Eq.\ 2.4)$$

$$\Delta Cq_{standard} = Cq_{standard1} - Cq_{standard2} \quad (Eq.\ 2.5)$$

$$\Delta Cq = Cq_{standard} - Cq_{sample} \quad (Eq.\ 2.6)$$

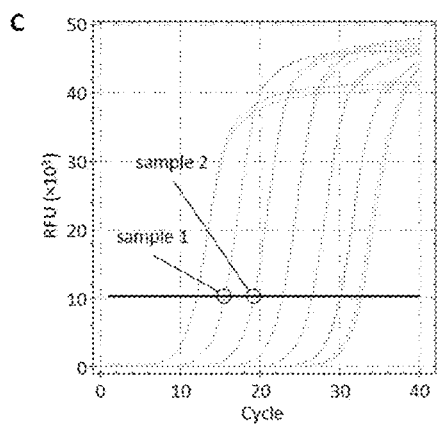

$$\frac{sample1}{sample2} = (2 \times PCR\ efficiency)^{\Delta Cq} \quad (Eq.\ 3.1)$$

$$\Delta Cq = Cq_{sample2} - Cq_{sample1} \quad (Eq.\ 3.2)$$

$$PCR\ efficiency = 95.0\%$$

--- samples with unknown 16S rRNA gene copy load
---- standards (e.g., $10^8$ 16S rRNA gene copies ml$^{-1}$)
— Cq threshold

FIG. 2

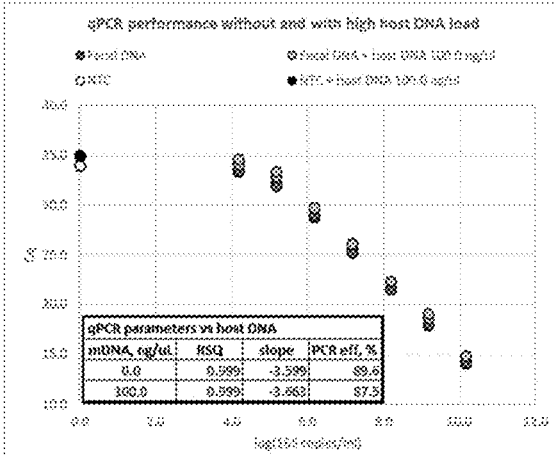
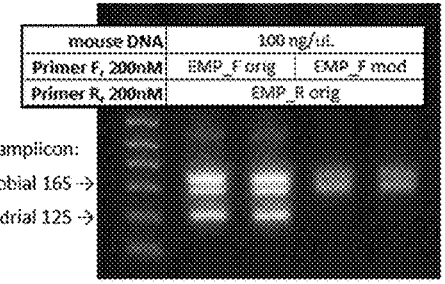
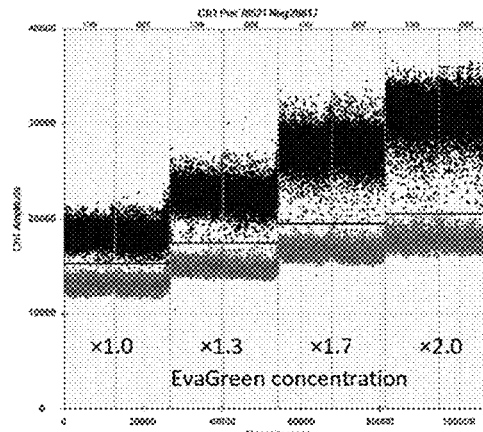
FIG. 3

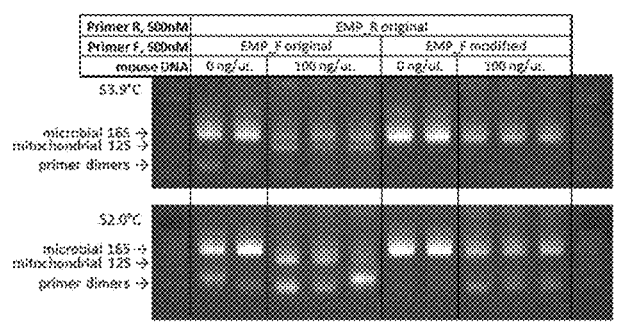
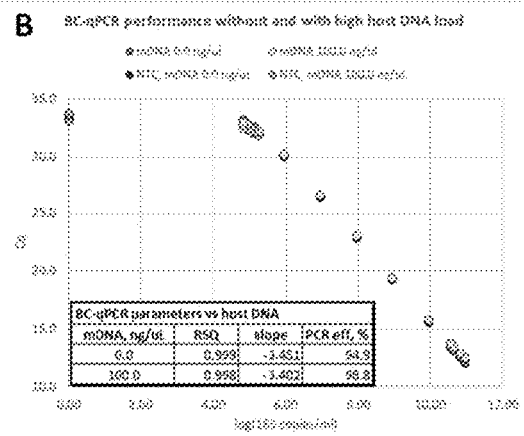
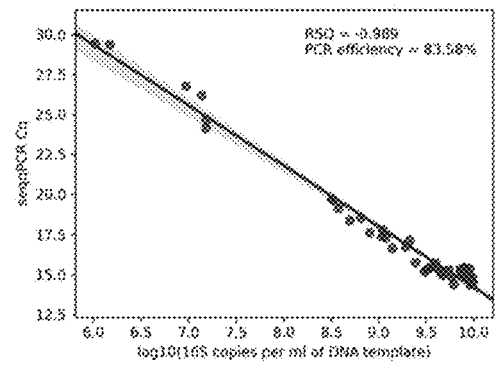
FIG. 4

| Contaminant Taxa | Percentage Abundance |
|---|---|
| Acinetobacter(g) | 31.38 |
| Pseudomonas(g) | 24.12 |
| Allorhizobium-Neorhizobium-Pararhizobium-Rhizobium(g) | 9.77 |
| Brevundimonas(g) | 5.86 |
| Massilia(g) | 2.84 |
| Delftia(g) | 2.52 |
| Dietzia(g) | 2.33 |
| Corynebacterium 1(g) | 2.08 |
| Xanthomononadaceae(f) | 2.06 |
| Anaerococcus(g) | 1.95 |
| Nubsella(g) | 1.94 |
| Lysobacter(g) | 1.91 |
| Comamonas(g) | 1.82 |
| Janthinobacterium(g) | 1.30 |
| Shinella(g) | 1.29 |
| Novosphingobium(g) | 1.23 |
| Sphingobium(g) | 1.15 |
| Taibaiella(g) | 1.02 |

FIG. 22

| Approach | Major Improvement to the Field | Demonstrated Limit of Quantification | Demonstrated Limit of Detection | Demonstrated Precision | Validated Sampling Locations | Validation Against PCR Amplification Bias | Bias-Free Validation with High Host DNA Loads | References |
|---|---|---|---|---|---|---|---|---|
| Flow Cytometry | Showed importance of quantifying absolute abundance in clinical samples | Not Discussed | Not Discussed | Not Discussed | Stool | Not Applicable | Not Shown | Vandeputte et al. 2017[1] |
| Sequencing Spike-ins | Generated a variety of spike-in standards that can be used. Provided comprehensive analysis of detection limits and accuracy | Not Discussed | Dependent on spike-in amount (~100 copies/reaction) | 1.5-1.7X with mock communities | Sludge, Soil | Show that it may skew total load measurement | Not Shown | Tourlousse et al. 2016[2] |
| qPCR Anchoring | Provided a simple and easy method for absolute quantification | Not Discussed | Not Discussed | High correlation at high DNA input levels | Stool | Not Discussed | Not Shown | Jian et al. 2018[3] |
| Total DNA | Provided a simple method for absolute quantification. Showed dramatic variability in loads across animal kingdom and clinical scenarios | Not Discussed | ~100 pg of DNA | Not Discussed | Stool | Not Applicable | Not Applicable for stool | Contijoch et al. 2019[4] |
| Digital PCR Anchoring | Quantitative assessment of accuracy and precision of absolute abundances in complex gut samples and their impact on differential taxon analyses | $4.2 \times 10^5$ 16S copies/g Stool $1.0 \times 10^7$ 16S copies/g Mucosa | $4.2 \times 10^4$ 16S copies/g Stool $1.0 \times 10^6$ 16S copies/g Mucosa | 2X across 6 orders of magnitude with low and high host DNA load | Stool, Mucosa, Small Intestine, Cecum, Stomach | Yes | Yes | This paper |

FIG. 23

|  | TD.150300 | TD.07797.PWD |
|---|---|---|
|  | Control Diet (g/kg) | Ketogenic Diet (g/kg) |
| Casein | 200 | 121 |
| Crisco | 61.25 | 605 |
| Corn Oil | 8.75 | 86.2 |
| Cellulose | 50 | 112.95 |
| Corn Starch | 389 | 0 |
| Maltodextrin | 100 | 0 |
| Sucrose | 150 | 0 |
| DL-Methionine | 3 | 1.56 |
| Vitamin Mix, Teklad (40060) | 10 | 17.8 |
| Choline Bitartrate | 0 | 2.5 |
| TBHQ, antioxidant | 0.07 | 0.14 |
| Mineral Mix, Ca-P Deficient (79055) | 13.37 | 23.8 |
| Calcium Phosphate, dibasic | 7.5 | 24.3 |
| Calcium Carbonate | 6.85 | 4.4 |
| Magnesium Oxide | 0.2 | 0.35 |

FIG. 24

| Taxon | Absolute Abundance Ketogenic Diet (16S copies/g) | Absolute Abundance Control Diet (16S copies/g) | log₂ Fold Change (Keto/Control) | Relative Abundance Ketogenic Diet (%) | Relative Abundance Control Diet (%) | Quantification Class |
|---|---|---|---|---|---|---|
| GCA-900066575(g) | 1.94E+09 | 8.71E+07 | 4.00 | 0.799 | 0.014 | Semi-Quant |
| Ruminococcaceae(f) | 2.02E+09 | 2.43E+08 | 2.87 | 0.909 | 0.033 | Semi-Quant |
| Lachnospiraceae NK4A136 group(g) | 5.34E+09 | 8.57E+08 | 2.58 | 2.362 | 0.135 | Quant |
| Acetatifactor(g) | 5.20E+08 | 6.19E+07 | 2.46 | 0.256 | 0.009 | Semi-Quant |
| Lachnospiraceae(f) | 8.29E+09 | 1.71E+09 | 2.25 | 3.708 | 0.226 | Quant |
| Ruminiclostridium 9(g) | 1.91E+09 | 5.01E+08 | 1.84 | 0.863 | 0.059 | Quant |
| Dorea(g) | 7.79E+07 | 0.00E+00 | 1.36 | 0.032 | 0.000 | Presence/Absence |
| Enterorhabdus(g) | 7.55E+08 | 3.51E+08 | 0.99 | 0.349 | 0.052 | Quant |
| [Eubacterium] xylanophilum group(g) | 8.69E+07 | 1.91E+07 | 0.87 | 0.037 | 0.003 | No Quant |
| Peptococcus(g) | 8.83E+07 | 2.29E+07 | 0.79 | 0.040 | 0.004 | Semi-Quant |
| Candidatus Soleaferrea(g) | 5.91E+07 | 6.21E+06 | 0.78 | 0.026 | 0.002 | No Quant |
| Marvinbryantia(g) | 5.67E+08 | 1.35E+09 | -1.26 | 0.226 | 0.218 | Quant |
| Bacteroides(g) | 8.81E+09 | 3.37E+10 | -1.93 | 3.990 | 5.578 | Quant |
| Faecalibaculum(g) | 1.01E+11 | 3.87E+11 | -1.93 | 46.724 | 54.268 | Quant |
| Prevotellaceae UCG-001(g) | 1.50E+07 | 7.87E+07 | -2.12 | 0.006 | 0.015 | No Quant |
| Bifidobacterium(g) | 3.18E+08 | 1.42E+09 | -2.15 | 0.153 | 0.100 | Quant |
| Muribaculaceae(f) | 1.25E+08 | 5.74E+08 | -2.16 | 0.056 | 0.091 | Quant |
| Ruminiclostridium 5(g) | 2.85E+08 | 1.38E+09 | -2.26 | 0.127 | 0.202 | Quant |
| Ruminococcaceae UCG-014(g) | 4.85E+08 | 2.45E+09 | -2.32 | 0.209 | 0.427 | Quant |
| Ruminococcaceae NK4A214 group(g) | 8.66E+06 | 6.64E+07 | -2.36 | 0.003 | 0.009 | No Quant |
| Lactococcus(g) | 3.34E+09 | 1.74E+10 | -2.38 | 1.528 | 2.715 | Quant |
| Muribaculaceae(f) | 8.04E+09 | 4.26E+10 | -2.40 | 3.520 | 6.506 | Quant |
| Anaerotruncus(g) | 2.23E+07 | 1.79E+08 | -2.68 | 0.010 | 0.031 | No Quant |
| Lactobacillus(g) | 1.45E+10 | 1.35E+11 | -3.22 | 6.632 | 19.295 | Quant |
| Butyricimonas(g) | 4.38E+08 | 4.39E+09 | -3.30 | 0.203 | 0.755 | Quant |
| Alistipes(g) | 1.11E+09 | 1.15E+10 | -3.36 | 0.526 | 2.018 | Quant |
| Mollicutes RF39(o) | 3.06E+07 | 3.99E+08 | -3.38 | 0.014 | 0.074 | Semi-Quant |
| Christensenellaceae(f) | 2.35E+07 | 3.69E+08 | -3.55 | 0.009 | 0.057 | Semi-Quant |
| Clostridiales vadinBB60 group(f) | 3.31E+07 | 5.68E+08 | -3.77 | 0.017 | 0.108 | Semi-Quant |
| ASF356(g) | 0.00E+00 | 2.44E+08 | -4.65 | 0.000 | 0.029 | Presence/Absence |
| Parabacteroides(g) | 9.26E+07 | 3.30E+09 | -5.01 | 0.040 | 0.457 | Quant |
| Gram-negative bacterium cTPY-13(g) | 0.00E+00 | 3.71E+08 | -5.20 | 0.000 | 0.050 | Presence/Absence |

FIG. 25

| Taxon | Absolute Abundance Ketogenic Diet (16S copies/g) | Absolute Abundance Control Diet (16S copies/g) | log₂ Fold Change (Keto/Control) | Relative Abundance Ketogenic Diet (%) | Relative Abundance Control Diet (%) | Quantification Class |
|---|---|---|---|---|---|---|
| Lachnoclostridium(g) | 1.64E+07 | 7.07E+05 | 3.57 | 0.293 | 0.006 | Semi-Quant |
| Lachnospiraceae(f) | 9.60E+06 | 4.05E+05 | 3.16 | 0.171 | 0.006 | Semi-Quant |
| A2(g) | 2.29E+07 | 2.08E+06 | 3.06 | 0.441 | 0.025 | Semi-Quant |
| Akkermansia(g) | 2.57E+08 | 3.77E+07 | 2.74 | 5.576 | 0.419 | Quant |
| Escherichia-Shigella(g) | 2.96E+06 | 0.00E+00 | 2.21 | 0.059 | 0.000 | Presence/Absence |
| Dorea(g) | 2.94E+06 | 0.00E+00 | 2.20 | 0.062 | 0.000 | Presence/Absence |
| Bacteroides(g) | 5.51E+06 | 8.09E+05 | 1.94 | 0.112 | 0.009 | Semi-Quant |
| Desulfovibrionaceae(f) | 4.29E+06 | 5.91E+05 | 1.82 | 0.097 | 0.005 | Semi-Quant |
| uncultured Bacteroidales bacterium(g) | 1.55E+07 | 3.98E+06 | 1.76 | 0.365 | 0.041 | Quant |
| Enterorhabdus(g) | 1.12E+07 | 2.74E+06 | 1.73 | 0.245 | 0.022 | Semi-Quant |
| Lachnospiraceae NK4A136 group(g) | 1.38E+06 | 3.38E+05 | 0.65 | 0.031 | 0.005 | No Quant |
| Ruminococcaceae(f) | 8.48E+05 | 6.76E+04 | 0.51 | 0.017 | 0.001 | No Quant |
| uncultured Lachnospiraceae bacterium(g) | 6.46E+05 | 0.00E+00 | 0.35 | 0.013 | 0.000 | Presence/Absence |
| Marvinbryantia(g) | 4.62E+06 | 3.33E+06 | 0.27 | 0.127 | 0.037 | Semi-Quant |
| Ruminiclostridium(g) | 5.41E+05 | 0.00E+00 | 0.17 | 0.011 | 0.000 | Presence/Absence |
| Muribaculaceae(f) | 1.22E+08 | 3.48E+08 | -1.51 | 2.585 | 3.041 | Quant |
| Lactococcus(g) | 1.20E+08 | 4.31E+08 | -1.84 | 2.533 | 4.582 | Quant |
| Lactobacillus(g) | 9.05E+08 | 3.70E+09 | -2.03 | 16.956 | 35.988 | Quant |

FIG. 26

|  | *Akkermansia muciniphila* | Bacteroidales | *Lachnospiraceae* | *Lactobacillaceae* | 519F-806R |
|---|---|---|---|---|---|
| Forward Primer | CAGCACGTGAAGGTGGGGAC (SEQ ID NO: 6) | GGTGTCGGCTTAAGTGCCAT (SEQ ID NO: 7) | CGGTACCTGACTAAGAAGC (SEQ ID NO: 8) | GCAGCAGTAGGGAATCTTCCA (SEQ ID NO: 9) | CAGCMGCCGCGGTAA (SEQ ID NO: 10) |
| Reverse Primer | CCTTGCGGTTGGCTTCAGAT (SEQ ID NO: 11) | CGGAYGTAAGGGCCGTGC (SEQ ID NO: 12) | AGTTTYATTCTTGCGAACG (SEQ ID NO: 13) | CACCGCTACACATGGAG (SEQ ID NO: 14) | GGACTACHVGGGTWTCTAAT (SEQ ID NO: 15) |
| Taxonomy Level | Species | Order | Family | Family | Kingdom |
| Annealing Temp (°C) | 65 | 65 | 55 | 60 | 52 |
| Concentration (nM) | 500 | 500 | 500 | 500 | 500 |
| Coverage (n=1 mismatch) | 100% | 75% | 86% | 91% | 94% Bacteria, 95% Archaea |
| Potential Undetected Taxa | None | Rikenellaceae(f); Alistipes(g) | UCG-010(g) | None | None |
| Potential non-specific interactions (n=1 mismatch) | None | None | None | Leuconostocaceae(o) | None |
| Citation | Collado *et al.* (2007)[5] | Rinttilä *et al.* (2004)[6] | Kennedy *et al.* (2014)[7] | Castillo *et al.* (2006)[8] | Bogatyrev & Ismagilov (2020)[9]  Bogatyrev *et al.* (2020)[10]  Bogatyrev (2020)[11] |

FIG. 27

| Primer | Oligonucleotide sequence | Assay | Reference |
|---|---|---|---|
| UN00F2 | CAGCMGCCGCGGTAA (SEQ ID NO: 16) | 16S rRNA gene DNA qPCR 16S rRNA gene DNA ddPCR | [9] |
| UN00R0 | GGACTACHVGGGTWTCTAAT (SEQ ID NO: 17) | | [12, 13] |
| UN00F2_BC | AATGATACGGCGACCACCGA GATCTACACTATGGTAATTGT CAGCMGCCGCGGTAA (SEQ ID NO: 18) | 16S rRNA gene DNA amplicon barcoding | [9] |
| UN00R0_BC | CAAGCAGAAGACGGCATACGAGA T [NNNNNNNNNNN] AGTCAGTCAGCC GGACTACHVGGGTWTCTAAT (SEQ ID NO: 19) | | [12, 13] |
| ILM00F(P5) | AATGATACGGCGACCACCGA (SEQ ID NO: 20) | Barcoded amplicon and NGS library quantification ddPCR | [12-16] |
| ILM00R(P7) | CAAGCAGAAGACGGCATACGA (SEQ ID NO: 21) | | |
| Seq_UN00F2_Read_1 | TATGGTAATTGTCAGCMGCCGCG GTAA (SEQ ID NO: 22) | MiSeq read 1 | [9] |
| Seq_UN00R0_Read_2 | AGTCAGTCAGCCGGACTACHVGG GTWTCTAAT (SEQ ID NO: 23) | MiSeq read 2 | [12, 13] |
| Seq_UN00R0_RC_Index | ATTAGAWACCCBDGTAGTCCGGC TGACTGACT (SEQ ID NO: 24) | MiSeq index read | [12, 13] |

FIG. 38

| Step | Repeats | Temperature, °C | Time, sec |
|---|---|---|---|
| Initial denaturation | × 1 | 95 | 120 |
| Cycle | × 40 | 95 | 15 |
| | | 53 | 10 |
| | | 68 | 45 |

FIG. 39

| Step | Repeats | Temperature, °C | Time, sec | Ramp, °C/sec |
|---|---|---|---|---|
| Initial denaturation | × 1 | 95 | 300 | 2.0 |
| Cycle | × 40 | 95 | 30 | 2.0 |
| | | 52 | 30 | 2.0 |
| | | 68 | 60 | 2.0 |
| Dye stabilization | × 1 | 4 | 300 | 2.0 |
| | | 90 | 300 | 2.0 |
| | | 12 | ∞ | 2.0 |

FIG. 40

| Step | Repeats | Temperature, °C | Time, sec |
|---|---|---|---|
| Initial denaturation | × 1 | 94 | 180 |
| Cycle | × var. | 94 | 45 |
| | | 54 | 60 |
| | | 72 | 105 |
| Final extension | × 1 | 72 | 600 |

FIG. 41

| Step | Repeats | Temperature, °C | Time, sec | Ramp, °C/sec |
|---|---|---|---|---|
| Initial denaturation | × 1 | 95 | 300 | 2.0 |
| Cycle | × 40 | 95 | 30 | 2.0 |
| | | 60 | 90 | 2.0 |
| Dye stabilization | × 1 | 4 | 300 | 2.0 |
| | | 90 | 300 | 2.0 |
| | | 12 | ∞ | 2.0 |

FIG. 42

| Bile acid | Reference # | Vendor | LOT |
|---|---|---|---|
| TαMCA | C1893-000 | Steraloids | B1439 |
| TβMCA | C1899-000 | Steraloids | B1594 |
| TωMCA | C1889-000 | Steraloids | B1731 |
| THCA | C1887-000 | Steraloids | B1621 |
| αMCA | C1890-000 | Steraloids | B1529 |
| βMCA | C1895-000 | Steraloids | B1725 |
| ωMCA | C1888-000 | Steraloids | B1710 |
| HCA (gMCA) | C1850-000 | Steraloids | B0696 |
| HDCA | C0860-000 | Steraloids | B0684 |
| MCA | C0910-000 | Steraloids | B1711 |
| GDCA | C1087-000 | Steraloids | B2122 |
| GCA | C1927-000 | Steraloids | |
| GHDCA | C0865-000 | Steraloids | B1667 |
| GHCA | C1860-000 | Steraloids | L1105 |
| TCA | 13232UNL | Isosciences | EH1-2015-111A1 |
| CA | 13098UNL | Isosciences | EH1-2014-075A1 |
| DCA | 13100UNL | Isosciences | EH1-2014-076A1 |
| TCDCA | 13105UNL | Isosciences | EH1-2015-110A1 |
| TDCA | 13225UNL | Isosciences | EH1-2015-112A1 |
| TUDCA | 13106UNL | Isosciences | EH1-2014-027A1 |
| TLCA | 13230UNL | Isosciences | EH1-2014-077A1 |
| CDCA | 13101UNL | Isosciences | PG1-2014-149A1 |
| UDCA | 13102UNL | Isosciences | EH1-2015-113A1 |
| LCA | 13099UNL | Isosciences | EH1-2014-030A1 |
| D4-TCA | 13232 | Isosciences | SJ5-2015-035A1 |
| D4-DCA | 13100 | Isosciences | RS6-2014-168A1 |
| D4-CA | 13098 | Isosciences | SJ5-2015-100A1 |
| D4-TDCA | 13225 | Isosciences | SJ5-2015-034A1 |
| D4-GLCA | 13231 | Isosciences | SR3-2015-203A1 |
| D4-GUDCA | 13224 | Isosciences | SJ5-2017-206A1 |
| D4-GCDCA | 13104 | Isosciences | SJ4-2012-070A1 |
| D4-GCA | 13443 | Isosciences | SJ5-2015-118A1 |
| D4-GDCA | 13226 | Isosciences | SJ5-2015-033A1 |

FIG. 43

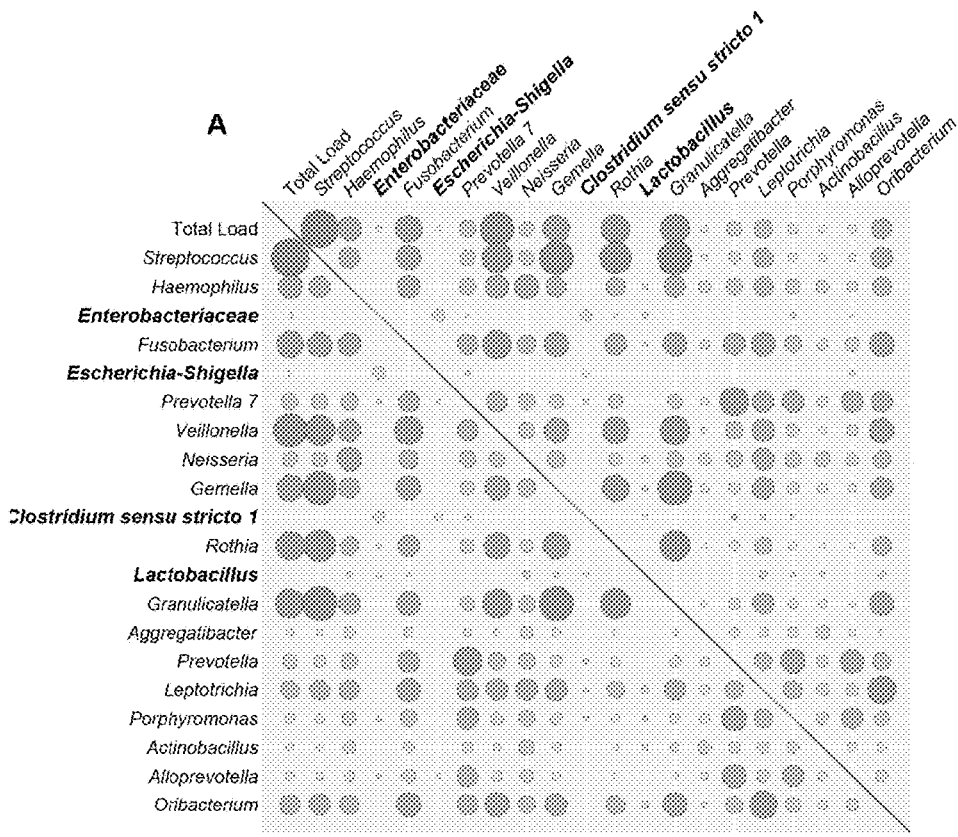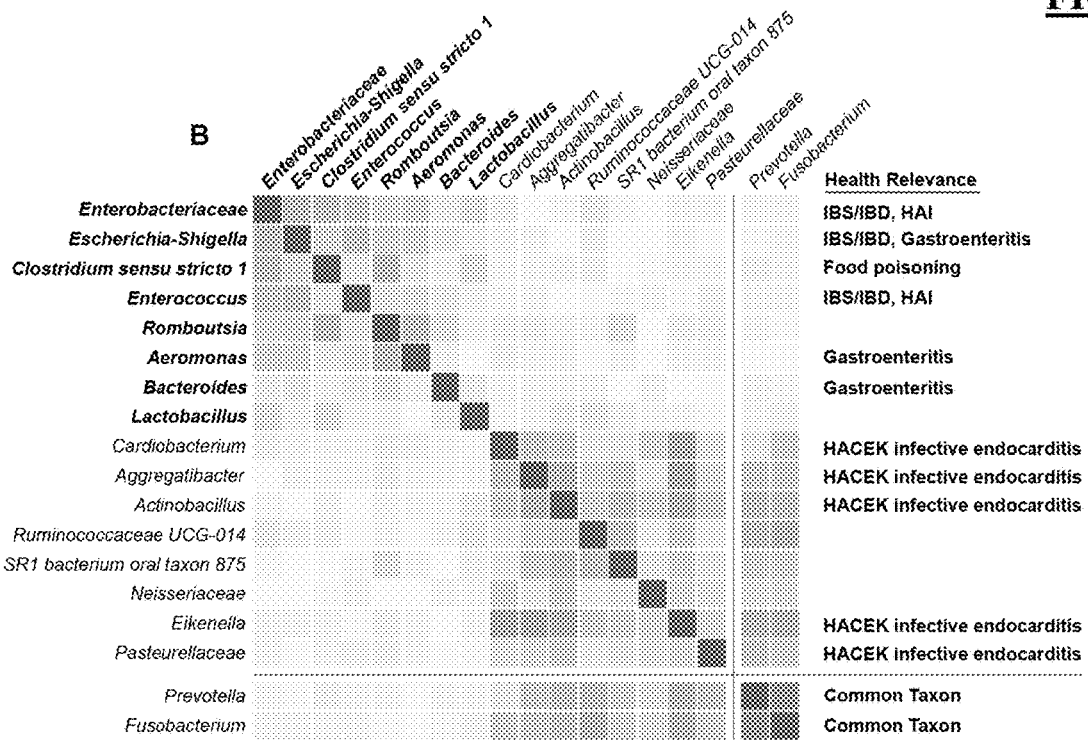
FIG. 54

RODENT MODEL AND RELATED DEVICE, COMPOSITIONS, METHODS AND SYSTEMS

CROSS-REFERENCE TO RELATED APPLICATION

The present application is a continuation-in-part of and claims priority to U.S. application Ser. No. 16/927,496 entitled "Absolute Quantification of Nucleic Acids and Related Methods and Systems" filed on Jul. 13, 2020 and to PCT application S/N PCT/US2020/041787 entitled "Absolute Quantification of Nucleic Acids and Related Methods and Systems" filed on Jul. 13, 2020, each of which in turn further claim priority to U.S. Provisional Application No. 62/961,584, entitled "A Method For Absolute Quantification of Nucleic Acids" filed on Jan. 15, 2020, to U.S. Provisional Application No. 62/873,838, entitled "A Method For Absolute Quantification of Nucleic Acids" filed on Jul. 12, 2019, to U.S. Provisional Application No. 62/873,410, entitled "A method for developing a more humanized rodent model" filed on Jul. 12, 2019, and to the above mentioned U.S. Provisional Application No. 62/960,527, entitled "A method for developing a more humanized rodent model" filed on Jan. 13, 2020, the contents of each of which are also incorporated by reference in its entirety. The present application further claims priority to U.S. Provisional Application No. 62/960,527, entitled "A method for developing a more humanized rodent model" filed on Jan. 13, 2020 and to U.S. Provisional Application No. 62/961,584, entitled "A Method For Absolute Quantification of Nucleic Acids" filed on Jan. 15, 2020, the contents of each of which are incorporated by reference in its entirety.

STATEMENT OF GOVERNMENT GRANT

This invention was made with government support under Grant No. W911NF-17-1-0402 awarded by the US Army and Grant No. EFMA1137089 awarded by the National Science Foundation. The government has certain rights in the invention.

FIELD

The present disclosure relates generally to rodent models and related use. In particular, the present disclosure relates to a rodent model and related devices, composition methods and systems.

BACKGROUND

Rodent models are used extensively in microbiome research and enable the spatial, temporal, compositional, and functional interrogation of the gastrointestinal microbiota and its effects on the host physiology and disease phenotype.

Challenges however remain for developing rodent models having a microbiome closely mimicking microbiomes of interest and in particular human gut microbiome when associated to physiological or pathological conditions of interest, which can provide more reliable model to investigate the causal roles of human microbiomes on the host physiology and disease predisposition and phenotype, as well as drugs pharmacokinetic and personalized medicine.

SUMMARY

Provided herein are customized rodent models and related devices, compositions methods and systems which in several embodiments allow production of customized rodent models having a gut microbiome with controlled presence, proportion and/or total load of target prokaryotes According to a first aspect, a method is described to provide a rodent model having a target microbiome profile formed by a target presence, a target proportion and/or a target total load of a target prokaryote of a target taxon, the target taxon having a taxonomic rank lower than a sample taxon in a same taxonomic hierarchy, the method comprising
    providing a rodent having a rodent microbiome;
    obtaining a sample of the rodent comprising the rodent microbiome to provide a rodent sample;
    quantifying absolute abundance of the target prokaryotes in the rodent sample, to obtain a rodent detected presence, a rodent detected proportion and/or a rodent detected total load of the target prokaryotes in the rodent, each target prokaryote being of a target taxon having a taxonomic rank lower than a sample taxon in a same taxonomic hierarchy; and
    comparing the rodent detected presence, the rodent detected proportion of and/or the rodent detected total load of the target prokaryotes with the target presence, the target proportion and/or the target total load of the target prokaryotes in the target microbiome profile.

In the method to provide a rodent model herein described, the quantifying absolute abundance of the target prokaryotes comprises
    amplifying a 16S rRNA recognition segment comprising a 16S rRNA variable region specific for the target taxon flanked by target 16S rRNA conserved regions specific for the sample taxon, by performing amplification of nucleic acids extracted from the sample with primers comprising a primer target sequence specific for the target 16S rRNA conserved regions to quantitatively detect an absolute abundance of prokaryotes of the sample taxon in the sample and to provide an amplified 16S rRNA recognition segment,
    sequencing the amplified 16S rRNA recognition segment with primers comprising the primer target sequence specific for the target 16S rRNA conserved region and the 16S rRNA variable regions to detect a relative abundance of the prokaryotes of the target taxon with respect to the prokaryotes of the sample taxon in the sample, and
    multiplying the relative abundance of the prokaryotes of the target taxon in the sample times absolute abundance of the prokaryotes of the sample taxon in the sample to quantify the absolute abundance of the prokaryotes of the target taxon in the sample.

In the method to provide a rodent model herein described, the detected presence of the target prokaryote in the rodent is provided by the detected relative abundance and/or absolute abundance wherein presence is detected when the relative abundance is greater than a threshold.

In the method to provide a rodent model herein described, the detected proportion is provided by the relative abundance of the target prokaryote and/or by the quantified absolute abundance in combination with the detected relative abundance providing the detected proportion of the target prokaryote in the rodent.

In the method to provide a rodent model herein described the total load of the target prokaryote is provided by detected absolute abundance of the target prokaryote of the target taxa and/or by the detected absolute abundance of prokaryotes of the sample taxon.

The method to provide a rodent model according to the disclosure can optionally further comprise modifying the rodent microbiome by introducing, enriching and/or depleting prokaryotes in the rodent microbiome to provide the rodent microbiome with the target prokaryotes with the target presence, the target proportion, and/or the target total load;

obtaining a sample of the rodent comprising the rodent microbiome following the modifying to obtain a rodent modified sample;

quantifying absolute abundance of the target prokaryotes in the rodent modified sample, to obtain a detected rodent modified presence, a detected rodent modified proportion and/or a detected rodent modified total load of the target prokaryotes in the rodent, each target prokaryote being of a target taxon having a taxonomic rank lower than a sample taxon in a same taxonomic hierarchy; and comparing the detected rodent modified presence, the detected rodent modified proportion and/or the detected rodent modified total load of the target prokaryotes with the target presence, the target proportion and/or the target total load of the target prokaryotes in the target microbiome profile.

The method to provide a rodent model according to the disclosure can optionally further comprise repeating the modifying, the obtaining to provide a rodent modified sample and the quantifying absolute abundance of the target prokaryotes in the rodent modified sample until the detected rodent modified presence, the detected rodent modified proportion and/or the detected rodent modified total load of the target prokaryote is substantially the same of the target presence, the target proportion and/or the target total load of the target prokaryotes, to obtain the rodent model having the target microbiome profile. In preferred embodiments, the microbiome is a microbiome of the gastrointestinal tract of an individual, and the modifying comprises or consist of preventing coprophagia of the rodent.

According to a second aspect, a system is described to provide a rodent model having a target gut microbiome profile formed by a target presence, a target proportion and/or a target total load of a target prokaryote of a target taxon. The system comprises primers comprising the target primer sequence specific for the target 16S rRNA conserved regions specific for the sample taxon, reagents to perform polymerase chain reaction, and reagents to perform amplicon sequencing for simultaneous combined or sequential use to detect an absolute abundance of target prokaryotes of the target taxon in the sample according to the method herein described. The system can further comprise means for preventing coprophagia preferably a tail cup according to the present disclosure.

According to a third aspect, a customized rodent model is described having a target gut microbiome profile formed by a target presence, a target proportion and/or a target total load of a target prokaryote of a target taxon, and obtained by methods herein described to provide a customized rodent model.

According to a fourth aspect methods and systems are described to perform testing of effects of a compound on physiological and/or pathological conditions associated with a target microbiome, having a target microbiome profile, the method comprises providing a customized rodent model according to the present disclosure having the target microbiome profile, and performing the testing on the customized rodent model.

The system comprises the customized rodent model in combination with the compound and/or reagents to perform the testing for simultaneous combined or sequential use in the method to perform the testing herein described.

According to a fifth aspect methods and systems are described to perform testing of effects of a target microbiome having a target microbiome profile on physiological and/or pathological conditions associated with a target microbiome, having a target microbiome profile, the method comprises providing a customized rodent model according to the present disclosure having the target microbiome profile, and performing the testing on the customized rodent model.

The system comprises the customized rodent model in combination with reagents to perform the testing for simultaneous combined or sequential use in the method to perform the testing herein described.

According to a sixth aspect, a tail cup device is described for animals with tails, the tail cup device comprising: a tubular-shaped cup for trapping excreted feces of an animal, the tubular-shaped cup having a proximal surface configured to fit around a posterior end of the animal and a distal surface and a tail sleeve configured to cover a portion of a tail of the animal and engageable with the tubular-shaped cup through the distal surface of the tubular-shaped cup, for mounting of the tubular-shaped cup at a tail base of the animal.

In the tail cup device, the distal surface of the tubular-shaped cup comprises an orifice operating as a locking opening of the tubular-shaped cup to allow passing through of the tail sleeve from an inside to an outside of the tubular-shaped cup, the orifice having a diameter smaller than a diameter of the tail sleeve in order to allow a locking engagement of the tail sleeve with the tubular-shaped cup when applied to the tail of the animal.

The tail cup device further comprises an unlocking slit for a pressure-based opening of the tubular-shaped cup to engage and disengage the tail sleeve to and from the tubular-shaped cup.

Customized rodent models, and related devices, compositions methods and systems herein described, allow in several embodiments, a more accurate testing of compounds and related properties in connection with target physiological and/or pathological conditions which are associated to a target gut microbiome, such as various gastrointestinal disorders such as SIBO, Crohn's disease, Ulcerative Colitis, Colon cancer, primary sclerosing cholangitis, ulcers, and Celiac disease.

Customized rodent models, and related devices, compositions methods and systems herein described, allow in several embodiments a more accurate testing of compounds and related properties following administration through an individual gastrointestinal tract, such as testing of pharmacokinetic of a drug, toxicology studies, drug interaction studies and additional testing identifiable by a skilled person.

Customized rodent models, and related devices, compositions methods and systems herein described, allow in several embodiments a more accurate testing of the role of microbiome in connection with target physiological and/or pathological conditions such as cancer, autoimmune diseases, obesity, neurological diseases and additional conditions identifiable by a skilled person.

Customized rodent models, and related devices, compositions methods and systems herein described, allow in several embodiments to prepare individualized model mimicking the target microbiome of specific individuals, and therefore allowing a more accurate testing in particular when performed in connection with personalized medicine.

The customized rodent models and related devices methods and systems herein described can be used in connection with various applications wherein a model with a customized gut microbiome is desired. For example, the customized rodent models and related devices methods and systems herein described can be used for quantitative microbiome profiling in human and animal microbiome research, research and investigation in various areas human and veterinary medicine, such as Immuno-Oncology, Immunology, Infectious Disease, Inflammation, Metabolic Disease, Neuroscience, Oncology and additional areas identifiable by a skilled, drug research in particular when focused on drug effectiveness and pharmacokinetics, personalized medicine and additional applications identifiable by a skilled person.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

(FIG. 1 Panel A) Sample collection and DNA extraction. (FIG. 1 Panel B) BC-qPCR reactions are prepared in replicates for more accurate quantification and uniform amplicon barcoding. (FIG. 1 Panel C) Amplification and barcoding of the V4 region of microbial 16S rRNA gene are performed under real-time fluorescence measurements on a real-time PCR instrument. Pr-F—forward primer, Pr-R—reverse primer, IA-P5 and IA-P7—Illumina adapters P5 and P7 respectively, BC—barcode. (FIG. 1 Panel D) Quantitative PCR data (Cq values) are recorded. Mock data are shown for illustration. (FIG. 1 Panel E) Barcoded samples are quantified, pooled, purified, and sequenced on an NGS instrument. (FIG. 1 Panel F) NGS sequencing results provide data on relative abundances of microbial taxa (mock chart data were constructed only for illustrative purposes). Microbial taxa relative abundance profiles are converted to microbial absolute or absolute fold-difference abundance profiles using the absolute or absolute fold-difference data (16S rRNA gene DNA loads) measured in the corresponding samples in step (D) (FIG. 1 Panel D) (mock chart data were constructed only for illustrative purposes).

FIG. 2 shows schematic drawings describing anchoring approaches for deriving the absolute abundances or absolute abundance fold differences implemented with the single-step 16S rRNA gene DNA quantification and amplicon barcoding workflow (BC-qPCR). (FIG. 2 Panel A) Anchoring with a single standard and assumed BC-qPCR efficiency. (FIG. 2 Panel B) Anchoring with two or more standards and calculated batch-specific BC-qPCR efficiency. (FIG. 2 Panel C) Estimation of the absolute fold difference among samples with unknown total 16S rRNA gene DNA copy load in the absence of standards.

FIG. 3 shows an exemplary optimization of the protocol for microbial 16S rRNA gene DNA copy quantification in samples without and with high mammalian DNA background. (FIG. 3 Panel A) Sequence alignment of the original EMP and modified forward primers targeting the V4 region of microbial 16S rRNA gene are shown with the E. coli 16S rRNA gene and mouse and human mitochondrial 12S rRNA gene sequences (SEQ ID NO: 1 to SEQ ID NO: 5). (FIG. 3 Panel B) Amplification products of the complex microbiota DNA sample containing 100 ng/μL of GF mouse DNA obtained with the original EMP or modified forward primers. (FIG. 3 Panel C) Performance of the quantitative PCR reaction with the modified non-barcoded primers performed on serial 10-fold dilutions of the complex microbiota DNA sample with and without 100 ng/μL of mouse DNA. (FIG. 3 Panel D) Improvement of the 16S rRNA gene DNA copy ddPCR quantification assay performance in the presence of 100 ng/μL of mouse DNA background as a result of the supplementation of intercalating dye to the commercial droplet digital PCR (ddPCR) master mix.

FIG. 4 shows in some embodiments the optimization of the single-step protocol for microbial 16S rRNA gene DNA copy quantification and amplicon barcoding in samples without and with high mammalian DNA background. (FIG. 4 Panel A) Amplification products of the complex microbiota DNA sample containing 100 ng/μL of GF mouse DNA with the barcoded original EMP (UN00F0+UN00R0) and barcoded modified (UN00F2+UN00R0) primer sets. (FIG. 4 Panel B) Barcoding quantitative PCR reaction performance with the serial 10-fold dilutions of the complex microbiota DNA sample (SPF mouse fecal microbiota) with and without 100 ng/μL of mouse DNA. (FIG. 4 Panel C) Correlation of the BC-qPCR Cq values (Y-axis) with the absolute 16S rRNA gene DNA copy numbers (X-axis) previously determined in the same set of samples with and without high host DNA background (data in panel C are taken from [1, 2]) using the UN00F2+UN00R0 qPCR assay.

(FIG. 7 Panel a) Taxon A increases in abundance while Taxon B remains the same; (FIG. 7 Panel b) Taxon A remains unchanged while Taxon B decreases in abundance, and (FIG. 7 Panel c) Taxon A and Taxon B both decrease, but Taxon B decreases by a greater magnitude.

(FIG. 8 Panel a) A comparison of theoretical and measured copies of the 16S rRNA gene with digital PCR using an eight-member microbial community spiked at a range of dilutions into germ-free (GF) mouse tissue from small-intestine (SI) mucosa, cecum, and stool. Each bar plot shows a single technical replicate for each matrix. (FIG. 8 Panel b) Relative abundance of the eight taxa as predicted and measured after 16S rRNA gene amplicon sequencing. (FIG. 8 Panel c) Correlation between the mean (n=4) relative abundance of each taxon and the coefficient of variation (% CV) using a cecum sample from a mouse on a chow diet with an initial template input of either $1.2 \times 10^7$ or $1.2 \times 10^4$ 16S rRNA gene copies. Each analysis comprised four technical (sequencing) replicates. Taxa found only in the low-input sample were labeled contaminants (markers with an x); taxa found in the high-input sample but not low input sample were labeled dropouts (marker with a plus sign). Shading indicates the Poisson sampling 95% confidence interval (10,000 bootstrapped replicates) at a sequencing read depth of 28,000. (FIG. 8 Panel d) Relationship between relative abundance threshold (see text for details) and sequencing read depths at 30%, 40%, and 50% CV thresholds.

(FIG. 9 Panel a) Correlation between the Logo abundance of four bacterial taxa as determined by taxa-specific dPCR and 16S rRNA gene sequencing with dPCR anchoring (relative abundance of a specific taxon measured by sequencing * total 16S rRNA gene copies measured by dPCR). (FIG. 9 Panel b) The $Log_2$ ratio of the absolute abundance of four bacterial taxa as determined either by taxa-specific dPCR or by 16S rRNA gene sequencing with dPCR anchoring (N=32 samples). Data points are overlaid on the box and whisker plot. The body of the box plot goes from the first to third quartiles of the distribution and the center line is at the median. The whiskers extend from the quartiles to the minimum and maximum data points within the 1.5× interquartile range, with outliers beyond. All dPCR measurements are single replicates. (FIG. 9 Panel c) Analysis of beta diversity in cecum samples at a series of 1× dilutions (n=1 for each dilution). Mean Aitchison distance for six pairwise comparisons of n=4 sequencing replicates of the undiluted ($10^8$ copies) sample is shown for reference (error bar is standard deviation). Individual data points are overlaid on the replicates bar plot.

(FIG. 10 Panel a) Overview of experimental setup and sample-collection protocol. Gastrointestinal tract (GIT) samples were collected from the following regions: stomach, upper small intestine (SI), lower SI, cecum, colon, and stool. (FIG. 10 Panel b) Comparison of total microbial loads between ketogenic and control diets in lumenal (top) and mucosal (bottom) samples collected after 10 days on each diet. The body of the box plot goes from the first to third quartiles of the distribution and the center line is at the median. The whiskers extend from the quartiles to the minimum and maximum data point within 1.5× interquartile range, with outliers beyond. (FIG. 10 Panel c) Principal component analysis (PCA) on the centered log-ratio transformed absolute abundances of microbial taxa shows separation by GI location and diet (Ketogenic, circles and triangles; Control, X's and crosses). (FIG. 10 Panel d) Ranked order of the eigenvector coefficients scaled by the square root of the corresponding eigenvalue (feature loadings) for the top two principal components. The two most positive and most negative taxa are shown.

(FIG. 11 Panel a) PCA on centered log-ratio transformed relative abundance data and log transformed absolute-abundance data (only the vectors of the five features with the largest magnitude are shown). (FIG. 11 Panel b) The impact of each taxon in the principal-component space, with two taxa indicated to illustrate the comparison. (FIG. 11 Panel c) A comparison of the taxa determined to be significantly different between diets using relative versus absolute quantification (N=6 mice per diet). P-values were determined by Kruskal-Wallis. Each point represents a single taxon; dark greypoints indicate taxa with the absolute value of P-value ratios greater than 2.5; red points indicate two taxa that disagreed significantly between the relative and absolute analyses. (FIG. 11 Panel d) For illustrative purposes, a comparison of *Akkermansia*(g) relative abundance (percentage of *Akkermansia*), absolute abundance (*Akkermansia* load), and total microbial load between stool samples from one mouse on each diet (Ketogenic, light-grey; Control, dark-grey). Whitebars indicate loads prior to the diet switch when all mice were on the chow diet.

(FIG. 16 Panel a) Relationship between the relative abundance of each taxon and % coefficient of variation (CV) using four technical (sequencing) replicates of a mouse cecum sample with an initial template input of $1.2 \times 10^4$ 16S rRNA gene copies. The red shading indicates the bootstrapped (B=104) Poisson sampling confidence interval of the input 16S rRNA gene copies. (FIG. 16 Panel b) Bootstrapped Poisson sampling relationship between % CV and percentage abundance as a function of read depth.

(FIG. 18 Panel a) Principal coordinates analysis (PCoA) plot using Bray-Curtis dissimilarity metric of all samples collected 10 days after the diet switch. (FIG. 18 Panel b) Principal component analysis (PCA) plot using log-transform of absolute abundance data after adding a pseudocount of 1 read to all taxa.

FIG. 22 shows a table listing the contaminant taxa with greater than 1% abundance in negative-control extraction.

FIG. 23 shows a table comparing digital PCR anchoring method for absolute abundance measurements and other published absolute abundance methods [4-7].

FIG. 24 shows a table with composition of ketogenic and control diets used in this study based on previously reported diets (Envigo, Indianapolis, IN, USA) [8].

FIG. 25 shows a table listing the absolute abundance, relative abundance, fold change and quantification class for each differentially abundant taxon in the stool 10 days after diet switch.

FIG. 26 shows a table listing the absolute abundance, relative abundance, fold change, and quantification class for each differentially abundant taxon in the lower small-intestine mucosa 10 days after diet switch.

FIG. 27 shows a table listing the primers used in this study, relevant conditions, and specificity. All primers (SEQ ID NO: 6-15) were tested in silico for coverage of their desired taxonomic group and specificity [1, 2, 9-13].

(FIG. 28 Panel A) Mice from two age cohorts (4-months-old and 8-months-old) were raised co-housed (four mice to a cage) for 2-6 months. One mouse from each cage was then assigned to one of the four experimental conditions: (functional tail cups (TC-F), mock tail cups (TC-M), housing on wire floors (WF), and controls housed in standard conditions (CTRL). All mice were singly housed and maintained on each treatment for 12-20 days (N=24, 6 mice per group). (FIG. 28 Panel B) Samples were taken from six sites throughout the gastrointestinal tract. Each sample was analyzed by quantitative 16S rRNA gene amplicon sequencing of lumenal contents (CNT) and mucosa (MUC) and/or quantitative bile-acid analyses of CNT. FIG. 28 Panel B is adapted from [14, 15]).

(FIG. 29 Panel A) Total 16S rRNA gene DNA copy loads, a proxy for total microbial loads, were measured along the GIT of mice of all groups (STM=stomach; SI1=upper third of the small intestine (SI), SI2=middle third or the SI, SI3=lower third of the SI roughly corresponding to the duodenum, jejunum, and ileum respectively;

CEC=cecum; COL=colon). Multiple comparisons were performed using a Kruskal-Wallis test, followed by pairwise comparisons using the Wilcoxon-Mann-Whitney test with false-discovery rate (FDR) correction. Individual data points are overlaid onto box-and-whisker plots; whiskers extend from the quartiles (Q2 and Q3) to the last data point within 1.5× interquartile range (IQR). (FIG. 29 Panel B) Correlation between the microbial loads in the lumenal contents (per g total contents) and in the mucosa (per 100 ng of mucosal DNA) of the mid-SI. N=6 mice per experimental group.

(FIG. 30 Panel A) Principal components analysis (PCA) of the $\log_{10}$-transformed and standardized (mean=0, S.D.=1) absolute microbial abundance profiles in the stomach, mid-small intestine, and cecum. Loadings of the top contributing taxa are shown for each principal component. (FIG. 30 Panel B) Mean relative and absolute abundance profiles of microbiota in the mid-SI (order-level) for all experimental conditions. Functional tail cups (TC-F), mock tail cups (TC-M), housing on wire floors (WF), and controls housed in standard conditions (CTRL). N=6 mice per experimental group, 4 of which were used for sequencing. (FIG. 30 Panel C) Absolute abundances of microbial taxa (order-level) compared between coprophagic and non-coprophagic mice along the mouse GIT. *Chloroplast and *Richettsiales (mitochondria) represent 16S rRNA gene DNA amplicons from food components of plant origin. Multiple comparisons were performed using the Kruskal-Wallis test.

(FIG. 32 Panel A) Total bile acid levels (conjugated and unconjugated; primary and secondary) and (FIG. 32 Panel B) the fraction of unconjugated bile acids in gallbladder bile and throughout the GIT (STM=stomach; SI1=upper third of the small intestine (SI), SI2=middle third or the SI, SI3=lower third of the SI roughly corresponding to the duodenum, jejunum, and ileum respectively; CEC=cecum; COL=colon). In all plots, individual data points are overlaid onto box-and-whisker plots; whiskers extend from the quartiles (Q2 and Q3) to the last data point within 1.5× interquartile range (IQR). Multiple comparisons were performed using the Kruskal-Wallis test; pairwise comparisons were performed using the Wilcoxon-Mann-Whitney test with FDR correction. N=6 mice per group.

(FIG. 33 Panels A, B, C) Functional (TC-F, left) and mock (TC-M, right) tail cups as viewed from different perspectives. (FIG. 33 Panel D) The standard cages with wire mesh floors used in this study (WF). (FIG. 33 Panels E, F) Ventral view of the functional (TC-F; left) and mock (TC-M, right) tail cups 24 hours after emptying (TC-F) or mock emptying (TC-M).

(FIG. 34 Panels A, B) Ventral and dorsal view of the tail sleeve mounted at the tail base. (FIG. 34 Panels C, D) Ventral and dorsal view of the functional tail cup installed and locked in place using the tail sleeve.

(FIG. 35 Panel A) Body weights of each individual animal at the beginning and at the endpoint of the study. (FIG. 35 Panel B) Normalized food intake per gram of body weight per day measured over the entire duration of the study. Multiple comparisons of the normally-distributed homoscedastic data were performed using one-way ANOVA; pairwise comparisons were performed using the Student's t-test with FDR correction. N=6 mice per group.

(FIG. 36 Panel A) Culturable microbial loads in contents along the gastrointestinal tract were evaluated using the most probable number (MPN) assay performed in anaerobic BHI-S broth (N=5 mice per group, P-values were calculated using the Wilcoxon-Mann-Whitney test). (FIG. 36 Panel B) PCA analysis of the CLR-transformed relative microbial abundance profiles (16S rRNA gene amplicon sequencing) along the entire GIT in TC and CT mice (N=1 mouse from each group).

(FIG. 37 Panel A) Total secondary bile acid levels (conjugated and unconjugated) and (FIG. 37 Panel B) the fraction of secondary bile acids (conjugated+unconjugated) in gallbladder bile and throughout the GIT (STM=stomach; SI1=upper third of the small intestine (SI), SI2=middle third or the SI, SI3=lower third of the SI roughly corresponding to the duodenum, jejunum, and ileum respectively; CEC=cecum; COL=colon). In all plots, individual data points are overlaid onto box-and-whisker plots; whiskers extend from the quartiles (Q2 and Q3) to the last data point within 1.5× interquartile range (IQR). Multiple comparisons were performed using the Kruskal-Wallis test; pairwise comparisons were performed using the Wilcoxon-Mann-Whitney test with FDR correction. N=6 mice per group.

FIG. 38 shows a table listing the primer oligonucleotide sequences (SEQ ID NO: 16-24) used in the study. [NNNNNNNNNNNN]— 12-base barcode sequences "806rcbc" (SEQ ID NO: 25) according to [16]. Additional description of the primers is provided in the following references UN00F2 [17], UN00R0 [16, 18], UN00F2_BC [17], UN00R0_BC [16, 18], ILM00F(P5) [16, 18-21], ILM00R(P7), Seq_UN00F2_Read_1 [17], Seq_UN00R0_Read_2 [16, 18], Seq_UN00R0_RC_Index [16, 18].

FIG. 39 shows a table listing thermocycling parameters for the quantitative PCR (qPCR) assay for 16S rRNA gene DNA copy quantification.

FIG. 40 shows a table listing the thermocycling parameters for the digital PCR (dPCR) assay for absolute 16S rRNA gene DNA copy quantification.

FIG. 41 shows a table listing thethermocycling parameters for the 16S rRNA gene DNA amplicon barcoding PCR reaction for next generation sequencing (NGS).

FIG. 42 shows a table listing the thermocycling parameters for the digital PCR (dPCR) assay for barcoded amplicon and Illumina NGS library quantification.

FIG. 43 shows a table listing the reagents and chemical standards used in the bile acid metabolomics assay.

(FIG. 49 Panel A) Histogram of the total microbial load in 250 duodenal aspirate samples overlaid with a kernel-density estimate. (FIG. 49 Panel B) Quantile-quantile plot comparing the sample distribution of the $\log_{10}$-transformed total microbial load in duodenal aspirate samples to a normal distribution. (FIG. 49 Panel C) Kernel-density estimate plots showing the absolute abundance distribution for the taxa with greater than 50% prevalence in duodenal aspirates. Prevalence (defined as a taxon's frequency of occurrence in our dataset) and number of samples with each genus are labeled next to the distribution. A legend indicates strict anaerobes (gray line through O2) and the location each genus is commonly found (saliva and/or stool)[22, 23].

(FIG. 52 Panel A) Scatterplot comparing aerobic culture load from MacConkey plates to total load from 16S quantitative sequencing of only the subset of bacteria that are known to grow on MacConkey plates (*Escherichia-Shigella, Enterobacteriaceae, Enterococcus*, and *Aeromonas*)[24]. (FIG. 52 Panel B) Scatterplot comparing anaerobic culture load, from blood agar plates, to total load from sequencing of prevalent bacteria that are expected to grow on blood agar plates (*Prevotella, Streptococcus, Fusobacterium, Escherichia-Shigella*)[25]. Gray dashed line indicates limit of detection of quantitative sequencing method. N=244. (Six patients in the study were lacking culture data.)

(FIG. 53 Panel A) Total microbial load of 21 paired duodenal aspirate and saliva samples. (FIG. 53 Panel B) No significant correlation between the total microbial load of 21 paired duodenal aspirate and saliva samples. (FIG. 53 Panel C) Percentage of taxa in duodenal aspirate samples also present in paired (same patient) vs randomly paired saliva samples. (FIG. 53 Panel D) Volcano plot showing the ratio of relative abundances of species in duodenum vs saliva samples. The dashed line indicates a significance threshold at q=0.1 (Kruskal-Wallis with Benjamini-Hochberg correction).

FIG. 54 illustrates in an exemplary embodiment the taxa co-correlations. In particular, the co-correlations reveal which taxa co-occur in high abundance and which can be considered disruptor taxa. (FIG. 54 Panel A) Co-correlation matrix of the top 20 most abundant genera and total microbial load. Only significant correlations (q<0.1, Benjamini-Hochberg correction) are shown. Size of each marker is determined by the Spearman correlation coefficient. The eight disruptor taxa are bolded. (FIG. 54 Panel B) Clustered co-correlation matrix of the top 16 genera ranked by the difference between their maximum abundance and mean abundance. Two common genera in the dataset are shown at the bottom for reference. Darker squares indicate a higher Spearman correlation coefficient. Disruptor taxa labels are bolded. Genera are labeled with known relevance to human health. HAI=hospital acquired infection, IBD=inflammatory bowel disease.

(FIG. 55 Panel A) PCA plot of absolute microbial abundances at the genus level with the top two correlated metadata variables overlaid. (FIG. 55 Panel B) Feature loadings for principal component 2. Top five value-ranked genera in each direction (positive and negative) are in light grey and labeled. (FIG. 55 Panel C) Correlation between the strict anaerobic microbial load and facultative anaerobic microbial load. (FIG. 55 Panel D) Relationship between the percentage abundance of strict anaerobes and Shannon diversity index.

(FIG. 56 Panel A) Principal component analysis (PCA) of absolute microbial abundances at the genus level. Colors indicate non-SIBO (grey) or SIBO (black) participants as determined by culture. "X" markers indicate samples from non-SIBO participants that contained *Lactobacillus*. The PC1 axis correlates with total load and the PC2 axis correlates with the abundance of disruptor taxa. (FIG. 56 Panel B) Volcano plot indicating the taxa that differed between SIBO and non-SIBO samples. The dashed line indicates the significance threshold at q=0.01. (FIG. 56 Panel C) Correlation between PC2 (disruptor axis) and patient-reported symptom scores (on a 0-100 scale). The dashed line represents significance threshold at q=0.05. (FIG. 56 Panel D) Correlation between PC2 and patient serum cytokine levels. The dashed lines represent the significance thresholds at q=0.05. (FIG. 56 Panel E) Boxplot indicating increasing average total microbial load with increasing number of disruptor taxa with loads greater than $10^4$ rRNA gene copies/mL (not including *Lactobacillus*). A significant difference between total load in samples with zero disruptor taxa and total load in samples with at least 1 disruptor taxa was observed (P<0.001). (FIG. 56 Panel F) Percentage of samples from patients with either 0 symptoms or 5-6 symptoms (out of 6 categories) for individuals with varying loads of disruptor taxa (not including *Lactobacillus*).

(N=24), and *Campylobacter* (N=59) in high load samples vs *Lactobacillus* (N=42) and the common taxa *Prevotella* (N=104).

Figure 59:
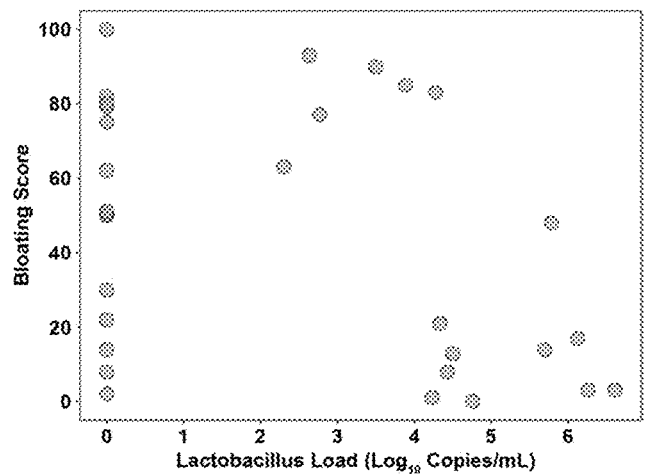

FIG. 59 shows in an embodiment a plot demonstrating the relationship between *Lactobacillus* load and bloating symptoms in samples containing additional (non-*Lactobacillus*) disruptor taxa.

Figure 60:
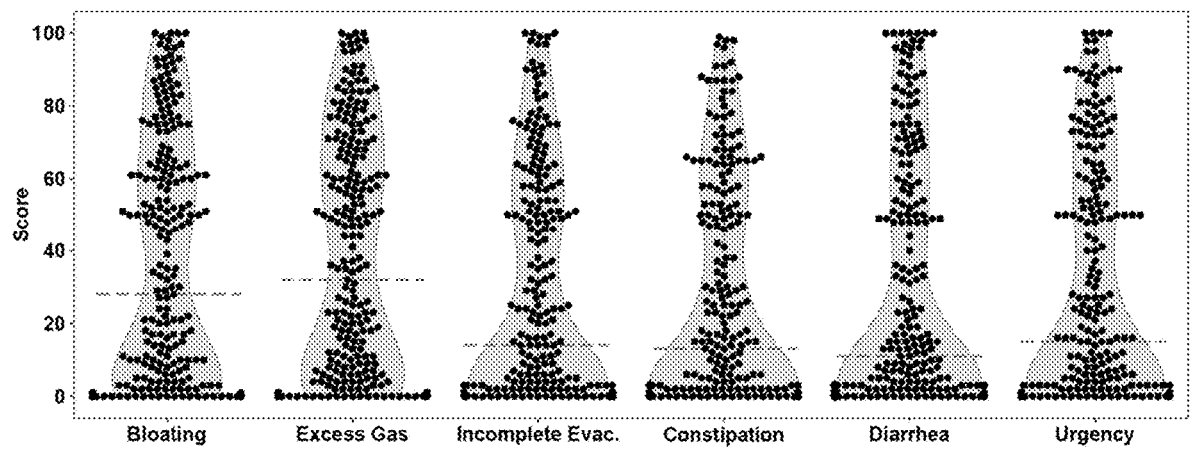

FIG. 60 shows in an embodiment the violin plots with data points overlaid for patient-reported symptom scores. Binary threshold for determining whether severe symptoms exist was set at the median score reported of each symptom, shown by the dashed lines.

Figure 61:
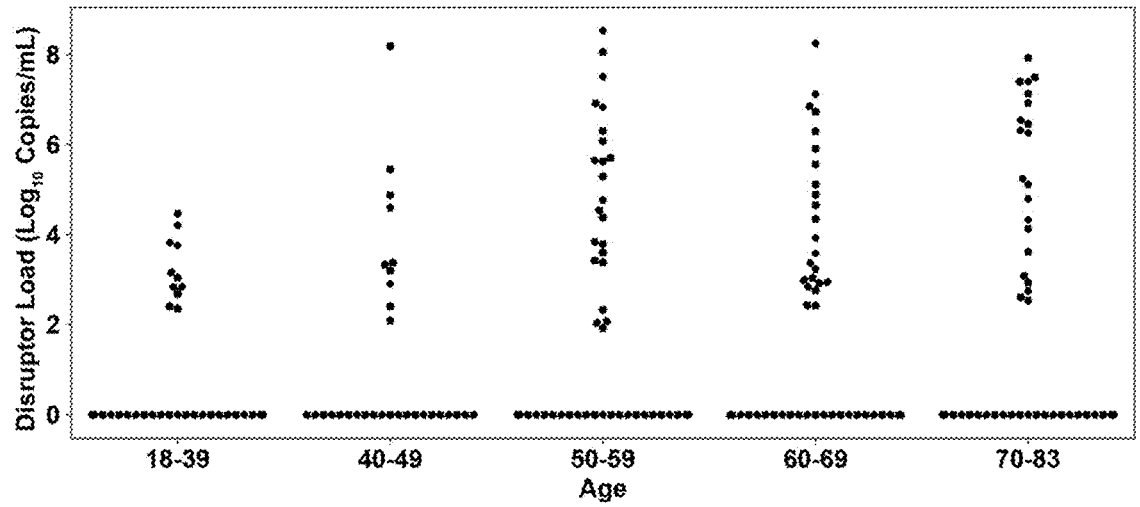

FIG. 61 illustrates in an embodiment the disruptor taxa load separated by patient age: 18-39 (N=40), 40-49 (N=31), 50-59 (N=58), 60-69 (N=67), 70-83 (N=54).

Figure 62:
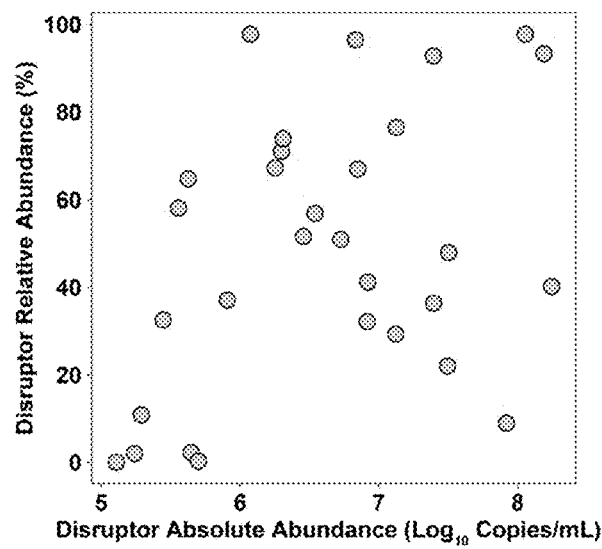

FIG. 62 shows in an embodiment the relationship between absolute abundance (greater than $10^5$ copies/mL) and relative abundance of disruptor loads (Spearman, P=0.09, not significant)

DETAILED DESCRIPTION

Provided herein are a customized rodent model and related methods and systems for providing a rodent with customized microbiome through as absolute quantification of a corresponding prokaryote in the microbiome.

The term "microbial" "microbe" or "microorganism", as used herein indicates a microscopic living organism, which can exist in a single-celled form or in a colony of cells form. Microorganisms comprise extremely diverse unicellular organisms, including prokaryotes and in particular bacteria, but also including fungi (yeast and molds), and protozoal parasites as will be understood by a skilled person.

The term "prokaryote" is used herein interchangeably with the terms "cell" and refers to a microbial species which contains no nucleus or other membrane-bound organelles in the cell. Exemplary prokaryotic cells include bacteria and archaea.

The term "bacteria" or "bacterial cell", used herein interchangeably with the term "cell" indicates a large domain of prokaryotic microorganisms. Typically a few micrometers in length, bacteria have a number of shapes, ranging from spheres to rods and spirals, and are present in most habitats on Earth, such as terrestrial habitats like deserts, tundra, Arctic and Antarctic deserts, forests, savannah, chaparral, shrublands, grasslands, mountains, plains, caves, islands, and the soil, detritus, and sediments present in said terrestrial habitats; freshwater habitats such as streams, springs, rivers, lakes, ponds, ephemeral pools, marshes, salt marshes, bogs, peat bogs, underground rivers and lakes, geothermal hot springs, sub-glacial lakes, and wetlands; marine habitats such as ocean water, marine detritus and sediments, flotsam and insoluble particles, geothermal vents and reefs; man-made habitats such as sites of human habitation, human dwellings, man-made buildings and parts of human-made structures, plumbing systems, sewage systems, water towers, cooling towers, cooling systems, air-conditioning systems, water systems, farms, agricultural fields, ranchlands, livestock feedlots, hospitals, outpatient clinics, health-care facilities, operating rooms, hospital equipment, long-term care facilities, nursing homes, hospice care, clinical laboratories, research laboratories, waste, landfills, radioactive waste; and the deep portions of Earth's crust, as well as in symbiotic and parasitic relationships with plants, animals, fungi, algae, humans, livestock, and other macroscopic life forms. Bacteria in the sense of the disclosure refers to several prokaryotic microbial species which comprise Gram-negative bacteria, Gram-positive bacteria, Proteobacteria, Cyanobacteria, Spirochetes and related species, Planctomyces, *Bacteroides, Flavobacteria, Chlamydia,* Green sulfur bacteria, Green non-sulfur bacteria including anaerobic phototrophs, Radioresistant micrococci and related species, *Thermotoga* and Thermosipho thermophiles as would be understood by a skilled person. Taxonomic names of bacteria that have been accepted as valid by the International Committee of Systematic Bacteriology are published in the "Approved Lists of Bacterial Names" [26] as well as in issues of the International Journal of Systematic and Evolutionary Microbiology. More specifically, the wording "Gram positive bacteria" refers to cocci, nonsporulating rods and sporulating rods that stain positive on Gram stain, such as, for example, *Actinomyces, Bacillus, Clostridium, Corynebacterium, Cutibacterium* (previously *Propionibacterium*), *Erysipelothrix, Lactobacillus, Listeria, Mycobacterium, Nocardia, Staphylococcus, Streptococcus, Enterococcus, Peptostreptococcus,* and *Streptomyces.* Bacteria in the sense of the disclosure refers also to the species within the genera *Clostridium, Sarcina, Lachnospira, Peptostreptococcus, Peptoniphilus, Helcococcus, Eubacterium, Peptococcus, Acidaminococcus, Veillonella, Mycoplasma, Ureaplasma, Erysipelothrix, Holdemania, Bacillus, Amphibacillus, Exiguobacterium, Gracilibacillus, Halobacillus, Saccharococcus, Salibacillus, Virgibacillus, Planococcus, Kurthia, Caryophanon, Listeria, Brochothrix, Staphylococcus, Gemella, Macrococcus, Salinococcus, Sporolactobacillus, Marinococcus, Paenibacillus, Aneurinibacillus, Brevibacillus, Alicyclobacillus, Lactobacillus, Pediococus, Aerococcus, Abiotrophia, Dolosicoccus, Eremococcus, Facklamia, Globicatella, Ignavigranum, Carnobacterium, Alloiococcus, Dolosigranulum, Enterococcus, Melissococcus, Tetragenococcus, Vagococcus, Leuconostoc, Oenococcus, Weissella, Streptococcus, Lactococcus, Actinomyces, Arachnia, Actinobaculum, Arcanobacterium, Mobiluncus, Micrococcus, Arthrobacter, Kocuria, Nesterenkonia, Rothia, Stomatococcus, Brevibacterium, Cellulomonas, Oerskovia, Dermabacter, Brachybacterium, Dermatophilus, Dermacoccus, Kytococcus, Sanguibacter, Jonesia, Microbacteirum, Agrococcus, Agromyces, Aureobacterium, Cryobacterium, Corynebacterium, Dietzia, Gordonia, Skermania, Mycobacterium, Nocardia, Rhodococcus, Tsukamurella, Micromonospora, Propioniferax, Nocardioides, Streptomyces, Nocardiopsis, Thermomonospora, Actinomadura, Bifidobacterium, Gardnerella, Turicella, Chlamydia, Chlamydophila, Borrelia, Treponema, Serpulina, Leptospira, Bacteroides, Porphyromonas, Prevotella, Flavobacterium, Elizabethkingia, Bergeyella, Capnocytophaga, Chryseobacterium, Weeksella, Myroides, Tannerella, Sphingobacterium, Flexibacter, Fusobacterium, Streptobacillus, Wolbachia, Bradyrhizobium, Tropheryma, Megasphera, Anaeroglobus, Escherichia-Shigella, Klebsiella, muribaculum, alloprevotella, paraprevotella, oscillibacter, candidatus arthromitus, aeromonas, romboutsia, campylobacter, salmonella, faecalibacterium, roseburia, blautia, oribacterium, ruminococcus.*

The term "Archaea" as used herein refers to prokaryotic microbial species of the division Mendosicutes, such as Crenarchaeota and Euryarchaeota, and include but is not limited to methanogens (prokaryotes that produce methane); extreme halophiles (prokaryotes that live at very high concentrations of salt (NaCl); extreme (hyper) thermophiles (prokaryotes that live in extremely hot environments), Methanobrevibacter, and methanosphaera.

Accordingly, the term "microbial community" as used herein refers to a group of microorganisms sharing an environment which can comprise one or more prokaryotes or individual genera or species of prokaryotes. A microbial community in the sense of the disclosure can thus include two or more microorganisms two or more strains, two or more species. two or more genera, two or more families, or any mixtures of microorganisms in the sense of the disclosure with additional life form such as viruses, comprised in the shared environment. The interaction between the two or more community members may take different forms and can be in particular commensal, symbiotic and pathogenic as will be understood by a skilled person. An exemplary microbial community is the 'microbiome" of an individual which is an aggregate of all microbiota (all microorganisms found in and on all multicellular organisms) residing on or within tissues and biofluids of the individual.

The term "individual" as used herein indicates any multicellular organism that can comprise microorganisms, thus providing a shared environment for microbial communities, in any of their tissues, organs, and/or biofluids. Exemplary individual in the sense of the disclosure include plants, algae, animals, fungi, and in particular, vertebrates, mammals more particularly humans.

In particular, in individual having a digestive tract (e.g. all vertebrates and in particular humans, as well as most invertebrates including sponges, cnidarians, and ctenophores) the microbiome residing in or within the digesting tract, (generally comprising bacteria and archaea), is also indicated as "gastrointestinal microbiome" or gut microbiome.

Additional fluids hosting a microbial community in individuals such as vertebrates and human comprise tear fluid, saliva, nasal, oral, tonsillar, and pharyngeal swabs, sputum, bronchoalveolar lavage (BAL), gastric, small-intestine, and large-intestine contents and aspirates, feces, bile, pancreatic juice, urine, vaginal samples, semen, skin swabs, tissue and tumor biopsy, blood, lymph, cerebrospinal fluid, amniotic fluid, mammary gland secretions/breast milk and tumor tissues.

Accordingly in a human individual, in addition to gastrointestinal microbiome, further microbiomes comprise eye microbiome, skin microbiome, mammary glands microbiome, placenta microbiome, seminal fluid microbiome, uterus microbiome, ovarian follicles microbiome, lung microbiome, saliva microbiome, oral mucosa microbiome, conjunctiva microbiome, biliary tract microbiome, tumor microbiome and additional microbiomes.

Additional exemplary microbiome in individuals comprise insect microbiome plant root microbiome (rhizosphere), aquaculture (fisheries, clam farms) and others identifiable to a person skilled in the art.

Microbial communities in the sense of the disclosure can also be found in a target environment outside an individual and comprising a medium (a substance, either solid or liquid) including components such as nutrients allowing growth of microbes in the sense of the disclosure Exemplary target environments comprise soil for plant growth, water, sediment, oil well samples, bioreactors (e.g., complex/mixed probiotics) and additional environment identifiable by a skilled person. Exemplary microbiomes in a target environment include, ocean microbiome, living space microbiome, clean room microbiome, and others identifiable to a person skilled in the art.

Microbial communities and in particular microbiome are characterized by the prokaryote composition and in particular by microbiome features that characterize and distinguish the microbiome providing a related profile.

The term "microbiome profile" as used herein indicates a combination of features that characterize a microbiome and can be used to identify and distinguish the microbiome over different microbiome or the same microbiome under different conditions. Features that can be used to provide a microbiome profile comprise, presence, proportion and total load of prokaryotes comprised in the microbiome which are associated with and characterize the microbiome under certain conditions. Prokaryotes whose presence, proportions and/or total load can form a microbiome profile under certain conditions, can be identified by a skilled person.

For example, the microbiome profile in the sense of the disclosure of a microbiome of a species, an organ and/or an individual with a disease typically comprise presence proportion and/or total load of a prokaryote associated with the species, organ, and/or diseases respectively. Exemplary prokaryote whose presence proportion or total load are associated with a condition comprise gut pathogens such as *Escherichia, Serratia, Salmonella, Clostridium difficile* associated with gastrointestinal pathologies, Exemplary prokaryote whose presence proportion or total load are associated with a microbiome of a species comprise, Clostridiales, Bacteroidales, Erysipelotrichale associated with the gut microbiome of a rodent in view of as a result of self-inoculation (see Example 14) Exemplary prokaryote whose presence proportion or total load are associated with an organ in the individual probiotics such as *Lactobacillus*[27] associated with the gastrointestinal tract (Example 14).

In particular the presence of a prokaryote in the microbiome can be determined based on an absolute abundance of the prokaryote and/or of a relative abundance of the prokaryote in the microbiome. In particular, presence can be detected when the relative abundance and/or the absolute abundance are above a certain threshold. In some embodiments the threshold is arbitrarily, set or set in view of considerations related to experimental settings. In some embodiments, the threshold can be determined in view of statistical considerations to reduce or minimize inaccurate detection (e.g. application of Poisson statistics), In some embodiments the threshold can be a low value number (e.g. 0.01% relative abundance). In some embodiments the threshold can be zero.

In particular the proportion of a prokaryote in the microbiome can be determined based on relative abundance and/or by absolute abundance of the prokaryote in combination a relative abundance of the prokaryote in the microbiome to provide a proportion value indicative of the proportion of the prokaryote with respect to one or more of additional prokaryotes, typically all prokaryotes of the microbiome.

The total load of the prokaryotes can be determined based on an absolute abundance of the prokaryote in the microbiome. In particular, the total load of prokaryote can comprise one or more prokaryotes of interest, and typically comprises all prokaryotes of a microbiome.

Prokaryotes that can be used to identify features of a microbiome profile can comprise one or more types of prokaryotes and can advantageously identified with the absolute quantification method in accordance with the present disclosure.

In methods and systems described herein and a rodent model is provided which has a rodent microbiome profile formed by a rodent presence, a rodent proportion and/or a rodent total load of a rodent prokaryote of a rodent taxon, The term "rodent" as used herein, rodents indicates mammals of the Rodentia order, which are characterized by a single pair of continuously growing incisors in each of the upper and lower jaws as will be understood by a person skilled in the art. Examples of rodents include mice, rats, squirrels, prairie dogs, porcupines, beavers, guinea pigs, hamsters, gerbils and others identifiable to a person skilled in the art. Rodents commonly used for experimental purpses comprise mice, rats, guinea pigs, hamsters, and rabbits. Common commercially available strains are *Mus musculus, Rattus norvegicus, Cricetus auratus,* and *Oryctolagus cuniculus.*

A "rodent model" in the sense of the disclosure is animal model wherein the animal is a rodent. An animal model is a living, non-human species used in medical research and investigation of human disease because it can mimic aspects of the disease found in humans. Animal models are typically used to obtain information about a disease and its prevention, diagnosis, and treatment. By using animal models, researchers can carry out experiments that would be impractical or ethically prohibited with humans. Animal models can be altered or genetically engineered to have an existing, inbred or induced disease or injury that is similar to a human condition. For example, experimental models are models of disease that resemble human conditions in phenotype or response to treatment but are induced artificially in the laboratory as will be understood by a person skilled in the art.

Methods are herein described comprise providing a rodent which is typically selected in view of the relevant aspect of human physiology and or disease to be modeled in the customized rodent model.

In embodiments herein described, the rodent selected has a rodent microbiome and a corresponding rodent microbiome profile formed by a rodent prokaryote presence, a rodent prokaryote proportion and/or a rodent prokaryote total load of the target prokaryote of the target taxon. The term rodent prokaryote is used herein to indicate any prokaryote whose presence, proportion and/or total load is associated with and characterize a microbiome of a rodent animal. Preferred microbiomes comprise the microbiomes of the gastrointestinal tract (GIT) or of any portion thereof, such as oral cavity, small intestine, colon stomach, duodenum, jejunum and additional portions identifiable by a skilled person.

In some embodiments the rodent microbiome can be a naturally occurring microbiome. In some embodiments, the rodent microbiome can be modified through various treatments identifiable by a skilled person. For example, in some embodiments. germ free (gnotobiotic) mice can be used or mice treated with a cocktail of antibiotics to have a microorganism free background which can then be colonized by specific microbes [28].

In particular, the rodent microbiome is the microbiome of a model organ selected to simulate a target microbiome. Common organs are those of the gastrointestinal tract: oral cavity, stomach, small intestine (duodenum, jejunum, ileum), colon or the entire GI tract. Additional model organs are identifiable by a skilled person.

In some embodiment, providing a rodent is performed by providing a rodent further having a selected genetic background as will be understood by a skilled person.

In particular, in some embodiments, a rodent can be selected that have a genetic background emulating a particular human disease genotype. Several common examples are the IL10-/- mouse model for human colitis[29], the ob/ob mouse for human obesity[30], the SAMP1/YitFc mouse for human ileitis[31], and the NOD mouse for non-obese diabetes in humans[32] and additional genetic background emulating a particular human disease.

In some embodiments, a rodent can be selected that has a genetic background commonly used in research of human conditions and are commercially available laboratory mouse strains. Several common examples are C57BL/6, BALB/c, and Swiss Webster mice.

In some embodiments, a rodent can be selected with a genetic background resulting in in a defective immune system, such as immunocompromised mice[33]. Several common examples are nude mice that lack a thymus, SCID mice that are T and B cell deficient, and RAG knockout mice also deficient in T and B cells.

In some embodiments, a rodent can be selected with any genetic background and additional induced disease. For example, the DSS-colitis model can be used with any genetic background. Dextran sodium sulfate is added to the drinking water and results in colitis that can simulate human colitis.[34]

In methods and systems herein described, the rodent microbiome is modified to obtain a rodent with target microbiome associated with a physiological and/or pathological condition to be modeled in the resulting customized rodent model.

The term "target microbiome" as used herein indicates a microbiome to be simulated in the customized rodent model of the present disclosure. Target microbiome have profile formed by presence, proportion, and/or total load of one or more target prokaryotes, which are prokaryote associated with the target microbiome to be simulated. Exemplary target microbiome comprise, any microbiome of an individual preferably human beings, or microbiome of an environment such as soil microbiome or marine microbiome In preferred embodiments a target microbiome can be one or more of microbiomes of an individual, most preferably human being, associated with a physiological or a pathological condition of the individual.

In some embodiments, a target prokaryote can comprise a microorganism that has been associated with some form of pathological condition. For example, the Proteobacteria phylum consists of many opportunistic pathogens that are linked or directly cause disease (*Escherichia, Serratia, Campylobacter, Enterococcus, Klebsiella, Pseudomonas, Staphylococcus, Salmonella, Yersinia*). Additional gut pathogens beyond the Proteobacteria phylum can also be used like *Clostridium difficile.*

In some embodiments, a target prokaryote can comprise any prokaryote that is known to cause a change in the immune system. For example, many *Clostridium* species are known to induce an immune response that has been linked to the effectiveness of cancer treatments[35].

In some embodiments, a target prokaryote can comprise any prokaryote used as a probiotic or food additive. Common examples are *Lactobacillus*[27] and *Bifidobacterium* [36] strains.

In preferred embodiments, target prokaryotes can be any prokaryote associated with a target physiological or pathological condition to be simulated, (e.g. a disease) including physiological or pathological condition identified by one or more target phenotypic features (such as one or more specific symptoms of a disease). A target prokaryote can be identified by comparing microbiomes of individuals with that physiological or pathological condition against individuals without the physiological or pathological condition and finding prokaryotes that differ between these two groups. For example, identification of target prokaryote in gut microbiome was performed in human patients with and without Crohn's disease to find that Enterobacteriaceae, Pasteurellaceae, Fusobacteriaceae, and Neisseriaceae are enriched in Crohn's disease patients[37]. Accordingly, in exemplary embodiments, prokaryote for each of Enterobacteriaceae, Pasteurellaceae, Fusobacteriaceae, and Neisseriaceae taxa, and/or the related combination can be used as target prokaryotes for a target gut microbiome of a hman individual having Crohn's disease. Additional, target prokaryotes for human gut microbiome or other microbiome of human or other individuals selected to be target microbiome can be identified by a skilled person upon reading of the present disclosure.

In embodiments herein described presence or absence of one or more target prokaryotes, proportion of the of one or more target prokaryotes with respect to one or more preferably all additional prokaryotes in the target microbiome and/or total load of the target prokaryote in the target microbiome provide features of the target microbiome which form a profile of the target microbiome, as will be understood by a skilled person upon reading of the present disclosure.

An exemplary presence of a target prokaryote of a target prokaryote which can be used alone or in combination with proportion of the same or other target prokaryote and/or total load of the same and/or other target prokaryote to provide a microbiome profile, is the presence of *bacteroides* genus with respect to the target microbiome of the small intestine of coprophagic mice (see e.g. Examples 20-26) showing *bacteroides* presence is not detected after prevention of coprophagy performed with the preferred tailcups of the present disclosure.

An additional exemplary presence of a target prokaryote of a target prokaryote which can be used alone or in combination with proportion of the same or other target prokaryote and/or total load of the same and/or other target prokaryote to provide a microbiome profile, is the presence of *Clostridium difficile* with respect to a target gut microbiome associated with a *Clostridium difficile* infection.

An exemplary proportion of a target prokaryote of a target prokaryote which can be used alone or in combination with presence of the same or other target prokaryote and/or total load of the same and/or other target prokaryote to provide a microbiome profile, is provided by the relative abundance of any target prokaryote (of any taxonomic level) with respect to target gut microbiome of coprophagic animals (such as any rodents) and non-coprophagic animals (such as human beings). For example, the relative abundance of any target prokaryote is higher in coprophagic animal compared to non-coprophagic animals. In particular, according to a coprophagy dataset the relative abundance of the *Lactobacillus* genus has been detected to approximately 98% after the utilization of tail cups while it detected to be approximately roughly 15% without utilization of tail cups and related coprophagy prevention.

An additional exemplary proportion of a target prokaryote which can be used alone or in combination with presence of the same or other target prokaryote and/or total load of the same and/or other target prokaryote to provide a microbiome profile, is provided by the relative abundance of the top 10 or preferably of the top 50 or more preferably of the top 100 most abundant taxa of the target microbiome preferably in combination with a total load (see e.g. the human gut microbiome as a target microbiome to be provided in the rodent.

An exemplary total load of a target prokaryote of a target prokaryote which can be used alone or in combination with presence of the same or other target prokaryote and/or proportion of the same and/or other target prokaryote to provide a microbiome profile, is provided by the absolute abundance of total prokaryotes a target microbiome normalized to some sample input mass in a target microbiome, such as small intestine target microbiome of coprophagic animal (see Examples 20-26) showing that the coprophagy dataset the total load of prokaryotes was roughly $1\times10^{\wedge}6$ 16S copies/g in the small intestine after utilization of tail cups while it was roughly $1\times10^{\wedge}9$ 16S copies/g without utilization of tail cups preventing coprophagy).

An additional exemplary total load of a target prokaryote of a target prokaryote which can be used alone or in combination with presence of the same or other target prokaryote and/or proportion of the same and/or other target prokaryote to provide a microbiome profile, is provided by the total microbial load with respect to human small intestine microbiome in individual having Small Intestine Bacterial Overgrowth (SIBO). In particular in such target microbiome the total microbial load is at least 2 orders of magnitude higher than those of human small intestine of human individuals without SIBO. In such target microbiome A high total microbial load of specific target prokaryotes provided by subsets of taxa (Enterobacteriaceae) is associated with target microbiome of human individuals with SIBO having worse gastrointestinal symptoms.

In methods and systems to provide a customized rodent model herein described, a sample from the rodent is obtained comprising the rodent microbiome. The obtained sample can comprise any sample herein described providing an environment for the rodent microbiome. Different regions of the body of the rodent will require different sample collection methodologies.

For example, if the environment is comprised in the first part of the small intestine (duodenum), a sample from this region is collected from the host with proper collection techniques identifiable by a skilled person. Stool can be used as a sample comprising rodent microbiome of the lumen of the colon. Small intestinal aspirates can be used for the lumen of the small intestine. Stool can simply be collected upon passage from the body while small intestinal aspirates will require an endoscopic procedure where a catheter is placed down the throat or nasal cavity, through the stomach and into the duodenum before a suction tube is pushed through the catheter and utilized to suck up a portion of liquid from the desired region.

In some embodiments of the methods and system to provide a customized rodent according to the disclosure, a collected sample can preferably be appropriately stored to limit DNase mediated degradation of DNA in the sample. Examples of adequate storage include immediate transport to a freezer, snap freezing with liquid nitrogen, or DNase inactivation via mixing with a chaotropic agent (e.g., guanidinium thiocyanate).

The methods and systems to provide a customized rodent model herein described, further comprise quantifying in the obtained sample absolute abundance the target prokaryotes to obtain a detected presence, proportion and/or total load of the target prokaryotes in the rodent, each target prokaryote being of a target taxon having a taxonomic rank lower than a sample taxon in a same taxonomic hierarchy.

In order to perform the quantifying portion of the collected sample can typically be removed be removed from the collection tube, weighed, and subjected to nucleic acid extraction and purification, wherein nucleic acids can be extracted/purified via a nucleic acid extraction kit. Examples of kits include Qiagen DNeasy Powersoil Pro, Zymobiomics DNA miniprep, and magmax microbiome ultra nucleic acid isolation.

In particular the method to provide a rodent model herein described the quantifying is performed by methods and systems for absolute quantification of the disclosure which can be performed to provide an absolute quantification of a prokaryote within a microbial community through absolute quantification of the related 16SrRNA.

The term "16S rRNA" indicates the 16S ribosomal ribonucleic acid of component of the ribosome 30S subunit of a prokaryote, or a DNA encoding therefor (herein 16S rRNA gene). A 16S rRNA of a prokaryote can be identified by its a sedimentation coefficient which, an index reflecting the downward velocity of the macromolecule in the centrifugal field. 16S rRNA performs various functions in a prokaryote such as providing scaffolding for the immobilization of ribosomal proteins, binds the shine Dalgarno sequence of mRNAs, interacts with 23S to help integrate two ribosome units (50S+30S). Accordingly, the 16S ribosomal RNA is a necessary for the synthesis of all prokaryotic proteins and is therefore comprised in all prokaryotes as will be understood by a skilled person.

The 16S rRNA is highly prevalent and highly conserved (overall) across a broad diversity of prokaryotes/in view of its role in the physiology of prokaryotes, 16S ribosomal RNA is the most conserved among prokaryotes. Accordingly, 16S rRNA is a key parameter in molecular classification and phylogenetic analysis of prokaryote possibly applied to the identification of clinical bacteria, sequence analysis and related therapeutic and/or diagnostic application. In particular classification and grouping of prokaryotes can be performed based on a sequence similarity in the 16S rRNA varying among prokaryotes based on their taxonomical ranks.

The term "taxonomy" or "taxon" refers to a group of one or more microbial organisms that are classified into a group based on their common characteristics. Taxonomic hierarchy refers to a sequence of categories arranging various organisms into successive levels of the biological classification either in a decreasing or increasing order from domain to species or vice versa. Taxonomic rank is the relative level of a group of organisms (a taxon) in a taxonomic hierarchy. Examples of taxonomic ranks include strain, species, genus, family, order, class, phylum, kingdom, domain and others as will be understood by a person skilled in the art. Species is the basic taxonomic group in microbial taxonomy. Groups of species are then collected into genus. Groups of genera are collected into family, families into order, orders into class, classes into phylum, phyla into kingdom, and kingdoms into domain.

As a person skilled in the art will understand, each taxonomic level has increasing sequence similarity between individual members of the same taxonomic level from domain down to species. Individual taxonomic groups at a specific rank can be defined by the conservation of their 16S rRNA gene sequence.

Accordingly, 16S rRNA in the sense of the disclosure comprises conserved regions and variable regions. The conserved regions being conserved among prokaryotes with different degree of conservation among different taxa based on their taxonomic rank. The variable regions are instead specific for specific taxa with different degree of specificity among different taxa based on their taxonomic rank, as will be understood by a skilled person.

16S rRNA conserved and variable region of a target taxon having a taxonomic rank can be identified by comparing 16S rRNA sequences of the target taxon and 16S rRNA sequences for a reference taxon having a taxonomic rank higher than the taxonomic rank of the target taxon to provide a 16S rRNA sequence comparison. Identification of 16S rRNA variable regions of the target taxon can be performed by selecting regions of the 16S rRNA sequences having at least 70% homology among the 16S rRNA sequences of the reference taxon. Identification of 16S rRNA variable regions of the target taxon can be performed by selecting regions of the 16S rRNA sequences having less than 70% homology with the 16S rRNA sequences of the reference taxon.

Preferably 16S rRNA sequences are all available 16S rRNA sequences of the target taxon (e.g. known and/or through detection of 16S rRNA in prokaryotes of the target taxon) and encompass the entire length of the 16S rRNA. More preferably the 16S rRNA sequences are DNA sequences and the homology is detected among 16S rRNA DNA sequences.

As used herein, "homology", "sequence identity" or "identity" in the context of two or more nucleic acid or polypeptide sequences makes reference to the nucleotide bases or residues in the two or more sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A person skilled in the art would understand that similarity between polynucleotide sequences is typically measured by a process that comprises the steps of aligning the two sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two or more optimally aligned sequences over a comparison window, wherein the portion of the polynucleotide sequence in the comparison window may comprise additions or deletions (gaps) as compared to the reference sequence (which does not comprise additions or deletions) for optimal alignment of the two or more sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable a database such as GenBank and UniProt and others identifiable to those skilled in the art.

As understood by those skilled in the art, determination of percent identity between any two sequences can be accomplished using a mathematical algorithm. Non-limiting examples of such mathematical algorithms are the algorithm of Myers and Miller [38], the local homology algorithm of Smith et al. [39]; the homology alignment algorithm of Needleman and Wunsch [40]; the search-for-similarity-method of Pearson and Lipman [41]; the algorithm of Karlin and Altschul [42], modified as in Karlin and Altschul [43]. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA [42], and TFASTA in the Wisconsin Genetics Software Package, Version 8 (available from Genetics Computer Group (GCG), Madison, Wis., USA). Alignments using these programs can be performed using the default parameters.

Accordingly, the term "conserved" as used herein in connection with nucleic acid regions indicates regions with homology of at least 70%, more preferably at least 80%, more preferably at least 90%, and most preferably 95%, more preferably 98% or 100%.

Conversely, the term "variable" as used herein in connection with nucleic acid regions indicates regions with homology of less than 70% possibly lower than 50%, lower than 30% or lower than 20% as will be understood by a skilled person.

In 16S rRNA in the sense of the disclosure, the conserved regions and the variable regions are comprised in a configuration where the variable regions are flanked by conserved regions. In particular in a 16S rRNA according to the disclosure can comprise multiple conserved regions sequences flanking and/or interspaced with nine hypervariable regions. In particular, the 16S rRNA is atypically about 1500 bp and comprises V1-V9 ranging from about 30 to 100 base pairs long flanked and interspaced by conserved regions. The variable regions are involved in the secondary structure of the encoded small ribosomal subunit as will be understood by a person skilled in the art.

In 16S rRNA in the sense of the disclosure the configuration of conserved and variable regions can be perform by detecting variability for each base position within aligned 16S rRNA sequences by detecting the frequency of the most common nucleotide residue and determining a frequency distribution by calculating one minus the frequency of the most common nucleotide residue. The resulting frequency distribution can be adjusted by taking the mean frequency within a 50-base sliding window, moving 1 base position at a time along the alignment. Peaks correspond to the hypervariable regions. Methods on how to locate the conserved and variable regions in 16S rRNA gene DNA can be found in, for example, reference [44].

In a 16S rRNA in accordance with the disclosure formed by a 16S rRNA the 16S rRNA gene is typically a DNA polynucleotide naturally occurring in a prokaryote and comprising variable regions flanked by conserved regions in the configuration of the encoded 16S rRNA ribonucleotide. Accordingly, typically the length of the 16S rRNA gene is about 1500 bp. Prokaryotic cells can contain 1-20 copies, often 5 to 10 copies, of 16S rRNA each, which impact the detection sensitivity when detection is directed to detection of prokaryotes of set taxon based on detection of 16S rRNA in accordance with the present disclosure. Tools for predicting 16S gene copy number of prokaryotes and related databases can be found in public domains including published tools such as PICRUSt [45, 46], CopyRighter [47], PAPRICA [48], rrnDB [49] and others identifiable to a person skilled in the art.

In embodiments herein described, tools for predicting 16S rRNA gene copy number and/or databases can be used to detect a number of cells of a prokaryote of a target taxon based on a detected absolute number of 16S rRNA gene copies for that taxon, in addition or in place of detection of 16S rRNA gene as will be understood by a skilled person upon review of the present disclosure. In particular, it will be understood by a skilled person detection of 16S rRNA gene allows for a more accurate quantitation when the number of 16S rRNA gene copies per genome of the target prokaryote is not known, or it is desired to account for a variation of numbers of cells for a single prokaryote depending on its physiological state or growth rate.

Accordingly a 16S rRNA and related gene comprises conserved regions highly prevalent and highly conserved across a broad diversity of prokaryotes (about >80% of known bacterial and >80% of known archaeal 16S sequences) A 16S rRNA and related gene also comprises variable regions which can allow differentiation/identification among prokaryote members of a same taxonomic rank.

In some embodiments herein described, detection of a 16S rRNA recognition segment comprising conserved and variable regions identifying a target 16S rRNA, is performed to obtain an absolute quantification of the target 16S rRNA and/or a corresponding prokaryote target taxon within a microbial community in a sample.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "qualitative" when it refers, relates to, or involves identification of a quality or kind of the target or signal in terms of relative abundance to another target or signal, which is not quantified, such as presence or absence. A detection is "quantitative" when it refers, relates to, or involves the measurement of quantity or amount of the target or signal (also referred as quantitation), which includes but is not limited to any analysis designed to determine the amounts or proportions of the target or signal. A quantitative detection in the sense of the disclosure comprises detection performed semi-quantitatively, above/below a certain amount of nucleic acid molecules as will be understood by a skilled person and/or using semiquantitative real time isothermal amplification methods including real time loop-mediated isothermal amplification (LAMP) (see e.g. semi quantitative real-time PCR). For a given detection method and a given nucleic acid input, the output of quantitative or semiquantitative detection method that can be used to calculate a target nucleic acid concentration value is a "concentration parameter".

The wording "absolute quantification" as used herein in connection with a nucleic acid such as 16S rRNA indicates detecting absolute numbers of copies of the nucleic acid within a target environment such as a sample. Accordingly, absolute quantification of a 16S rRNA as used herein indicates the total number of 16S rRNA ribonucleotide or 16S rRNA gene within a target environment, herein also indicated as "absolute abundance". Absolute quantification of a nucleic acid can be provided by direct detection of the nucleic acid (by a digital amplification method such as digital PCR which directly detect absolute copy numbers of a target nucleic acid) and/or based on a comparative quantification of the nucleic acid in combination with a standard measurement (herein also "anchor" and/or by detecting fold differences between sample (e.g. by real-time/qPCR).

Absolute quantification of a nucleic acid can be provided using a fluorescence or spectrophotometric based method (e.g., Nanodrop or Qubit) which is considered to be proportional to the levels of the nucleic acid to be quantified. Absolute quantification of a nucleic acid can be provided by cell counting based methods such as flow cytometry, optical density, plating which is also considered to be proportional to the desired 16S nucleic acid levels. Absolute quantification of a nucleic acid can be provided by sequencing spike-in (adding a 16S sequence not in the sample at a known level, usually determined by dPCR/qPCR and then use the relative abundance after sequencing and the known abundance level that was inputted as the anchor) as will be understood by a skilled person.

Absolute quantification of a nucleic acid can also be directed to quantify a fold difference between a first quantity of the target nucleic acids and one or more second quantities of the same target nucleic acid in a different environment (e.g. a sample) or in the same environment at different times. In particular, absolute fold difference quantification can indicate a fold change in the nucleic acid abundance between two samples taken from a same environment at different times. When qPCR is used, absolute quantification can be performed by providing a calibration curve for a detected 16S rRNA based on a series of purified 16S rRNA standards of known concentrations, which is then used to estimate the 16S rRNA concentration in the samples of interest and then comparing the normalized numbers between samples to obtain a fold change or fold difference between those samples. Alternatively, the absolute fold difference quantification can be performed entirely without a standard curve. In such case, the qPCR reaction efficiency is assumed to be consistent with the previously characterized one (for example, 95-99%) for a given set of reagents, primers, and the type of samples. Absolute fold difference between two (or among many samples) is then calculated based exclusively on the Cq values and the assumed PCR efficiency value using the equations 3.1 and 3.2 of FIG. 2 (see Example 1 as example of BC-qPCR: qPCR with barcoding primers).

The wording "relative quantification" of a nucleic acid such as 16S rRNA quantification indicates a quantity of a target nucleic acid relative to a quantity of a different nucleic acid. In particular, relative quantification can indicate a quantity of the target nucleic acids relative to the quantity of one or more nucleic acids (typically a plurality of nucleic acids) in a same environment (e.g. a sample).

In relative quantification of a 16S rRNA, a relative abundance a target 16S rRNA is determined (e.g. within a group of 16S rRNAs), but the absolute amount of 16S rRNA is not necessarily known. Accordingly, relative quantification" refers to measuring proportions (fractions, %) of target 16S sequences within the sample plurality of 16S rRNA sequences.

Relative abundances obtained by relative quantification can be multiplied with a standard herein also identified as an "anchor", to obtain absolute quantification value as will be understood by a skilled person. Suitable anchors comprise a measure of an unchanging parameter in the target environment where the detection is made (e.g. a sample or samples) such as the total concentration of cells, DNA, or amplicons as determined by flow cytometry or qPCR or dPCR.

The term "sample" as used herein indicates a limited quantity of something that is indicative of a larger quantity of that something, including but not limited to fluids from a specimen such as biological environment, cultures, tissues, commercial recombinant proteins, synthetic compounds or portions thereof. In particular, biological sample can comprise one or more cells of any biological lineage including microbial and in particular prokaryotic cells, as being representative of the total population of similar cells in the sampled individual. Exemplary biological samples comprise the following: whole venous and arterial blood, blood plasma, blood serum, dried blood spots, cerebrospinal fluid, lumbar punctures, nasal secretions, sinus washings, tears, corneal scrapings, saliva, sputum or expectorate, bronchoscopy secretions, transtracheal aspirate, endotracheal aspirations, bronchoalveolar lavage, vomit, endoscopic biopsies, colonoscopic biopsies, bile, vaginal fluids and secretions, endometrial fluids and secretions, urethral fluids and secretions, mucosal secretions, synovial fluid, ascitic fluid, peritoneal washes, tympanic membrane aspirate, urine, clean-catch midstream urine, catheterized urine, suprapubic aspirate, kidney stones, prostatic secretions, feces, mucus, pus, wound draining, skin scrapings, skin snips and skin biopsies, hair, nail clippings, cheek tissue, bone marrow biopsy, solid organ biopsies, surgical specimens, solid organ tissue, cadavers, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, nasal swab, nasopharyngeal swab, oropharyngeal swab, cheek or buccal swab, urethral swab, vaginal swab, cervical swab, genital swab, anal swab, rectal swab, conjunctival swab, skin swab, and any wound swab. Depending on the type of biological sample and the intended analysis, biological samples can be used freshly for sample preparation and analysis, or can be fixed using fixative.

Exemplary samples according to the instant disclosure samples comprise tear fluid, saliva, nasal, oral, tonsillar, and pharyngeal swabs, sputum, bronchoalveolar lavage (BAL), gastric, small-intestine, and large-intestine contents and aspirates, feces, bile, pancreatic juice, urine, vaginal samples, semen, skin swabs, tissue and tumor biopsy, blood, lymph, cerebrospinal fluid, amniotic fluid, mammary gland secretions/breast milk. Examples of environmental and industrial samples: soil and other media for (agricultural) plant growth, water, sediment, oil well samples, bioreactors (e.g., complex/mixed probiotics). Samples can also include clean room swabs, hospital surfaces, and mucosal brush biopsies.

In methods and systems herein described, absolute quantification of a target 16S rRNA within a sample further comprising prokaryotes and related 16S rRNA (herein also sample 16S rRNA) is performed through detection of a 16S rRNA recognition segment.

In methods and systems of the present disclosure a 16S rRNA recognition segment can be a 16S rRNA polyribonucleotide or 16S rRNA DNA as will be understood by a skilled person. Selection between a 16S rRNA polyribonucleotide or 16S rRNA DNA can be performed based on the experimental design and features of the sample, 16S rRNA segment and related amplifying and sequencing. For example since 16S rRNA is 100-10,000 times more abundant per cell than 16S rRNA gene, 16S rRNA can be preferred in samples with very low microbial loads. Additionally, since abundance of 16S rRNA polyribonucleotide per cell varies with the growth state a 16S rRNA polyribonucleotide recognition segment can be used to obtain as an indication of the growth state of a taxon. A higher ratio of 16S rRNA polyribonucleotide to 16S rRNA gene can indicate a higher growth rate for that taxon. Furthermore, in general 16S rRNA polyribonucleotide is much less stable than 16S rRNA gene and thus can be used as a live/dead marker for a taxon. A low or zero level of 16S rRNA polyribonucleotide in the presence of 16S rRNA gene can indicate that the taxon was not alive in the sample. Additional features, reaction constraints in connection with quantification of target 16S rRNA can be identified by a skilled person upon reading disclosure.

The term "target" as used herein indicates a reference item (such as a nucleic acid and/or a prokaryote) that is aim of a method, step or reaction herein described.

In methods and systems herein described a target 16S rRNA comprises a 16S rRNA recognition segment in which a 16S rRNA variable region specific for the target 16S rRNA is flanked by 16S rRNA conserved regions specific for a plurality of sample 16S rRNA, the plurality of sample 16S rRNAs comprising the target 16S rRNA.

In embodiments herein described a "16S rRNA recognition segment" indicates a region of 16S rRNA comprising a variable region flanked by target conserved regions each independently having 8 to 50 bp in various configurations as will be understood by a skilled person upon reading of the present disclosure.

The term "flank" and "flanking" as used herein with respect to regions of RNA and/or DNA indicates a polynucleotide configuration where "flanking" segment/sequences are located at both sides of a "flanked' reference segment/sequence. The "flanking" segment/sequences can comprise a same or different sequence, be adjacent to the second reference sequence and/or separated by an intermediate sequence as will be understood by a skilled person. In some embodiments, the two flanking regions are no more than 500 bp apart.

In some embodiments, the 16S rRNA recognition segment can comprise additional conserved regions between the two target conserved regions. In some embodiments, the 16S rRNA recognition segment can comprise a plurality of variable regions interspaced by conserved regions in a configuration wherein conserved regions are located in between one or more variable regions as will be understood by a skilled person.

In particular in a 16S rRNA recognition segment according to the disclosure, a polynucleotide typically up to 1,500 bp comprises two or more conserved regions of the 16S rRNA gene sequences flanking one or more variable regions. For example the one or more variable regions can comprise one or more of nine hypervariable regions V1-V9 ranging from about 30 to 100 base pairs long in various configurations, in which conserved regions can flank and possibly be interspersed between variable V1-V9 regions as will be understood by a skilled person. The number of variable and conserved regions and related configuration is determined by the 16S rRNA to be quantified by methods and systems of the present disclosure.

In particular, in the 16S rRNA recognition segment, variable 16S rRNA regions can be selected to provide signature sequences unique for a target taxon and useful for identification of the target taxon and/or corresponding 16S rRNA.

In the 16S rRNA recognition segment, the 8 to 50 bp 16S rRNA conserved regions can be selected to provide sequences conserved in the majority of the prokaryotes within a taxa of a taxonomic rank higher than the target taxon (e.g. a sample prokaryotic taxa known or expected to possibly be comprised in a microbial community of target environment) Different degrees of conservation in the conserved sequence allow grouping of different prokaryotes. The degree of conservation also varies widely between hypervariable regions, with more conserved regions correlating to higher-level taxonomy and less conserved regions to lower levels, such as genus and species. In some embodiments, the variable region ideally has a unique sequence between the two conserved regions for each species of interest.

In embodiments described, the 16S rRNA segment can comprise a plurality of 16S rRNA segment of a same length but typically different lengths, each having the same 8 to 50 bp conserved regions and a same or different type and number of variable regions.

In some embodiments, in a 16S r RNA recognition segment two conserved regions are <500 nt apart from each other and therefore a plurality of 16S r RNA recognition segment can independently have a length <500 nt, higher than <1,000 nt. In some embodiments, the 16S rRNA recognition segment can comprise the entire 16S rRNA sequence. The maximum length of a 16S rRNA recognition is limited by the sequencing technology as will be understood by a skilled person. For example nanopore sequencing performs "long read" sequencing which allows sequencing the whole ~1500-1600 nts of the 16S rRNA. Other sequencing methods can limit the length of the 16S rRNA to approximately up to 600 nts and preferably up to 500 nts, of variable regions between the flanking target conserved regions, in a 16S rRNA recognition segment of up to 650 nts or 550 nts.

In embodiments, herein described absolute quantification of a target 16S rRNA within a sample is performed through detection of a 16S rRNA recognition segment using primers specific for conserved regions of the 16S rRNA recognition segment which are conserved within plurality of sample 16S rRNAs and related taxa, if any can be associated to the selected plurality of 16S rRNAs.

The wording "primer" as used herein indicates a short, single-stranded polynucleotide configured to complementary and capable of complementary binding a target polynucleotide region. Primers in the sense of the disclosure can be used to define the region of the DNA that will be amplified in PCR reactions and/or sequencing reactions. Primers are also referred to as oligonucleotides. Typically, a primer can range in length from 8-50 nucleotides, most preferred between 15-25 nucleotides (e.g. 20 nts) as will be understood by a skilled person.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Exemplary functional groups that can be comprised in an analog include methyl groups and hydroxyl groups and additional groups identifiable by a skilled person. Exemplary monomers of a polynucleotide comprise deoxyribonucleotide, ribonucleotides, LNA nucleotides and PNA nucleotides as will be understood by a skilled person.

Accordingly, the term "polynucleotide" includes nucleic acids of any length, and in particular DNA, RNA, analogs thereof, such as LNA and PNA, and fragments thereof, each of which can be isolated from natural sources, recombinantly produced, or artificially synthesized. Polynucleotides can typically be provided in single-stranded form or double-stranded form (herein also duplex form, or duplex). A "single-stranded polynucleotide" refers to an individual string of monomers linked together through an alternating sugar phosphate backbone. The 5'-end of a single strand polynucleotide designates the terminal residue of the single strand polynucleotide that has the fifth carbon in the sugar-ring of the deoxyribose or ribose at its terminus (5' terminus). The 3'-end of a single strand polynucleotide designates the residue terminating at the hydroxyl group of the third carbon in the sugar-ring of the nucleotide or nucleoside at its terminus (3' terminus). A "double-stranded polynucleotide" or "duplex polynucleotide" refers to two single-stranded polynucleotides bound to each other through complementarily binding. The duplex typically has a helical structure, such as a double-stranded DNA (dsDNA) molecule or a double stranded RNA, which is maintained largely by non-covalent bonding of base pairs between the strands and by base stacking interactions. The term "5'-3' terminal base pair" with reference to a duplex polynucleotide refers to the base pair positioned at an end of the duplex polynucleotide that is formed by the '5 end of one single strand of the two single strand forming the duplex polynucleotide base-paired with the 3' end of the single strand forming the duplex polynucleotide complementary to the one single strand.

The term "complementary" as used herein indicates a property of single stranded polynucleotides in which the sequence of the constituent monomers on one strand chemically matches the sequence on another strand to form a double stranded polynucleotide. Chemical matching indicates that the base pairs between the monomers of the single strand can be non-covalently connected via two or three hydrogen bonds with corresponding monomers in the another strand. In particular, in this disclosure, when two polynucleotide strands, sequences or segments are noted to be complementary, this indicates that they have a sufficient number of complementary bases to form a thermodynamically stable double-stranded duplex. Double stranded of complementary single stranded polynucleotides include dsDNA, dsRNA, DNA: RNA duplexes as well as intramolecular base paring duplexes formed by complementary sequences of a single polynucleotide strand (e.g., hairpin loop).

The terms "complementary bind", "base pair", and "complementary base pair" as used herein with respect to nucleic acids indicates the two nucleotides on opposite polynucleotide strands or sequences that are connected via hydrogen bonds. For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions and additional interactions identifiable by a skilled person. The wording "specific" "specifically" or "specificity" as used herein with reference to a computer supported tool, such as a software indicates a tool capable of identifying a target sequence (such as the nucleic acids of the target organism herein described) among a group of sequences e.g. within a database following alignment of the target sequence with the sequences of the database. Exemplary software configured to specifically detect target sequences comprise Primer-3 [50-52], Perl-Primer [53] and Primer-BLAST [54].

In embodiments of method and systems herein described, the wording "specific" when used in connection with a primer and a target sequence indicates a primer capable of complementary bind the target sequence forming a duplex polynucleotide more thermodynamically stable under a reaction condition than other duplex polynucleotides resulting from complementary binding of the primers with additional polynucleotides possibly present.

The term "thermodynamic stability" as used herein indicates a lowest energy state of a chemical system. Thermodynamic stability can be used in connection with description of two chemical entities (e.g., two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can include, but are not limited to, chemical compositions, base compositions, neighboring chemical compositions, and geometry of the chemical entity.

The strand melting temperature (Tm) of the double-stranded duplex formed by the primer and a target polynucleotide region can be experimentally tested or measured.

In methods and systems herein described, primers used to perform absolute quantification of a target 16S rRNA, are engineered to comprise a target primer sequence specific for a target conserved regions of a 16S rRNA recognition segment which are conserved in a plurality of sample 16S rRNA and flank variable regions which re conserved in the target 16S rRNA.

In methods and systems herein described, selection of specific primers to quantify a target 16S rRNA with the method of the disclosure can comprise for example selecting candidate primers in silico before experimentally testing specificity of candidate primers selected in silico. For example, the performance of a primer can be tested in silico by running in silico PCR on the SILVA database using the TestPrime function [9, 55, 56]. From the results of the PCR, the program computes coverages for each taxonomic group in the taxonomies offered by SILVA. These coverages can then be inspected so that one can identify strengths and weaknesses of a particular pair of primers. In addition or in the alternative, in silico testing can be performed by BLAST or Primer BLAST against any expected off-target DNA potentially present in the sample such as human genomic or mitochondrial DNA to guide the optimization against the off-target amplification.

In methods and systems herein described, selection of specific primers to quantify a target 16S rRNA with the method of the disclosure can comprise modifying the target primer sequence of a base primer to modify the related specificity for a target conserved region in the 16S rRNA recognition segment. The base primer can be known primer or a candidate primer selected in silico and/or experimentally.

In methods and systems herein described, modification of a base primer to quantify a target 16S rRNA with the method of the disclosure the modification can include modification of the length with an increased length providing higher specificity for the template and a shorter length providing lower specificity as will be understood by a skilled person. Typically the length of the primer is selected to maintain specificity of the sample 16S rRNA taking account potential mismatches with the -target regions of the 16S rRNA potentially present in the sample due to the diversity of 16S rRNA within the sample 16S rRNAs. Accordingly primers of the disclosure can comprise a primer target sequence with a degeneracy depending on the taxonomic coverage desired. In embodiments herein described, the length of the targeting sequence complimentary to the target sequences of the target 16S rRNA recognition segment is typically 15-25 nucleotides.

In methods and systems herein described, modification of a base primer to quantify a target 16S rRNA with the method of the disclosure, the modification can include modification of the sequences by introducing mismatches or reducing degeneracy to narrow the taxonomic coverage of the target conserved regions or to improve primer specificity against off-target amplification (e.g., human or animal genomic or mitochondrial DNA). The modification can include modification of the sequences by introducing degenerate bases and/or universal bases to broaden the taxonomic coverage of the target conserved regions. Exemplary "universal" bases comprise as 2'-deoxyinosine, 2'-deoxynebularine, 3-nitropyrrole 2'-deoxynucleoside, 5-nitroindole 2'-deoxynucleoside. Primer mismatches with the known off-target DNA (e.g., human or animal genomic or mitochondrial DNA) can be reinforced by using primers comprising modified nucleotides (e.g. LNA) which would increase the primer specificity against off-target amplification.

In particular in embodiments herein described, the target sequence of the primer should be designed target amplification to preferably have no more than 3 mismatches with the target 16S rRNA sequence and no mismatches at the 3' end of the sequence. In most preferred embodiments, the primers have no mismatches with the target conserved sequence of the 16S rRNA recognition segment, throughout the entire length of the target sequence of the primer.

In methods and systems herein described, modification of a base primer to quantify a target 16S rRNA with the method of the disclosure mismatches can be introduced in base primers to increase specificity of the primers for the target 16S rRNA with respect to known off-target sequences of contaminant polynucleotides potentially present in the sample (e.g., host genomic or mitochondrial DNA). Accordingly, primers can be designed such that those mismatches between the primer and the off-target template. Preferably mismatched are located closer to the 3' end of the primer target sequence to provide stronger specificity for the target template during amplification.

In methods and systems herein described, modification of a base primer to quantify a target 16S rRNA with the method of the disclosure, the modification can include modification of the sequences and/or length of the primers in view of a target annealing temperature and/or other conditions. Preferably forward and reverse primers used herein are designed to have annealing temperature as close to each other as possible. Exemplary annealing temperatures range from 45° C. to 75° C., preferably 60° C.

In methods and systems herein described, modification of a base primer to quantify a target 16S rRNA with the method of the disclosure, selection of the primers can be performed to optimize use of the specific primers in combination with additional primers that can be used in the amplifying and/or sequencing such as a TagMan probe that targets a conserved region between the two conserved regions targeted by the forward and reverse primers in 16S rRNA. In general, TaqMan probes are designed to have a higher annealing temperature (~5° C.) compared with primers that can be used in combination with the TaqMan probes as will be understood by a skilled person.

In methods and systems herein described, modification of a base primer to quantify a target 16S rRNA with the method of the disclosure, selection of the primers can be performed to optimize the sequencing step of the method. For example, in some embodiments, primers flank an amplicon region of a length that configured to perform for a single- or paired-end amplicon sequencing using a desired next generation sequencing technique. In some cases, the amplicon region is within 500 bp, while in other cases longer regions can also be amplified and sequenced by Nanopore sequencing [57-59].

In methods and systems herein described, modification of a base primer to quantify a target 16S rRNA with the method of the disclosure, selection of the primers can be performed to optimize specificity of the primers to exclude polynucleotide possibly present in the sample other than 16S rRNA (herein also contaminant polynucleotides) such as polynucleotide of host cells when the target environment hosting a microbial community is an individual, or polynucleotide present in a target environment outside the individual.

Computational methods can be used to perform in silico testing and/or modification of candidate primers targeting the conserved regions of 16S rRNA gene DNA herein described. Exemplary computational methods include mopo16S [60]. For example, modifying a base primer such as the EMP (Earth Microbiome Project) forward primer by shortening it resulted in increasing its microbial coverage.

In some embodiments, the target primer sequence of the 16S rRNA primers used in method and systems of the disclosure is a modified version of a base primer sequence, such as EMP primer and/or a TaqMan probe.

In particular, in an exemplary embodiments primers specific for a target 16S rRNA can be engineered from a EMP primer set in which the EMP forward primer at its 5' end is redesigned to start at the position 519 of the V4 region of microbial 16S rRNA gene sequence.

For example in an exemplary embodiment the 16S rRNA primers can be made specific for the target 16S rRNA by redesigning the EMP forward primer so that the nonspecific annealing to the host rRNA such as the mouse and human mitochondrial 12S rRNA gene DNA will be reduced or eliminated, which is the main competing template of mammalian origin identified by amplicon sequencing of PCR products obtained with mouse germ-free tissue DNA. Such change increases the primer's specificity for low copy number microbial templates in samples with high content of mouse or human host DNA background (see Examples 2 and 3).

In some of those embodiments, the modification of the EMP primer set broadened its taxonomical coverage of the microbial diversity (86.0% Archaea, 87.0% Bacteria) compared with the original EMP primer set (52.0% Archaea, 87.0% Bacteria) based on the SILVA (version 132) 16S rRNA gene sequence reference database [9, 55, 56] (Example 2 and Example 3). The broader coverage of microbial diversity maximizes the completeness of microbial detection and quantification and richness of diversity profiling.

In some embodiments, a primer set has been obtained specific for all prokaryotes comprises a forward primer having a sequence of 5'-CAGCMGCCGCGGTAA-3') (SEQ ID NO: 26) and a reverse primer having a sequence of 5'-GGACTACHVGGGTWTCTAAT-3' (SEQ ID NO: 27).

Broad-coverage universal 16S primers can be optimized for higher specificity for a taxon of choice. In particular, one introduces nucleotide substitutions or eliminates degeneracy according to the consensus sequence of the conserved priming sites of the taxon of interest. The length of the primers can be adjusted for them to extend into less overall conserved regions but conserved for the taxon of interest. The position of the primers can be adjusted to extend and cover the less overall conserved regions but conserved for the taxon of interest. The above approaches can be combined with the optimization against the known potential off-target templates likely present in the sample (e.g. human genomic or mitochondrial DNA). Alternatively, a taxon-specific TaqMan probe can be introduced which can be used in combination with the same forward and reverse primers with broad coverage. Absolute quantification (dPCR or qPCR) will be based on the TaqMan probe signal.

Table 1 includes an exemplary list from [61] of universal and specific primers for 16S rRNA gene in some microbial groups.

TABLE 1

| Primer | Sequence (5'-3') | Target Group | Reference | SEQ ID NO |
|---|---|---|---|---|
| 8F | AGAGTTTGATCCTGGCTCAG | Universal | [62] | 28 |
| 27F | AGAGTTTGATCMTGGCTCAG | Universal | [63] | 29 |
| CYA106F | CGGACGGGTGAGTAACGCGTGA | Cyanobacteria | [64] | 30 |
| CC[F] | CCAGACTCCTACGGGAGGCAGC | Universal | [65] | 31 |
| 357F | CTCCTACGGGAGGCAGCAG |  | [62] | 32 |
| CYA359F | GGGGAATYTTCCGCAATGGG | Cyanobacteria | [64] | 33 |
| 515F | GTGCCAGCMGCCGCGGTAA | Universal | [62] | 34 |
| 533F | GTGCCAGCAGCCGCGGTAA | Universal | [66] | 35 |
| 895F | CRCCTGGGGAGTRCRG | Bacteria exc. plastids & Cyanobacteria | [67] | 36 |
| 16S.1100.F16 | CAACGAGCGCAACCCT | Universal | [62] | 37 |
| 1237F | GGGCTACACACGYGCWAC | Universal | [62] | 38 |
| 519R | GWATTACCGCGGCKGCTG | Universal | [62] | 39 |
| CYA781R | GACTACWGGGGTATCTAATCCCWTT | Cyanobacteria | [64] | 40 |
| CD[R] | CTTGTGCGGGCCCCCGTCAATTC | Universal | [65] | 41 |
| 902R | GTCAATTCITTTGAGTTTYARYC | Bacteria exc. plastids & Cyanobacteria | [67] | 42 |
| 904R | CCCCGTCAATTCITTTGAGTTTYAR | Bacteria exc. plastids & Cyanobacteria | [67] | 43 |
| 907R | CCGTCAATTCMTTTRAGTTT | Universal | [63] | 44 |
| 1100R | AGGGTTGCGCTCGTTG | Bacteria | [62] | 45 |

TABLE 1-continued

| Primer | Sequence (5'-3') | Target Group | Reference | SEQ ID NO |
|---|---|---|---|---|
| 1185mR | GAYTTGACGTCATCCM | Bacteria exc. plastids & Cyanobacteria | [67] | 46 |
| 1185aR | GAYTTGACGTCATCCA | Lichen-associated Rhizobiales | [67] | 47 |
| 1381R | CGGTGTGTACAAGRCCYGRGA | Bacteria exc. Asterochloris sp. plastids | [67] | 48 |
| 1381bR | CGGGCGGTGTGTACAAGRCCYGRGA | Bacteria exc. Asterochloris sp. plastids | [67] | 49 |
| 1391R | GACGGGCGGTGTGTRCA | Universal | [62] | 50 |
|  | GGTTACCTTGTTACGACTT | Universal | [62] | 51 |
| 1492R(s) | ACCTTGTTACGACTT | Universal | [63] | 52 |

Additional primers that can be used as base primers to select specific primers suitable in methods and systems of the disclosure are identifiable by a skilled person upon reading of the present disclosure in view of specific target 16S rRNA and sample 16S rRNA.

In some embodiments, a method of the disclosure comprises amplifying the target 16S rRNA recognition segment by performing polymerase chain reaction (PCR) on nucleic acids from the sample with primers specific for the 16S rRNA conserved regions to quantitatively detect an absolute abundance of the plurality of sample 16S rRNAs in the sample and to provide an amplified 16S rRNA recognition segment.

In embodiments wherein the 16S rRNA is a polyribonucleotide, specific primers are used for generation of cDNA from an RNA template via reverse transcription. In particular, in those embodiments a primer can be used to reverse transcription which is a reverse primer used in amplifying step according to the instant disclosure as will be understood by a skilled person.

The term "amplify" or "amplification" as used herein indicates a usually massive replication of a polynucleotide in particular of a gene or DNA sequence. Accordingly, amplifying indicated in connection with a reference polynucleotide indicates the replication of the referenced polynucleotide to provide a greater number of the referenced polynucleotide and increase representation of the reference polynucleotide in a target environment. Amplification can be conducted through methods such as: Polymerase Chain Reaction, ligase chain reaction, transcription-mediated amplification, methods and additional methods identifiable by a skilled person. Copies of a particular nucleic acid sequence generated in vitro in an amplification reaction are called amplicons or amplification products.

In embodiments of the disclosure amplification is performed by Polymerase Chain Reaction (PCR) on nucleic acids extracted from the sample.

The term "polymerase chain reaction" as used herein indicates a reaction amplifying copies a polynucleotide in a series of cycles of temperature changes. In particular, in various PCR methods repeated cycles of heating and cooling exposes reactants of temperature-dependent reactions which result in amplification of the polynucleotide. PCR can amplify polynucleotides of up to 40 kilo base pairs (kbp) and typically amplifies between 0.1 and 10 kbp in length, as will be understood by a skilled person.

In all PCR methods the amplification is performed by using primers and a polymerase. The term "polymerase" as used herein indicates an enzyme capable of synthesizes long chains of polymers or nucleic acids, replicating a target polynucleotide or template strand using base-pairing interactions. Exemplary polymerase comprises heat stable DNA polymerase such as Taq polymerase or high fidelity polymerases such as Pfu polymerase. Commercial modification of these base polymerases and their associated master mixes work well (e.g., Bio-Rad SsoFast EvaGreen Supermix (Bio-Rad Laboratories, Hercules, CA), 5PRIME HotMaster Taq DNA Polymerase and 5PRIME HotMasterMix (Quantabio, Beverly, MA), KAPA HiFi polymerase (KAPA Biosystems, Woburn, MA), JumpStart Taq DNA Polymerase (Sigma-Aldrich, St. Louis, Mo.).

Accordingly, in a PCR reaction the primers determine the region of target polynucleotide that will be copied or amplified. In particular, in a PCR a forward primer contains a nucleotides complementary and capable of complementary binding a region of the target polynucleotide upstream of the sequence to be amplified, and a reverse primer contains nucleotides complementary and capable of complementary binding nucleotides on the target polynucleotide that are downstream of the sequence to be amplified as will be. Upstream refers to a 5' location to the sequence to be amplified relative to the coding strand and downstream refers to a 3' location to the sequence to be amplified relative to the coding strand as will also understood by a skilled person.

In embodiments of the present disclosure polymerase chain reaction (PCR) is performed with primers specific for the 16S rRNA conserved regions to quantitatively detect an absolute abundance of the plurality of sample 16S rRNAs in the sample and to provide an amplified 16S rRNA recognition segment. For example, various combinations of the forward and reverse primers from Table 1 can be used to amplify various regions of 16S rRNA gene sequences. Using various combinations of such primers will result in variable taxonomic coverage of the microbial diversity and variable taxonomic resolution as will be understood by a person skilled in the art.

In some embodiments, primers specific for a target sequence of the 16S rRNA to be used in methods and systems of the disclosure, can further comprises in addition to the target primer sequence described above, a barcode and/or an adapter sequence.

The term "barcode" or "barcoding" when used as a verb with reference to a reaction, indicates a reaction performed to covalently attach a barcode in the sense of the disclosure to the reference item, in a configuration allowing detection of the barcode. Accordingly, barcoding in the sense of the disclosure refers to coupling a unique set of tags or identifiers in order to mark molecules for downstream detection and identification. In particular, in embodiments herein described barcoding in particular refer to a coupling reaction of molecules within a same sample in case multiple samples are provided for analysis in order to label these molecules for downstream detection and identification. In some embodiments, suitable tags or identifiers for barcoding can be oligonucleotide label. As used herein, "unique" means different from any other. Exemplary reactions that can be used to barcode a molecule in the sense of the disclosure comprise ligation binding of antibody covalently attaching an oligonucleotide, addition of DNA by transposase and additional reactions identifiable by a skilled person.

In some embodiments, a barcode can be obtained by sequential direct covalent linkage of a tag with another tag until formation of a barcode comprising a series of two or more tags directly attached one to another through covalent linkage.

In embodiments herein described, the primer construct can also contain an adapter sequence, and in particular an adapter compatible to a next-generation sequencing platform.

An "adapter or a linker is a short, chemically synthesized, single-stranded or double-stranded oligonucleotide that can be ligated to the ends of other DNA or RNA molecules. An adapter can be designed to comprise overhangs specific to the complementary sequence of the target molecule of interest. The overhang can be used for subsequent processing of the nucleic acid and/or protein complex for tagging, ligation, elongation, and additional downstream analysis as will be understood by a skilled person. The overhang sequence can be at least 1 bp in length. The adapter sequence can be located at one or both ends of other DNA or RNA molecules. In some embodiments, the barcode is ligated onto nucleic acids with a DNA or RNA ligase via an adapter as will be understood by a person skilled in the art. Overhangs can be generated by restriction digestion as will be understood by a skilled person.

In some embodiments, a primer can comprise a specific adapter sequence ligated to the 5' end of the target specific sequence portion of the primer. This adapter (also referred to as a sequencing adapter) is a short oligonucleotide of known sequence that can provide a priming site for both amplification and sequencing of the target nucleic acid. As such, adapters allow binding of a fragment to a flow cell for next generation sequencing.

Any adapter sequence required by a sequencing platform of a choice can be included in a primer used herein. In some embodiments of the method, the adapter sequence is an Illumina P5 adapter, P7 adapter, P1 adapter, A adapter, or Ion Xpress™ barcode adapter.

In some embodiments, a primer set used herein can further comprise a linker and/or pad sequence suitable for next-generation sequencing as will be understood by a skilled person. The primer pad sequence is used to extend the region over which the sequencing primer anneals and increases the $T_m$ of the sequencing primer to fit that of the sequencing platform such as Illumina platform as will be understood by a skilled person.

In particular, in some embodiments, a primer can be engineered for Barcoding qPCR (BC-qPCR) a single-step amplicon barcoding-quantification in which a qPCR reaction performed with primers that include barcode and/or adapter sequences. Additionally, BC-qPCR can be run with a single-step (one set of primers carrying barcodes and adapters) [16, 18] and two(multi)-step (two sets of primers: 1st set carrying common adapters, 2nd set carrying barcodes and sequencing adapters) [68-70].

In embodiments of the methods and systems herein described, a primer set specific for the 16S rRNA conserved regions of the 16S rRNA recognition segment, and preferably comprising a barcode and/or an adaptor, is used to perform the amplifying the 16S rRNA recognition segment by performing polymerase chain reaction to obtain a total number of the sample 16S rRNA.

Figure 1:
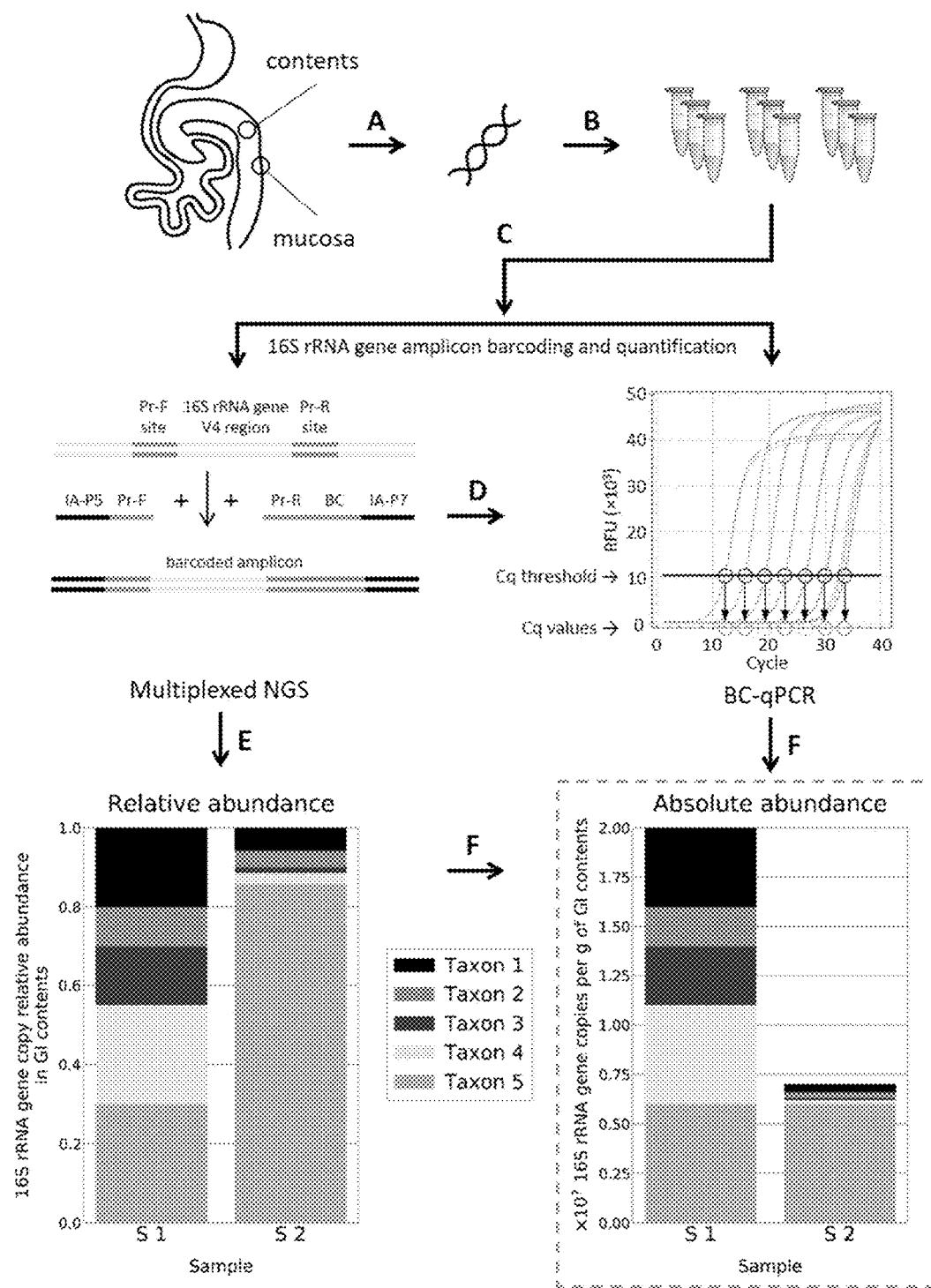
FIG. 1 shows a schematic illustration of the single-step 16S rRNA gene DNA quantification and amplicon barcoding workflow (BC-qPCR) implementation for quantitative microbiome profiling.

In some embodiments herein described, the PCR reaction is set up with 16 S rRNA gene primer containing the target primer sequence specific for the conserved regions in the 16S rRNA recognition segments together with barcodes, adapters, linker, pad, and/or frameshifting sequences configured for next-generation sequencing (see e.g. Example 1 and "B" in FIG. 1).

The PCR reaction mix further comprises conventional commercial reagents for 16S rRNA gene amplicon library preparation as will be understood by a person skilled in the art. Reactions can be run in replicates to improve the real-time PCR quantification precision and resolution and amplicon barcoding uniformity [18].

In some embodiments, the parameters used in the PCR and/or barcoding-PCR procedures herein described are optimized to minimize primer dimer formation and host DNA amplification while reducing amplification biases and ensuring uniform amplification of diverse 16S rRNA gene sequences from complex microbiomes.

In some embodiments, the amplification PCR reaction is conducted at the highest possible annealing temperature to minimize the primer dimer formation and non-specific host mitochondrial DNA amplification both of which would be competing with specific prokaryote 16S rRNA gene DNA template for reaction resources (see Example 3). In some embodiments, the temperature of 40-80° C. is selected as optimal for the PCR reaction, preferably between 50-70° C., and more preferably about 60° C. In some of those embodiments, even in the presence of high host DNA background, the reaction efficiency is ~95.0% and the assay is able to resolve 1.25 to 1.67-fold differences in total 16S rRNA gene copy loads among samples within the range of ~$10^{4.83}$-$10^{10.95}$ copies/mL (see Example 3).

99 In methods and systems herein described the amount of amplified product which is determined by the available substrates in the reaction, which become limiting as the reaction progresses will provide absolute abundance of the plurality of sample 16S rRNAs in the sample and an amplified 16S rRNA recognition segment (16S rRNA amplicon) as will be understood by a skilled person.

In embodiments wherein the primer set used in the amplifying, is an adapter-ligated and/or barcoded primers, the adapter sequence and/or barcode sequence are incorporated into the 16S rRNA amplicon along with the target 16S rRNA primer sequence during amplification. Therefore, the resulting amplicons comprise both the 16S rRNA target sequence and the barcode and/or adapter sequence, which are suitable for the subsequent sequencing and do not require the traditional library preparation protocol.

In some embodiments wherein the primer set used in the amplifying, comprises a barcode, the presence of the barcode also permits the differentiation of sequences from multiple sample sources, the amplified 16S rRNA derived from a single sample further comprise an identical barcode sequence that indicates the source from which the amplicon is generated, the barcode sequence for each sample being different from the barcode sequences from all other samples. As such, in those embodiments, the use of barcode sequences permits multiple samples to be pooled per sequencing run and the sample source subsequently ascertained based on the barcode sequence. In some embodiments, the 16S rRNA amplification and barcoding is performed simultaneously in one set up to generate a barcoded amplicon library that can be used in sequencing directed to detect a relative abundance of the target 16S rRNA with respect to the plurality of sample 16S rRNAs in the sample according to the methods and systems of the present disclosure (see Example 1).

In embodiments wherein the primer set used in the amplifying, comprises an adapter, amplicons corresponding to specific regions of 16S rRNA are amplified using primers that contain an oligonucleotide sequencing adapter to produce adapter tagged amplicons to be used in sequencing directed to detect a relative abundance of the target 16S rRNA with respect to the plurality of sample 16S rRNAs in the sample according to the methods and systems herein described.

In embodiments, wherein the primer set used in the amplifying does not contain an a barcode and/or adapter sequences, the amplicons produced can be ligated to an oligonucleotide sequencing adapter on one or both ends of the amplicons as will be understood by a person skilled in the art to allow sequencing directed to detect a relative abundance of the target 16S rRNA with respect to the plurality of sample 16S rRNAs in the sample according to the methods and systems herein described [71, 72].

In embodiments, wherein the primer set used in the amplifying does not contain a barcode and/or adapter sequences, a two-step recognition segment amplification and barcoding can be performed consisting of two consecutive PCR steps as previously described [69, 73, 74]. The first PCR step uses a pair of primers that have two parts: sequences targeting the 16S rRNA and adapter overhangs. The second PCR step uses a pair of primers that target the adapter sequences added to the 16S amplicons in the first step and also carry barcodes and flow-cell adapters on their ends [45] as will be understood by a skilled person.

In embodiments wherein the 16S rRNA is a 16S rRNA polyribonucleotide, RNA templates can first be reverse transcribed into cDNA before following the same amplification steps described for DNA. The reverse transcription step generally consists of a reverse transcriptase enzyme, associate buffers, dNTPs, and an RNase inhibitor.

In embodiments wherein the 16S rRNA is a 16S rRNA polyribonucleotide, exemplary reverse transcriptase enzymes consist of the base and modified enzymes of the following forms: Bst, M-MLV, AMV, and HIV-1. Additionally, thermostable reverse transcriptases can be used (eg., RapiDxFire (Lucigen), RocketScript (Bioneer)). Associated buffers are generally provided by the manufacturer but can also be homemade mixtures of salts. dNTP mixtures contain the fours nucleotides (dATP, dCTP, dGTP, and dTTP) at equimolar concentration. RNase inhibitors consist of small molecules or enzymes that inhibit the activity of RNAse enzymes (e.g., RNase A, RNase B, RNase C).

In embodiments wherein the 16S rRNA is a 16S rRNA polyribonucleotide, the reverse transcription thermocycling step can include a low temperature (20-50 C) primer annealing step followed by the mandatory cDNA synthesis step. cDNA synthesis is run at a temperature range specific to each reverse transcriptase enzyme. In general cDNA synthesis occurs between 40 C and 80 C with thermostable enzymes preferring 60-80 C and non-thermostable enzymes preferring 40-55 C. Most preferably 70 C and 55 C respectively. The cDNA synthesis step is generally run for 5-120 mins, more preferably, 10-60 mins. A heat denaturation step of the RT enzyme can be included as well which occurs between 70-95 C, preferably 80 C.

In embodiments wherein the 16S rRNA is a 16S rRNA polyribonucleotide, the primer concentration in the reverse transcription step can range from 100 nM-25 uM, more preferably 500 nm-1 uM.

In some embodiments wherein the 16S rRNA is a 16S rRNA polyribonucleotide, a reaction clean-up step can be performed following cDNA synthesis before the DNA amplification, barcoding, and quantification steps. The clean-up generally consists of either a silica column based or magnetic bead based clean-up similar to those described in DNA extraction.

In some embodiments of the methods and systems herein described, amplifying the 16S rRNA recognition segment can be performed with touchdown PCR a PCR method that can be used for increased specificity and sensitivity in PCR amplification as will be understood by a person skilled in the art [75].

In some embodiments of the methods and systems herein described, amplifying the 16S rRNA recognition segment can be performed with qPCR. The term "qPCR","quantitative polymerase chain reaction", "real-time polymerase chain reaction" or "real-time PCR' as used, herein indicated indicates a polymerase chain reaction performed to monitor amplification of a target polynucleotide during the PCR (in real time). qPCR can be used to detect a target polynucleotide quantitatively (quantitative real-time PCR) or semi-quantitatively (above/below a certain amount of target polynucleotide) (semi-quantitative real-time PCR). Typically in qPCR monitoring is performed through use of non-specific fluorescent dyes that intercalate with any double-stranded DNA or sequence-specific polynucleotide probes consisting of oligonucleotides that are labelled with a fluorescent reporter, which permits detection only after hybridization of the probe with its complementary sequence.

In embodiments of the methods and systems herein described wherein the amplifying the 16S rRNA recognition segment is performed with qPCR, the cycling conditions can be optimized. Generally, the thermocycling program can be set up as follows: initial denaturing at 95° C. for 30s, annealing at 54° C. for 30s, and final extension at 68° C. for 30s. The concentration of primers can also be changed. In general, a concentration of primers is in a range between 100 nM and 2.5 µM depending on the primers and detection methods, and is typically around 500 nM.

In embodiments of the methods and systems herein described wherein the amplifying the 16S rRNA recognition segment is performed with r real-time PCR, real-time fluorescence monitoring also enables terminating the amplification of each sample upon reaching the mid-exponential phase to maximize the amplicon yield and minimize the over-amplification artifacts [76].

In embodiments of the methods and systems herein described wherein the amplifying the 16S rRNA recognition segment is performed with real-time PCR (qPCR), the concentration of the fluorescent dye can be increased in particular with samples having high background (e.g. host) amounts of DNA.

In embodiments of the methods and systems herein described wherein the amplifying the 16S rRNA recognition segment is performed with qPCR, fluorescence can be used only to prevent "over-amplification" of 16S amplicons without exact quantification of the target, according to approaches such as the one used in a commercial microbiome 16S sequencing library preparation kit to prevent overamplification [73, 74].

In embodiments of the methods and systems herein described wherein the amplifying the 16S rRNA recognition segment is performed with qPCR, real-time amplification procedures with barcoding for next generation sequencing are well known in the art. The same amplification protocols used by the Earth Microbiome Projects (earthermicrobiome.org/emp-standard-protocols/16s) can be used herein as will be understood by a skilled person.

In some embodiments, amplification of the 16S rRNA recognition segment can be performed under real-time fluorescence measurements on a real-time PCR instrument (see Example 1, in FIG. 1, Panel C), thus enabling a single-step 16S rRNA gene copies quantification and amplicon barcoding approach. This approach is referred to as "barcoding qPCR" or "BC-qPCR".

Accordingly, quantitative real-time PCR data (Cq values) are recorded (see Example 1 and FIG. 1 panel D) and used to calculate the absolute abundance of the sample 16S rRNAs in each sample based on the sample 16S rRNA standards (or anchors) included within the same BC-qPCR run (see Example 1 and FIG. 2, panels A-B) or to calculate the absolute fold-differences in the 16S rRNA gene DNA copy load among the samples in the absence of the standards (or anchors) (see Example 1 and FIG. 2, panel C). These data are further used to calculate the absolute abundances or fold differences in the absolute abundances of single 16S rRNA of the sample 16S rRNA in the analyzed samples.

In some embodiment, wherein the amplifying is performed with BC-qPCR, single 16S rRNA gene DNA standard (or anchor) with known target template concentration can be included with a 96-well (96 PCR tube) run (see Example 1 and FIG. 2, panel A). In some other embodiments, wherein the amplifying is performed with BC-qPCR, two or more 16S rRNA gene DNA standards (e.g., serial dilutions) with known target template concentrations can be utilized in a similar manner (see Example 1 and FIG. 2, panel B). Including more than one standard will allow estimating the exact BC-qPCR efficiency (according to the equations 2.2 and 2.5 or 2.3, 2.4, and 2.5 of FIG. 2) for any given batch of samples and reagents.

In some embodiments, wherein BC-qPCR is performed it can provide a valuable information about the fold difference in the absolute load of 16S rRNA gene copies among compared samples (in a single batch and potentially across multiple batches of samples from a single PCR run or multiple separate PCR runs) without standards (anchors) included (see Example 1 and FIG. 2, panel C). Such fold difference between samples can be calculated using the equations 3.1 and 3.2 of FIG. 2 and assuming the empirical BC-qPCR efficiency of 95.0%. Such absolute fold difference values can then be converted to the absolute fold differences among samples for each individual taxon based on their relative abundance values obtained from the sequencing step as will be understood by a skilled person upon reading of the present disclosure.

In embodiments, wherein PCR is performed by qPCR the total number of sample 16S rRNAs can be obtained by detecting a concentration parameter such as Cq (PCR cycle number at which a signal is detected), reaction time, fluorescence intensity, and comparing the detected concentration parameter with a standard calibration curve to obtain the nucleic acid concentration value.

Several different anchoring approaches can be utilized to convert the Cq values obtained from the qPCR to provide the absolute abundance of sample 16S rRNA in the samples. For example multiple uncharacterized samples (ideally with distant Cq values) can be quantified using the dPCR assay and used as anchoring "standards" for the batch of samples. Any of the multiple anchoring points then can be used to calculate the sample 16S rRNAs copy load in the remaining samples from the batch using equations 2.1 and 2.6 of FIG. 2.

In addition or in the alternative, a single uncharacterized sample from the batch can be analyzed using e.g. a dPCR assay and thus can serve as a single anchoring "standard" sample. In this scenario all calculations of the absolute concentrations of the remaining samples can be done using the equations 1.1. and 1.2 of FIG. 2 and would rely on the empirical BC-qPCR efficiency (e.g., 95.0%) to provide absolute abundance values of sample 16S rRNAs.

In some embodiments, the 16S rRNA gene amplification and barcoding can be performed via two separate PCR reactions ("two-step barcoding") as in [69, 73, 74] as will be understood by a person skilled in the art.

In some embodiments in which absolute abundance is obtained by BC-qPCR (which allows target amplification+barcoding+simultaneous quantification based on Cq) the "two-step barcoding" can be performed by recording the real-time fluorescent signal during both of the real-time barcoding PCR reactions and combining for each sample a complete time series of the fluorescent signal from the fluorescent signal values obtained from the first and from the second PCR reactions. Combined fluorescent signal time series can then be used to plot the fluorescence profiles (fluorescence values over the number of cycles) and calculate the corresponding Cq values for each sample as in [77].

In some embodiments, the absolute abundance of 16S rRNAs can be provided as a direct measurement from experiments. For example, the total number of sample 16S rRNAs can be provided by detecting a nucleic acid with digital quantification methods.

As used herein the term, "digital" in connection amplification and/or quantification methods, indicates polynucleotides amplification methods, in which Single molecules can be isolated by dilution and individually amplified; each product is then separately analyzed. Exemplary digital quantification methods comprise digital PCR (dPCR), or with correction for amplification efficiency by digital LAMP or digital RPA or other digital isothermal amplification chemistries.

In particular some embodiments herein described, the absolute abundance of 16S rRNAs can be provided by amplifying the 16S rRNA recognition segment with digital polymerase chain reaction to quantitatively detect an absolute abundance of the plurality of sample 16S rRNAs.

As used herein, "digital PCR" refers to an assay that provides an end-point measurement that provides the ability to quantify nucleic acids without the use of standard curves, as is used in real-time PCR. In a typical digital PCR experiment, the sample is randomly distributed into discrete partitions, such that some contain no nucleic acid template and others contain one or more template copies. The partitions are amplified to the terminal plateau phase of PCR (or end-point) and then read to determine the fraction of positive partitions. If the partitions are of uniform volume, the number of target DNA molecules present can be calculated from the fraction of positive end-point reactions using Poisson statistics, according to the following equation: $\lambda=-\ln(1-p)$ (1) wherein $\lambda$, is the average number of target nucleic acid molecules per replicate reaction and p is the fraction of positive end-point reactions. From $\lambda$, together with the volume of each replicate PCR and the total number of replicates analyzed, an estimate of the absolute target nucleic acid concentration is calculated. Digital PCR includes a variety of formats, including droplet digital PCR, BEAMing (beads, emulsion, amplification, and magnetic), and microfluidic chips.

As a person skilled in the art will understand, digital PCR (dPCR) builds on traditional PCR amplification and fluorescent-probe-based detection methods to provide a sensitive absolute quantification of nucleic acids without the need for standard curves.

In embodiments wherein dPCR is used to quantify the total number of sample 16S rRNAs, a sample is typically split into two separate PCR reactions: one reaction is used for absolute quantification through dPCR and the second reaction is used for amplicon barcoding for next-generation sequencing.

Accordingly, in embodiments wherein dPCR is used to quantify the total number of sample 16S rRNAs, amplifying the 16S rRNA recognition segment comprises performing digital PCR to quantitatively detect an absolute abundance of the plurality of sample 16S rRNAs in the sample and performing real-time PCR to provide an amplified 16S rRNA recognition segment.

In some embodiments dPCR reactions are set up with 16 S rRNA gene primer containing the target primer sequence sequences configured for the sequencing according to methods and systems herein described. The PCR reaction mix further comprises conventional commercial reagents for 16S rRNA gene amplicon library preparation as will be understood by a person skilled in the art. Reactions can be run in replicates to improve quantification precision and resolution and amplicon barcoding uniformity.

In embodiments herein described, the methods and systems of the disclosure also comprise b) sequencing the 16S rRNA recognition segment with the primers comprising the target specific for the 16S rRNAs conserved region to detect a relative abundance of the target 16S rRNA with respect to the plurality of sample 16S rRNAs in the sample, As a person skilled in the art will understand, the sequencing in methods and systems herein described is used to detect the order of nucleotides present in the 16S rRNA recognition segment and to differentiate among the sample 16S rRNAs to detect a relative abundance of the target 16S rRNA with respect to the total 16S rRNAs in the sample. As a person skilled in the art will understand, a relative abundance used herein is the percent composition of the target 16S rRNA relative to the total number of sample 16S rRNA in the sample.

The word "sequencing" as used herein indicates massive parallel sequencing performed via spatially separated, clonally amplified polynucleotide templates or single polynucleotide molecules, as will be understood by a skilled person. In particular, in embodiments herein described sequencing can be performed by Next Generation Sequencing performed by generating sequencing libraries by clonal amplification of a target polynucleotide by PCR in vitro to provide amplified templates or providing single target polynucleotides; spatially segregating, amplified templates or single target polynucleotide; and sequencing the spatially segregated target polynucleotide by synthesis, such that the sequence is determined by the addition of nucleotides to the complementary strand rather than through chain-termination chemistry. While these steps are followed in most NGS platforms, each utilizes a different sequencing approach such as Pyrosequencing, Sequencing by reversible terminator chemistry, Sequencing-by-ligation mediated by ligase enzymes, and Phospholinked Fluorescent Nucleotides or Real-time sequencing as will be understood by a skilled person. Exemplary NGS kits commercially available include Illumina™ sequencing, Roche 454™ sequencing, Ion torrent: Protein/PGM™ sequencing, Nanopore sequencing, and SOLiD™ sequencing. Next generation sequencing methods are known in the art, and are described, e.g., in Metzker, M. Nature Biotechnology Reviews 11:31-46 (2010).

Accordingly in some embodiments sequencing is performed by performing next-generation sequencing of a 16S rRNA comprising the recognition segment the amplified 16S rRNA recognition segment with the same primers described herein for the PCR, which are specific for the 16S rRNAs conserved region.

In some embodiments sequencing can be performed by performing long read sequencing (Nanopore) which is a sequencing method based on measuring changes in voltage as the bases pass through a membrane protein pore. In those embodiments typically up to nearly full length 16S sequence is amplified using non-barcoded primers. Amplicons are then end-repaired, dA-tailed, ligated with barcodes, and then pooled (from multiple samples) barcoded amplicons were ligated with sequencing adapters before sequencing. [58, 59].

In the embodiments herein described, the primers used for sequencing the 16S rRNA comprise a forward and a reverse primer sequence. In particular, in methods and systems herein described the forward and reverse primer sequence comprise the same target primer sequences that are specific to the 16S rRNA conserved regions of the 16S rRNA recognition segment flanking the variable region of the same 16S rRNA recognition segment.

Accordingly, both the forward and reverse primers used for next-generation sequencing and the forward and reverse primers used in PCRs described above comprise the same target primer sequences that are substantially complementary to the 16S rRNA conserved regions of the 16S rRNA recognition segment.

In some embodiments, the primers used for next generation sequencing comprise a forward primer having a sequence of 5'-CAGCMGCCGCGGTAA-3') (SEQ ID NO: 53) and a reverse primer having a sequence of 5'-GGACTACHVGGGTWTCTAAT-3' (SEQ ID NO: 54).

Additional exemplar primers are listed in Table 2 below,

TABLE 2

| Primer name | Sequence | Orientation | SEQ ID NO: |
|---|---|---|---|
| UN00F02.1 | CAGCMgCCGCGGTaA | Forward | 55 |
| UN00F02.2 | CAGCNgCCGCGGTaA | Forward | 56 |

TABLE 2-continued

| Primer name | Sequence | Orientation | SEQ ID NO: |
|---|---|---|---|
| UN00F03.1 | AGCMgCCGCGGTaA | Forward | 57 |
| UN00F03.2 | AGCNgCCGCGGTaA | Forward | 58 |
| UN00F04.1 | GTGYCAGCMgCCGC | Forward | 59 |
| UN00F04.2 | GTGNCAGCNgCCGC | Forward | 60 |
| UN00F05.1 | GTGYCAGCMgCCG | Forward | 61 |
| UN00F05.2 | GTGNCAGCNgCCG | Forward | 62 |
| UN00F06.1 | GTGYCAGCMgCC | Forward | 63 |
| UN00F06.2 | GTGNCAGCNgCC | Forward | 64 |
| UN00F07.1 | GCMgCCGCGGTaA | Forward | 65 |
| UN00F07.2 | GCNgCCGCGGTaA | Forward | 66 |
| UN00F08.1 | CMgCCGCGGTaA | Forward | 67 |
| UN00F08.2 | CNgCCGCGGTaA | Forward | 68 |
| UN00F09.1 | GCMgCCGCGGTa | Forward | 69 |
| UN00F09.2 | GCNgCCGCGGTa | Forward | 70 |
| UN00F10.1 | AGCMgCCGCGGTa | Forward | 71 |
| UN00F10.2 | AGCNgCCGCGGTa | Forward | 72 |
| UN00R00.1 | gGacTAcHVGGGTWTCTAAT | Reverse | 73 |
| UN00R00.2 | gGacTAcNNGGGTNTCTAAT | Reverse | 74 |

Y, M, H, V, and W indicate degenerate bases according to the IUPAC notation;
N indicates degenerate base according to IUPAC notation, or a universal base (as described in the text of the disclosure), or a combination of these two (when sequence has multiple N),
Lowercase letters indicate LNA modifications at a single location, various combinations of more than one location, or all locations within a sequence.

The primers shown in Table 2 can form primer pairs to be used in method and systems herein described in any combination of forward and reverse primers as will be understood by a skilled person. In particular, primers comprising LNA have been designed to facilitate the primer binding to specific microbial 16S rRNA polynucleotides while reduce its binding to animal mitochondrial polynucleotides, as will be understood by a skilled person upon reading of the present disclosure.

A person skilled in the art will understand, the primers used for sequencing 16S rRNAs can further comprise an index sequencing primer that carries a reverse complement of the sequence that targets 3' end of the 16S rRNA amplicon.

In some embodiments, the next-generation sequencing approach used herein is amplicon sequencing. "Amplicon sequencing" as used herein refers to a targeted sequencing method in which a discrete region of a genome is first amplified from the entire genome using PCR and the generated amplicons are used as templates for subsequent sequencing. Sequencing can be carried out in a sample containing amplification products of a single amplicon. Alternatively, the sample can contain mixtures of multiple amplicons pooled together, as will be understood by a skilled person. Amplicon Sequencing is a method where multiple amplicons are pooled together and co-sequenced.

"Amplicons" as used herein are defined as replicated DNA (or ribonucleic acid—RNA) strands that are formed by polymerase chain reaction (PCR), ligase chain reactions (LCR), or other DNA duplication methods, where the strands are copies of a target region of a genome. In order to multiplex PCR amplification, each amplicon has to be unique and independent (no overlapping amplicons), which requires careful selection of the primers used to tag the regions to be amplified. Amplicons for sequencing have a length typically in the range between 100 bp and 500 bp.

The processing and sequencing of amplicons with different sequencing platforms can be flexible and allows for a range of experimental designs. A variety of options regarding design parameters can be selected, such as the length of amplicons, the number of amplicons pooled together, the number of reads desired for a given amplicon or a pool of amplicons, whether to read from one end (unidirectional sequencing) or both ends (bi-directional sequencing) of the amplicon and other factors identifiable to a skilled person in the art.

In some embodiments herein described, the 16S rRNA amplicon samples generated from real-time PCR are quantified, pooled, purified, and sequenced on an NGS instrument. NGS sequencing results provide the sequence read and count data which enable taxa identification and calculation of the corresponding taxa relative abundance profiles for the analyzed samples ("E" in FIG. 1).

The terms "read" or "reads" used herein are defined as a sequenced range of DNA or RNA. A read can be a sequence that is output by a sequencing instrument, where the read attempts to match a range of DNA that was input to the instrument. Each set of reads maps to a particular amplicon, with a read being a sequence for the complete amplicon or, typically, a range of bases comprising a subset of the amplicon. The total set of reads in the input data for the filter pipeline can include multiple amplicons, each having multiple reads mapped to them. The range of the read lengths depends upon the primers chosen for a given library. The mapping of reads to an amplicon can be determined by overlapping paired-end reads (generally shorter than the length of the amplicon) for each sequenced amplicon to obtain the complete 16S amplicon sequences. Complete 16S amplicon sequences are used in downstream analysis to identify their proportions in the entire 16S amplicon pool and to identify their taxonomic origin. The mapping of reads to an amplicon can also be determined during alignment/assembly using a sequencing alignment tool, for example the Bowtie™ 2 read alignment tool from Johns Hopkins University (see "Fast gapped-read alignment with Bowtie 2" by Ben Langmead and Steven L. Salzberg, *Nat Methods, Author manuscript*; PMC 2013 Apr. 1).

In some embodiments, the complete 16S amplicon sequences can be obtained by combining overlapping paired-end reads (generally shorter than the length of the amplicon) for each sequenced amplicon to obtain the complete 16S amplicon sequences. Complete 16S amplicon sequences can then be used in downstream analyses to identify their proportions in the entire 16S amplicon pool and to identify their taxonomic origin as will be understood by a skilled person.

In some embodiments, a one-step quantification can be performed by detecting the absolute abundance of the plurality of sample 16S rRNA by qPCR with either with one-step or two-step barcoding as described herein, and by monitoring a library barcoding reaction fluorescence in real-time like qPCR. The Cq of each sample can be used with a standard curve or a defined number of standards (or anchors: multiple, two, or only one) to determine the absolute abundance of each sample or can be used without any standards (anchors) to calculate an absolute fold-difference.

In some embodiments, a two-step quantification can be performed can be performed by detecting the absolute abundance of the plurality of sample 16S rRNA by dPCR or digital LAMP or digital RPA with non-barcoded primers in a portion of the sample, and by detecting the relative abundance by sequencing in another portion of the sample used to prepare the barcoded sequencing library.

In both the one-step quantification and two step quantification embodiments according to the instant disclosure, barcoded libraries are typically sequenced and the relative abundance of the target 16S rRNA (and/or target taxon) in the sample detected through sequencing is then multiplied by the absolute abundance of the plurality of sample 16S rRNA (and/or sample taxon).

In some embodiments of the methods and systems herein described the reads from the sequencing can be used to determine relative abundances of a target 16S rRNA.

In particular, the relative abundances of each target 16S rRNA can be determined by dividing the number of read counts associated with each target 16S rRNA or 16S rRNA of each taxon by the total read counts of the 16S rRNAs in the sample. Methods for analyzing amplicon sequences from the next generation sequencing are well known in the art. Open-source bioinformatic platforms for such analysis include MOTHUR [78] and QIIME [79] and others identifiable to a person skilled in the art. For example, QIIME2 can be used with the DADA2 package for ASV determination as will be understood by a person skilled in the art [3, 80].

In embodiments, where the 16SrRNA is a polyribonucleotide after generation of cDNA via the reverse transcription step all sequencing methodologies described for DNA sequencing are applicable and identical for RNA.

In embodiments herein described absolute abundance values of sample 16S rRNAs can be converted to the absolute abundances of target 16S rRNA based on the target 16S rRNA relative abundance values for the obtained from the sequencing.

In particular in methods and systems of the disclosure by c) multiplying the relative abundance of the target 16S rRNA in the sample times the absolute abundance of the plurality of sample 16S rRNAs in the sample, to quantify the absolute abundance of the target 16S rRNA in the sample.

Accordingly, in some embodiments, the absolute abundance of the target 16S rRNA can be obtained by multiplying the relative abundance of the target 16S rRNA in the sample from the sequencing times absolute abundance of the plurality of 16S rRNAs in the sample obtained from digital PCR or qPCR (see Example 1 and FIG. 1 panels E and F).

In some embodiments, method and a system to quantify a target 16S rRNA in a sample further comprises extracting nucleic acids from the sample to provide nucleic acids extracted from the sample for the amplifying step. As a person skilled in the art will understand, the extraction process generally comprises mechanical lysis via bead beating, capturing nucleic acids either on a silica column or magnetic beads, purifying nucleic acids by washing with ethanol, and eluting nucleic acids off of column or beads with water.

In some embodiments, mechanical lysis can be supplemented/enhanced or substituted with chemical lysis (e.g., phenol/chloroform, etc.). Nucleic acids can be also precipitated or phase-separated without the use of a column. Washing can be done with ethanol and many other solvents Elution/dissolution of washed nucleic acid can be done with water or many different stabilizing buffers (e.g., TE buffer).

Figure 6:
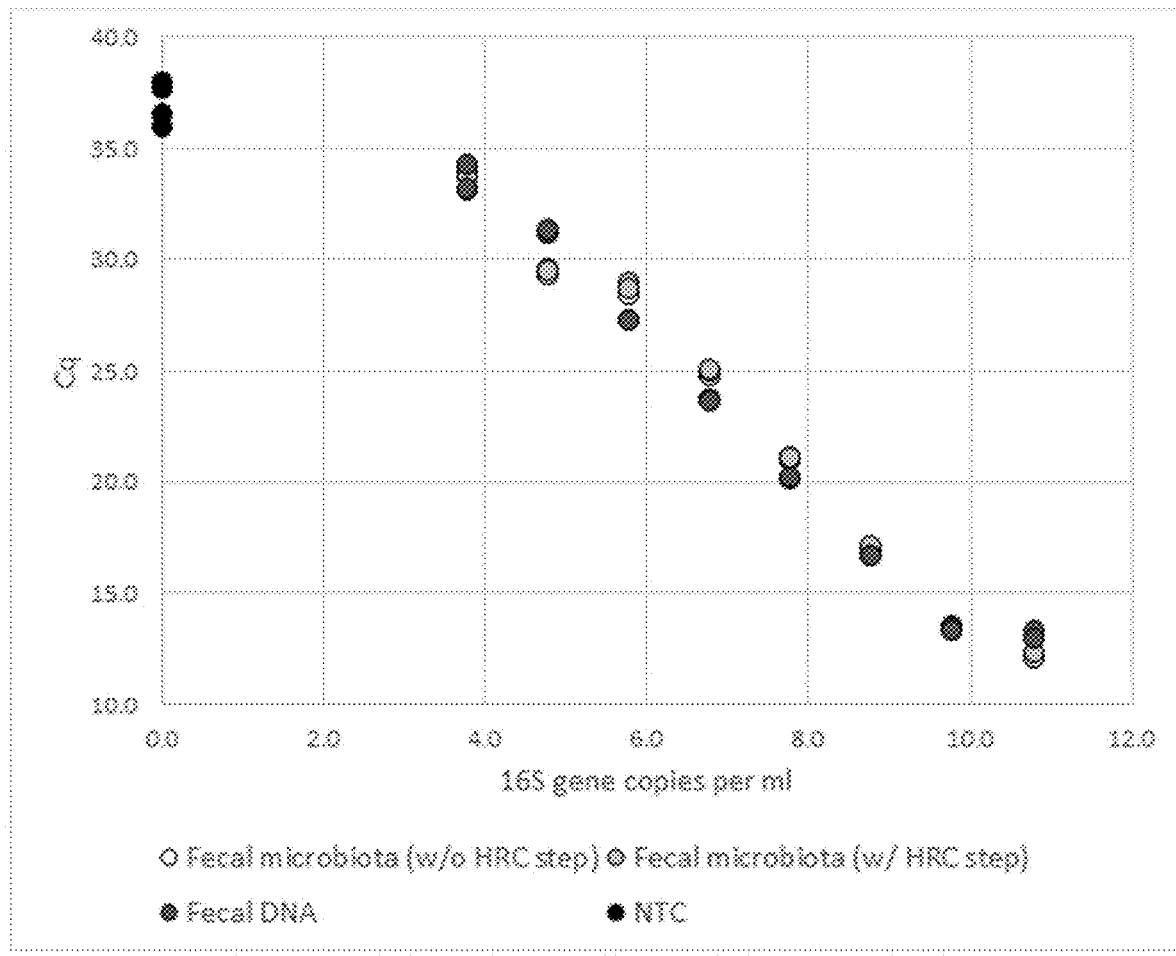
FIG. 6 shows in an embodiment quantitative DNA recovery using commercial extraction and purification kit (Zymo-BIOMICS) from samples containing fecal microbial cells in the range of concentrations evaluated with a qPCR assay. "Fecal microbiota (w/o HRC step)"-serial 10-fold dilutions of mouse fecal microbial suspension extracted with the kit with the HRC purification step omitted (N=1 extraction per dilution, N=3 PCR replicates). "Fecal microbiota (w/HRC step)"—serial 10-fold dilutions of mouse fecal microbial suspension extracted with the kit and purified from PCR inhibitors using the "HRC" columns included with the kit (N=1 extraction per dilution, N=3 PCR replicates). "Fecal DNA"—serial dilutions of the single extracted DNA sample from the undiluted mouse fecal microbial suspension extracted with the kit according to the manufacturer's protocol (N=1 sample per dilution, N=3 PCR replicates). "NTC"—no-template control (N=4 PCR replicates).

In some embodiments, the nucleic acids extracted from the sample can be a total DNA extracted and purified from samples such as feces, gastrointestinal contents or aspirates, intestinal mucosa biopsy, using commercially-available kits (see Example 1 and FIG. 1 panel ("A") validated for uniform DNA extraction from complex microbiota (e.g., Zymo-BIOMICS) and for quantitative recovery of microbial DNA from samples with microbial loads across multiple orders or magnitude as will be understood by a person skilled in the art (see for example FIG. 6).

In some embodiments, the amplifying and/or the sequencing can be performed on extracted polynucleotides from the sample. Preferably information the amount of matter the nucleic acids were extracted from is taken into account, in order to provide magnitude of the absolute quantification per sample mass/volume In particular mass or volume of the sample being extracted can be recorded and the quantified number of 16S rRNA copies can be normalized to the recorded input mass or volume as will be understood by a skilled person.

In some embodiments herein described the 16S rRNA primers can be optimized to be specific for a plurality of sample 16S rRNA based on the shared conserved sequences which can be also associated with a specific taxon grouping different prokaryotes as will be understood by a skilled person.

In those embodiments the target 16S rRNA can be the 16S rRNA of a prokaryote of a target taxon, and the plurality of sample 16S rRNA is associated to a sample taxon, the target taxon having a taxonomic rank lower than a sample taxon in a same taxonomic hierarchy.

In those embodiments, the absolute abundance of the target 16S rRNA can be converted into the absolute abundance of the target prokaryotes of the target taxon if the 16S gene copy number in that prokaryote is known.

In those embodiments, method and a system herein described can be performed to quantify in a sample a target prokaryote of a target taxon, the target taxon having a taxonomic rank lower than a sample taxon in a same taxonomic hierarchy.

In those embodiments the method comprises amplifying a 16S rRNA recognition segment comprising a 16S rRNA variable region specific for the target taxon flanked by 16S rRNA conserved regions specific for the sample taxon, by performing polymerase chain reaction on nucleic acids extracted from the sample with primers specific for the 16S rRNA conserved regions to quantitatively detect an absolute abundance of prokaryotes of the sample taxon in the sample.

In some embodiments of methods and systems to quantify in a sample a prokaryote of a target taxon within a sample taxon, the 16S rRNA recognition segment herein described can comprise a 16S rRNA variable region specific for a phyla (a target taxon) in the prokaryotic bacteria such as Bacillales, Lactobacillales, Clostridiales, Pseudomonadales, and other phyla, in which the 16S rRNA variable region is flanked by 16S rRNA conserved regions specific all the prokaryotic bacteria in the sample.

In some embodiments of methods and systems to quantify in a sample a prokaryote of a target taxon within a sample taxon, the 16S rRNA recognition segment herein described can comprise a 16S rRNA variable region specific for a species (a target taxon) which belongs to a genus (a sample taxon), in which the 16S rRNA variable region is flanked by 16S rRNA conserved regions specific for that genus.

In some embodiments of methods and systems to quantify in a sample a prokaryote of a target taxon within a sample taxon, the 16S rRNA recognition segment herein described can comprise a 16S rRNA variable region specific for a genus (a target taxon) which belongs to a family (a sample taxon), in which the 16S rRNA variable region is flanked by 16S rRNA conserved regions specific for that family.

In some embodiments of methods and systems to quantify in a sample a prokaryote of a target taxon within a sample taxon, the 16S rRNA recognition segment herein described can located in the V4 region of the 16S rRNA gene.

Accordingly, in some embodiments of methods and systems to quantify in a sample a prokaryote of a target taxon within a sample taxon the 16S rRNA primers used herein comprise a target primer sequence specific to the conserved regions in the V4 region of the microbial 16S rRNA gene.

In some embodiments of methods and systems to quantify in a sample a prokaryote of a target taxon within a sample taxon, the target primer sequence of the 16S rRNA primers used can be an optimized version of the original EMP primer set in which the EMP forward primer at its 5' end is redesigned to start at the position 519 of the V4 region of microbial 16S rRNA gene sequence (FIG. 3, panel A).

In some embodiments of methods and systems to quantify in a sample a prokaryote of a target taxon within a sample taxon the 16S rRNA primers can be optimized by redesigning the EMP forward primer so that the nonspecific annealing to the host rRNA such as the mouse and human mitochondrial 12S rRNA gene DNA will be reduced or eliminated, which is the main competing template of mammalian origin identified by amplicon sequencing of PCR products obtained with mouse germ-free tissue DNA. Such change increases the primer's specificity for low copy number microbial templates in samples with high content of mouse or human host DNA background.

Embodiments of the methods according to the disclosure, allow to perform an absolute quantification of a target 16S rRNA and/or of a target prokaryotic taxon herein described with accuracy, precision and/or resolution.

The term "accuracy" and "accurate" as used herein indicates a measure of the difference between a detected value and true value of a parameter. Accuracy of a method of quantification of a nucleic acid in accordance with the instant disclosure can be determined by detecting a difference between quantification of the nucleic acid performed with the method and the quantification obtained via primer specific digital PCR An accurate method can be one with at least 2× accuracy, with 95% confidence, for most taxa in a sample.

The term "precision" as used herein indicates a measure of the difference between detected values of a parameter among different measurements on a same reference item. Therefore precision is a measure of how similar multiple measured values (performed on the same exact sample) are to one another as will be understood by a skilled person. in order to have a precise method at least 50% coefficient of variation should be achieved for samples within the limits of quantification. The term "resolution" as used herein indicates a measure of the difference between detected values of a parameter between two reference items. Accordingly, resolution of a measurement indicates how far apart two samples measured values must be to know that they are truly different values.

In particular, embodiments of the methods according to the disclosure, allow to perform an absolute quantification of target 16S rRNA and/or of a target prokaryotic taxon herein described with an increased accuracy, precision and/or resolution with respect to know methods. This is in view of performance on a same 16S rRNA recognition segment of the detection of the absolute abundance of the a plurality of sample 16S rRNAs and/or of the sample prokaryotic taxon performed by the amplifying and detection of the relative abundance of the target 16S rRNA and/or of a target prokaryotic performed by the sequencing.

In this connection, a skilled person will understand that multiplication of the absolute abundance and relative abundance so detected allow obtaining the absolute quantification in accordance with method and systems of the disclosure which will have an increased accuracy, precision and/or resolution with respect to known methods.

In methods and systems to provide a customized rodent model herein described amplifying a 16S rRNA recognition segment comprising a 16S rRNA variable region specific for the target taxon flanked by target 16S rRNA conserved regions specific for the sample taxon, by performing amplification of nucleic acids extracted from the sample with primers comprising a primer target sequence specific for the target 16S rRNA conserved regions to quantitatively detect an absolute abundance of prokaryotes of the sample taxon in the sample and to provide an amplified 16S rRNA recognition segment, sequencing the amplified 16S rRNA recognition segment with primers comprising the primer target sequence specific for the target 16S rRNA conserved region and the 16S rRNA variable regions to detect a relative abundance of the prokaryotes of the target taxon with respect to the prokaryotes of the sample taxon in the sample; and multiplying the relative abundance of the prokaryotes of the target taxon in the sample times absolute abundance of the prokaryotes of the sample taxon in the sample to quantify the absolute abundance of the prokaryotes of the target taxon in the sample, are performed in connection with the detection of in one or more target prokaryotes and related presence, proportion of and total load in a sample obtained from the rodent.

In particular, in preferred embodiments, the absolute abundance of detected target prokaryote of detected taxa is typically normalized to the input sample weight into extraction.

In some embodiments, the method can further comprise separating (e.g. through filtering out) low abundant likely contaminant taxa before detection of presence/absence and/or analysis if desired.

In the method to provide a rodent model herein described, the detected presence of the target prokaryote in the rodent is provided by the detected relative abundance and/or absolute abundance wherein presence is detected when the relative abundance is greater than a threshold.

In some embodiments, the threshold for determination of the detected presence or absence of the target prokaryote, can be determined in view of the experimental consideration such as limit of detection of the absolute quantification method. For example, the limit of detection can be determined via Poisson statistics. Accordingly, one can define a confidence level (a common one is to use a 95% confidence interval but lower confidence can be used), and a total load can be used to determine the limit of detection. For example, if a sample has a total load of 100 copies of a prokaryote then Poisson statistics indicates that to have a 95% confidence of detection one can measure a prokaryote that has 3 copies. A taxon with 3 copies out of 100 copies has a relative abundance of 3%. Therefore, the threshold for this sample would be 3%.

In some embodiments, the threshold for determination of the detected presence or absence of the target prokaryote, can be arbitrary.

In some embodiments, the threshold for determination of the detected presence or absence of the target prokaryote, can be zero.

In the method to provide a rodent model herein described, the detected proportion is provided by the relative abundance of the target prokaryote and/or by the quantified absolute abundance in combination with the detected relative abundance providing the detected proportion of the target prokaryote in the rodent.

In the method to provide a rodent model herein described the total load of the target prokaryote is provided by detected absolute abundance of the target prokaryote of the target taxa and/or by the detected absolute abundance of prokaryotes of the sample taxon as will be understood by a skilled person.

In some embodiments, herein described the load of all taxa can be determined by the absolute abundance determined from amplification and quantification of the 16S rRNA gene segment through an absolute abundance of prokaryotes of the sample taxon or through combination of detected absolute abundances of more than one target prokaryotes.

In preferred embodiments, the target microbiome can be the microbiome of one individual (herein individual microbiome) and the target presence, target proportion and/or target total load of the one or more target prokaryotes forming part of the target microbiome profile is provided by the presence, proportion and/or target load of the one or more target prokaryotes detected in the microbiome of the individual.

In some preferred embodiments, wherein the target microbiome is an individual microbiome, the method can further comprise determining the individual microbiome profile by absolute quantification method.

In those embodiments, the method can further comprise quantifying absolute abundance of the target prokaryotes in a sample from the individual comprising the individual microbiome. In particular, the quantifying is preferably performed by the amplifying, the sequencing and the multiplying herein described on an individual sample comprising the individual microbiome to provide absolute quantification of the target prokaryotes in the individual sample, and to further provide a detected presence, detected proportion and/or detected total load of the target prokaryotes in the sample of the individual based on the relative abundance and/or absolute abundance so obtained.

The detected presence, detected proportion and/or detected total load of the target prokaryotes in in the sample of the individual can provide or be used to provide following a plurality of measurements) the individual presence, individual proportion and/or the individual total load of the target prokaryotes forming or comprised in the individual microbiome profile.

In further preferred embodiments, the target microbiome can be a target microbiome obtained by averaging the individual microbiome of a plurality of individuals (herein target averaged microbiome), and the target presence, target proportion and/or target total load of the one or more target prokaryotes forming part of the target microbiome profile, is provided by the averaged presence, averaged proportion and/or averaged target load of the one or more target prokaryotes detected in the microbiome of each individual of the plurality of individuals.

In those embodiments, the method can further comprise determining an individual microbiome in each individual of the plurality of the individuals, by quantifying absolute abundance of the target prokaryotes in a sample from each individual of the plurality of the individuals the sample comprising the target microbiome, according to methods and systems herein described. The individual presence, individual proportion and/or the individual total load of the target prokaryotes forming part of the individual microbiome profile of each individual of the plurality of individuals are then averaged to provide the averaged presence, averaged proportion and/or averaged target load of the target averaged microbiome.

In methods and systems to provide a rodent, the method further comprises comparing the detected presence, the detected proportion of and/or the detected total load of the target prokaryotes with the target presence, the target proportion and/or the target total load of the target prokaryotes in the target microbiome profile to detect differences between the detected presence, detected proportion of and/or the detected total load of the target prokaryotes with the target presence, the target proportion and/or the target total load of the target prokaryotes and the target presence, the target proportion and/or the target total load of the target prokaryotes, to obtain the rodent model having the target microbiome profile.

Accordingly, the detected microbiome profile and the target microbiome profile can be considered substantially the same of when the detected presence, proportion and/or total load of target prokaryote and corresponding target presence, proportion and/or total load of target prokaryote are substantially the same.

The term "substantially same" between two values indicates that the difference between these two values is below a threshold. The threshold can either be an arbitrary value or a value defined based on the limit of detection methods and/or factoring in the related biological and/or technical variability. The threshold can be determined in view of statistical considerations to reduce or minimize inaccurate detection such as the application of Poisson statistics as will be understood by a person skilled in the art. For example, the threshold can be defined according to a confidence interval which is typically selected to be 95% or lower. In some embodiments, the threshold can be an arbitrary value such as 0.01% relative abundance. In some embodiments, the threshold can be zero.

In particular, in embodiments herein described, since presence, proportion and total load of target prokaryotes is provided by their relative and/or absolute abundance, the comparing is performed by comparing the detected relative abundances and/or absolute abundance providing the detected presence detected proportion and/or detected total load of the target prokaryote, with corresponding target relative abundances and/or absolute abundance providing the target presence target proportion and/or target total load of the target prokaryote to establish whether they are substantially the same.

In particular, in some embodiments, the comparing between two microbiome profiles, comprises comparing a total microbe load of a detected microbiome to a total microbe load of a target microbiome and comparing a relative abundance of each taxon in the detected microbiome to a relative abundance of the same target prokaryotes in the target microbiome.

In some embodiments, the comparing between two microbiome profiles comprises comparing the detected relative abundance of each target prokaryote in the detected microbiome to a relative abundance of the same target prokaryote in the target microbiome.

In some embodiments, the comparing between two microbiome profiles comprises comparing a total load of target prokaryote in an absolute abundance of each target prokaryote in the detected microbiome to an absolute abundance of the same target prokaryote in the target microbiome.

A person skilled in the art will understand, a relative abundance of a target prokaryote (or taxon) in a sample is a ratio of an absolute abundance of the taxon in the sample to the total microbe load of the sample. In particular, to detect whether a target prokaryote is present in a microbiome or not, one can determine the presence of the target prokaryote by detecting if the relative abundance of the target prokaryote is greater than zero or an arbitrary threshold value as described herein.

In some embodiments, methods to compare two microbiome profiles can be performed using beta-diversity metrics. Common beta-diversity metrics include bray-curtis, Euclidean, jaccard, unweighted unifrac, and weighted unifrac. When using these metrics they commonly scale from 0-1 where 0 means completely different and 1 means identical. In general, one can compare two profiles by first measuring both with the quantitative sequencing method herein described, then comparing the two profiles with one of the beta-diversity metrics, then determining if they are substantially the same by seeing if the metric is greater than an arbitrary threshold.

In some embodiments, the method to provide a rodent model according to the disclosure can optionally further comprise
- modifying the rodent microbiome by introducing, enriching and/or depleting prokaryotes in the rodent microbiome to provide the rodent microbiome with the target prokaryotes with the target presence, the target proportion, and/or the target total load;
- obtaining a sample of the rodent comprising the rodent microbiome following the modifying to obtain a rodent modified sample;
- quantifying absolute abundance of the target prokaryotes in the rodent modified sample, to obtain a detected rodent modified presence, a detected rodent modified proportion and/or a detected rodent modified total load of the target prokaryotes in the rodent, each target prokaryote being of a target taxon having a taxonomic rank lower than a sample taxon in a same taxonomic hierarchy; and
- comparing the detected rodent modified presence, the detected rodent modified proportion and/or the detected rodent modified total load of the target prokaryotes with the target presence, the target proportion and/or the target total load of the target prokaryotes in the target microbiome profile.

Those embodiments are preferably performed when the detected presence, proportion and/or total load of the target prokaryote, are not substantially the same, and more preferably substantially different from corresponding target presence, proportion and/or total load of the target prokaryote of the target microbiome.

The term "substantially different" between two values indicates that the difference between these two values is statistically significant. Statistical significance indicates that the difference between these two values is statically significant over the related biological and/or technical variability. A difference has statistical significance when it is very unlikely to have occurred given the null hypothesis which is a default hypothesis that a quantity (herein difference) to be measure is zero as will be understood by a person skilled in the art. Statistical analysis of the data comprises testing the null hypothesis as a skilled person would understand and then reject the null hypothesis if the probability of generating the observed data is less than the p-value, a threshold for statistical significance chosen by a practitioner according the standards of the field. Common choices for the p-value would be 0.05, 0.025, and 0.01. Additional description of statistical analysis used in single-molecule (digital) measurements to resolve differences between two distributions can be found in published literatures such as in Kreutz et al 2011[81].

In those embodiments, and in general any time it is desired in view of experimental design, the method to provide a rodent model according to the disclosure can optionally further comprise
- repeating the modifying, the obtaining to provide a rodent modified sample and the quantifying absolute abundance of the target prokaryotes in the rodent modified sample until the detected rodent modified presence, the detected rodent modified proportion and/or the detected rodent modified total load of the target prokaryote is substantially the same of the target presence, the target proportion and/or the target total load of the target prokaryotes, to obtain the rodent model having the target microbiome profile.

Methods and systems of the present disclosure directed to modify a rodent microbiome to provide a rodent model having a target microbiome, are based on modifying the rodent microbiome, by introducing target prokaryotes or prokaryotes nutrients in the rodent microbiome and quantifying absolute abundance of target prokaryotes of the target microbiome with absolute quantification methods and systems herein described to detect presence, proportion and/or total load of one or more target prokaryotes of the target microbiome in the rodent.

In some embodiments the modifying is preceded by quantifying absolute abundance of rodent prokaryotes of the target microbiome with absolute quantification methods and system herein described to detect presence, proportion and/or total load of one or more rodent prokaryotes of the rodent microbiome in the rodent.

In embodiments of methods and systems to provide a customized rodent model herein described, the modifying can be performed with any methods directed to introduce, enrich and/or deplete prokaryotes of the rodent microbiome to provide the rodent microbiome with the target prokaryotes with the target presence, the target proportion and/or the target total load.

In some embodiments, the modifying can comprise introducing prokaryotes and in particular target prokaryote, and/or introducing prokaryotes' nutrients in the rodent microbiome to be modified.

In some embodiments, prokaryotes can be introduced into the rodent either via a single, repeated, or continuous administration.

In some embodiments, prokaryotes can be introduced into the rodent via one or more of the following routes supplementation into the diet or drinking water, application onto the body/fur followed by the rodent grooming, application onto the rodent cage parts or bedding, temporary co-housing with a pre-colonized rodent of the same species with permitted allo-coprophagy (between the animals), oral gavage or intrarectal administration.

In some embodiments, the introducing can be performed by providing a pure or mixed culture of a target prokaryote, possibly by growing the culture in laboratory and introducing the culture in the rodent microbiome.

In some embodiments, prokaryotes can be introduced into the rodent in a vegetative or spore form.

In some embodiments, prokaryotes can be obtained either from an in vitro cell culture or from an in vivo ("raw") sample (e.g., human saliva, gastrointestinal contents, stool, mucosal biopsy, gastrointestinal lavage fluid/aspirate, mucosal wash, or any other human-associated sample type).

In some embodiments, prokaryotes can be introduced into the rodent either as single species/strains or as a part of complex microbial mixture.

In some embodiments, prokaryotes can be introduced into the rodent either via a single administration, repeated, or continuous administration.

For example, in preferred embodiment, where the target microbiome is a GIT microbiome of a human individual introducing prokaryotes: can be performed by obtaining a sample from the gastrointestinal tract of a human modifying the sample to provide the same in an administrable form such as a slurry with a buffer (e.g., PBS) and then introducing the sample in the administrable form to the rodent animal through gavage or enema[82]. In particular, in this embodiment the sample is typically from the gastrointestinal organ one wants to model in the rodent.

In some embodiments, the modifying comprises direct or indirect enrichment or depletion of prokaryotes by administering the rodents with agents influencing the prokaryote growth and physiology, such as prokaryotes nutrients or other agents identifiable by a skilled person.

In some embodiments the modifying can comprise administering nutrients to the rodent through a route allowing contacting of the route with the rodent microbiome wherein the nutrients are selected to increase the presence, proportion and/or total load of target prokaryotes and/or to reduce the presence, proportion and/or total load of prokaryotes other than target prokaryotes.

In particular, in some embodiments, nutrients to be introduced in the rodent microbiome can be formulated into pellets, powder, or paste and fed to the rodent, and if water soluble, dissolved in the drinking water and given to the rodent and/or administered through oral gavage or enema.

In preferred embodiment, where the target microbiome is a GIT microbiome of a human individual administering prokaryotes nutrients to the rodent can be performed by orally and/or rectally administering nutrients to the rodent, to modify microbiome composition of the rodent GIT microbiome.

In some embodiments, the administering can comprise providing the rodent with modified diets (e.g. with adjusted ratios of macronutrients, such as proteins, carbohydrates, and fats), dietary compounds (e.g., vitamins, dietary fiber or simple carbohydrates non-digestible by the rodents), or xenobiotics (non-antimicrobial drugs or chemical compounds).

In some embodiments, the specific diets can be administered in various forms of enteral nutrition, such as: pellets, powder, pastes, solution or liquid.

In some embodiments, the administering the specific diets can be administered in various modes, such a "ad libitum": the rodent has access to the unlimited amounts of diet at all times; "timed-controlled" (e.g., timed feeding, intermittent feeding, intermittent fasting): the rodent has access to the diet regulated over time; "amount-controlled": the rodent has an access to a predefined amount of diet per unit of time; and/or "forced": the rodent is administered with a predefined amount of diet (e.g., liquid) via forced feeding (gavage) at a predefined schedule.

In some embodiments, specific diets can be administered in the form of parenteral nutrition. The diet can also be administered to the rodent as a sterile solution via a repeated or continuous injection.

In some embodiments, the modifying comprises direct or indirect enrichment or depletion of prokaryotes by administering the rodents with agents influencing the prokaryote growth and physiology.

In some of embodiments, the administering the rodents with agents influencing the prokaryote growth and physiology, can comprise setting the oxygen levels in the rodent (and consequently in the GIT) by means of exposure of the rodent to hypoxic/hypobaric or hyperoxic/hyperbaric atmosphere.

In some of embodiments, the administering the rodents with agents influencing the prokaryote growth and physiology, can comprise manipulating the prokaryote enzymatic activity via administration of non-antimicrobial drugs/compounds (e.g. inhibitors of beta-glucuronidases or bile salt hydrolases).

In some of embodiments, the administering the rodents with agents influencing the prokaryote growth and physiology, can comprise administering agent directed to obtain targeted or broad-spectrum enrichment and/or elimination of prokaryotes: For example, in some embodiments, the agent can comprise an antimicrobial agents with or without non-antimicrobial agents known to amplify or reduce the antimicrobial effects of the antimicrobial agents. In those embodiments antimicrobial agents can be delivered as individual compounds or in the form of mixtures in some embodiments the antimicrobial agent comprises one or more prokaryotic viruses (phages).

In some embodiments, the modifying comprises direct or indirect enrichment or depletion of prokaryotes by manipulating the rodent's physiology to modify the rodent microbiome composition.

For example, in preferred embodiment wherein the rodent microbioate is the GIT microbiota, the modifying can comprise one or more of
  administering to the rodent of pharmaceutical agents decreasing (e.g., loperamide) or increasing (e.g., metoclopramide, domperidone) the GIT motility;
  administering to the rodent pharmaceutical agents decreasing (e.g., omeprasol, ranitidine) or increasing (e.g., linaclotide, lubiprostone) the secretory function;
  administering to the rodent agents impacting the rodents digestive/enzymatic and absorptive function resulting in altered retention of macronutrients in the GIT (e.g. acarbose, orlistat);
  administering to the rodent exogenous bile acids or administration of bile acids sequestrants (e.g., cholestyramine, colestipol, colesevelam), to modify the bile acid levels in the rodent's gastrointestinal tract;
  administering viruses (e.g., LP-BM5 murine leukemia virus (MuLV)), drugs (e.g., cytostatic/anticancer drugs, steroid immunosuppressants, antibodies (e.g., anti-CD4 or anti-CD8 antibodies), or ionizing radiation to modify the rodent's immune status and function; and
  surgically modifying the rodent GIT, such as: bile duct ligation, pancreatic duct ligation, resection and/or anastomoses of the GIT segments, creation of blind loops.

In preferred embodiment, the microbiome modeled in the customized rodent model of the present disclosure is a GIT microbiome and modifying the rodent microbiome comprises preventing coprophagia of the rodent.

A main purpose of preventing coprophagy is to eliminate re-introduction of fecal (large intestine) microbiota into the upper gastrointestinal tract (mouth, pharynx, esophagus, stomach, small intestine) of rodents as will be understood by a skilled person.

A further the main purpose of preventing coprophagy is to compartmentalize the upper gastrointestinal microbiota from contamination with the fecal (large intestine) microbiota.

Accordingly, preventing coprophagia allows compartmentalization of the upper gastrointestinal microbiota of the rodent and therefore provides a rodent model with true GI compartment-specific microbiota with its GI compartment-specific function present in each individual sequential segment of the GIT.

Accordingly preventing coprophagia as used herein encompass any procedure directed to reduce, minimize or eliminate re-introduction of fecal microbiota into the upper gastrointestinal tract of rodents as will be understood by a skilled person, and/or to compartmentalize the upper gastrointestinal microbiota from contamination with the fecal (large-intestine) microbiota.

Preventing coprophagia can comprise using of known devices, methods and system such as tail cups devices, Elizabethan collars device, or rodent jackets can be affixed to the rodent throughout a set duration.

Preventing coprophagy can also be performed by devices methods and systems such as restraining cages (e.g., tubular or circular cage) with the dimensions not allowing the rodent to reach its hind end and access their fecal excretions (such as those described in Ref.[83-86], Wearable restraining devices such as those described in Ref. [87], Wearable jackets: such as those described in Ref. [86, 88], Wearable Elizabethan collars in combination with wire/grid/mesh floors[89], Wearable tail/anal cups: such as those described in Ref. [90] [86, 91-101].

If multiple rodents are used concurrently, all rodents are most preferably be single-housed to prevent one rodent from eating another rodent's feces in.

A preferred device for preventing coprophagia in a rodent is provided by a tail cup device of the present disclosure. An additional description is provided with reference to FIGS. 45-48 showing an exemplary a tail cup device (100) for animals such as rodents, the device comprised of a cup (110) for trapping excreted feces and a tail sleeve (120) for mounting of the cup (110) at a tail base of a rodent having a sufficiently long tail, such as mice (including deer mouse, Natal multimammate mouse, vesper mouse, long-tailed pocket mouse, little pocket mouse, canyon mouse, members of the genus harvest mouse) or rats (including cotton rat, obese sand rat, rice rat, white-tailed rat, kangaroo rat, desert woodrat), degu, voles (bank, red-backed vole, meadow vole, mountain vole, tundra vole, prairie vole, woodland/pine vole, Brandt's vole, California vole), gophers (e.g., pocket gophers), mole-rats (e.g., naked mole-rat, Damaraland mole-rat), and moles, the tail sleeve (120) being configured to be applied to the tail of the rodent.

In the illustration of FIGS. 45-48, the cup (110) is a tubular-shaped component configured to trap fecal matter and prevent the rodent from accessing it, with an exemplary length of 2-5 cm and an exemplary diameter of 1-3 cm. While FIGS. 45-48, show a circular or oval cross section by way of example, any other shape, e.g. rectangular, can be devised by the person skilled in the art. Additionally, while the drawings show a generally uniform cross-section of the cup along its length, embodiments are also possible where larger cross-section areas are provided close to one end of the cup (110) and smaller cross-section areas are provided close to the other end of the cup (110).

In the illustration of FIGS. 45-48, the distal end or surface (130) of the tubular cup (110) comprises an orifice (140) operating as a locking opening of the cup (110) to allow passing through of the tail sleeve (120) from the inside to the outside of the cup (110). The orifice (140) may be round, oval or of similar shape with an exemplary 0.5-0.7 cm diameter. In order to allow a proper locking engagement of the tail sleeve (120) when applied to the tail of the rodent and when pressure is not applied to the sides of the cup (110), the diameter (or at least one of the two axes) of the orifice (140) is smaller than the diameter of the tail sleeve (120). While the figures show a central placement of the orifice (140) on the distal surface (130), off-center placements are also possible. Off-center placement of the orifice, for example closer to the dorsal side of the cup, would allow for an increased size (centrally asymmetric on the cross-section and linearly asymmetric on a longitudinal section) cup compartment on the ventral side of the cup where fecal matter may accumulate under gravity when animals spend most of their time in their natural prone position.

In the illustration of FIGS. 45-48, distal surface (130) also includes an unlocking slit (150A-D) for opening of the cup (110) before or after use. Unlocking slit (150A-D) has a narrow diameter when compared with other dimensions of the cup (110), usually less than 1.0 mm. While the unlocking slit includes portions (150A), (150B) across the orifice (140) on the distal surface (130), intersecting the orifice (140) and spanning along a diametral extension of the distal surface (130), it also includes side portions (150C), (150D) extending along opposite side walls of the cup (110). Other embodiments can also be provided (e.g. in case the locking orifice is placed off-center) where the unlocking slit crosses the orifice along a chord extension (for circular devices) of the distal surface. The purpose of the unlocking slit is to install/unlock the tail sleeve (120) in/from the orifice (140) by increasing the gap formed by the orifice (140) through pression (e.g. with fingers, such as thumb on one side and index on the other while holding the cup) alongside portions (150C), (150D), e.g. on pressing points (150CC) and (150DD), corresponding to the ends of their respective side portions. These pressing points can have no specific shape at all and just be located at the straight end of their respective side portions, or can have a shape (e.g. circular with a 1-2 mm diameter) to address deformation stress dissipation concerns upon enlargement of the orifice. If desired, as also shown in the drawings, the pressing points (150CC), (150DD), can be placed on opposite sides of the cup (110) (e.g. 180 degrees apart in case of a cylindrical embodiment) to allow for a stronger hold of the cup (110) while applying pressure, thus providing better structural integrity and responsiveness to the pressing force. The length of side portions (150), (150D) depends on parameters such as cup length, shape, cross section profile, size and material and should be chosen to allow a sufficient increase of the orifice and unlocking slit when unlocking the cup (110) from the tail sleeve (120) upon application on the pressing points (150CC), (150DD) to allow removal of the cup (110) from the rodent and/or related emptying of the cup (110), while not compromising the mechanical integrity of the device, not increasing the risk of the locking mechanism failure, and the cup's purpose to effectively entrap fecal matter. While the figures exemplary show a flat arrangement of the distal surface (130), such surface can also be spherical, conical or differently shaped, if required.

In the illustration of FIGS. 45-48, reference will now be made to the proximal end or surface (160) of the cup (110), the proximal end having a cross sectional dimension sufficiently wide to fit around a posterior end of the rodent more proximal than the anus to ensure falling of the fecal pellets into the cup, but also preferably more distal than the urethral opening and genitals to prevent urine from accessing the cup and from discomfort or damage to the genital area of the animal. While the proximal surface (160) can be shaped as a straight/flat cut as shown in the figures, embodiments are also possible where the proximal surface is carved or shaped to better fit around the rodent's posterior end and better accommodate for the genital anatomy of the rodent, varying between genders.

In the illustration of FIGS. 45-48, a reinforcement and/or protective ring (170) is located along the proximal end (160) and is configured to come in contact with a body (skin) portion close to and/or around the genital area of the rodent, which portion the rodent may be able to reach with its mouth and/or teeth. The reinforcement and/or protective ring (170) is made from an inert (in order not to corrode or leak any chemical compounds) material hard enough to prevent the animal from damaging it by chewing (which would necessitate cup replacement), such as metal (e.g. medical grade stainless steel, titanium and/or suitable metal alloys), ceramic, glass, tough plastic (such as PTFE/Teflon or Kevlar) and/or combinations of the same. Usage of soft materials would likely result in deterioration of the proximal end of the cup due to rodents chewing on it, thus resulting in the proximal edge of the cup becoming jagged or sharp and potentially leading to severe skin damage when the rodent moves around and the cup's edge rubs against the skin.

In the illustration of FIGS. 45-48, the reinforcement and/or protective ring (170) comprises a proximal flange, an internal conical (funnel) or round section and a distal cylindrical part.

The internal section of the reinforcement and/or protective ring (170) fitting around the animal body may have a conical shape to allow for a more effective fecal entrapment inside the cup in cases where the rodent is allowed to freely mode around, frequently resulting in the tail cup and the animal's tail tilting to the sides away from the longitudinal body axis. On the other hand, a round shape of the internal section has the advantage of serving as a joint surface when the animal moves around and the cup rubs against the animal's body/skin. Overall the design of the proximal end of the cup should allow for some degree of freedom/motion (not only axial rotation) relatively to the animal's posterior end, at least partially matching the degree of freedom/motion characteristic for the tail base, in order to minimize or eliminate any inhibition of animal's physical activity/motion.

On the other hand, in the illustration of FIGS. 45-48, the outside diameter of the flange of the reinforcement and/or protective ring (170) is comparable to or larger than the cross-sectional extension (e.g. diameter) of the cup to ensure that the edge of the proximal surface (end) (160) of the cup (110) is not exposed to chewing. To further prevent animals from chewing on the proximal edge of the cup, the reinforcement and/or protective ring (170) may be installed to allow for some gap (e.g. 2-3 mm) between the flared edge of the ring and the edge of the proximal surface (edge) of the cup. If desired, the flared edge of the ring (170) may also be configured to wrap around the edge of the cup. Given that the material of the ring is harder than the material of the cup this provides better protection from the animal's teeth.

Additionally, placement of the reinforcement and/or protective ring (170) at the proximal end of the cup (110) may be adjustable in order to control the snug fit of the cup (110) against the animal's posterior end after installation of the tail sleeve (120).

In its current exemplary implementation, reinforcement and/or protective ring (170) is made by a stainless steel grommet with reduced flange edge diameter and length, performed with a cutter on a lathe to improve size and reduce weight, thus resulting in a straight proximal edge of the cup (110). The person skilled in the art will understand that if the proximal edge is carved more anatomically than the reinforcement and/or protective ring, it will have to be shaped accordingly.

As shown in the illustration of FIGS. 45-48, reinforcement and/or protective ring (170) is preferably coupled (e.g. attached) to cup (110) using a coupling ring (175) (made of e.g. latex or plastic tubing). Presence of the coupling ring (175) also allows adjusting the depth and placement of the reinforcement and/or protective ring (170) inside the cup (110), thus tuning the fit or snugness of the cup (110). Embodiments are also possible where coupling ring (175) is not needed when the cup itself is made such that the reinforcement and/or protective ring (170) can be attached to the cup directly. It should be noted that a simple soldering and/or gluing of the ring would not be preferred, as it would not allow an adjustable arrangement.

Cup (110) may be made from a clear (e.g. transparent, such as polypropylene) material to allow for an easier observation of the device degree of filling with animal excretions. However, an opaque (e.g. non-transparent) material may be preferred in cases where the excretions need to be protected from light, e.g. for further analysis. The material can be, for example, a mesh material with an exemplary mesh size of up to 1 mm.

Cup (110) may also comprise venting perforations or boreholes (180) to allow for the fecal excretions to accelerate the desiccation of trapped fecal excretions and prevent moisture entrapment. Advantageously, drying fecal pellets distribute uniformly within the cup when the animal moves around. If fecal excretions are not allowed to dry, they could potentially stick to the inside surface of the cup and build up around the anus, likely imposing some resistance for further defecation, an important animal welfare consideration. The venting perforations (180) can be of different shape, size, number, and distribution considering that: a) their size should be small enough and their shape (e.g. round) should be designed to prevent the fecal pellets from falling out, especially after drying and/or shrinking. The number of the perforations should be sufficiently large and their distribution should be sufficiently uniform to allow faster fecal matter desiccation.

Reference will now be made to the tail sleeve (120) of the illustration of to FIGS. 45-48, which is configured to hold the cup snugly against the posterior end of the animal while at the same time maximizing distributing the opposing force over a larger surface area of the tail skin to reduce the damaging effects of such shear force on the skin and other potential negative effects such as tail strangulation. At the same time the sleeve (if made from a stiffer material) should only cover a fraction of the tail (e.g. less than a half of the total length) to allow for some degree of freedom/motion of the distal part of the tail and not to inhibit the animal's movement.

Figure 47:
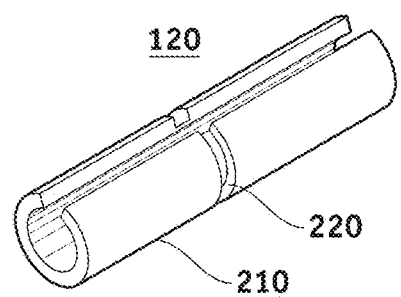
Figure 46:
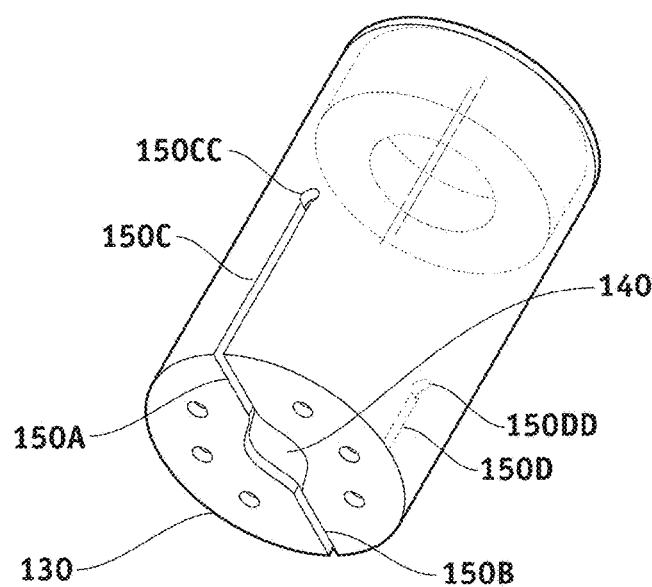
Figure 48:
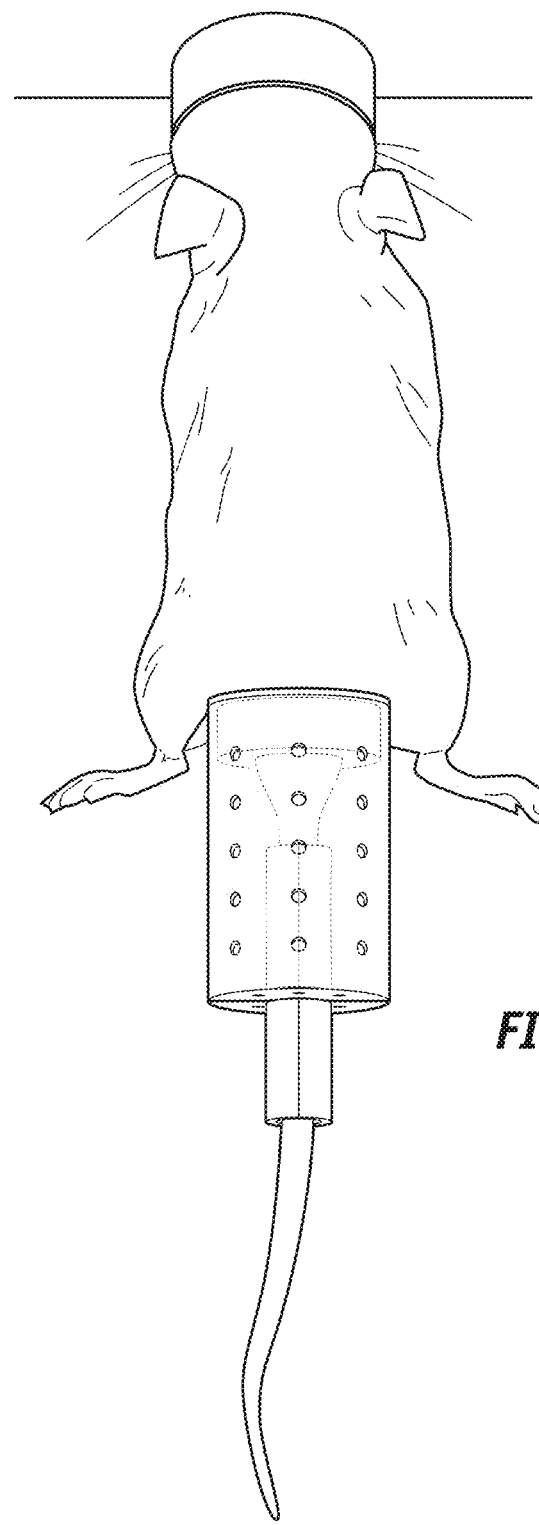

As shown in FIG. 47, tail sleeve (120) comprises a longitudinally split or open tubular component (210) (having an exemplary length of 2-5 cm, an exemplary inside diameter of ⅛"-comparable to or slightly smaller than the tail outside diameter at the tail base- and an exemplary outside diameter of ¼") and an intermediate locking groove (220) on its outside surface, the latter configured to allow locking of the tail sleeve (120) through the orifice (140) of the cup (110). In particular, the outside diameter of the groove (220) can be smaller than the outside diameter of the tubular component (210) and also slightly smaller than the orifice or locking opening (140) of the cup (110). In order to accommodate for variable tail diameters among animals along the tail length, a longitudinal strip of the wall of the sleeve (e.g. 1-2 mm wide) can be optionally removed to prevent uneven tail compression and to facilitate uniform application of adhesive force as later explained.

In the illustration of FIGS. 45-48, the tubular component can be cylindrically or conically shaped (to accommodate the slightly conical tail shape) and may have various degrees of softness or stiffness, but it should be sufficiently soft to conform to the tail shape upon installation without applying excessive pressure and sufficiently stiff not to overstretch or deform in order to withstand the shear force from the snugly fit cup (110) when locked onto it. As with the cup (110), also the sleeve (120) may be opaque or clear for easier tail health monitoring. In accordance with an embodiment of the disclosure, the tubular component is made from a material devoid of components that upon leaking from the material can be toxic to the animal (e.g., plasticizer-free tubing) as it can come in contact, in some cases, with the tail skin through a layer of curable adhesive or adhesive tape, both of which can potentially aid the extraction of toxic components from the material of the tubular component. Potential alternatives can include surface patterning, e.g. nano- or micro-perforations to provide gecko-like adhesion. More generally, any other means that allows the inside surface of the sleeve to be sufficiently adhesive and/or sticky can be devised by the person skilled in the art.

In the illustration of FIGS. 45-48, while the figures show a tail sleeve made of a tubular component cut along its entire length, other realizations are possible where the cut partially occurs only for a set length starting at the proximal end, in order to accommodate the portion of the tail immediately following the tail base, i.e. the part of the tail that is largest in diameter.

The intermediate locking groove (220) extends perpendicularly to the longitudinal direction of the sleeve (120) along the outside surface of the sleeve (120). As already noted above, the groove allows locking of the tail sleeve (120) through the orifice (140) of the cup (110). If desired, multiple such locking grooves (220) can be provided in a parallel arrangement along the longitudinal extension of the tail sleeve (120) in order to provide for adjustable locking degrees and extensions of the sleeve (120) on the cup (110) thus allowing an easy adjustment of the snugness of the cup fit once the sleeve is installed on the animal's tail.

Alternatively to the one or more locking grooves (220), the tail sleeve can have a tubular component with a variable outside diameter along its length, where the proximal (relatively to the desired locking point/level) portion of the tail sleeve has an outside diameter slightly smaller than the locking opening of the cup, and the distal (relatively to the desired locking point/level) portion of the sleeve has an outside diameter larger than the locking opening of the cup.

Additionally, if desired, the distal edge of the tail sleeve may be tapered along its inside diameter to prevent distal tail skin (at the distal edge of the tail sleeve) from bulging up due to the applied shear force (directed distally) from snug cup fitting and strangulating the distal end of the tail.

If necessary and/or required, the tail sleeve (120) can be secured to the tail skin surface of the animal by an adhesive, such as curable adhesive, curable glue, double-sided adhesive tape, the alternative adhesion means described above. Use of double-sided adhesive tape (opaque or clear for easier tail health monitoring) appears to be preferable as it allows instantaneous tail sleeve installation. In particular, the tape can be pre-applied to the inside surface of the tail sleeve which can be then be almost instantaneously placed onto the animal's tail while the animal is restrained for a very short amount of time (about 5-15 seconds). Additionally, with the double-sided adhesive the tail sleeve and the tail cup can be easily removed and placed back at desired times without causing any skin surface damage.

Advantageously, when mounted, the tail cup (110) may freely rotate along its longitudinal axis in order to ensure that the edges of the locking opening (140) do not press too hard on the tail sleeve (120), do not strangulate the animal's tail and at the same time are not under an excessive shear force or stress due to the snugness of the cup fit.

Accordingly, in preferred embodiments of methods and systems of the present disclosure, preventing coprophagia in the rodent animal is performed with a tail cup in accordance with any one of the following enumerated embodiments.

Embodiment 1. A tail cup device (100) for animals with tails is described, the tail cup device (100) comprising:
 a tubular-shaped cup (110) for trapping excreted feces of an animal, the tubular-shaped cup having a proximal surface (160) configured to fit around a posterior end of the animal and a distal surface (130), and
 a tail sleeve (120) configured to cover a portion of a tail of the animal and engageable with the tubular-shaped cup through the distal surface of the tubular-shaped cup, for mounting of the tubular-shaped cup (110) at a tail base of the animal,
 the distal surface of the tubular-shaped cup comprising
 an orifice (140) operating as a locking opening of the tubular-shaped cup to allow passing through of the tail sleeve (120) from an inside to an outside of the tubular-shaped cup, the orifice having a diameter smaller than a diameter of the tail sleeve in order to allow a locking engagement of the tail sleeve with the tubular-shaped cup when applied to the tail of the animal, and
 an unlocking slit (150A-D) for a pressure-based opening of the tubular-shaped cup to engage and disengage the tail sleeve to and from the tubular-shaped cup.

Embodiment 2. The device of Embodiment 1, wherein the unlocking slit includes portions (150A), (150B) across the orifice on the distal surface, intersecting the orifice and spanning along a diametral extension of the distal surface of the tubular-shaped cup.

Embodiment 3. The device of Embodiment 2, wherein the unlocking slit further includes side portions (150C), (150D) extending along opposite side walls of the tubular-shaped cup.

Embodiment 4. The device of Embodiment 3, wherein the side portions comprise pressing points (150CC, 150DD) at respective ends of said side portions, for the pressure-based opening of the tubular-shaped cup.

Embodiment 5. The device of Embodiment 4, wherein the pressing points have a circular shape.

Embodiment 6. The device of Embodiment 4, wherein the pressing points are located at opposite sides of the tubular-shaped cup.

Embodiment 7. The device of Embodiment 1, wherein the orifice has a round or oval shape.

Embodiment 8. The device of Embodiment 1, wherein the orifice is centrally placed on the distal surface of the tubular-shaped.

Embodiment 9. The device of Embodiment 1, wherein the orifice is placed off-center on the distal surface of the tubular-shaped cup.

Embodiment 10. The device of Embodiment 9, wherein the unlocking slit crosses the orifice along a chord extension of the distal surface of the tubular-shaped cup.

Embodiment 11. The device of Embodiment 1, wherein a cross section of the tubular-shaped cup is selected from a group consisting of circular cross section, oval cross section and rectangular cross section.

Embodiment 12. The device of Embodiment 1, wherein the tubular-shaped cup has a uniform cross section along a length of the tubular-shaped cup.

Embodiment 13. The device of Embodiment 1, wherein the tubular-shaped cup has a non-uniform cross section along a length of the tubular-shaped cup, a larger cross section being provided close to one end of the tubular-shaped cup and a smaller cross section being provided close to another end of the tubular-shaped cup.

Embodiment 14. The device of Embodiment 1, wherein the tubular-shaped cup has a length of 2-5 cm and a diameter of 1-3 cm.

Embodiment 15. The device of Embodiment 1, further comprising a reinforcement and/or protective ring (170) located along the proximal surface of the tubular-shaped cup.

Embodiment 16. The device of Embodiment 15, wherein the reinforcement and/or protective ring comprises an anatomically carved proximal flange, an internal conical or round section and a distal cylindrical part.

Embodiment 17. The device of Embodiment 15, wherein placement of the reinforcement and/or protective ring along the proximal surface of the tubular-shaped cup is adjustable.

Embodiment 18. The device of Embodiment 15, wherein the reinforcement and/or protective ring is controllably coupled to the tubular-shaped cup through a coupling ring (175).

Embodiment 19. The device of Embodiment 1, wherein the tubular-shaped cup is made of a transparent material.

Embodiment 20. The device of Embodiment 1, wherein the tubular-shaped cup comprises venting perforations (180).

Embodiment 21. The device of Embodiment 1, wherein the tail sleeve is rotatable along its longitudinal axis.

Embodiment 22. The device of Embodiment 1, wherein the tail sleeve comprises a first portion inside the tubular-shaped cup and a second portion outside the tubular-shaped cup.

Embodiment 23. The device of Embodiment 22, wherein the tail sleeve further comprises at least one locking groove between the first portion and the second portion, the at least one locking groove configured to allow locking of the tail sleeve through the orifice of the tubular-shaped cup.

Embodiment 24. The device of Embodiment 23, wherein the at least one locking groove are a plurality of locking grooves to allow an adjustable engagement of the tail sleeve with the tubular-shaped cup.

Embodiment 25. The device of Embodiment 22, wherein the second portion of the tail sleeve comprises a distal edge tapered along an inside diameter of the second portion.

Embodiment 26. The device of Embodiment 22, wherein the tail sleeve comprises a tubular component with a variable outside diameter along its length, wherein a proximal portion of the tail sleeve has an outside diameter smaller than a diameter of the orifice, and a distal portion of the tail sleeve has an outside diameter larger than the diameter of the orifice.

Additional embodiments, of the preferred tail cup device according to the disclosure are identifiable by a skilled person.

In several embodiments, the modifying as described herein is typically followed by the quantifying absolute abundance of the target prokaryotes on a rodent modified sample from the modified rodent to provide a detected rodent modified presence, rodent modified proportion and/or rodent modified total load of target prokaryotes to be compared with the target presence, proportion and/or total load of target prokaryotes, according to the method of the disclosure.

In some embodiments, the quantifying absolute abundance of the target prokaryotes, can further be performed on a rodent sample before the modifying to obtain a detected rodent presence, rodent proportion and/or rodent total load of target prokaryotes to be compared with the target presence, proportion and/or total load of target prokaryotes and/or to possibly be used as a reference presence, proportion and/or reference total load of target prokaryotes to guide selection of type and amount of compounds agents and/or prokaryotes to be introduced enriched and/or depleted in the modifying according to the methods and systems of the disclosure.

Described herein are also customized rodent models having a target gut microbiome profile formed by a target presence, a target proportion and/or a target total load of a target prokaryote of a target taxon, obtained by methods herein described to provide a customized rodent model.

In preferred embodiments, customized rodent models are customized to comprise target individual microbiome or target averaged microbiome as will be understood by a skilled person. In some of those embodiments, the target individual or average microbiome mimicks the microbiome of the individual or plurality of the individuals under selected physiological and/or pathological conditions, such as any one of the conditions herein described and additional conditions identifiable by a skilled person.

In some embodiments, customized rodents according to the present disclosure comprise rodent model modified before or after quantifying absolute abundance of target prokaryotes according to method of the present disclosure.

In some exemplary embodiments, customized rodent model of the present disclosure comprise germ-free rodents (understood as a rodents devoid of microbial flora, including eukaryotes, prokaryotes, and viruses) [www.taconic.com/prepare-your-model/microbiome-solutions-and-germ-free-mice/germ-free-mice/]; Rodents pre-treated with antimicrobial agents (e.g., antibiotics and antibiotic cocktails) to deplete or even eliminate their native microbiota; Gnotobiotic rodents which are rodents carrying a defined microbiome, consisting of multiple or individual prokaryotes modified through microbiome and/or genomic modification procedures, before or after quantifying absolute abundance of target prokaryotes according to method of the present disclosure.

In some exemplary embodiments, customized rodent model of the present disclosure further comprise humanised rodents—(chimeric) rodents carrying human donor (or specific-patient)-derived cells in their tissues/organs obtained via transplantation of human peripheral blood, bone marrow, lymphoid, liver [102, 103] [www.herabiolabs.com/humanized-liver-mice/, www.yecuris.com/frg-ko-mice/], spleen cells and cells from other tissues, including donor/patient skin.

Patient-Derived Xenograft (PDX) model can be developed by means of inoculating the rodent with patient-derived tumor cells/tissues for pre-clinical oncology research, including the discovery of tumor presence biomarkers, biomarkers of the tumor susceptibility to drugs, and screening of anticancer therapeutics [www.criver.com/products-services/discovery-services/pharmacology-studies/oncology-immuno-oncology-studies/oncology-study-models/patient-derived-xenografts-pdx-models?region=3601], modified through microbiome and/or genomic modification procedures, before or after quantifying absolute abundance of target prokaryotes according to method of the present disclosure.

In some preferred embodiments, customized rodent model obtained by the method of the disclosure comprises a customized microbiome of the GIT of an individual, preferably a human being.

In some preferred embodiments, customized rodent model obtained by the method of the disclosure comprises a customized rodent model wherein the rodent model has been modified by preventing coprophagia to provide the rodent with a "human-like pattern" of microbial colonization such as the rodents obtained by preventing coprophagia with preferred tail cup of the disclosure.

Customized rodent with a "human-like pattern" of microbial colonization model have a microbiota compartmentalization in the GIT mimicking the microbial distribution of human beings. Such customized model is rodent model with compartmentalized gastrointestinal microbiome" which can be used in testing which affect the microbial function and phenotype (including metabolism and response to xenobiotics).

Customized rodent models can be used in methods and systems to perform testing of effects of a compound on physiological and/or pathological conditions associated with a target microbiome, having a target microbiome profile, the method comprises providing a customized rodent model according to the present disclosure having the target microbiome profile, and performing the testing on the customized rodent model.

Exemplary testing comprises testing of impact of diets, test of molecules, and in particular, diet, testing of sleep cycle and additional testing identifiable by a skilled person.

Methods and systems herein described can also be used to identify target prokaryotes whose presence of one or more physiological or pathological condition. In some of those embodiments, if certain prokaryotes in the microbiome of an individual having a disease have a relative or an absolute abundance that is substantially different from that of the prokaryotes in a healthy individual, these prokaryotes can be identified as signature prokaryotes of that disease. For example, reference is made the procedure reported in Examples 20-26 wherein detection of prokaryotes performed in patients with and without Crohn's disease to find that Enterobacteriaceae, Pasteurellaceae, Fusobacteriaceae, and Neisseriaceae are enriched in Crohn's disease patients and can be used as target prokaryotes whose presence, proportion and total load can be a signature of a target microbiome associated with Crohn's disease.

All methods of the present disclosure can be performed with a corresponding system comprising a rodent, a customized rodent, and/or primers specific for the 16S rRNA conserved regions specific for the plurality of sample 16S rRNAs, reagents to perform polymerase chain reaction, and/or reagents to perform amplicon sequencing, and/or testing of a compound or performing other testings, for simultaneous combined or sequential use to detect an absolute abundance of the target 16S rRNAs in the sample according to the method herein described.

In some embodiments, the system comprises primers specific for 16S rRNA conserved regions specific for the sample taxon, reagents to perform polymerase chain reaction, and reagents to perform amplicon sequencing for simultaneous combined or sequential use to detect an absolute abundance of the target taxon in the sample according to the method herein described.

The primers used herein comprise the target primer sequence specific for 16S rRNA conserved regions alone or in combination with adapter, barcode, tag, linker, pad and/or frameshifting sequence described herein.

In some embodiments, the systems further comprise buffers, enzymes having polymerase activity, enzymes having polymerase activity and lacking 5'-3' exonuclease activity or both 5' to 3' and 3' to 5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of alterations in target nucleic acid sequences corresponding to the specific 16S rRNA described herein.

In some embodiments, the systems of the disclosure to be used in connection with methods herein described, the reagents comprise DNA extraction, RNA extraction kit and amplification mix. The system can also include reagents required for preparing the sample, such as one or more of buffers e.g. lysis, stabilization, binding, elution buffers for sample preparation, enzyme for removal of DNA e.g. DNase I, and solid phase extraction material for sample preparation, reagents required for quantitative detection such as intercalating dye, reverse-transcription enzyme, polymerase enzyme, nuclease enzyme (e.g. restriction enzymes; CRISPR-associated protein-9 nuclease; CRISPR-associated nucleases as described herein) and reaction buffer. Sample preparation materials and reagents may include reagents for preparation of RNA and DNA from samples, including commercially available reagents for example from Zymo Research, Qiagen or other sample preparations identifiable by a skilled person. The system can also include means for performing DNA or RNA quantification such as one or more of: container to define reaction volume, droplet generator for digital quantification, chip for digital detection, chip or device for multiplexed nucleic acid quantification or semi-quantification, and optionally equipment for temperature control and detection, including optical detection, fluorescent detection, electrochemical detection.

In some embodiments where the system can be used to perform a single step quantification (BC-qPCR) according to the disclosure the system can comprise a "standard" (anchor)—sample containing either single or complex microbial 16S DNA of known concentration (copy number), such as the one (ZymoBIOMICS Microbial Community DNA Standard, Zymo Research, Irvine, CA, USA) described in [104] and additional standards identifiable by a skilled person. In some exemplary embodiments, the standard can consists of 10 microorganisms, 8 of which are bacteria (*Listeria monocytogenes*, 12%; *Pseudomonas aeruginosa*, 12%; *Bacillus subtilis*, 12%; *Escherichia coli*, 12%; *Salmonella enterica*, 12%; *Lactobacillus fermentum*, 12%; *Enterococcus faecalis*, 12%; *Staphylococcus aureus*, 12%) with 16S genes. These taxa are mixed together at defined concentrations so that the expected outcome of extraction and sequencing is known. The absolute concentration of 16S copies in such standard can be either estimated from the total DNA concentration (e.g., 10 ng/microL) and the approximate genome size of the members of this defined community. Alternatively, the absolute concentration of 16S copies in such standard can be directly measures by digital PCR as will be understood by a skilled person. Additional exemplary standard comprise samples of nucleic acids extracted from other complex mixtures of microorganisms (e.g., stool) or from pure microbial cultures (e.g., E. coli) can be quantified using digital PCR and serve as absolute quantification standards for qPCR and BC-qPCR assays described herein.

The systems herein describe can also include other necessary reagents to perform any of the NGS techniques disclosed herein. For example, the systems can further comprise one or more of: adapter sequences, barcode sequences, reaction tubes, ligases, ligase buffers, wash buffers and/or reagents, hybridization buffers and/or reagents, labeling buffers and/or reagents, and detection means. The buffers and/or reagents are usually optimized for the particular amplification/detection technique for which the system is intended. Protocols for using these buffers and reagents for performing different steps of the procedure can also be included in the system.

In some embodiments, the system can comprise a device combining all aspects required for the absolute quantification of the 16S rRNA herein described.

The systems herein disclosed can be provided in the form of kits of parts. In kit of parts for performing any one of the methods herein described, the primers and the reagents for the related detection and quantification can be included in the kit. The kit can further contain oligonucleotide (oligo) sequences of barcodes, adapters, linkers, pad and/or frameshifting bases compatible for next-generation sequencing platforms.

In a kit of parts, the primers and the reagents for the related detection, quantification and sequencing, and additional reagents identifiable by a skilled person are comprised in the kit independently possibly included in a composition together with suitable vehicle carrier or auxiliary agents. For example, one or more probes can be included in one or more compositions together with reagents for detection also in one or more suitable compositions.

Additional components can include labeled polynucleotides, labeled primer such as barcoded with an adapter sequence for next generation sequencing, labels, microfluidic chip, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods of the disclosure and related compositions, and systems herein described are further illustrated in the following examples, which are provided by way of illustration and are not intended to be limiting.

In particular, the following examples illustrate exemplary methods and protocols for performing methods directed to detect absolute quantification of nucleic acids and particularly 16S rRNA nucleic acids.

In particular, Examples 1-4 below describe general protocols and experimental procedures conducted for quantitative microbiome profiling in luminal and tissue samples with broad coverage and dynamic range using simultaneous real-time PCR quantification of 16S rRNA gene DNA copy and amplicon barcoding for multiplexed next-generation sequencing from the same analyzed sample performed in a combined workflow.

Examples 5-10 below describe general protocols and experimental procedures conducted for detecting absolute abundance measurements of mucosal and luminal microbial communities using the methods and systems herein described. In particular, these examples describe a quantitative framework to measure absolute abundances of individual bacterial taxa by combining the digital PCR with the high-throughput 16S rRNA gene amplicon sequencing. In a murine ketogenic-diet study, microbial loads in lumenal and mucosal samples along the GI tract were compared. Quantitative measurements of absolute abundances reveal decreases in total microbial loads on the ketogenic diet and enable one to determine the differential effects of diet on each taxon in stool and small-intestine mucosa samples. This quantitative microbial analysis framework, suitable for diverse GI locations, enables mapping microbial biogeography of the mammalian GI tract and more accurate analyses of changes in microbial taxa in microbiome studies.

Examples 11-17 below describe general protocols and experimental procedures conducted for self-reinoculation with fecal flora in mice using the methods and systems herein described. In particular, these examples used quantitative 16S rRNA gene amplicon sequencing, quantitative microbial functional gene content inference, and metabolomic analyses of bile acids to evaluate the effects of self-reinoculation on microbial loads, composition, and function in the murine upper gastrointestinal tract.

Examples 18-19; below describe a tail-cup device of the disclosure providing a preferred mean to prevent coprophagia in rodents according to the present disclosure and general description of a Rodent Model with a "humanized" digestive tract obtained by the combined used of absolute quantification method and the tail cup device of the disclosure.

Examples 20-25 below describe an exemplary detection of absolute microbial loads in the human duodenum and their potential relationship with factors related to health and disease in 250 individuals from the REIMAGINE study [105], as well in the oral microbiome in a subset of 21 individuals from this cohort. The total load of the e human duodenal and oral microbiome can be used to provide customized rodent model with target duodenal and oral microbiome that can be used in testing of the makeup of the human duodenal microbiome, improve the understanding of the underlying community structure of SIBO, and determine how microbial load and composition correlate with upper GI symptoms.

A person skilled in the art will appreciate the applicability and the necessary modifications to adapt the features described in detail in the present section, to additional methods and related compositions and systems according to embodiments of the present disclosure.

Example 1: General Protocols for Performing 16S rRNA Gene DNA Quantification and Amplicon Barcoding Workflow for Quantitative Microbiome Profiling An exemplary quantitative microbiome profiling was performed according to the general protocol schematically illustrated in FIG. 1.

Samples were collected from mice and the related DNA extracted (FIG. 1 Panel A).

In particular, all animal handling and procedures were performed in accordance with the California Institute of Technology (Caltech) Institutional Animal Care and Use Committee (IACUC).

Fecal samples were collected from SPF C57BL6/J mice of 2-12 months of age originally purchased from Jackson Laboratory (Sacramento, CA, USA) and housed in the Caltech animal facility for up to 10 months. Germ free mouse intestinal mucosal samples from germ free C57BL6/J mice of 2-5 months of age obtained from the germ-free mouse colony maintained in the Caltech animal facility were collected and processed as in [1, 2].

The total DNA was extracted from fecal and mucosal samples preserved in DNA/RNA Shield (DRS) solution (R1100-250, Zymo Research, Irvine, CA, USA) or fresh using ZymoBIOMICS DNA Miniprep Kit (D4300, Zymo Research) as described in [1, 2].

Quantitative (linear) recovery of DNA in the range of 16S rRNA gene copies of $10^3$-10 per ml was verified in using a series of 10-fold dilutions of specific-pathogen-free (SPF) mouse fecal microbial suspension in saline.

The absolute abundance of the microorganisms of the microbiome was performed by BC-qPCR reactions prepared in replicates for more accurate quantification and uniform amplicon barcoding. (FIG. 1 Panel B).

In particular, Quantitative PCR (qPCR) for 16S rRNA gene DNA copy enumeration was performed according to the method described in detail in [1, 2] which are incorporated by reference in their entirety.

Briefly, each qPCR reaction was set up with 1.5 µL of DNA sample, qPCR master mix (SsoFast EvaGreen Supermix, #172-5200, Bio-Rad Laboratories, Hercules, CA, USA), forward (UN00F2, 5'-CAGCMGCCGCGGTAA-3') (SEQ ID NO: 25) and reverse (UN00R0, 5'-GGAC-TACHVGGGTWTCTAAT-3' [16, 18]) primers (SEQ ID NO: 26) (Integrated DNA Technologies, San Diego, CA, USA) at the final concentration of 500 nM each, and ultrapure water (Invitrogen UltraPure DNase/RNase-Free Distilled Water 10977-015, Thermo Fisher Scientific) to the final volume of 15 µL.

The thermocycling program was set up as follows: initial denaturation at 95° C. for 5 min. followed by 40 cycles each consisting of denaturation at 95° C. for 15 sec., annealing at 53° C. for 10 sec., and extension at 68° C. for 45 sec.

Assay was performed on a real-time PCR instrument (CFX96 Real-Time PCR Detection System, Bio-Rad Laboratories). The raw fluorescence data were processed and the Cq values were extracted with the accompanying software (Bio-Rad CFX Manager 3.1, #1845000, Bio-Rad Laboratories).

Amplification and barcoding were performed under real-time fluorescence measurements on a real-time PCR instrument (FIG. 1 Panel C).

In particular, 16S rRNA gene DNA amplicon barcoding for next generation sequencing (NGS) was performed with a method is described in detail in [1, 2]. Briefly, all DNA samples were amplified and barcoded in triplicates for. Each reaction was set up with 3 µL of DNA sample combined with the PCR master mix (5PRIME HotMasterMix, #2200400, Quantabio, Beverly, MA, USA), ×1 DNA intercalating dye (EvaGreen, #31000, Biotium, Fremont, CA, USA), bar-coded forward (UN00F2_BC, 5'-AATGATACGGCGAC-CACCGAGATCTACACTATGGTAAT-TGTCAGCMGCCGCGGTAA-3') (SEQ ID NO: 75) and reverse (UN00R0, 5'-CAAGCAGAAGACGGCAT-ACGAGAT[NNNNNNNNNNNN] AGTCAGTCAGCCGGACTA CHVGGGTWTCTAAT-3' [16, 18], (SEQ ID NO: 76) where [NNNNNNNNNNNN]— 12-nucleotide barcode sequences from [16]) primers (Integrated DNA Technologies) at the final concentration of 500 nM each, and ultrapure water (Thermo Fisher Scientific) to the final volume of 30 µL.

The thermocycling program was set up similarly to the EMP protocol [16, 18] as follows: initial denaturation at 94° C. for 3 min. followed by variable for each sample number of cycles each consisting of denaturation at 94° C. for 45 sec., annealing at 54° C. for 60 sec., extension at 72° C. for 105 sec.; followed by a final extension step at 72° C. for 10 min.

Assay was performed on a real-time instrument (CFX96 Real-Time PCR Detection System, Bio-Rad Laboratories). Samples were amplified for a variable number of cycles and each sample was removed from the heating block during the last 15 sec. of the current cycle extension step upon reaching the mid-exponential amplification phase. Each removed sample was maintained on a secondary heating block at 72° C. until all samples from the amplification series were amplified and returned to the primary heating block for the final extension step. The raw fluorescence data were processed and the fluorescence profiles over time were extracted with the accompanying software (Bio-Rad CFX Manager 3.1, #1845000, Bio-Rad Laboratories).

Endpoint amplification products from whole PCR reactions were diluted 4-fold in ultrapure water (Invitrogen) and analyzed by gel electrophoresis using 1% (E-Gel EX, #G401001, Thermo Fisher Scientific) and 2% agarose gels (E-Gel, #G501802, Thermo Fisher Scientific).

Barcoding PCR real-time data processing was performed by processing raw fluorescence data using Python tools (Python tools used are described and referenced in [1, 2]).

Amplification profiles (fluorescence) for each PCR sample replicate were baseline-corrected by subtracting the minimal fluorescence value from the first 15 amplification cycles for each amplification replicate. Baseline-corrected amplification profiles from all replicates were averaged for each sample. Baseline-corrected and averaged amplification profiles were then used to find the Cq values (cycle numbers) at which they reached the fluorescence threshold (chosen as 2000 RFU) by interpolation.

The quantitative PCR data (Cq values) so obtained were recorded (FIG. 1 Panel D).

Cq values were converted to absolute fold-difference values in total 16S rRNA gene copy load using the equations 3.1 and 3.2 (FIG. 2) and assuming the BC-qPCR efficiency of 95.0%. The absolute fold difference values were then used to convert the taxa 16S rRNA gene relative abundance data obtained from the next generation sequencing to the taxa 16s rRNA gene absolute fold-difference data.

Barcoded samples were then quantified, pooled, purified, and sequenced on an NGS instrument (FIG. 1 Panel E).

In particular, Digital PCR (dPCR) for Illumina library quantification: was performed as described in detail in [1, 2]. Briefly, a home-brew digital PCR library quantification assay was set up using the Illumina P5 and P7 adapter sequences as priming sites [16, 18-21].

Each reaction was set up with 2.0 µL of the diluted amplicon sample ligated with the Illumina adapters, ddPCR master mix (QX200 ddPCR EvaGreen Supermix, #186-4033, Bio-Rad Laboratories), forward (ILM00F(P5), 5'-AATGATACGGCGACCACCGA-3' (SEQ ID NO: 77),) and reverse (ILM00R(P7), 5'-CAAGCAGAAGACGGCAT-ACGA-3' (SEQ ID NO: 78)) primers (Integrated DNA Technologies) at the final concentration of 125 nM each, and ultrapure water (Invitrogen) to the final volume of 20 µL.

Thermocycling program was set up as follows: initial denaturation at 95° C. for 5 min, followed by 40 cycles each consisting of denaturation at 95° C. for 30 sec. and annealing-extension at 60° C. for 90 sec.; followed by the dye stabilization step consisting of 5 min incubation at 4° C., 5 min incubation at 90° C., and incubation at 12° C. for at least 5 min.

This step was performed to sequence multiple samples barcoded with different unique barcodes to quantify the concentration of each barcoded sample 9 (e.g. using PCR assay or with other alternative non-PCR methods). and to quantify the amplicon concentration in the library not to overload/underload the sequencing flow cell as will be understood by a skilled person.

Hardware setup and droplet analysis were performed as in "Digital PCR (dPCR) for absolute 16S rRNA gene DNA copy enumeration".

Library pooling, purification, and quality control were performed according to the method described in detail in [1, 2]. Briefly, triplicates of each barcoded amplicon sample were combined. After each sample was quantified with the home-brew ddPCR library quantification assay and KAPA SYBR FAST Universal qPCR Library Quantification Kit (#KK4824, Kapa Biosystems, Wilmington, MA, USA), all samples were pooled in equimolar quantities. The library was purified with Agencourt AMPure XP beads (#A63880, Beckman Coulter, Brea, CA, USA) and eluted with ultrapure water (Invitrogen). Quality control on the pooled library was performed using light absorbance at 260/280 nm (NanoDrop 2000c, Thermo Fisher Scientific) and the mean amplicon size of ~400 nucleotides was confirmed with a High Sensitivity D1000 ScreenTape System (#5067-5584 and #5067-5585, Agilent Technologies, Santa Clara, CA, USA) on a 2200 TapeStation instrument (Agilent Technologies) supported with the Agilent 2200 TapeStation Software A02.01. (Agilent Technologies).

Next generation sequencing was then performed according to the: s method described in detail in [1, 2]. Briefly, paired-end 300-base reads were generated on a MiSeq instrument (Illumina, San Diego, CA, USA) using a MiSeq Reagent Kit v3 (#MS-102-3003, Illumina) with a PhiX control spiked in at 15%.

The following sequencing primers were used:

```
MiSeq read 1:
Seq_UN00F2_Read_1,
                                  (SEQ ID NO: 79)
5'-TATGGTAATTGTCAGCMGCCGCGGTAA-3'.

MiSeq read 2:
Seq_UN00F2_Read_1,
                                  (SEQ ID NO: 80)
5'-AGTCAGTCAGCCGGACTACHVGGGTWTCTAAT-3'

MiSeq index read:
Seq_UN00R0_RC_Index,
                                  (SEQ ID NO: 81)
5'-ATTAGAWACCCBDGTAGTCCGGCTGACTGACT-3'
```

NGS sequencing results provide data on relative abundances of microbial taxa (FIG. 1 Panel F).

With respect to the sequencing read processing and sequencing data processing, all processed and analyzed NGS data were obtained from [1, 2].

NGS data and sequencing data analysis scripts were obtained and are available from [1, 2].

Microbiota relative abundance profiles were converted to microbiota absolute or absolute fold-difference abundance profiles using the absolute or absolute fold-difference data on 16S rRNA gene DNA loads in the corresponding samples measured in the step schematically illustrated in (FIG. 1 Panel D). (FIG. 1 Panel G).

The validated the accuracy of the quantitative 16S rRNA gene amplicon profiling obtained using the single-step BC-qPCR approach was confirmed comparing the related result with the quantitative 16S rRNA gene amplicon profiling results obtained using real-time and digital PCR 100421 In particular, the Digital PCR (dPCR) for absolute 16S rRNA gene DNA copy enumeration was performed according to the: method is described in detail in [1, 2]. Briefly, each reaction was set up with 2.0 µL of DNA sample, ddPCR master mix (QX200 ddPCR EvaGreen Supermix, #1864033, Bio-Rad Laboratories), forward (UN00F2, 5'-CAGCMGCCGCGGTAA-3') (SEQ ID NO: 25) and reverse (UN00R0, 5'-GGACTACHVGGGTWTCTAAT-3' [16, 18]) primers (SEQ ID NO: 26) (Integrated DNA Technologies) at the final concentration of 500 nM each, and ultrapure water (Thermo Fisher Scientific) to the final volume of 20 µL.

In some experiments, additional DNA intercalating dye (EvaGreen, #31000, Biotium, Fremont, CA, USA) was added to the reactions up to ×1 final concentration (to achieve up to ×2 overall concentration).

Each reaction volume was converted to droplets using a QX200 droplet generator (#1864002, Bio-Rad Laboratories).

Droplet samples were amplified on a thermocycler (C1000 Touch, #1841100, Bio-Rad Laboratories) according to the program: initial denaturation at 95° C. for 5 min. followed by 40 cycles each consisting of denaturation at 95° C. for 30 sec., annealing at 52° C. for 30 sec., and extension at 68° C. for 60 sec.; followed by the dye stabilization step consisting of 5 min incubation at 4° C., 5 min incubation at 90° C., and incubation at 12° C. for at least 5 min.

Droplet samples were quantified on a QX200 Droplet Digital PCR System (#1864001, Bio-Rad Laboratories) The raw data were analyzed and the target molecule concentrations were extracted using the accompanying software (QuantaSoft Software, #1864011, Bio-Rad Laboratories).

Example 2: Design of Primers Specific for Low Copy Number Microbial Templates in Samples with High Content of Mouse or Human Host DNA Background Primers from the Earth Microbiome Project (EMP) 16S rRNA gene amplicon profiling protocol [16, 18] were optimized for use in the absolute quantification according to the method described in Example 1 to improve broad-coverage 16S rRNA gene DNA quantification via real-time and digital PCR in the presence of high host DNA background.

Accordingly the EMP 16S rRNA gene amplicon profiling protocol [16,18] is well-known for having broad microbial coverage and has been widely adopted in the field of basic and clinical microbiome research.

It was hypothesized that by redesigning the EMP forward primer (designated by Applicant as UN00F0) at its 5' end to start at position 519 (UN00F2) of the V4 region of microbial 16S rRNA gene sequence (FIG. 3, panel A) its nonspecific annealing to the mouse and human mitochondrial 12S rRNA gene DNA—the main competing template of mammalian origin identified by amplicon sequencing of PCR products obtained with mouse germ-free tissue DNA—would be either reduced or eliminated. Such change would increase the primer's specificity for low copy number microbial templates in samples with high content of mouse or human host DNA background.

The effectiveness of these design considerations was confirmed by performing qPCR reactions in complex mouse microbiota DNA samples analyzed as-obtained or spiked with GF mouse small-intestine mucosal DNA at 100 ng/μL. The ~200-bp mitochondrial 12S rRNA gene amplicons were absent in the PCR reactions containing high amounts of mouse DNA and using the modified forward primer UN00F2 (FIG. 3, panel B).

The efficiency of the quantitative PCR reactions set up with the modified forward primer UN00F2 was similar (and high) with and without the presence of 100 ng/μL of mouse DNA in the template sample (FIG. 3, panel C) demonstrating the robust assay performance.

The qPCR experiments also suggested that the PCR reactions with high host DNA background are intercalating dye-limited: the increase in total fluorescence (Δ-RFU) in each reaction at the end of amplification was lower in samples containing 100 ng/μL of background mouse DNA whereas the total fluorescence levels were similar between samples with and without the background mouse DNA.

By combining the use of the new forward primer UN00F2 with the supplementation of commercial reaction mix with additional amounts of intercalating EvaGreen dye improved the digital PCR performance by increasing the separation between negative and positive droplets in the droplet digital PCR (ddPCR) reactions used for quantifying 16S rRNA gene DNA copies in samples with high host DNA background (100 ng/μL) (FIG. 3, panel D). This assay was used to establish or confirm the exact 16S rRNA gene DNA copy numbers in the standard samples, which were further utilized to build the standard curves in the qPCR assays.

Additionally, the modification of the primer set UN00F2+UN00R0 broadened its taxonomical coverage of the microbial diversity (86.0% Archaea, 87.0% Bacteria) compared with the original EMP primer set UN00F0+UN00R0 (52.0% Archaea, 87.0% Bacteria) based on the SILVA 16S rRNA gene sequence reference database [9, 55, 56].

The above results therefore demonstrate that optimized primers improve broad-coverage 16S rRNA gene DNA quantification via real-time and digital PCR in the presence of high host DNA background.

Example 3: Features of Primers Specific for Low Copy Number Microbial 16S rRNA Gene in the Amplification and Amplicon Barcoding of the 16S rRNA Recognition Segment in High Host DNA Background The modified barcoded primers used in the optimized workflow according to Example 2 were tested for the features enabling simultaneous 16S rRNA gene DNA copy quantification and amplicon barcoding in samples with high host DNA background Two essential and contrasting design principles in the BC-qPCR reaction optimization guide this work:

1. The amplification and barcoding reaction utilizing degenerate 16S rRNA gene primers (whether using the original EMP primers or improved EMP primers) should be conducted at the lowest possible annealing temperature (within the range of annealing temperatures for the specific primer variants within the degenerate primer mixture) to maximize the uniformity of amplification of diverse 16S rRNA gene DNA sequences and eliminate the amplification biases.

2. The amplification and barcoding reaction should be conducted at the highest possible annealing temperature to minimize the primer dimer formation and non-specific host mitochondrial DNA amplification both of which would be competing with specific microbial 16S rRNA gene DNA template for reaction resources (dNTPs, primers, polymerase, intercalating dye). Such competing reactions would inevitably have pronounced effects on the samples containing very low levels of specific microbial template and requiring high numbers of amplification cycles.

Compared with the improved primer set (UN00F2+UN00R0), the original EMP primer set (UN00F0+UN00R0) requires a higher annealing temperature to reduce primer dimer formation and amplification of mouse mitochondrial (MT) DNA.

Long "overhangs" (carrying the linker and Illumina adapter sequences) at the 5' end of the forward primer and non-complimentary to the specific 16S rRNA gene DNA template were not sufficient to prevent the EMP primer set from amplifying the mouse MT DNA. At 53.9° C. both primer dimers and MT DNA amplification persisted in the reactions using the EMP primers, which suggested that this primer set would require even higher annealing temperatures (>53.9° C.) to eliminate the amplification artifacts.

This in turn will likely introduce amplification biases across a range of specific 16S rRNA gene DNA templates. Using the improved primer set eliminated both artifacts in the reactions conducted at 53.9° C. (FIG. 4, panel A), while some primer dimer formation was still present in the reactions conducted at 52° C. Thus, the temperature of 54° C. was selected as optimal for the BC-qPCR reaction.

The BC-qPCR assay demonstrated good performance in samples with and without high host DNA background (GF mouse DNA spiked in at 100 ng/μL of the DNA template sample) and containing the specific complex microbiota template (SPF mouse fecal DNA) across multiple orders of concentration (FIG. 4, panel B). Regardless of the presence of high host DNA background, the reaction efficiency was ~95.0% and the assay was able to resolve 1.25 to 1.67-fold differences in total 16S rRNA gene copy loads among samples within the range of $10^4$-83-1010-95 copies/mL.

The data also confirmed the BC-qPCR assay can provide accurate quantification data for the amount of 16S rRNA gene DNA copy loads in the analyzed samples. The Cq values obtained based on the real-time fluorescence measurements during the BC-qPCR reaction were in a good agreement with the absolute 16S rRNA gene DNA copy values (FIG. 4, panel C) estimated in the same samples (samples and data were from [1, 2]) using the previously optimized qPCR assay (FIG. 3, panel C).

This example demonstrates features of specific barcoded primers od Example 2 enable simultaneous 16S rRNA gene DNA copy quantification and amplicon barcoding in samples with high host DNA background according to methods of the disclosure according to Example 1.

Example 4: Absolute Quantification of Microbiota and Microbiota Quantitative Microbiota Profiling by Detection of Absolute Fold Differences Absolute quantification of microbiota according to the method of Example 1 was performed by detecting absolute fold differences between different samples.

In particular, a single-step BC-qPCR approach was used to calculate the absolute fold differences (as in FIG. 2, panel C) for a number of taxa (FIG. 5) among samples from four experimental groups of mice described in [1, 2] using the NGS data from [1, 2] and the absolute fold difference data for the total 16S rRNA gene abundance in the corresponding samples from BC-qPCR assay (see Example 1).

The absolute fold difference data for each individual taxon that are yielded by the single step approach can be used for comparisons among groups subjected to different experimental conditions using non-parametric rank tests (e.g., Kruskal-Wallis).

Figure 5:
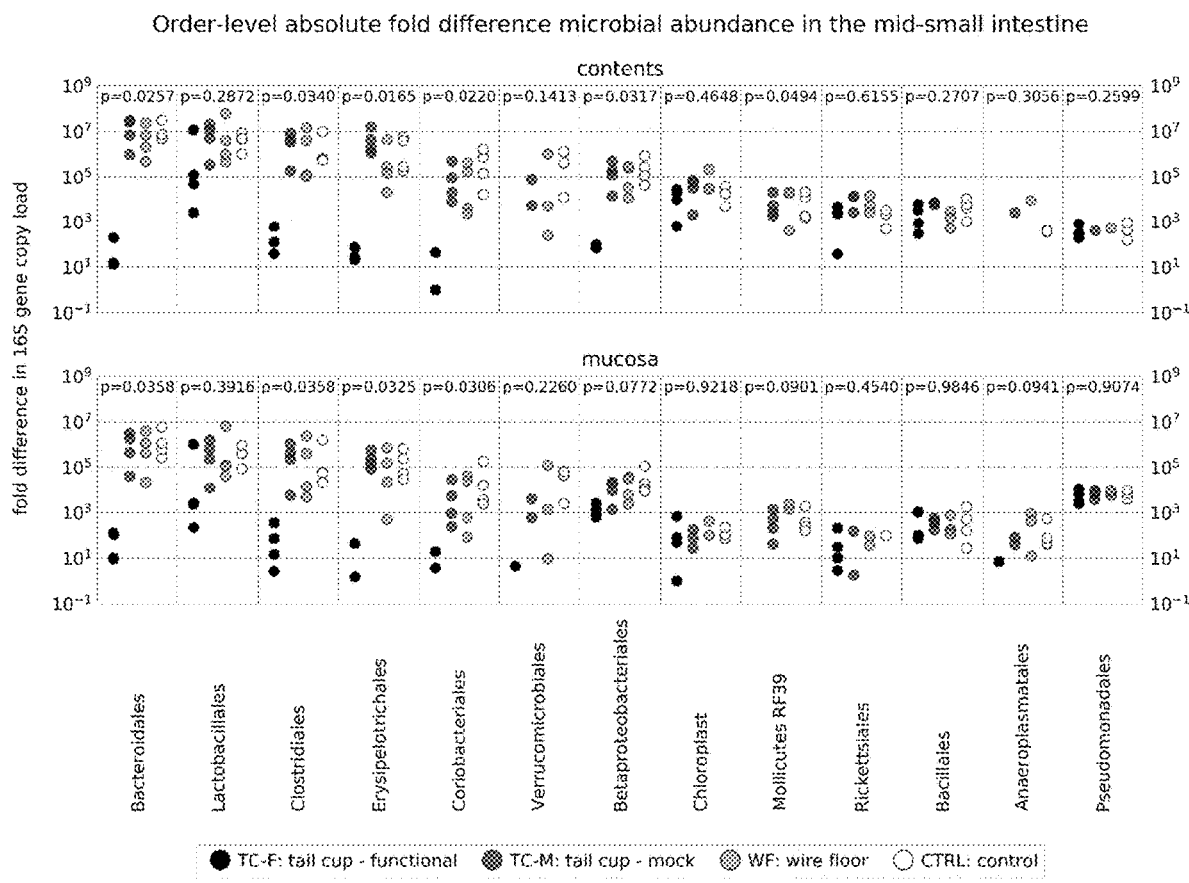
FIG. 5 shows the absolute fold differences in the abundances of taxa (16S rRNA gene copies) in mouse mid-small intestine mucosal and lumenal samples yielded by the BC-qPCR assay according to an exemplary method of the disclosure. NGS data obtained from [1, 2] were used to calculate the fold difference values among samples using the single-step fold-difference approach (this disclosure) for each individual taxon (order level). Multiple comparisons between the four experimental groups of mice were performed for each taxon using the Kruskal-Wallis test.

Such comparisons revealed that in both the mid-small-intestine contents and mucosal samples multiple taxa (e.g., Bacteroidales, Clostridiales, Erysipelotrichales, Coriobacteriales) were differentially abundant (on the absolute scale) among the four experimental groups of mice (FIG. 5). These results are in agreement with data previously obtained using a two-step approach (utilizing absolute 16S rRNA gene copy quantification with a dedicated qPCR assay performed separately from the barcoding PCR reaction) described in [1, 2].

Example 5: General Protocols for Detecting Absolute Abundance Measurements of Mucosal and Luminal Microbial Communities Absolute quantification of mucosal and luminal microbial community was detected according to an exemplary method herein described wherein absolute abundance of sample 16S rRNAs was performed by digital PCR.

In particular, samples were collected from mice and the related DNA extracted All animal husbandry and experiments were approved by the Caltech Institutional Animal Care and Use Committee (IACUC protocols #1646 and #1769). Male and female germ free (GF) C57BL/6J mice were bred in the Animal Research Facility at Caltech, and 4-week-old female specific-pathogen-free (SPF) Swiss Webster mice were obtained from Taconic Farms (Germantown, NY, USA). Mice were housed on heat-treated hardwood chip bedding (Aspen Chip Bedding, Northeastern Products, Warrensburg, NY, USA) and provided with tissue paper (Kleenex, Kimberly-Clark, Irving, TX, USA) nesting material. Experimental animals were fed standard chow (Lab Diet 5010), 6:1 ketogenic diet (Envigo TD.07797, Indianapolis, IN, USA; FIG. 24) or vitamin- and mineral-matched control diet (Envigo TD.150300; FIG. 24). Diet design and experimental setup were taken from a recently published study [8].

To minimize cage effects, mice were housed two per cage with three cages per diet group. Custom feeders, tin containers approximately 2.5 inches tall with a 1-inch diameter hole in the top, were used for the ketogenic diet as it is a paste at room temperature. Autoclaved water was provided ad libitum and cages were subjected to a daily 13:11 light:dark cycle throughout the study. Mice were euthanized via CO2 inhalation as approved by the Caltech IACUC in accordance with the American Veterinary Medical Association Guidelines on Euthanasia [106].

The mock microbial community (Zymobiomics Microbial Community Standard; D6300) was obtained from Zymo Research (Irvine, CA, USA). This community is stored in DNA/RNA Shield, which could interfere with extraction efficiency at high concentrations. It was found that a 100 μL input of a 10× dilution of the microbial community stock is the maximum input that the Qiagen DNeasy Powersoil Pro Kit can handle without recovery losses. Negative control blanks were also used which included 100 μL of nuclease free water instead of mock community.

Fresh stool samples were collected immediately after defecation from individual mice and all collection occurred at approximately the same time of day. For intestinal samples, the GIT was excised from the stomach to the anus. Contents from each region of the intestine (stomach, upper half of SI, lower half of SI, cecum, and colon) were collected by longitudinally opening each segment with a scalpel and removing the content with forceps. Terminal colonic pellets are referred to as stool. After contents were removed the intestinal tissue was washed by vigorously shaking in cold sterile saline. The washed tissue was placed in a sterile petri dish and then dabbed dry with a Kimwipe (VWR, Brisbane, CA, USA) before scraping the surface of the tissue with a sterile glass slide. These scrapings were collected as the mucosa samples. All samples were stored at −80° C. after cleaning and before extraction of DNA.

DNA was extracted from all samples by following the Qiagen DNeasy Powersoil Pro Kit protocol (Qiagen; Valencia, CA, USA). Bead-beating was performed with a Mini-BeadBeater (BioSpec, Bartlesville, OK, USA) for 4 min. To ensure extraction columns were not overloaded, we used ~10 mg of scrapings and ~50 mg of contents. Half of the lysed volume was loaded onto the column and elution volume was 100 μL. Nanodrop (NanoDrop 2000, ThermoFisher Scientific) measurements were performed with 2 μL of extracted DNA to ensure concentrations were not close to the extraction column maximum binding capacity (20 μg).

The absolute abundance of the microorganism from the sample was detected by digital PCR. The concentration of total 16S rRNA gene copies per sample was measured using the Bio-Rad QX200 droplet dPCR system (Bio-Rad Laboratories, Hercules, CA, USA). The concentration of the components in the dPCR mix used in this study were as follows: 1× EvaGreen Droplet Generation Mix (Bio-Rad), 500 nM forward primer, and 500 nM reverse primer.

Universal primers to calculate the total 16S rRNA gene concentrations were a modification to the standard 515F-806R primers [18] to reduce host mitochondrial rRNA gene amplification in mucosal and small-intestine samples (FIG. 27) [1, 2, 17]. Thermocycling for universal primers was performed as follows: 95° C. for 5 min, 40 cycles of 95° C. for 30 s, 52° C. for 30 s, and 68° C. for 30 s, with a dye stabilization step of 4° C. for 5 min and 90° C. for 5 min. All ramp rates were 2° C. per second.

The concentration of taxon-specific gene copies per sample was measured using a similar dPCR protocol, except with different annealing temperatures. Annealing temperatures during thermocycling for taxa-specific primers can be found in FIG. 27. The concentration of the components in the qPCR mix used in this study were as follows: 1× SsoFast EvaGreen Supermix (BioRad), 500 nM forward primer, and 500 nM reverse primer. Thermocycling was performed as follows: 95° C. for 3 min, 40 cycles of 95° C. for 15 s, 52° C. for 30 s, and 68° C. for 30 s. All dPCR measurements are single replicates.

Concentrations of 16S rRNA gene per microliter of extraction were corrected for elution volume and losses during extraction before normalizing to the input sample mass (Equation 1).

$$\text{Microbial Load} = \text{dPCR concentration} * \text{elution volume} * \frac{\text{dead volume}}{\text{extraction volume}} * \frac{1}{\text{sample mass}} \quad (1)$$

Absolute abundance of individual taxa was calculated either by dPCR with taxa-specific primers or multiplying the total microbial load from Equation 1 by the relative abundance from 16S rRNA gene amplicon sequencing.

16S rRNA Gene Amplicon Sequencing was then performed. In particular, extracted DNA was amplified and sequenced using barcoded universal primers and protocol modified to reduce amplification of host DNA [1, 2, 17]. The variable 4 (V4) region of the 16S rRNA gene was amplified in triplicate with the following PCR reaction components: 1×5Prime Hotstart mastermix, 1× Evagreen, 500 nM forward and reverse primers. Input template concentration varied. Amplification was monitored in a CFX96 RT-PCR machine (Bio-Rad) and samples were removed once fluorescence measurements reached ~10,000 RFU (late exponential phase).

Cycling conditions were as follows: 94° C. for 3 min, up to 40 cycles of 94° C. for 45 s, 54° C. for 60 s, and 72° C. for 90 s. Triplicate reactions that amplified were pooled together and quantified with Kapa library quantification kit (Kapa Biosystems, KK4824, Wilmington, MA, USA) before equimolar sample mixing. Libraries were concentrated and cleaned using AMPureXP beads (Beckman Coulter, Brea, CA, USA). The final library was quantified using a High Sensitivity D1000 Tapestation Chip. Sequencing was performed by Fulgent Genetics (Temple City, CA, USA) using the Illumina MiSeq platform and 2×300 bp reagent kit for paired-end sequencing.

16S rRNA Gene Amplicon Data Processing was then performed: Processing of all sequencing data was performed using QIIME 2 2019.1 [80]. Raw sequence data were demultiplexed and quality filtered using the q2-demux plugin followed by denoising with DADA2 [3]. Chimeric read count estimates were estimated using DADA2. Beta-diversity metrics (Aitchison distance [107], Bray-Curtis Dissimilarity) were estimated using the q2-diversity plugin after samples were rarefied to the maximum number of sequences in each of the relevant samples. Rarefaction was used to force zeros in the dataset to have the same probability (across samples) of arising from the taxon being at an abundance below the limit of detection.

Although rarefaction may lower the statistical power of a dataset [108] it helps decrease biases caused by different sequencing depths across samples [109]. Taxonomy was assigned to amplicon sequence variants (ASVs) using the q2-feature-classifier [110] classify-sklearn naïve Bayes taxonomy classifier against the Silva [56] 132 99% OTUs references from the 515F/806R region. All datasets were collapsed to the genus level before downstream analyses. All downstream analyses were performed in IPython primarily through use of the Pandas, Numpy and Scikit-learn libraries.

Data Transforms and Dimensionality Reduction was then performed: For dimensionality reduction techniques requiring a log transform, a pseudo-count of 1 read was added to all taxa. With relative abundance data, the centered log-ratio transform was used (Equation 2) to handle compositional effects whereas a log transform was applied to the absolute-abundance data to handle heteroscedasticity in the data.

$$x_{clr} = \left[ \log\left(\frac{x_1}{G(x)}\right), \log\left(\frac{x_2}{G(X)}\right), \ldots, \log\left(\frac{x_D}{G(X)}\right) \right] \text{ where } G(X) = \sqrt[D]{x_1 * x_2 * \ldots * x_D} \quad (2)$$

For comparative purposes, principal co-ordinates analysis (PCoA) was also performed using the Bray-Curtis dissimilarity metric. Principal component analysis (PCA) and PCoA were performed using scikit-learn decomposition methods. Feature loadings for each principal component were calculated by multiplying each eigenvector by the square root of its corresponding eigenvalue. All data were visualized using matplotlib and seaborn.

Taxa Limits of Quantification were then determined: Poisson confidence intervals were calculated by bootstrapping Poisson samples for rate parameters across the percentage abundance range (0-1) corresponding to either the input DNA copies or number of reads. to $10^4$ bootstrap replicates were taken with a Poisson sample size of 4 to match the number of replicates we sequenced. The % CV for each replicate was calculated and the middle $95^{th}$ percentile was shown as the confidence interval.

Thresholds for percentage abundance were calculated by first fitting a negative exponential curve $y=ax^{-b}$ to the plot of % CV versus percentage abundance using SciPy. Then the percentage abundance at a given % CV threshold was determined. This process was repeated after subsampling the data at decreasing read depths to find the relationship between percent abundance accuracy limits at sequencing depth.

When measuring the absolute abundance of a given taxon in a sample, many factors contribute to the uncertainty of the measurement. Two primary factors, extraction efficiency and average amplification efficiency for each taxon, should be equivalent for each taxon across samples processed under identical conditions and thus neither should impact the discovery of differential taxa. However, other factors contributing to the uncertainty of an absolute-abundance measurement vary among samples and can impact the discovery of differential taxa.

At least six independent errors can contribute to the overall uncertainty of a taxon's absolute abundance: (i) extraction error (ii) the Poisson sampling error of dPCR, (iii) the Poisson sampling error of sample input into an amplification reaction to make a sequencing library, (iv) the uncertainty in the amplification rates among sequences, (v) the Poisson sampling error of the sequencing machine, and (vi) the uncertainty in taxonomic assignment resulting from different software programs that differ in how they convert raw sequencing reads to a table of read counts per taxon.

To measure the total error in our absolute-abundance measurements, we compared the true absolute load value of four "representative" taxa (taxa that are common gut flora from different taxonomic ranks) as measured by taxa-specific dPCR, with the value obtained from our method of quantitative sequencing with dPCR anchoring (FIG. 9, panel b) and then analyzed the relative error in these measurements, defined as the log 2 of the observed taxon load over the true taxon load. Applicant constructed a quantile-quantile (Q-Q) plot (FIG. 21) of the mean-centered log 2 relative errors and found that the errors appeared normally distributed.

This was confirmed by running a Shapiro-Wilk test (P-value=0.272) on the mean-centered log 2 relative errors, which uses a null hypothesis that the dataset comes from a normal distribution. The standard deviation of the mean-centered $\log_2$ relative errors was 0.48, which results in a 95% confidence interval of ~(−1,1), indicating a 2× precision on each individual measurement. However, as seen with *Akkermansia*(g) (FIG. 9, panel b), accuracy offsets may exist for specific taxa. It is important to note that all samples used in this analysis had relative abundances above the 50% CV threshold defined in FIG. 8, panel d and thus no conclusions were made about the precision of absolute abundance measurements for taxa with relative abundances below the 50% CV threshold.

When measuring the absolute abundance of a taxon from a defined population (e.g., healthy adults, mice on a ketogenic diet) it is unlikely this abundance comes from a well-defined statistical distribution. Given this inherent limitation, non-parametric statistical tests were used, which do not rely on distributional assumptions, for our differential abundance analyses.

Figure 12:
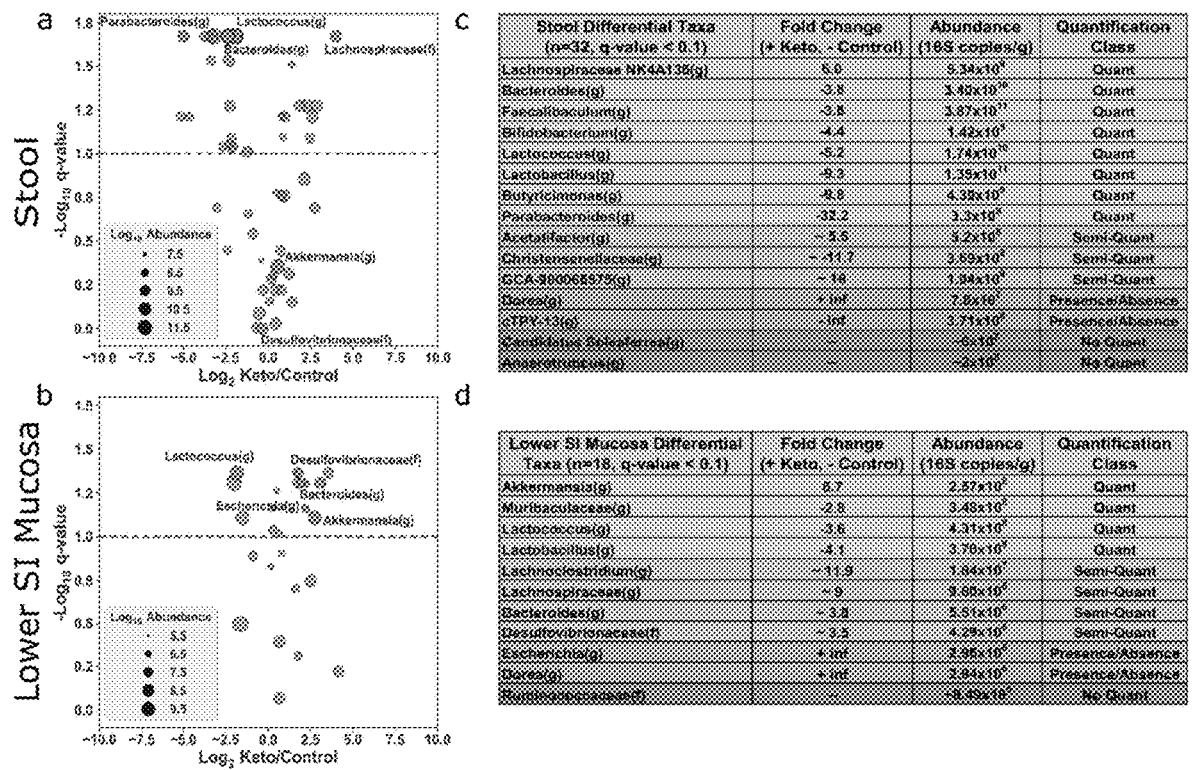
FIG. 12 demonstrates that incorporating quantification limits enhances differential taxon analysis as shown in stool and SI mucosa. A quantitative framework that explicitly incorporates limits of quantification separates differential microbial taxa into four classes, and for each GI location identifies a distinct set of differential taxa, including taxa with opposite patterns in stool and SI mucosa. (a-b) Microbial taxa in stool (FIG. 12 Panel a) or lower small-intestine (FIG. 12 Panel b) mucosa in mice on ketogenic (N=6) and control (N=6) diets. The fold change on the x-axis is the $Log_2$ ratio of the average absolute loads of taxon loads in each diet. Negative values indicate lower loads in ketogenic diet compared to control diet. The q-value for a taxon indicates the significance of the difference in absolute abundances between the two diets and were obtained by Kruskal-Wallis with a Benjamini-Hochberg correction for multiple hypothesis testing. The $Log_{10}$ absolute abundance of each taxon is indicated by circle size. The dashed line is shown at a q-value representing a 10% false-discovery rate. (c-d) A subset of taxa from stool (FIG. 12 Panel c) and lower SI mucosa (FIG. 12 Panel d) that were significantly different between diets (q-values <0.1) and their corresponding fold change, absolute abundance (larger of the average absolute abundances between the two diets), and quantification class. Quantification class is determined by whether one or both measurements were above or below the lower limit of quantification and the limit of detection.

Statistical comparisons between diet groups were analyzed using the Kruskal-Wallis [111] rank sums test with Benjamini-Hochberg [112] multiple hypothesis testing correction. All statistical tests were implemented using SciPy.stats Kruskal function and statsmodels.stats.multitest multipletests function with the fdr_bh option for Benjamini-Hochberg multiple-testing correction. When calculating differentially abundant taxa, only taxa present in at least 4 out of 6 mice in a group were considered to remove fold-change outliers when plotting (FIG. 12, panels a-b).

Figure 20:
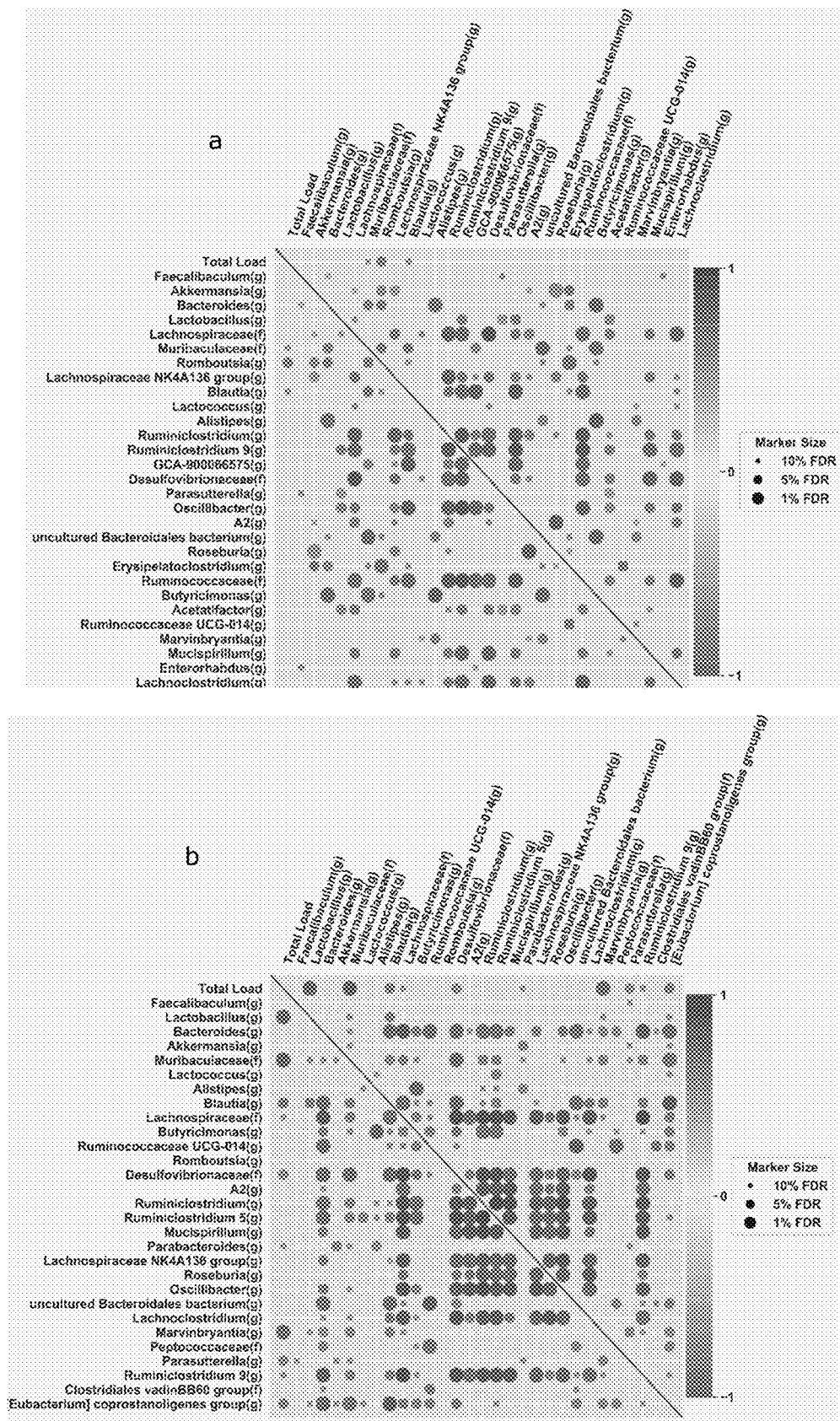
FIG. 20 demonstrates in two plots that absolute-abundance measurements enable unbiased determination of correlation structure in microbiome datasets. Correlation matrices, using Spearman's rank, for the total microbial load and the top 30 most abundant taxa in stool samples from mice on either a ketogenic diet (FIG. 20—Panel a) or control diet (FIG. 20 Panel b). The color of each marker is based on the correlation coefficient (darker indicates higher correlation coefficients) and the size is determined by the q-value of the correlation after Benjamini-Hochberg multiple testing correction. False-discovery rates (FDR) indicate the q-value at which the correlation was deemed significant: 1%, 5%, 10%. Abbreviations: (f), family; (g), genus; (o), order.

Samples were separated by diet (ketogenic and control) and only stool samples were used (days 4, 7, and 10). The total microbial load and top 30 taxa with the highest average absolute abundance were selected for analysis. Spearman's rank correlation coefficient and corresponding P-values were calculated for all pairwise interactions using the scipy.stats.spearmanr function. Benjamini-Hochberg procedure was to calculate q-values, which account for multiple hypothesis testing. A heatmap of the diagonal correlation matrix was plotted (FIG. 20) for q-values <10% FDR.

The complete sequencing data generated during this study are available in the National Center for Biotechnology Information Sequence Read Archive repository under study accession number PRJNA575097. Raw data for all figures available through CaltechDATA: data.caltech.edu/records/1371. Raw data for all figures is also provided as source data files.

The impact of extraction procedures, 16S rRNA sequencing and digital PCR, on the quantification of the 16S rRNA were tested with experiments described in Examples 6-8. The accuracy of the quantification performed with methods of the disclosure with respect to other approaches and in differential taxon analysis was tested with experiments described in Examples 9 and 10.

Example 6: Efficient DNA Extraction Across Microbial Loads and Sample Types

Figure 13:
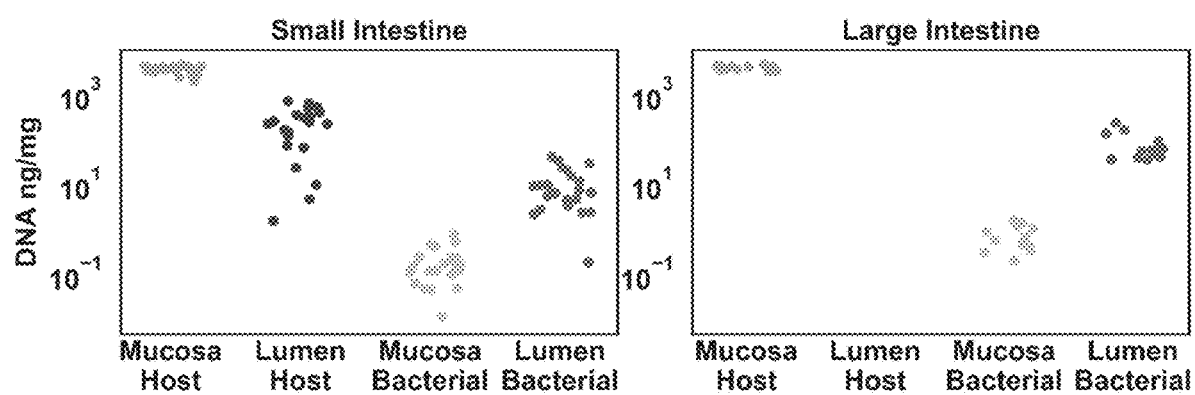
FIG. 13 shows two plots illustrating the total DNA loads in small intestine and large intestine mucosa and lumen. Extracted DNA samples from mice in the ketogenic-diet group were measured by Nanodrop (total DNA) and digital PCR (microbial DNA). The horizontal lines represent the means and the points represent individual biological replicates (N=24 for small intestine; N=12 for large intestine).

To estimate the maximum quantity of sample that could be extracted before overloading the 20-μg column capacity, total DNA and microbial DNA load were measured across small intestine and large intestine lumenal and mucosal samples (FIG. 13).

Extraction efficiency was then evaluated across three tissue matrices (mucosa, cecum contents, and stool) to assess whether variation in levels of PCR inhibitors and non-microbial DNA interfered with microbial quantification. A defined 8-member microbial community was spiked into GI samples taken from germ-free (GF) mice.

Figure 8:
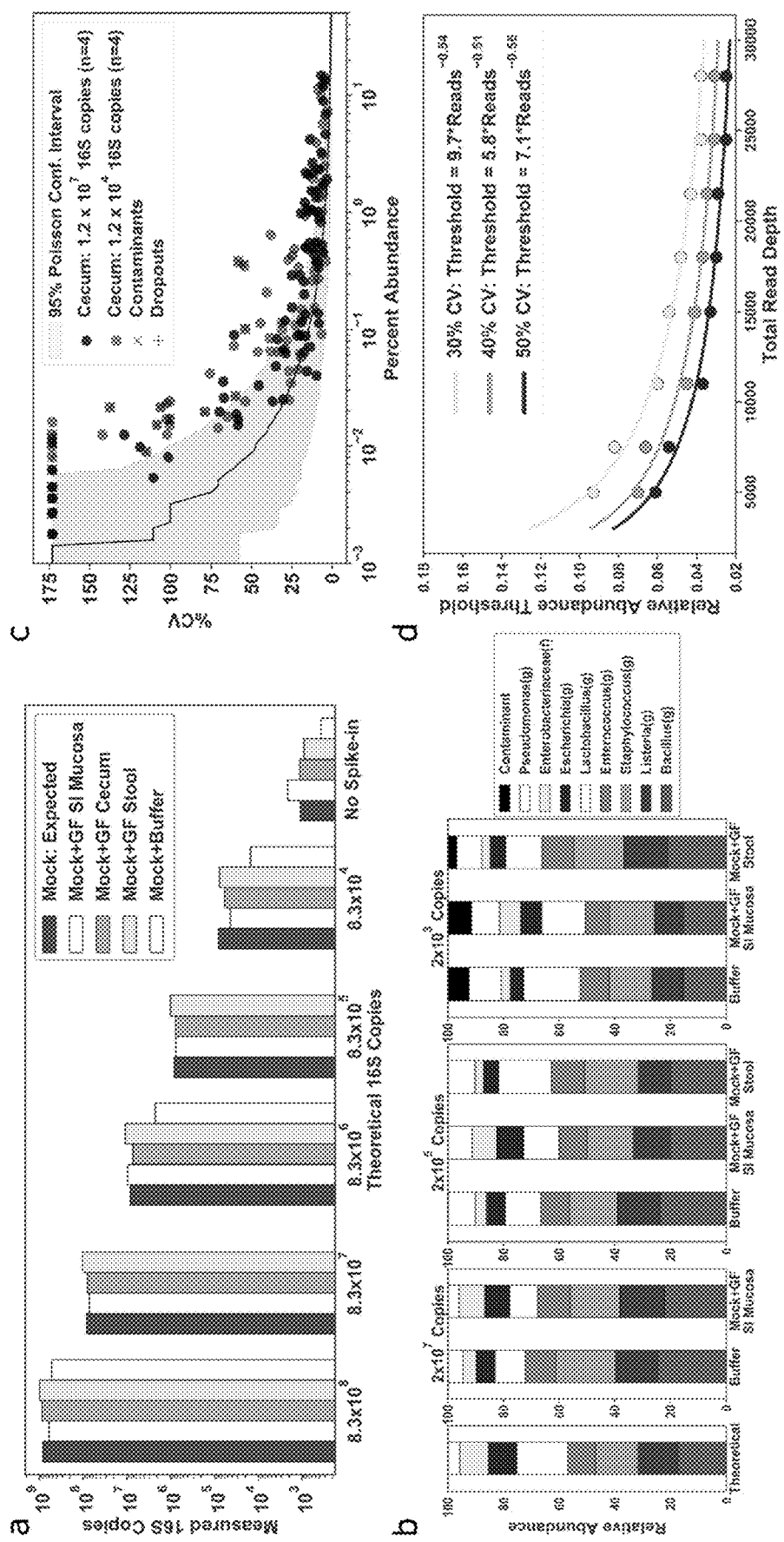
FIG. 8 shows in some embodiments the lower limits of quantification for total microbial DNA extraction and 16S rRNA gene amplicon sequencing.
Figure 14:
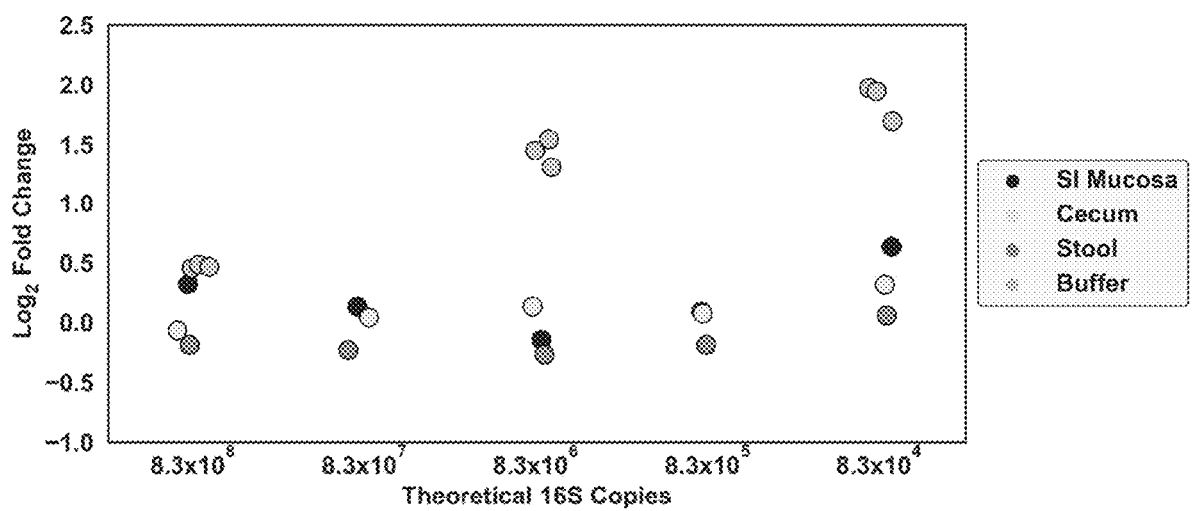
FIG. 14 shows a plot illustrating the extraction and total DNA measurement accuracy of an eight-member mock microbial community dilution spiked into extraction buffer or small-intestine mucosa, cecum, or stool from germ free mice. $Log_2$ fold change between theoretical and dPCR measured copies of 16S rRNA gene after extraction with varying input levels. Three technical replicates for buffer extractions are shown. All other sample types shown are N=1 to illustrate the biological noise among sample types.

To assess quantitative limits, a dilution series of microbial spike-in were performed from $1.4 \times 10^9$ CFU/mL to $1.4 \times 10^5$ CFU/mL. dPCR quantification showed near equal and complete recovery of microbial DNA over 5 orders of magnitude (FIG. 8, panel a). Overall, Applicant measured~2× accuracy in extraction across all tissue types (cecum contents, stool, SI mucosa) when total 16S rRNA gene input was greater than $8.3 \times 10^4$ copies (FIG. 14). Normalizing this sample input to the approximate maximum extraction mass (200 mg stool, 8 mg mucosa) yielded a lower limit of quantification (LLOQ) of $4.2 \times 10^5$ 16S rRNA gene copies per gram for stool/cecum contents and $1 \times 10^7$ 16S rRNA gene copies per gram for mucosa. Mucosal samples had a higher LLOQ because the high host DNA in this tissue type saturates the column, limiting total mass input.

Next, to ensure extraction performance was consistent for both Gram-negative and Gram-positive microbes, Applicant performed 16S rRNA gene amplicon sequencing using previously described improved primers and protocol [1, 2, 17] on a subset of the extracted samples (FIG. 8, panel b). It is important to note that all amplification reactions for 16S rRNA gene library prep were monitored with real-time qPCR and the reactions were stopped when they reached the late exponential phase to limit overamplification and chimera formation [1, 2, 17, 76, 113, 114]. Extraction appeared less even among microbial taxa at lower total microbial DNA inputs (FIG. 8, panel b).

Figure 15:
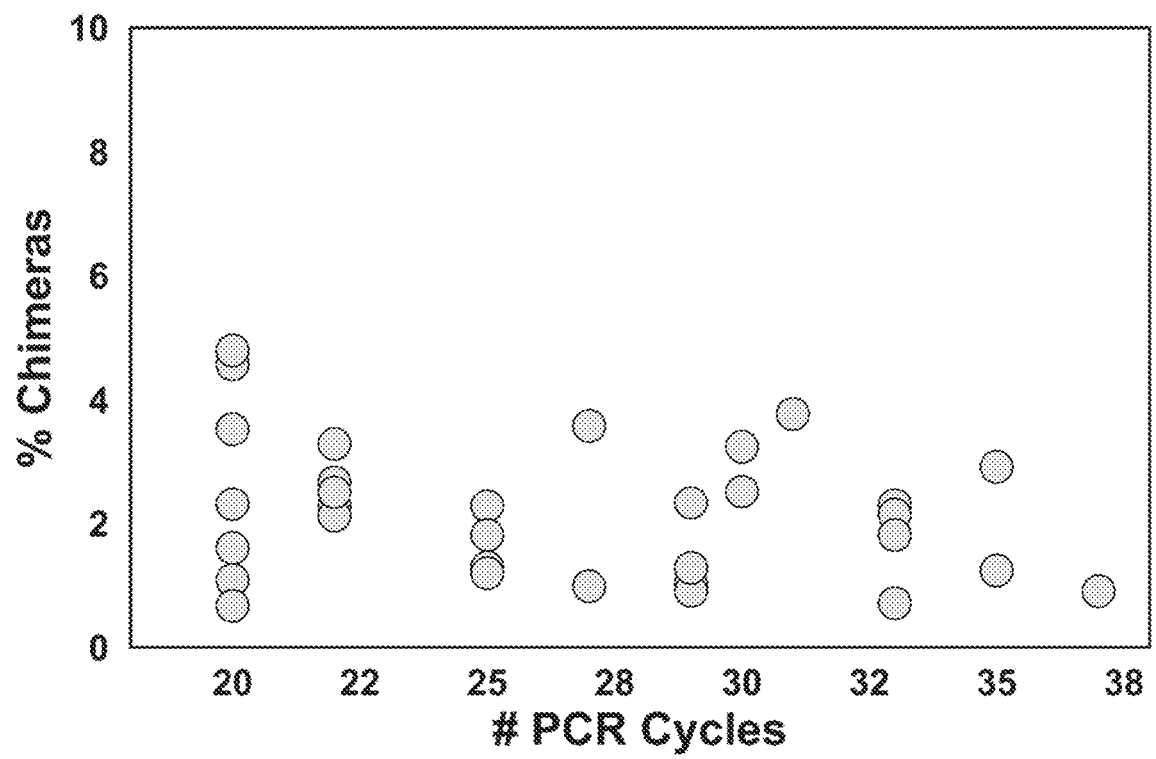
FIG. 15 shows the chimeric sequence prevalence as a function of the number of PCR cycles. The plot demonstrates that the chimeric sequence prevalence is not determined by the number of PCR cycles. Relationship between the number of PCR cycles during the amplification reaction for library prep and the percentage of chimeric sequences detected by Divisive Amplicon Denoising Algorithm 2 (DADA2) [3]. N=33 samples that were sequenced from mice in the ketogenic-diet group.

This discrepancy from the theoretical profile did not correlate with the presence of chimeric sequences (FIG. 15) and was likely a function of the reduced accuracy incurred when diluting complex microbial samples. Additionally, sequencing samples with low total microbial loads (<$1 \times 10^4$ 16S rRNA gene copies) resulted in the presence of contaminants, as confirmed by sequencing of negative-control extractions (FIG. 22).

FIG. 22 lists Contaminant taxa with greater than 1% abundance in negative-control extraction.

Example 7: Quantitative Limits of 16S rRNA Gene Amplicon Sequencing

The impact of the 16S rRNA gene amplicon sequencing on the 16S rRNA quantification was tested with the following experiments.

In particular to establish the precision of relative-abundance measurements, four replicates of DNA extractions from cecum samples were sequenced. Libraries from one DNA extraction were prepared with either an input of 1.2×10⁷ 16S rRNA gene copies or 1.2×10⁴ 16S rRNA gene copies to determine the impact of starting DNA amount on sequencing variability.

The coefficient of variation (% CV) was calculated for each taxon's relative abundance from amplicon sequencing the replicate samples. Each taxon's mean relative abundance (n=4) was then plotted against its corresponding coefficient of variation of the relative abundance (FIG. 8, panel c). "dropouts" were defined as taxa present only in the high-DNA-input sample whereas "contaminants" were defined as taxa present only in the low-DNA-input sample.

The two dropout taxa in the low input sample corresponded to the lowest abundance taxa from the high input DNA sample (markers with an "x", FIG. 8, panel c). Most of the contaminant taxa had a relative abundance <0.03%, but three taxa (*Pseudomonas*(g), *Acinetobacter*(g), Rhizobiales(f)) had relative abundances of 0.38%, 0.35%, and 0.1%, respectively. These three taxa were also the three most common contaminants in our negative-control extractions (FIG. 22).

Figure 16:
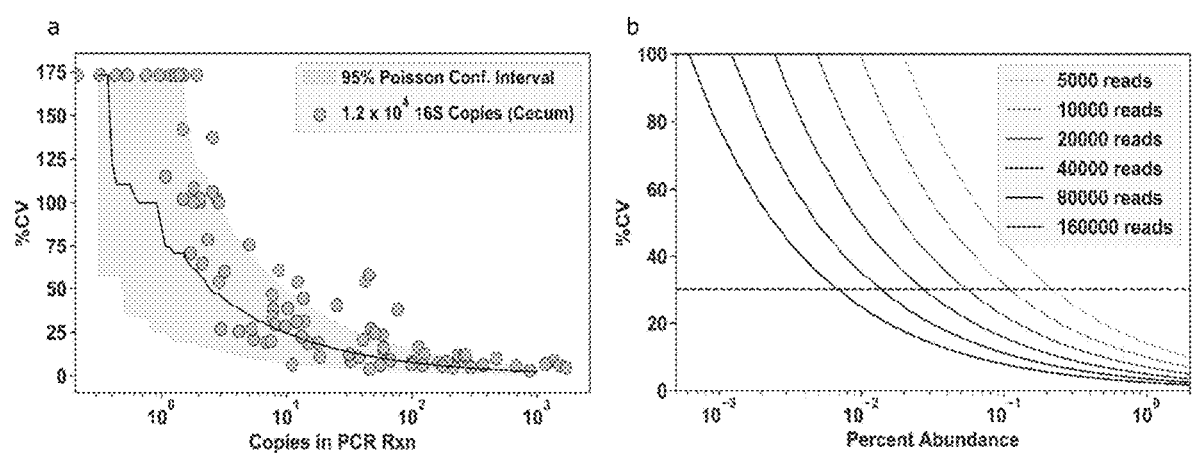
FIG. 16 shows the Poisson limits of sequencing accuracy.

The presence of contaminants in the sample containing 1.4×10⁴ 16S rRNA gene copies was consistent with the input amount at which we observed contaminants in the mixed microbial community dilutions (FIG. 8, panel b). A bootstrapped Poisson sampling confidence interval was calculated at our sequencing depth (28,000 reads) to assess how close the accuracy limits were to the theoretical limits (shading, FIG. 8, panel c). At the low DNA input level of 1.2×10⁴ 16S rRNA gene copies, Applicant began to reach the fundamental Poisson loading limit in the library-preparation reaction (FIG. 16, panel a).

A divergence of the % CV at ~0.01% abundance was expected because at a read depth of 28,000 a relative abundance of 0.01% is a measure of ~3 reads whereas at a total 16S rRNA gene copy input of 1.4×10⁴ a relative abundance of 0.01% is ~1 copy. Poisson statistics also helped us define the theoretical lower limits of relative-abundance measurements as a factor of sequencing depth (FIG. 16, panel b).

Next an approximate threshold was quantified, which would tell us, for a given sequencing depth, at what percentage of relative abundance one lose accuracy in the measurements (this threshold was defined as "relative abundance threshold"). To determine this threshold, a negative exponential was fit to the replicate data and the percentage abundance was identified at which 30% CV was observed. This threshold is a function of the sequencing depth, so Applicant subsampled the data at decreasing read counts and repeated the exponential fitting method to calculate the relationship between the relative abundance threshold and sequencing depth (FIG. 8, panel d). Greater sequencing depths yielded lower quantitative limits with diminishing returns, as expected. Applicant found that the threshold for percentage abundance decreases with increasing sequencing depth with a square root dependence analogous to the square-root dependence of Poisson noise. This trend follows for % CV thresholds of 40% and 50% as well (FIG. 8, panel d).

This analysis provides a framework with which to impose thresholds on relative-abundance data that are grounded on the calculated limits of quantitation.

Example 8: Absolute Quantification of Taxa Via Digital PCR (dPCR) Anchoring

Absolute abundances of taxa were determined from sequencing data using dPCR measurement of total microbial loads as an anchor. The accuracy of quantification through dPCR was then tested by the following experiments.

Briefly, relative abundance of each taxon was measured by sequencing and these numbers were multiplied by the total number of 16S rRNA gene copies (obtained using the same universal primers from amplicon sequencing, without the barcodes) from dPCR.

Next, the accuracy of this quantitative sequencing approach was evaluated. Typically, evaluation of quantitative accuracy and precision would involve the use of a mock microbial community (like the one used in FIG. 8).

However, because the absolute instead of relative abundances was computed, it is feasible to use the actual gut-microbiota samples and compare the results to the dPCR data obtained with relevant taxa-specific primers. The 16S rRNA gene copy amount was then normalized to the mass of each extracted sample after correcting for volume losses (Equation 1 in Example 5).

Figure 17:
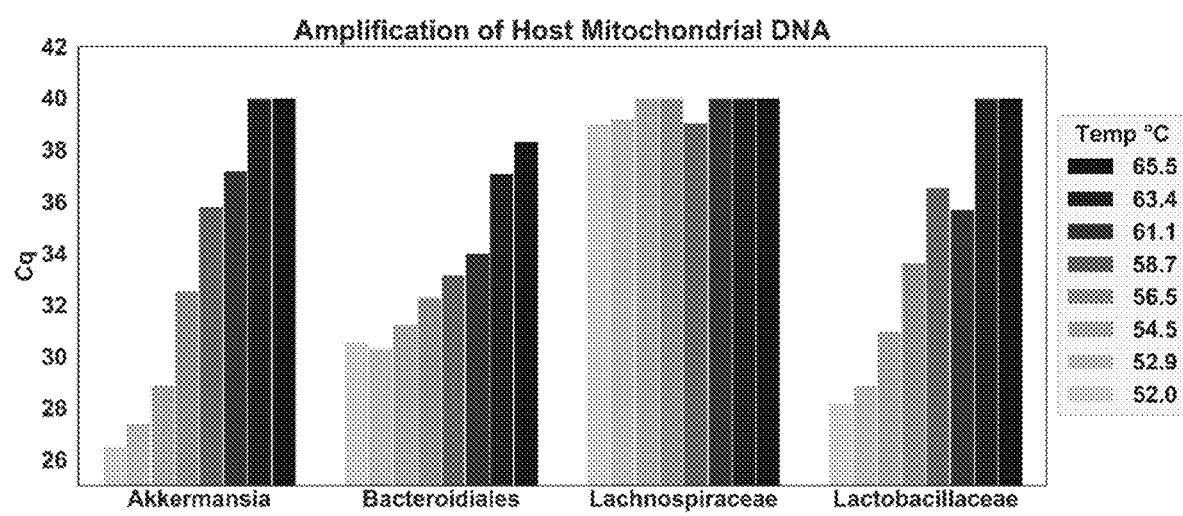
FIG. 17 shows in some embodiments the optimization of group-specific primers to eliminate amplification of host DNA. Relative abundance of non-specific product amplified from 20 ng/µL small-intestine mucosa sample from a germ-free mouse measured by qPCR. Lower Cq values indicate more amplification. Each color represents a different annealing temperature used during the cycling process. Samples were run in singlet at each temperature.

Four representative taxa were selected to encompass common gut flora of varying classification levels: *Akkermansia muciniphila*(s), Lachnospiraceae(f), Bacteroidales (o), and Lactobacillaceae(f). Like eubacterial primers, taxa-specific primer sets can (in principle) give rise to nonspecific amplification due to overlap with host mitochondrial DNA. To avoid nonspecific amplification, Applicant ran temperature gradients with GF mucosal DNA and taxa-specific microbial DNA to identify the optimal annealing temperature for each primer set (FIG. 17).

Figure 9:
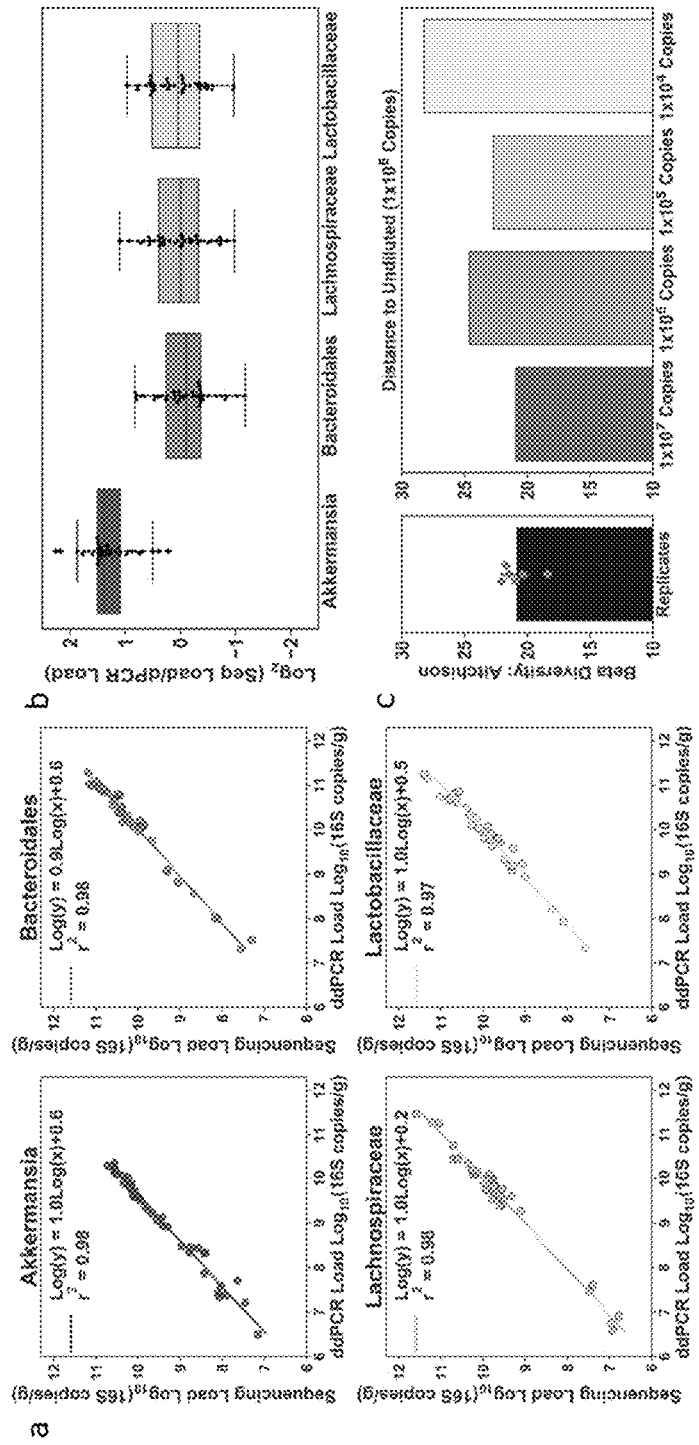
FIG. 9 shows exemplary embodiments of using digital PCR (dPCR) anchoring of 16S rRNA gene amplicon sequencing to provide microbial absolute abundance measurements. Taxon-specific dPCR demonstrates low biases in abundance measurements calculated by 16S rRNA gene sequencing with dPCR anchoring.
Figure 21:
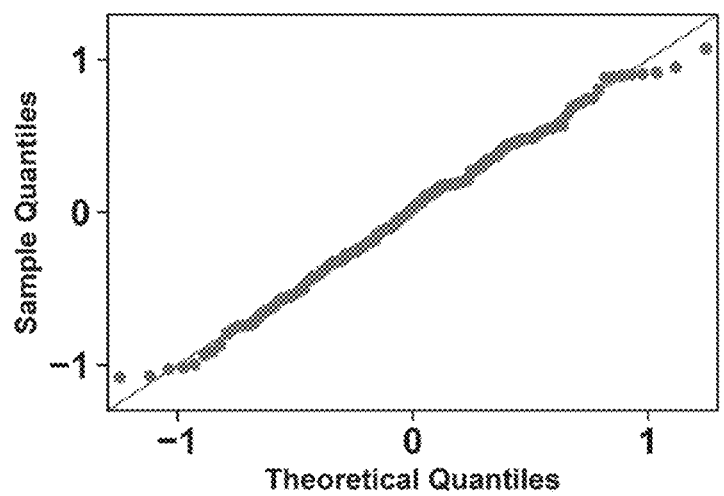
FIG. 21 shows a plot demonstrating that the uncertainty in taxon absolute-abundance measures approximately follows a normal distribution. The quantile-quantile (Q-Q) plot of the mean-centered $log_2$ relative error of absolute taxon abundances. The relative error is calculated as the ratio of the absolute taxon loads measured by our method of quantitative sequencing with dPCR anchoring over the absolute loads measured by taxon-specific primers in dPCR (data are from FIG. 9, panel b). The x-axis represents the theoretical quantiles from a normal distribution while the y-axis is the actual quantiles of the mean-centered $log_2$ relative errors.

Each taxa-specific primer targets a separate region of the 16S rRNA gene than the universal primer set, thus keeping the gene copy number equivalent across primers. High correlation coefficients were observed between the taxa load determined by quantitative sequencing with dPCR anchoring and the taxa load measured by dPCR with taxa-specific primers (all $r^2$>=0.97, FIG. 9, panel a) for all four taxa over a range of ~6 orders of magnitude. The ratio of the total load measurements obtained by quantitative sequencing with dPCR anchoring and by dPCR with taxa-specific primers showed unity agreement between three of the four primer sets with 2-fold deviation from the mean (FIG. 9, panel b and FIG. 21). Sequencing quantification was consistently 2.5-fold higher than dPCR quantification for the species *Akkermansia muciniphila* (FIG. 9, panel b).

Amplification bias as a factor cannot be confirmed because the error did not depend on the number of cycles used in library preparation. An alternative factor could be a discrepancy in coverage/specificity between the taxon-specific and universal primer sets. Applicant next tested the limits of the sequencing accuracy as a factor of input DNA load. A 10× dilution series of a cecum sample was created to cover input DNA loads of 1×10⁸ copies down to 1×10⁴ copies.

Minimal differences in beta diversity (Aitchison distance) between the undiluted and diluted samples were observed with a trend towards increasing difference with decreasing DNA load (FIG. 9, panel c). This negative correlation between beta diversity and microbial load is not unexpected due to the higher presence of contaminant species from our negative controls in the lower input samples (FIG. 8, panel b).

Example 9: Absolute Vs Relative Abundance Analysis in a Ketogenic-Diet Study

A ketogenic-diet study was performed to test the impact of using a quantitative framework for 16S rRNA gene amplicon sequencing.

In particular, the goals of this study were twofold. First, Applicant wished to test whether absolute instead of relative microbial abundances can more accurately quantify changes in microbial taxa between study groups. Second, Applicant wished to investigate how using a quantitative sequencing framework can guide the interpretation of changes in taxa across study conditions. The objective was not to make claims about the effect of a ketogenic diet on the microbiome, but rather to use this model as an illustration of the added benefits of using this quantitative sequencing framework.

Figure 10:
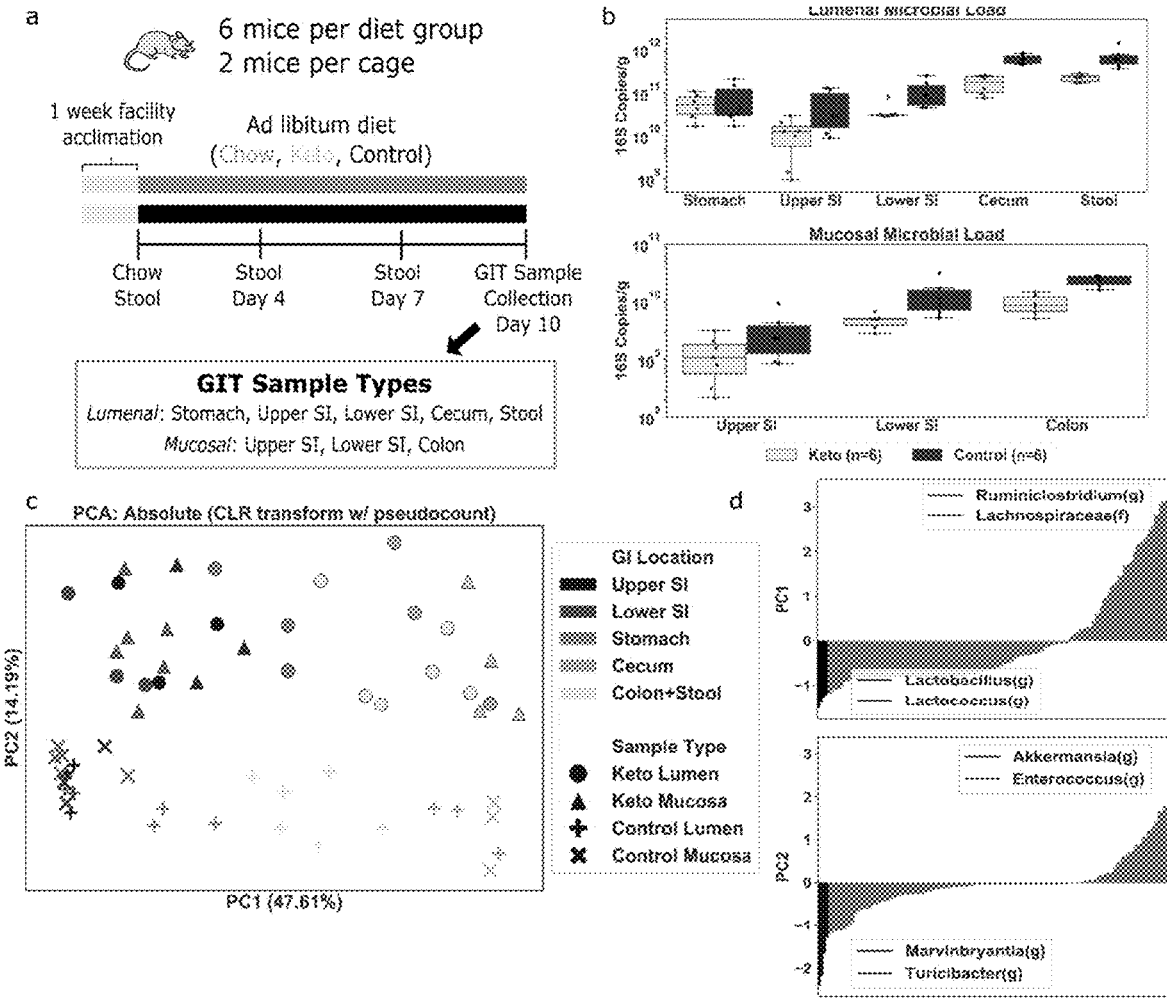
FIG. 10 demonstrates that microbial absolute abundances provide separation between GI locations of mice on ketogenic or control diets. Analysis of data comparing ketogenic and control diets provides changes of total microbial loads, separation of microbial communities by GI location and by diet in principal component analysis, and the top taxa driving the separation of samples along the principal components.

After one week on a standard chow diet, 4-week old Swiss Webster mice were split into two groups (n=6 each): one was fed a ketogenic diet and the other a vitamin and mineral matched control diet (FIG. 24). Stool was sampled immediately before the two diets were introduced (day 0), and again at days 4, 7 and 10. Additionally, on day 10, all mice were euthanized and lumenal and mucosal samples were collected from throughout the GI tract (FIG. 10, panel a). Microbial loads (quantified with dPCR) ranged from ~$10^9$ 16S rRNA gene copies/g in small intestinal mucosa to $10^{12}$ 16S rRNA gene copies/g in stool. On average, we observed lower microbial DNA loads in the mice on the ketogenic diet compared with mice on the control diet, except in the stomach, where loads were similar in mice on both diets (FIG. 10, panel b).

All stool samples and roughly half of the samples for all other GI sites (evenly distributed across mice on the two diets) underwent 16S rRNA gene amplicon sequencing. Ordination methods (PCA, PCoA, NMDS, etc.) are a common exploratory data analysis technique in the microbiome field. Common transformation techniques based on non-Euclidian distances (e.g., Bray-Curtis, UniFrac) can skew the accuracy of visualizations of relative data (FIG. 18, panel a) [115]. The centered log-ratio transformation (CLR, often used to compute the Aitchison distance) was used to handle compositional effects, and performed PCA on the transformed absolute abundance data for all samples from the final collection day (FIG. 10, panel c). A clear separation along the first two principal components (PC) was observed. Separation along PC1 was related to the location within the GI tract whereas separation along PC2 was related to the diet. The PCA analysis suggested that stomach samples were distributed somewhere in-between small-intestine and large-intestine samples, possibly resulting from coprophagy in mice [1, 2]. Additionally, the mucosal and lumenal samples from the small intestine on the control diet seemed to be closer together than on the ketogenic diet (FIG. 10, panel c).

Next, calculations were performed to investigate which taxa were contributing to separation in our principal component space. Applicant calculated the scaled covariance between each taxon and the first two principal components by multiplying the eigenvectors by the square root of their corresponding eigenvalues. These values are also known as "feature loadings." Plotting these feature loadings from smallest to highest shows that *Lactobacillus*(g) and *Lactococcus*(g) had the greatest impact on separation along PC in the direction of the small intestinal samples whereas RuminiClostridium(g) and Lachnospiraceae(f) separated in the direction of the large intestine (FIG. 10, panel d). This matches with what we know about the major genera commonly present in the small and large intestine [116]. Along PC2 (the "diet axis"), the top two contributing taxa towards the control diet were Turicibacter(g) and Marvinbryantia(g), while towards the ketogenic diet *Akkermansia*(g) and *Enterococcus*(g) had the greatest covariance.

Figure 7:
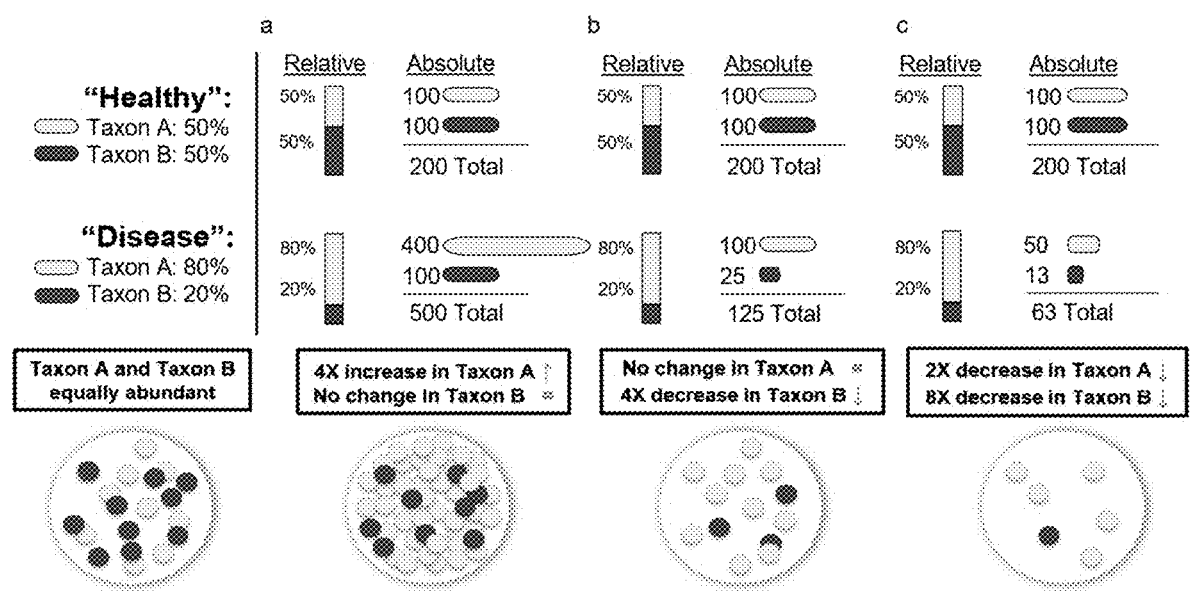
FIG. 7 illustrates in three hypothetical scenarios the value of absolute (compared with relative) quantification. In this hypothetical, two taxa (Taxon A and Taxon B) are found in equal abundance (50:50) in a "healthy" state but in an 80:20 ratio in the "disease" state. Three possible scenarios arise.
Figure 18:
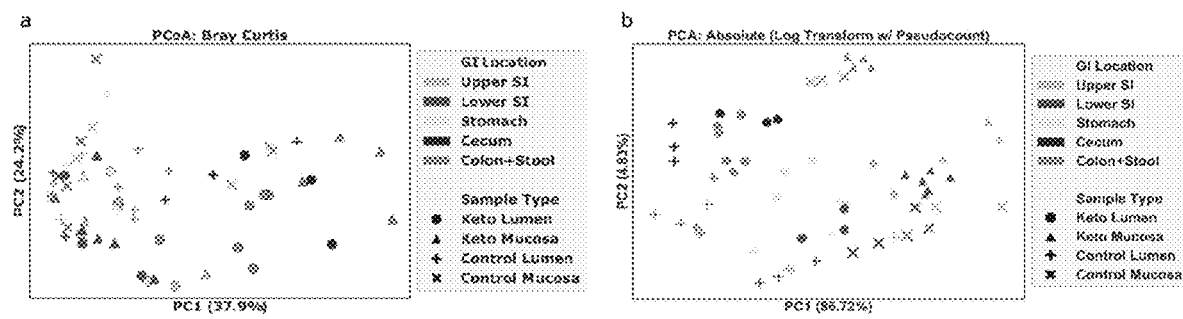
FIG. 18 demonstrates the impact of ordination method on data visualization.

Although the CLR transformation preserves distances in principal component space regardless of whether the starting data are relative or absolute, it normalizes out the differences in total loads by looking at log ratios between each taxon's abundance and the geometric mean of the sample (FIG. 18, panel b). In many cases, one wants to know if the absolute load of a taxon is higher or lower under different conditions (e.g., in mice on ketogenic and control diets). When the total microbial load varies among samples, analyses of relative abundance cannot determine which taxa are differentially abundant (FIG. 7).

Figure 11:
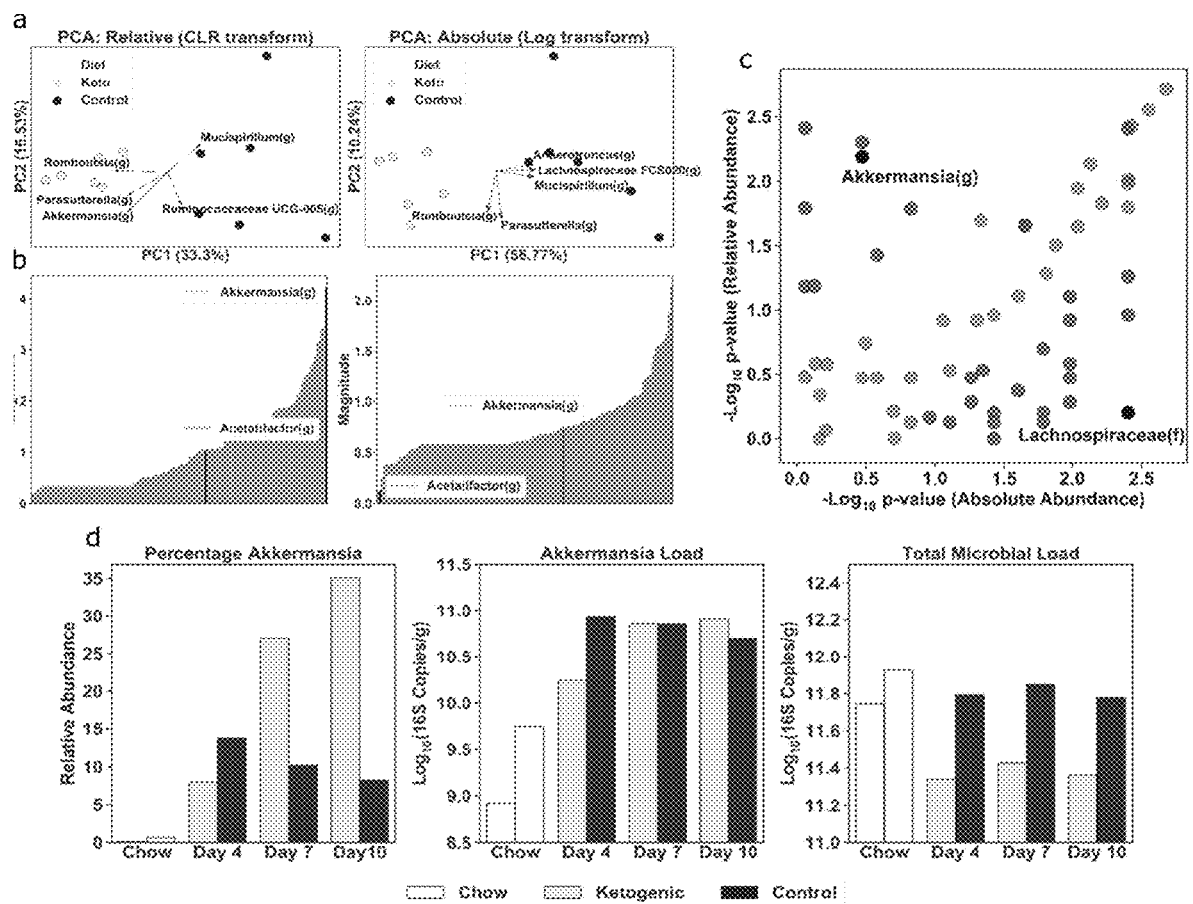
FIG. 11 demonstrates that analyses of relative and absolute microbial abundances from the same dataset result in different conclusions.

To assess the impact of using absolute quantification in analyses, microbiomes of stool samples from mice on ketogenic and control diets were analyzed. PCA analysis on the CLR-transformed relative abundances of microbial taxa showed separation between the two diets (FIG. 11, panel a). Feature loadings were analyzed as before, but this time total impact of each taxa on the PC space was plotted, which was defined as the sum of the feature loading vectors in PC1 and PC2 (FIG. 11, panel b). The same analysis was performed on the log-transformed absolute abundance data (FIG. 11, panel a). Separation between diets is clear in both relative and absolute abundance analyses, but the contribution of each taxon to the separation differed in direction and magnitude. Comparing the magnitude of feature loadings for two taxa, *Akkermansia*(g) and Acetatifactor(g), between the relative and absolute PCA plots showed obvious differences in the contribution of a given taxa to the separation in principal-component space. Analysis of relative-abundance data implies that *Akkermansia*(g) has the biggest contribution on separation between diets in PC space whereas the absolute abundance data implies that ~50% of the taxa in the sample have a greater contribution than *Akkermansia*(g) to the separation between the diets in PC space.

PCA is only an exploratory data-analysis technique, so next Applicant used a non-parametric statistical test to test for differentially abundant taxa in stool samples from mice on control and ketogenic diets (FIG. 11, panel c) [111]. Separate analyses of the relative and absolute abundance data were performed. The –log 10 P-value was plotted for each taxon's relative abundances against the corresponding –log 10 P-value for that taxon's absolute abundances. Points along the diagonal indicate congruence between the predictions from the relative and absolute abundance data. Points in the upper left corner indicate taxa that differed between the diets in the analysis of relative abundance but not in the analysis of absolute abundance. Conversely, points in the lower right corner indicate taxa that do not differ between diets in the analysis of relative abundance but do differ in the analysis of absolute abundance. *Akkermansia*(g) is an example of a microbe that appears to differ (P=$6.49\times10^{-3}$, Kruskal-Wallis) between mice on the two diets in the relative-abundance analysis but not in the absolute-abundance analysis (P=$3.37\times10^{-1}$, Kruskal-Wallis). Lachnospiraceae(f) showed the opposite trend; in the relative-abundance analysis it appears unchanged (P=$6.31\times10^{-1}$, Kruskal-Wallis) but in the absolute-abundance analysis it differs (P=$3.95\times10^{-3}$, Kruskal-Wallis) between the two diets.

Neither of these analyses is wrong, they are simply asking two different questions: with relative data, the question is whether the percentage of that microbe is different between two conditions whereas with absolute data, the question is whether the abundance of that microbe is different between two conditions.

Figure 19:
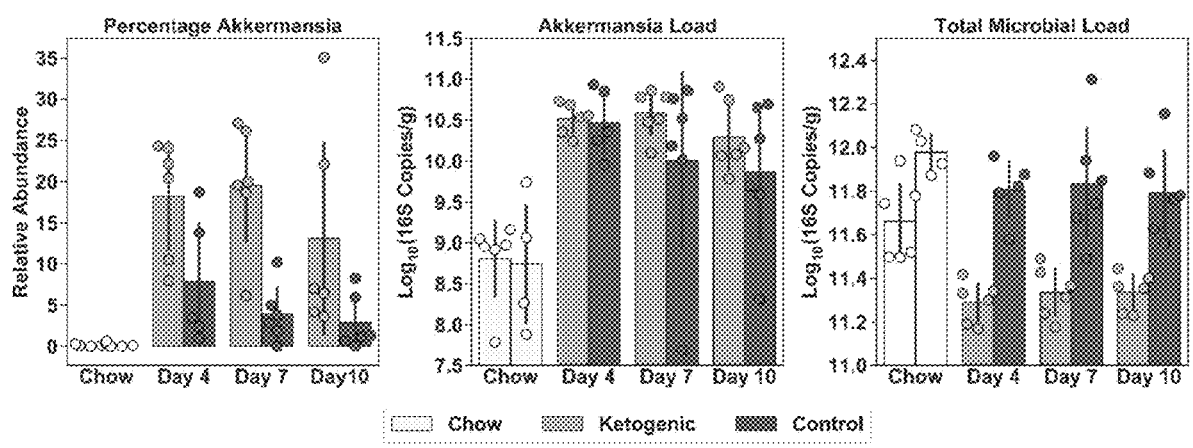
FIG. 19 shows the comparison of relative and absolute abundance quantification of Akkermansia(g) between mice on ketogenic and control diet. Average Akkermansia(g) load from stool of N=6 mice on control diet (dark grey) and N=6 mice on ketogenic diet (light-grey). White points and bars indicate loads prior to the diet switch when all mice were on the chow diet. Data points from mice without Akkermansia (g) are not shown. Bar plots show mean plus or minus the standard deviation. Individual data points are overlaid on the bar plots.

To explore one example of how different interpretations of how taxa differ between study conditions occur when using relative versus absolute abundance, Applicant analyzed *Akkermansia*(g) in stool across each of the three time points on experimental diets (days 4, 7, and 10) and day 0 on chow diet. For simplicity in this illustration, we compared data from one mouse on each diet, but the trends hold on average between all mice on the two diets (FIG. 19). Analysis of relative microbial abundance demonstrated ~3× higher abundance of *Akkermansia*(g) in samples from the ketogenic compared with the control diet on days 7 and 10.

However, when analyzing the difference in absolute abundance, more nuanced conclusions emerged. The rise in *Akkermansia*(g) results from switching mice from chow to experimental diets. The resulting *Akkermansia*(g) loads are similar in the two diets on days 7 and 10. However, the ketogenic diet reduces the total microbial load relative to both chow and control diets, therefore leading to the observed higher % of *Akkermansia*(g) in samples from mice on ketogenic diet.

Example 10: Absolute Abundances for Quantitative Differential Taxon Analysis

A microbiota abundance was analyzed to test the accuracy of method of the disclosure in differential taxon analysis.

In particular, the absolute microbiota abundances in stool and lower small intestinal mucosa samples from day 10 was analyzed. A volcano plot, akin to those used in gene expression studies, was used to represent the overall changes in taxa abundances between the two diets, and the absolute abundance of each taxon was indicated by the size of its symbol (FIG. 12, panel a). P-values from the Kruskal-Wallis tests were corrected for multiple hypothesis testing with the Benjamini-Hochberg method, resulting in q-values [111, 112]. A false discovery rate (FDR) of 10% was labeled on the volcano plot and q-values <0.1 were used as a cutoff for designating differential taxa for downstream analyses.

Comparisons between the two GI locations showed substantial differences in microbial response to diet by location. In stool, approximately 66% of the differential taxa were lower on the ketogenic diet vs the control diet whereas in the lower SI mucosa, >80% of the differential taxa were more abundant in the ketogenic diet than control diet (FIGS. 25-26).

Several specific differential taxa that were discordant between stool and lower SI mucosa were highlighted. (1) *Bacteroides*(g) was lower on ketogenic diet in stool and higher on ketogenic diet in lower SI mucosa. This type of result could lead researchers who analyze stool samples to believe that lower levels of *Bacteroides*(g) may be associated with a phenotype when it could be the opposite if the phenotype is driven by the SI mucosal microbiota. (2) Parabacteroides(g) and Lachnospiraceae GCA-900066575 (g) showed the highest fold changes (in opposite directions) in stool but were not detected in the lower SI mucosa. The opposite was observed for *Escherichia*(g), which was more abundant in the ketogenic diet than the control diet in the lower SI mucosa but was not detected in stool. (3) *Akkermansia*(g) and Desulfovibrionaceae(f) were more abundant in the ketogenic diet than the control diet in the lower SI mucosa but were similar between the two diets in stool. Such microbes could have a relationship with phenotype through the small intestine but would be missed if only stool samples are analyzed.

A further breakdown of the differential taxa, using the quantitative limits of sequencing accuracy (defined earlier), allowed one to categorize four distinct scenarios that describe how microbes differed between GI locations of mice on the two diets. We refer to these four scenarios as "quantification classes" (FIG. 12, panel b).

First, there were microbes that were present in one diet and absent in the other ("presence/absence" class). For example, Dorea(g), in stool, and *Escherichia*(g), in SI mucosa, were absent from the control diet but present in the ketogenic diet.

Second, there were microbes above the detection limit but below the quantitative limit in both diets ("no quant" class). For example, in stool, Candidatus Soleaferrea(g), ranges in relative abundance from 0.002% to 0.025%, well below the 30% CV quantification threshold of 0.04% (as defined in FIG. 8, panel d). Thus, the difference of this microbe between mice on the two diets cannot be quantitatively defined.

Third, microbes were above the detection limit in both diets but only above the quantitative limit in one of the diets ("semi-quant" class). For example, Desulfovibrionaceae(f) in the lower small-intestine mucosa was above the detection limit in mice on both diets but only above the quantitative limit in mice on the ketogenic-diet, so although one can be confident that a difference between the diets exists, one cannot be confident in the measurement of the magnitude of that difference.

Fourth, microbes were found above the quantitative limits in both diets ("quant" class). For example, for Parabacteroides(g) in stool, the results supported confidence in both the difference between the diets (it was more abundant in the control diet) and in the magnitude of that difference (a 32.2-fold difference). In particular, the lowest confidence was found in the measured absolute fold change of a taxon that is classified in the presence/absence class, and the greatest confidence in a taxon in the quant class.

Example 11: General Protocols for Absolute Quantification of Target 16S rRNA Following Modification Microbiota by Preventing Self-Reinoculation with Fecal Flora in Mice Absolute quantification of microbial community in mice following modification of the microbiota performed by preventing self re-inoculation was detected according to an exemplary method herein described.

All animal handling and procedures were performed in accordance with the California Institute of Technology (Caltech) Institutional Animal Care and Use Committee (IACUC). C57BL/6J male specific-pathogen-free (SPF) mice were obtained at the age of 7-8 weeks from Jackson Laboratory (Sacramento, CA, USA) and housed four mice per cage. Two cohorts of animals were used: the first cohort was allowed to acclimate in the Caltech animal facility for 2 months and mice were 4 months old at the start of the study; the second cohort acclimated for 6 months and mice were 8 months old at the start of the study.

All animals were maintained on chow diet (PicoLab Rodent Diet 20 5053, LabDiet, St. Louis, Mo., USA) and autoclaved water ad lib and subjected to a daily 13:11 light:dark cycle during acclimation and throughout the entire study. Mice were given measured amounts of food, and food intake during the experiment was measured by weighing the food during weekly cage changes and at the end time point for each animal. Body weight was measured at the start of the experiment, during weekly cage changes, and at the end time point.

During the experiment, all mice were singly housed in autoclaved cages (Super Mouse 750, Lab Products, Seaford, Del., USA). The mice in the control (CTRL), mock tail cup (TC-M) and functional tail cup (TC-F) treatments were housed on heat-treated hardwood chip bedding (Aspen Chip Bedding, Northeastern Products, Warrensburg, NY, USA) and provided with tissue paper (Kleenex, Kimberly-Clark, Irving, TX, USA) nesting material. The mice in the wire-floor (WF) treatment were housed on raised wire floors with a mesh size of 3×3 per square inch (#75016, Lab Products) and provided with floorless paper huts (#91291, Shepherd Specialty Papers, Watertown, Tenn., USA). A thin layer of woodchip bedding was added under the wire floors to absorb liquid waste from the animals (FIG. 33, panel D).

The tail cups were designed based on published literature [92-94, 117, 118], including the locking mechanism [117]. Each cup was locked in place around the hind end of animals by anchoring to a tail sleeve designed with a perpendicular groove. Such tail sleeves allow for the cup to be held snugly against the animal so that the total weight of the tail cup is distributed along a large surface area of the tail skin, which minimizes complications. When mounted, the tail cups can freely rotate along the longitudinal axis, which ensures the locking mechanism does not strangulate the tail.

Figure 33:
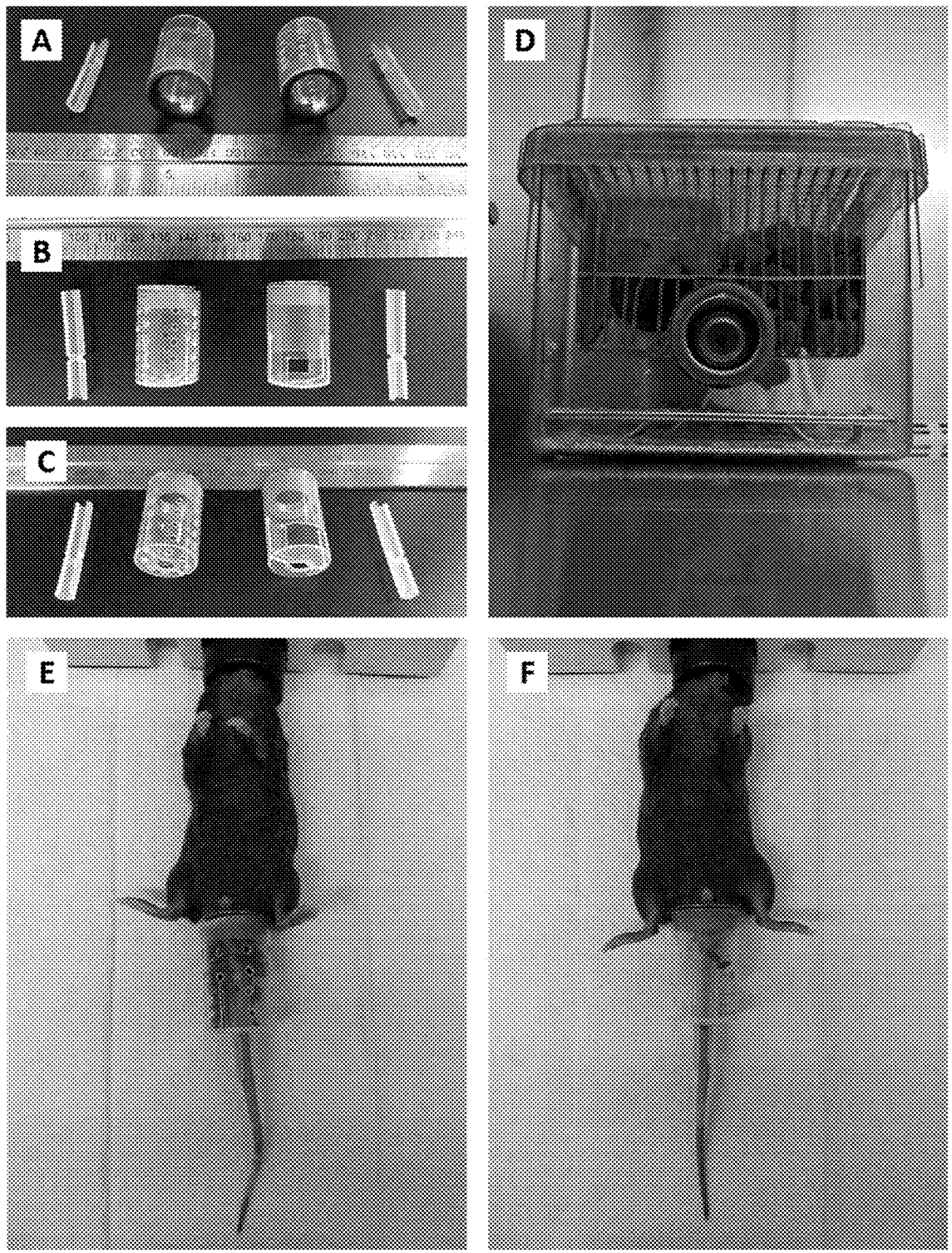
FIG. 33 shows the tail cup design and experimental setup for preventing coprophagy.
Figure 34:
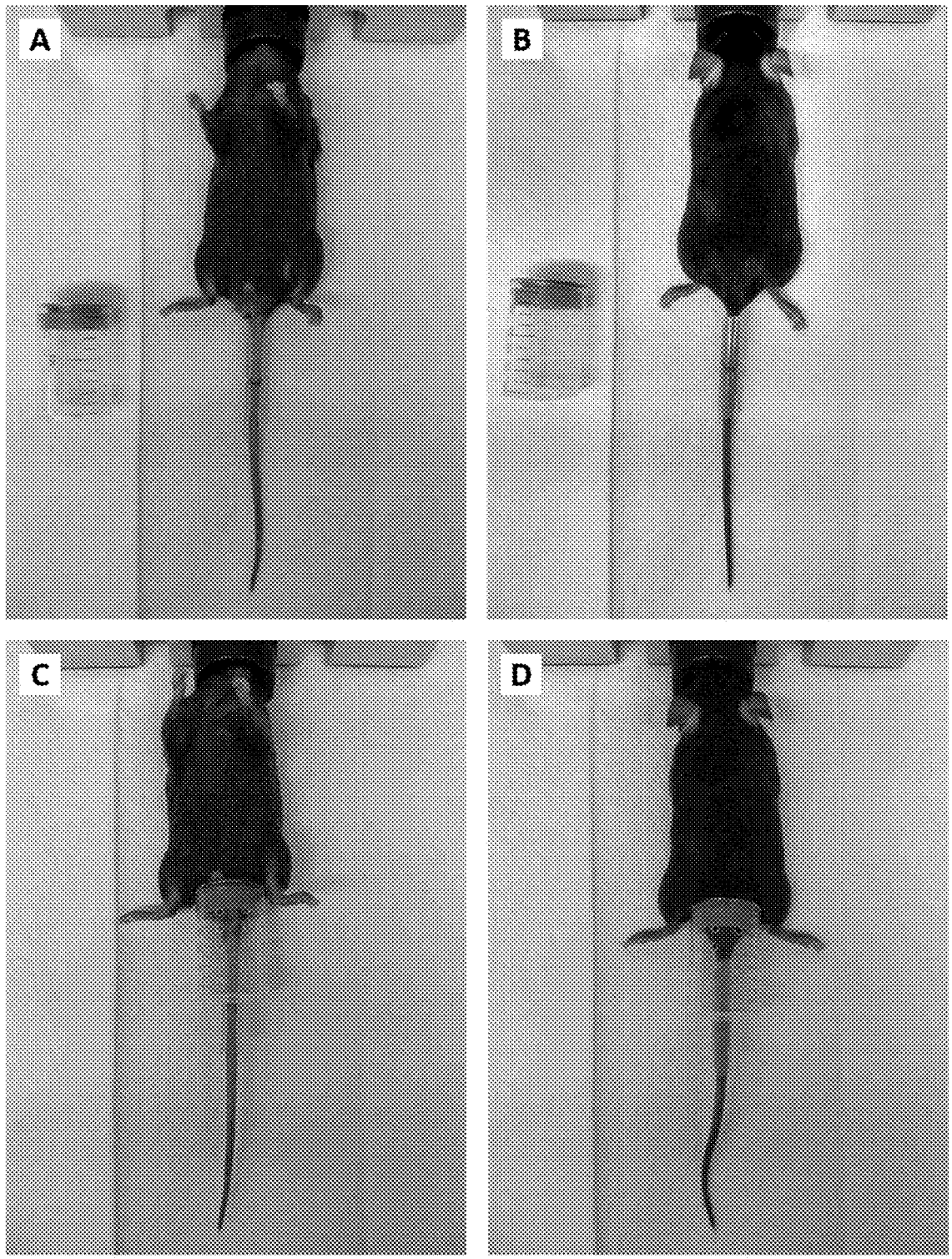
FIG. 34 shows the mounting of functional tail cups onto mice.

The tail cups were hand-made from 20 mL syringes (#4200.000V0 Norm-Ject 20 mL Luer-Lock, Henke-Sass Wolf GmbH, Tuttlingen, Germany) as depicted on FIG. 33, panels A-C. Multiple perforations were designed to accelerate desiccation of the captured fecal pellets. Lateral slits allowed for increasing the diameter of the locking edge; pressing on the slits with two fingers allowed tail cups to be quickly unfastened from tail sleeves. Mock tail cups were modified with wide gaps in the walls to allow the fecal pellets to fall out of the cup.

To prevent mice from gnawing on the plastic parts of the tail cups (which could create a jagged edge and lead to a subsequent injury), they were reinforced with metal flared rings made from stainless steel grommets (#72890, SS-4, C.S. Osborne, Harrison, NJ, USA) that were modified to reduce their size and weight. Metal rings were attached to tail cups using 4 mm-wide rubber rings cut from latex tubing (Amber Latex Rubber Tubing #62996-688, ½" ID, ¾" OD; VWR, Radnor, PA, USA).

Tail sleeves were made from high-purity silicone tubing (HelixMark 60-411-51, ⅛" ID, ¼" OD; Helix Medical, Carpinteria, CA, USA). The tubing was split longitudinally and a 2.0 mm wide strip of the wall was removed to accommodate for variable tail diameters among animals and along the tail length, to prevent uneven tail compression, and to facilitate uniform application of the tissue adhesive. The perpendicular tail-cup mounting groove was made using a rotary tool (Craftsman #572.610530, Stanley Black & Decker, New Britain, CT, USA) equipped with a cutting disc (RD1, Perma-Grit Tools, Lincolnshire, UK). Each tail cup and sleeve together weighed approximately 4.12 g empty.

Before mounting the tail cups, animals were anesthetized with 10 min isoflurane and placed on a heating pad to maintain body temperature. Sleeves were de-greased on the inside using 70% ethanol and a veterinary tissue adhesive (GLUture Topical Adhesive #32046, Abbott Laboratories, Lake Bluff, Ill., USA) was applied to the tail base. The adhesive was allowed to cure for 5 min and then tail cups were mounted. Mice were returned back to their cages and allowed to recover from the anesthesia and ambulate.

Tail cups were emptied of fecal pellets daily at 08:00 AM. Mice were prompted to enter a restrainer [119] made from a black polypropylene 50 mL conical tube (TB5000 Lite-Safe, Cole-Parmer, Vernon Hills, Ill., USA) and the tail cups were unclipped and quickly emptied. Any residue on the tail cup was cleaned using a paper towel and Rescue solution (Virox Technologies, Oakville, ON, Canada) prior to the cups being remounted. Animals fitted with the mock tail cups were subjected to the identical procedure to match the handling conditions.

Tail cups were mounted in animals for a duration of between 12 and 20 days. All TC-F animals were time-matched with TC-M animals, (i.e., each animal from the TC-F group had a time-matched animal from the TC-M group handled and euthanized at the same time).

All mice were euthanized as approved by the Caltech IACUC in accordance with the American Veterinary Medical Association Guidelines on Euthanasia [106]. Mice were euthanized while under isoflurane anesthesia (delivered via a calibrated gas vaporizer in an induction chamber followed by maintenance on a nose cone) via cardiac puncture followed by cervical dislocation. Blood was collected using a 1 mL syringe (#309659, Becton Dickinson) and 21G×1" needle (#26414, EXELINT International, Redondo Beach, CA, USA).

Blood was immediately placed into $K_2$EDTA plasma separation tubes (MiniCollect 450480, Greiner Bio-One GmbH, Kremsmunster, Austria), gently mixed, and stored on ice for up 1 h prior to centrifugation. Bile and urine were collected directly from the gall and urinary bladders respectively using a 1-mL syringe (#4010.200V0 Norm-Ject 1 mL Tuberculin Luer, Henke-Sass Wolf GmbH) and 27G×½" needle (#26400, EXELINT International) and stored on ice.

Fecal samples were collected if present at the time of euthanasia. The entire gastrointestinal tract was excised from the gastro-esophageal junction to the anal sphincter and stored on ice during processing.

Blood samples were centrifuged in the plasma separation tubes at 2000 RCF for 5 min at 4° C. Plasma was separated and stored at −80° C.

To prepare samples for the main experimental analyses (FIGS. 29-31), each mouse GIT was split into stomach, three equal-length thirds of the small intestine, cecum, and colon. Contents from each segment of the GIT were flushed out using 2-5 mL of cold (4° C.) sterile autoclaved saline solution (0.9% NaCl (#S5886, Sigma-Aldrich) in ultrapure water (Milli-Q, MilliporeSigma, Burlington, MA, USA)) followed by very gentle squeezing with tweezers to avoid mucosal damage. All samples were stored on ice during processing.

An aliquot of each sample diluted in saline was concentrated by centrifugation at 25000 RCF for 10 min at 4*C. The supernatant was removed and the pellet was reconstituted in 9 volumes of 1× DNA/RNA Shield (DRS) solution (R1100-250, Zymo Research, Irvine, CA, USA), mixed by vortexing and stored at −80° C. for future DNA extraction. Separate aliquots of each sample were stored at −80° C. for the metabolomic (bile acid) analysis.

Figure 36:
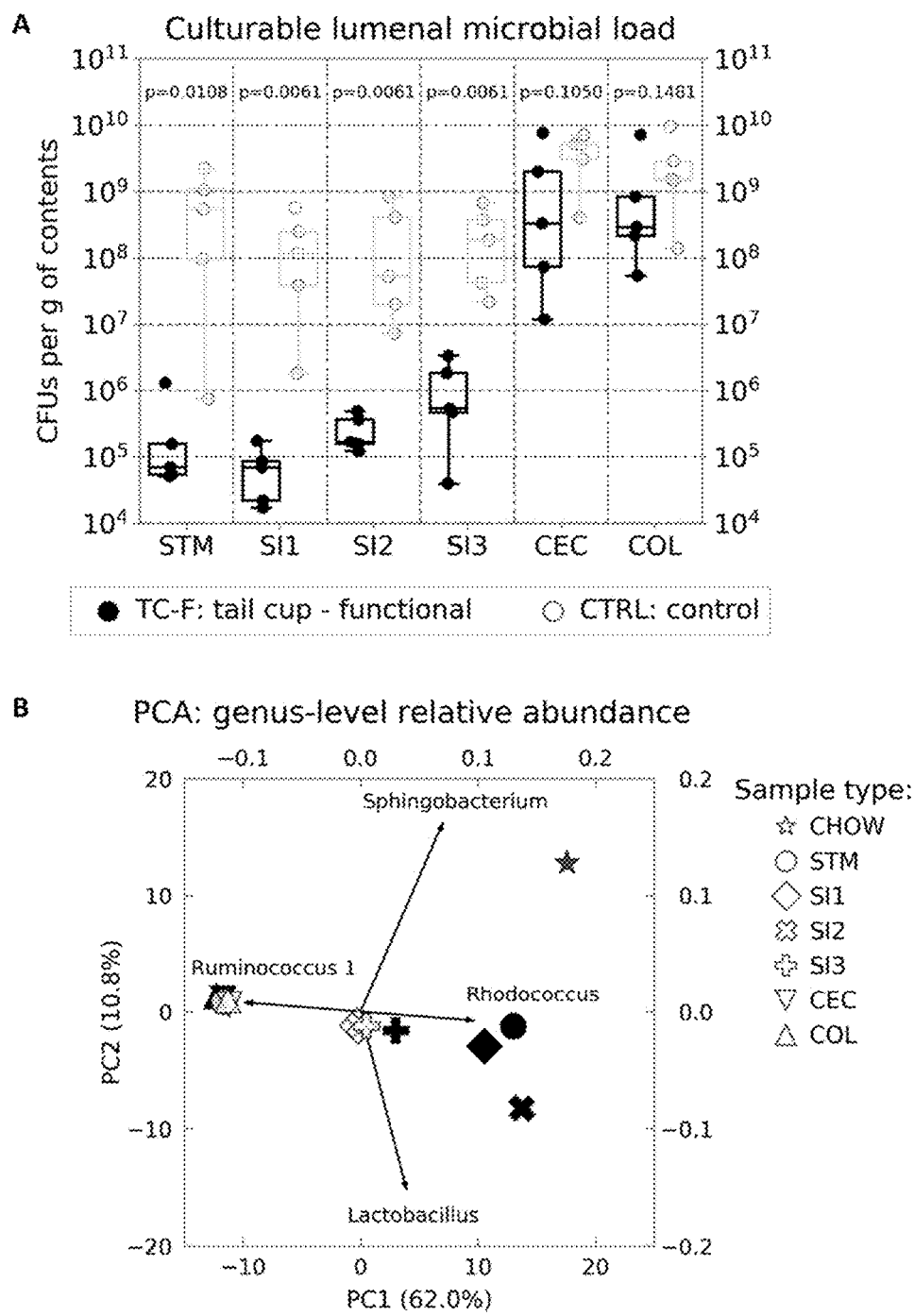
FIG. 36 shows the quantification of the culturable microbial load and microbiota profile along the entire GIT of mice fitted with functional tail cups (TC-F) and control mice (CTRL).

Preparation of GIT contents for the MPN-based microbial quantification and 16S rRNA gene amplicon sequencing (pilot study; FIG. 36, panel B) was the same as above, but conducted inside a vinyl anaerobic chamber (Coy Laboratory Products, Grass Lake, MI, USA) in an atmosphere of 5% hydrogen, 10% carbon dioxide, and 85% nitrogen. All samples were maintained on ice and immediately processed for the culture-based assay.

After flushing its contents, each segment of the GIT was gently rinsed in sterile cold (~4° C.) saline, cut longitudinally, and placed flat on a glass slide. The mucosa was scraped from the tissue gently using a second clean glass slide. Glass slides (VistaVision #16004-422, VWR) were sterilized by dry heat sterilization at 200° C. for at least 2 h. Mucosal scrapings were collected and combined with 9 volumes of DRS solution, mixed by vortexing, and stored at −80° C. in preparation for DNA and RNA extraction.

A Most Probable Number (MPN) assay was then performed. For the pilot study (FIG. 36, panel A), the MPN assays (adapted from [120-124]) were performed on each GIT section (stomach, three sub-sections of the small intestine, cecum, and colon) from five mice fitted with functional tail cups and five control mice. The growth medium was brain-heart infusion broth (Bacto BHI, #237500, Becton Dickinson, Franklin Lakes, NJ, USA), prepared in ultrapure water (Milli-Q), sterilized by autoclaving, allowed to cool to room temperature, and supplemented with 1.0 mg/L vitamin $K_1$ (#L10575, Alfa Aesar, Haverhill, MA, USA), 5 mg/L hematin (#H3281, Sigma-Aldrich St. Louis, Mo., USA), and 0.25 g/L L-cysteine (#168149, Sigma-Aldrich). The medium was allowed to equilibrate inside the anaerobic chamber for at least 24 hours before use.

MPN assays were performed in clear, sterile, non-treated polystyrene 384-well plates (Nunc 265202, Thermo Fisher Scientific, Waltham, MA, USA). Two series of eight consecutive 10-fold serial dilutions were prepared from each sample in sterile autoclaved saline solution (equilibrated inside the anaerobic chamber for at least 24 h) on clear sterile non-treated polystyrene 96-well plates (Corning Costar 3370, Corning, NY, USA). We injected 10 µL of each serial dilution from each series into four (eight total per dilution) culture-medium replicates (wells) filled with 90 µL of the BHI-S broth medium.

Plates were sealed with a breathable membrane (Breath-Easy BEM-1, Diversified Biotech) and incubated for 5 d at 37.0° C. inside the anaerobic chamber. The plates were lidless for the first 24 h to facilitate uniform gas equilibration, then from 24 h to the end of the incubation period (120 h), a plastic lid was kept over the plates.

At the end of the incubation, the plates were scanned using a flatbed scanner (HP ScanJet 8250, Hewlett-Packard, Palo Alto, CA, USA) in the reflective mode with black background at 300 dpi resolution. The positive wells (replicates) were called by visually observing each acquired high-resolution image. The MPN for each sample was calculated using Microsoft Excel with the "Calc_MPN" macro [125].

DNA was extracted from thawed GIT contents and mucosal sample aliquots preserved in DRS solution with the ZymoBIOMICS DNA Miniprep Kit (D4300, Zymo Research) according to the manufacturer's instructions. Samples were homogenized on a bead-beater (MiniBead-Beater-16, Model 607, Bio Spec Products, Bartlesville, OK, USA) for 5 min at the default speed of 3450 RPM. Quantitative recovery of DNA across multiple orders of microbial loads in the samples was previously verified in [1, 17].

DNA yield and purity in the extracts was evaluated via light absorbance (NanoDrop 2000c, Thermo Fisher Scientific) and via a fluorometric assay (Qubit dsDNA HS Assay Kit Q32854, Thermo Fisher Scientific) on a fluorometer (Invitrogen Qubit 3, Thermo Fisher Scientific).

Quantitative PCR (qPCR) for 16S rRNA gene DNA copy enumeration was then performed. In particular, the qPCR reactions were set up in triplicates for each DNA sample. A single replicate reaction volume of 15 µL contained 1.5 µL of the DNA extracts combined with the qPCR master mix (SsoFast EvaGreen Supermix, #172-5200, Bio-Rad Laboratories, Hercules, CA, USA), forward and reverse primers (synthesized by Integrated DNA Technologies, San Diego, CA, USA; FIG. 38) at a final concentration of 500 nM, and ultrapure water (Invitrogen UltraPure DNase/RNase-Free Distilled Water 10977-015, Thermo Fisher Scientific). Reactions were set up in white 96-well PCR plates (#HSP9655, Bio-Rad Laboratories) sealed with a PCR tape (#MSB1001, Bio-Rad Laboratories).

The standard curve was built for each qPCR run based on the included series of 10-fold dilutions of the "standard" SPF mouse fecal DNA extract (with the quantified absolute concentration of 16S rRNA gene copies using digital PCR).

Amplification was performed with real-time fluorescence measurements (CFX96 Real-Time PCR Detection System, Bio-Rad Laboratories). Thermocycling conditions were used according to FIG. 39. The qPCR data files were analyzed using Bio-Rad CFX Manager 3.1 (#1845000, Bio-Rad Laboratories) and the Cq data were exported to Microsoft Excel for further processing.

Digital PCR (dPCR) for absolute 16S rRNA gene DNA copy enumeration: was also performed. In particular, droplet digital PCR (ddPCR) reactions were set up according to [1, 17]. Single replicate reaction volume of 20 µL contained 2.0 µL of the DNA extracts combined with the ddPCR master mix (QX200 ddPCR EvaGreen Supermix, #1864033, Bio-Rad Laboratories), forward and reverse primers (synthesized by Integrated DNA Technologies; FIG. 38) at final concentration of 500 nM each, and ultrapure water (Thermo Fisher Scientific).

Droplets were generated using DG8 cartriges (#1864008, Bio-Rad Laboratories), droplet generation oil (#1864006, Bio-Rad Laboratories), and DG8 gaskets (#1863009, Bio-Rad Laboratories) on a QX200 droplet generator (#1864002, Bio-Rad Laboratories) and analyzed using a QX200 Droplet Digital PCR System (#1864001, Bio-Rad Laboratories) using droplet reader oil (#1863004, Bio-Rad Laboratories). The ddPCR data files were analyzed using QuantaSoft Software (#1864011, Bio-Rad Laboratories) and the raw data were exported to Microsoft Excel for further processing.

Thermocycling conditions were used according to [1, 17] and FIG. 40. Amplification was performed in PCR plates (#0030133374, Eppendorf, Hauppauge, NY, USA) sealed with pierceable heat seals (#1814040, Bio-Rad Laboratories) using PCR plate sealer (PX1, #1814000, Bio-Rad Laboratories) on a 96-deep well thermocycler (C1000 Touch, #1841100), Bio-Rad Laboratories).

16S rRNA gene DNA amplicon barcoding for next generation sequencing (NGS) was then performed. In particular, the PCR reactions was set up according to [1, 17], in triplicates for each DNA sample. Single-replicate reaction volumes of 30 µL contained 3 µL of the DNA extracts combined with the PCR master mix (5PRIME HotMaster-Mix, #2200400, Quantabio, Beverly, MA, USA), DNA intercalating dye (EvaGreen, #31000, Biotium, Fremont, CA, USA) at the suggested by the manufacturer concentration (×1), barcoded forward and reverse primers (synthesized by Integrated DNA Technologies; FIG. 38) at final concentration of 500 nM each, and ultrapure water (Thermo Fisher Scientific). Reactions were set up in 0.2 mL white PCR tubes (#TLS0851) with flat optical caps (#TCS0803, Bio-Rad Laboratories). Thermocycling conditions were used according to [1, 17] and FIG. 41. Amplification was performed with real-time fluorescence measurements (CFX96 Real-Time PCR Detection System, Bio-Rad Laboratories) and samples were amplified for a variable number of cycles until the mid-exponential (logarithmic) phase to maximize the amplicon yield and minimize artifacts related to over-amplification [76].

A Digital PCR (dPCR) for Illumina library quantification was then performed. In particular, a single replicate reaction volume of 20 uL contained 2.0 uL of the diluted amplicon sample ligated with the Illumina adapters, 10 uL of ddPCR master mix (QX200 ddPCR EvaGreen Supermix, #186-4033, Bio-Rad Laboratories), forward and reverse primers (synthesized by Integrated DNA Technologies; FIG. 38) targeting the Illumina P5 and P7 adapters respectively at the final concentration of 125 nM each, and ultrapure water (Invitrogen). Thermocycling conditions were used according to FIG. 42. PCR amplification and droplet analysis were performed as above.

Barcoded sample quantification, pooling, library purification and quality control were then performed. In particular, triplicates of each barcoded amplicon sample were combined. Each samples was diluted×$10^5$-$10^7$-fold and the molar concentration of barcoded amplicons was quantified using a home-brew ddPCR library quantification assay and KAPA SYBR FAST Universal qPCR Library Quantification Kit (#KK4824, Kapa Biosystems, Wilmington, MA, USA) according to the manufacturer's instructions (the qPCR reaction was set up same as above).

Barcoded samples were pooled in equimolar amounts. Pooled library was purified using Agencourt AMPure XP beads (#A63880, Beckman Coulter, Brea, CA, USA) according to the manufacturer's instructions and eluted with ultrapure water (Invitrogen).

The purified library was confirmed to have the 260 nm to 280 nm light absorbance ratio of >1.8 using a NanoDrop 2000c spectrophotometer (Thermo Fisher Scientific). The average amplicon size of approximately ~400 bp was confirmed with a High Sensitivity D1000 ScreenTape System (##5067-5584 and 5067-5585, Agilent Technologies, Santa Clara, CA, USA) using a 2200 TapeStation instrument (Agilent Technologies) and the Agilent 2200 TapeStation Software A02.01. (Agilent Technologies).

The molar concentration of the pooled library was measured using the ddPCR and KAPA qPCR assays and the library was submitted for next generation sequencing (NGS) with the sequencing primers described in FIG. 38.

Next generation sequencing was then performed. In particular, the library was sequenced on a MiSeq instrument (Illumina, San Diego, CA, USA) in a 300-base paired-end mode using a MiSeq Reagent Kit v3 (#MS-102-3003, Illumina). PhiX control spike-in was added at 15%.

The same universal microbial 16S rRNA gene V4 primers (modified from [16, 18] and validated in [1, 17]) targeting the V4 region of the 16S rRNA gene from the 519 to 806 positions were used as PCR primer oligonucleotides for 16S rRNA gene DNA copy quantification and multiplexed microbial community profiling based on 16S rRNA gene amplicon sequencing. Reverse barcoded primers for 16S rRNA gene DNA amplicon barcoding were according to [16]. (FIG. 38):

Primers targeting the P5 and P7 Illumina adapters for barcoded amplicon and pooled library quantification using the ddPCR assay were according to [16, 18-21].

Demultiplexed 2×300 reads were processed using the Qiime2-2019.01 pipeline [80]. DADA2 plugin [3] was used to filter (forward trimming—5, forward truncation—230, reverse trimming—5, reverse truncation—160), denoise, merge the paired-end sequences, and remove the chimeras. Taxonomic sequence (amplicon sequence variant, ASV) classification was performed using the classifier (available for download from [126]) trained [110] on the V4 515-806 bp regions of 16S rRNA gene sequences from the Silva rRNA reference database, release 132 [9, 55, 56](available for download from [127]).

Functional gene inference analysis with the PICRUSt2 [45, 46] was performed on the ASVs within the Qiime2 environment. Absolute and relative abundances of ASVs were normalized using the inferred 16S rRNA gene DNA copy counts. Obtained predicted metagenome data were used to calculate the normalized relative and absolute abundances of the gene orthologs of interest using Python tools (described below).

Sequencing Data handling, calculations, and statistical analyses were performed using Microsoft Excel with the Real Statistics Resource Pack [128], and the Python packages NumPy [129], Pandas [130], SciPy [131, 132], Statsmodels [133]. Plotting was performed with Matplotlib
and Seaborn [135]. All Python packages were run using
IPython [136] within Jupyter notebooks [137] distributed with the Anaconda environment [138].

Frequency data for the 16S rRNA gene ASVs assigned to taxa in each sample were converted to relative abundances for each sample. Relative abundances then were converted to absolute abundances using the corresponding values of total 16S rRNA gene DNA loads obtained from the qPCR and ddPCR assays for each sample.

Absolute abundance data were then collapsed to the genus (FIG. 30, panel A) or order (FIG. 30, panels B,C) taxonomical levels using a custom made Python function (confirmed to yield identical results to the "collapse" method of the Qiime2 "Taxa" plugin [80]). The contaminating taxa were defined (from sample handling during collection or from the DNA extraction kit or PCR reagents) using two methods: taxa that were not present in at least 1 out of 16 cecum contents samples (4 mice out of 6 from each group×4 groups), and taxa identified with a frequency-based contaminant identification [139] implemented by us in Python. Data for chloroplasts and mitochondria of plant origin (likely from the chow diet) were kept in the dataset for FIG. 30, panel A and panel C and removed for FIG. 30, panel B. Mean absolute abundances of taxa for each group were calculated, converted to relative abundances, and plotted in FIG. 30, panel B.

Principal components analysis (PCA) of the relative abundance data (FIG. 36, panel B) was performed on centered log-ratio (CLR)-transformed [140, 141] (after a pseudocount equal to the minimal non-zero sequence count in the dataset was added to all zero values) genus-level relative abundance data using the Python Scikit-learn package [142].

PCA of the absolute abundance data (FIG. 30, panel A) was performed on $\log_{10}$-transformed and centered-standardized (converted to normally-distributed data with mean=0 and standard deviation=1) [143] genus-level absolute abundance data using the Python Scikit-learn package [142].

Bile acid analysis was then performed. Reagents TαMCA, TβMCA, TωMCA, THCA, αMCA, βMCA, ωMCA, HCA, HDCA, MCA, GCDCA, GDCA, and GCA for bile acid analysis (FIG. 43) were obtained from Steraloids (Newport, R.I., USA). The reagents TCA, CA, DCA, TCDCA, TDCA, TUDCA, TLCA, CDCA, UDCA, LCA, $D_4$-TCA, $D_4$-DCA, $D_4$-CA, $D_4$-TDCA, $D_4$-GLCA, $D_4$-GUDCA, $D_4$-GCDCA, $D_4$-GCA, and $D_4$-GDCA (FIG. 43) were obtained from Isosciences (Ambler, PA, USA).

LC/MS grade acetonitrile (#A955-500), water (#W6500), and formic acid (#A117-50) were obtained from Thermo Fisher Scientific.

To overcome sample buffering (pH issues) in sample preparation, samples were extracted (using a protocol adapted and modified from [144-146]) in 9 volumes of ethanol with 0.5% formic acid and nine different heavy isotope ($D_4$) internal standards at 5 µM. $D_4$ internal standards were taurocholic acid (TCA), cholic acid (CA), deoxycholic acid (DCA), taurodeoxycholic acid (TDCA), glyco-cholic acid (GCA), glycolithocholic acid (GLCA), glycoursodeoxycholic acid (GUDCA), glycochenodeoxycholic acid (GCDCA), and glycodeoxycholic acid (GDCA). Samples were heated for one hour at 70° C. with orbital shaking at 900 RPM. Solids were precipitated by centrifugation at 17000 RCF for 15 minutes at 4° C. Supernatants were decanted as 10% of the original sample (e.g. 100 µL of a 1 mL extraction sample) and evaporated at approximately 100 mTorr at RT on a rotovap (Centrivap Concentrator #7810016, Labconco, Kansas City, Mo., USA). The evaporated samples were reconstituted at 100× dilution from the original sample (e.g. 100 µL decanted solution is resuspended at 1 mL) in 20% acetonitrile, 80% water with 0.1% formic acid.

Due to small volumes, gall bladder bile samples were first diluted in 10 volumes of 100% ethanol (#3916EA, Decon Labs, King of Prussia, PA, USA). The ethanol-based dilutions were combined with 9 volumes of ultrapure water (Invitrogen) and subjected to extraction as above.

Each 10 µL extracted and reconstituted sample injection was analyzed on a Waters Acquity UPLC coupled to a Xevo-qTOF Mass Spectrometer (Waters, Manchester, UK) using an Acquity UPLC HSS T3 1.8 micron, 2.1×100 mm column (#186003539) and Acquity UPLC HSS T3 1.8 micron Guard Column (#186003976). Needle wash was two parts isopropanol, one part water, and one part acetonitrile. Purge solvent was 5% acetonitrile in water. A pooled quality control sample was run every 8 injections to correct for drift in response.

Mass spectrometer instrument parameters were as follows: Capillary Voltage 2.4 kV, Collision Energy 6.0 eV, Sampling Cone 90V, Source Offset 40 V, Source 120° C., desolvation gas temperature 550° C., cone gas 50 L/Hr, and desolvation Gas 900 L/Hr. Time-of-flight mass spectra were collected in resolution mode, corresponding to 30000 m/$\Delta$m. The mass axis was calibrated with sodium formate clusters and locked using leucine enkephalin.

A seven point external calibration curve was collected three times within the run from 0.05 to 30 µM of the bile acid standards [0.05, 0.1, 0.5, 1, 5, 10, 30 µM]. External standards were taurocholic acid (TCA), tauro-alpha-muricholic acid (TaMCA), tauro-beta-muricholic acid (TOMCA), tauro-omega-muricholic acid (ToMCA), tauro-hyocholic acid (THCA), tauro-deoxycholic acid (TDCA), tauro-ursodeoxycholic acid (TUDCA), tauro-chenodeoxycholic acid (TCDCA), taurolithocholic acid (TLCA), glyco-cholic acid (GCA), glyco-hyocholic acid (GHCA), glyco-deoxycholic acid (GDCA), glyco-hyodeoxycholic acid (GHDCA), cholic acid (CA), alpha-muricholic acid (aMCA), beta-muricholic acid (OMCA), omega-muricholic acid (oMCA), hyocholic acid (HCA, also known as 7-muricholic acid), deoxycholic acid (DCA), chenodeoxycholic acid (CDCA), ursodeoxycholic acid (UDCA), hyodeoxycholic acid (HDCA), murocholic acid (murideoxycholic acid, MDCA), lithocholic acid (LCA), glycolithocholic acid (GLCA), glycoursodeoxycholic acid (GUDCA), and glycochenodeoxycholic acid (GCDCA). It was not possible to resolve UDCA and HDCA; so the sum was reported.

Integrated areas of extracted ion chromatograms were obtained using QuanLynx (Waters, Milford, MA, USA) and a mass extraction window of 10 mDa. Final corrections accounting for drift in instrumental sensitivity were performed in Microsoft Excel.

Elution Gradient: Samples were eluted using the following gradient of water with 0.1% formic acid ("A") and balance of acetonitrile with 0.1% formic acid:
1. 0 min, 0.55 mL/min at 68% A
2. 2 min, 0.55 mL/min at 60% A, 10 curve
3. 5 min, 0.55 mL/min at 40% A, 5 curve
4. 6 min, 1.1 mL/min at 0% A, 10 curve
5. 6.2 min, 1.2 mL/min at 0% A, 6 curve
6. 6.5 min, 1.47 mL/min at 0% A, 6 curve
7. 8.9 min, 1.5 mL/min at 0% A, 6 curve
8. 9.0 min, 0.9 mL/min at 68% A, 6 curve
9. 10 min, 0.55 mL/min at 68% A, 6 curve Bile acid data processing and analysis was performed using the software tools described for sequencing data processing.

Example 12: Absolute Quantification of Target Microbiota to Verify Effect of Coprophagy in Mice In this example, a pilot study was performed to confirm that preventing coprophagy in mice would result in decreased viable microbial load and altered microbiota composition in the small intestine.

A most probable number (MPN) assay utilizing anaerobic BHI-S broth medium was used to evaluate the live (culturable) microbial loads along the entire GIT of mice known to be coprophagic (housed in standard cages in groups, N=5) and mice known to be non-coprophagic (fitted with tail cups and housed in standard cages in groups, N=5).

Consistent with the published, classical literature [147, 148], it was found that coprophagic mice had significantly higher loads of culturable microbes in their upper GIT than mice that were non-coprophagic (FIG. 36, panel A). Moreover, the microbial community composition in the proximal GIT, particularly in the stomach, of coprophagic mice more closely resembled the microbial composition of the large intestine (FIG. 36, panel B) as revealed by 16S rRNA gene amplicon sequencing (N=1 mouse analyzed from each group) and principal components analysis (PCA) of the resulting relative abundance data.

Figure 28:
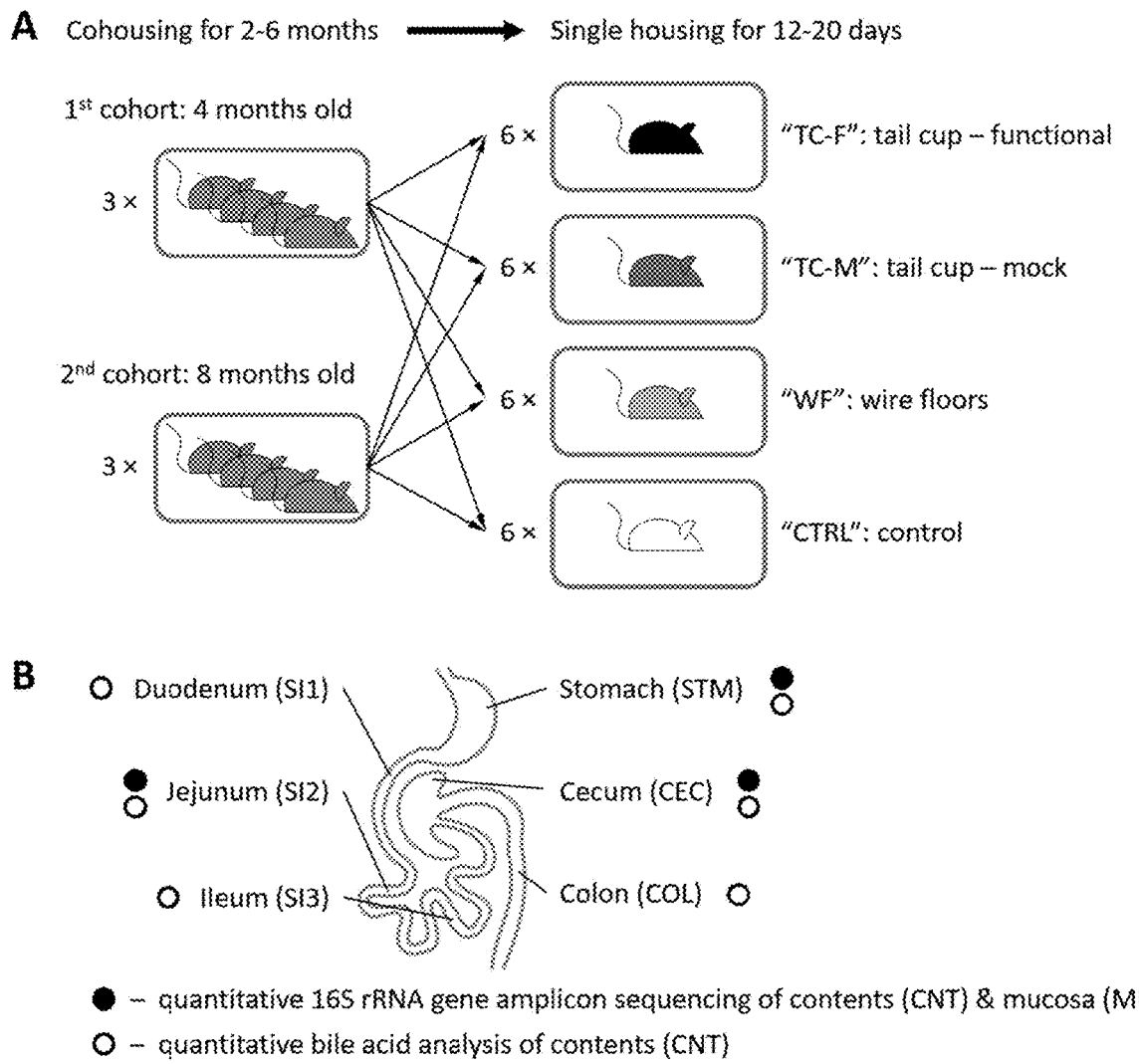
FIG. 28 shows an overview of the study design and timeline.

This pilot study confirmed that tail cups were effective at preventing the self-reinoculation of viable fecal flora in the upper GIT of mice. These results spurred the Applicant to design a rigorous, detailed study (FIG. 28) to answer the three questions using the quantitative 16S rRNA gene amplicon sequencing (to account for both changes in the total microbial load and the unculturable taxa), quantitative functional gene content inference, and targeted bile-acid metabolomics analyses: (1) Do quantitative 16S rRNA gene amplicon sequencing tools detect differences in small-intestine microbial loads between mice known to be coprophagic and non-coprophagic? (2) Does coprophagy impact the microbial composition of the small intestine? (3) Do differences in microbiota density and composition associated with self-reinoculation in mice impact microbial function (e.g., alter microbial metabolite production or modifications) in the small intestine?

Example 13: Absolute Quantification of Target Microbiota to Verify Effect of Coprophagy in Mice-Study Design A set of experiments was designed to provide a study directed to determine the effect of coprophagy in mice by performing absolute quantification of target microbiota in mice.

The study design (FIG. 28) consisted of six cages of four animals each that were co-housed for 2-6 months and then split into four experimental groups and singly housed for 12-20 days.

The four experimental conditions were: animals fitted with functional tail cups (TC-F) and singly housed in standard cages, animals fitted with mock tail cups (TC-M) and singly housed in standard cages, animals singly housed on wire floors (WF), and control animals singly housed in standard conditions (CTRL).

At the end of the study, gastrointestinal contents and mucosal samples were collected from all segments of the GIT of each animal and we evaluated total microbial loads (entire GIT) and microbiome composition (stomach (STM), jejunum (SI2), and cecum (CEC)).

The cecum segment of the large intestine was selected for quantitative 16S rRNA gene amplicon sequencing because the analysis of the contents of this section can provide a complete snapshot of the large-intestine and fecal microbial diversity in response to environmental factors [149-151]. Cecal contents also enabled us to collect a more consistent amount of sample from all animals across all experimental conditions (whereas defecation may be inconsistent among animals at the time of terminal sampling).

Example 13: Absolute Quantification of Microbiota Indicates that Self-Reinoculation Increases Microbial Loads in the Upper Gut The study set up according with the indications of Example 12 was performed to answer the a first question: can quantitative sequencing tools detect the difference in 16S rRNA gene DNA copy load in the upper GIT of mice known to be coprophagic and non-coprophagic?

Figure 29:
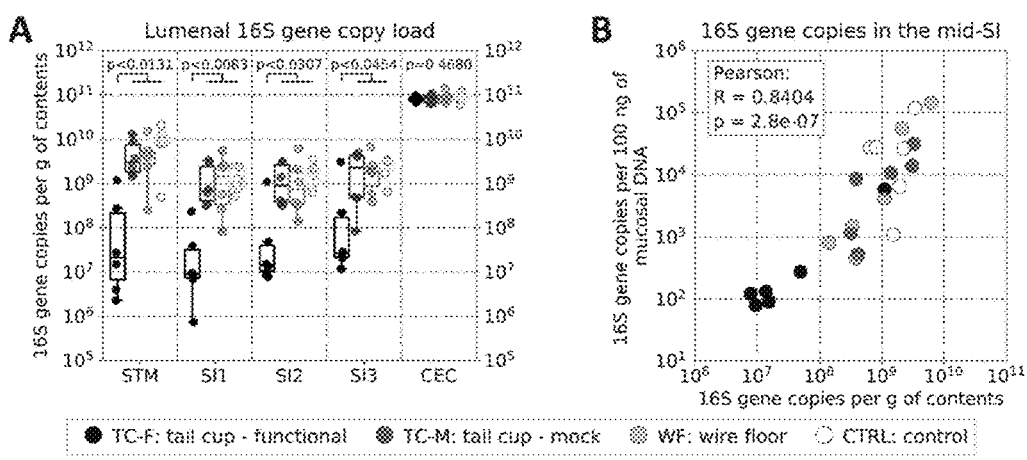
FIG. 29 shows the quantification of microbial loads in lumenal contents and mucosa of the gastrointestinal tracts (GIT) of mice in the four experimental conditions: (functional tail cups (TC-F), mock tail cups (TC-M), housing on wire floors (WF), and controls housed in standard conditions (CTRL).

With this goal in mind, total quantifiable microbial loads were analyzed across the GIT using 16S rRNA gene DNA quantitative PCR (qPCR) and digital PCR (dPCR). Preventing self-reinoculation in mice equipped with functional tail cups dramatically decreased the lumenal microbial loads in the upper GIT but not in the lower GIT (FIG. 29, panel A). Total quantifiable microbial loads in the upper GIT were reduced only in mice equipped with functional tail cups. All other experimental groups of singly-housed animals (those equipped with mock tail cups, housed on wire floors, or housed on standard woodchip bedding) that retained access to fecal matter and practiced self-reinoculation had similarly high microbial loads in the upper GIT, as expected from the published literature [117, 152-157].

Across all test groups, mucosal microbial loads in the mid-small intestine demonstrated high correlation (Pearson's $R=0.84$, $P=2.8 \times 10^{-7}$) with the microbial loads in the lumenal contents (FIG. 29, panel B).

Stomach (STM) and small-intestine (SI1, SI2, and SI3) samples from one (out of six) of the TC-F mice showed higher microbial loads compared with the other TC-F mice. The total microbial load in the upper GIT in this TC-F mouse was similar to mice from all other groups (TC-M, WF, CTRL), which emphasizes the crucial importance of performing analyses of both microbial load and composition (discussed below) on the same samples.

Example 14: Absolute Quantification Indicates that Self-Reinoculation Substantially Alters the Microbiota Composition in the Upper Gut but has Less Pronounced Effects in the Large Intestine The study set up according with the indications of Example 12 was performed to answer the a second question: does self-reinoculation with fecal microbiota impact upper GIT microbial composition?

With this goal in mind, quantitative 16S rRNA gene amplicon sequencing [1, 17] was performed on stomach (STM), jejunum (SI2), and cecum (CEC) samples.

Figure 30:
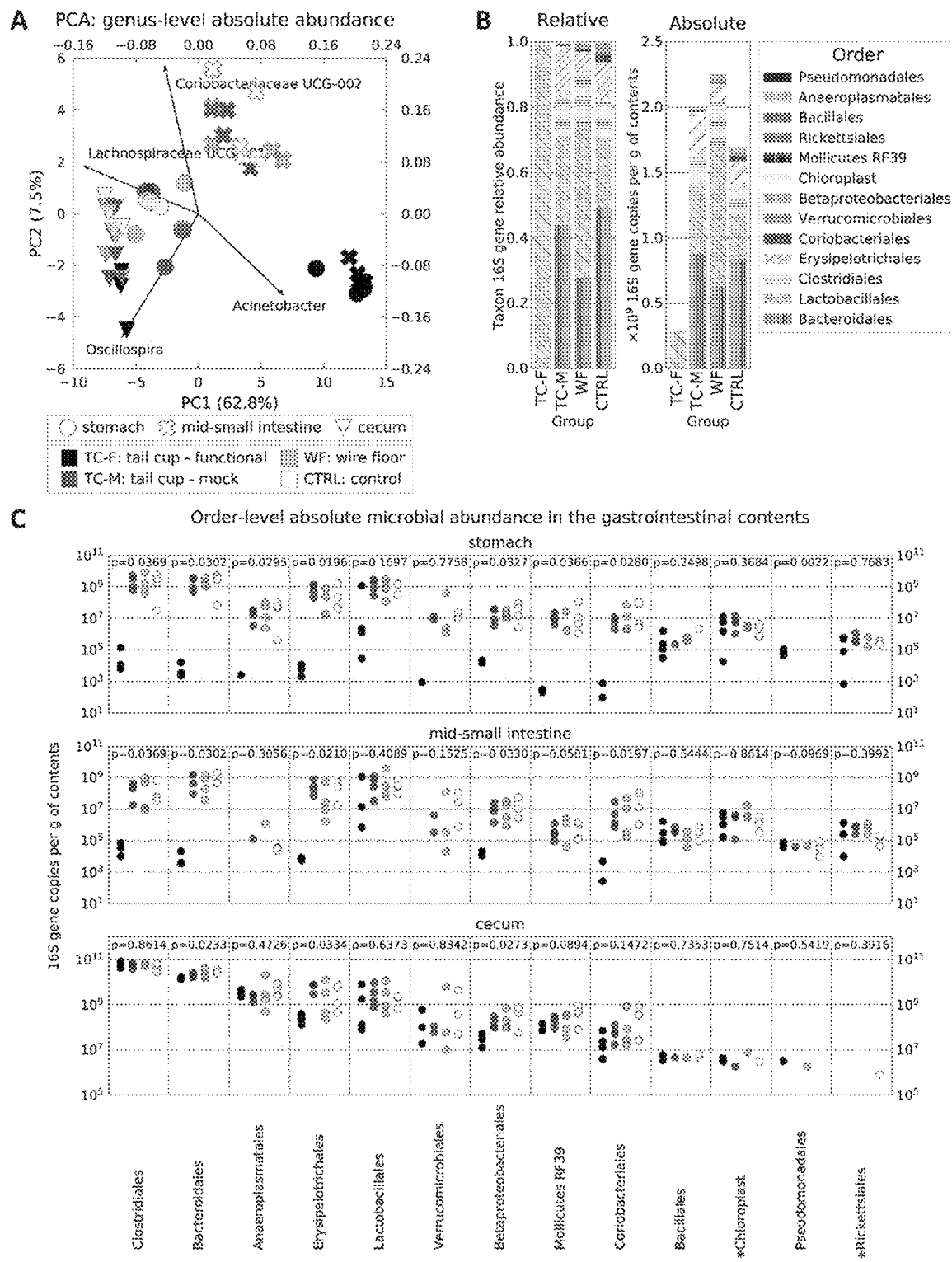
FIG. 30 shows the compositional and quantitative 16S rRNA gene amplicon sequencing of the gut microbiota.

Qualitative sequencing revealed dramatic overall changes in the upper GIT microbiota caused by self-reinoculation (FIG. 30). An exploratory PCA performed on the multidimensional absolute microbial abundance profiles highlights the unique and distinct composition of the upper GIT microbiome of non-coprophagic mice (FIG. 30, panel A). It is noteworthy that the stomach (STM) and small-intestine (SI2) microbiota in all coprophagic mice clustered closer to the large-intestine microbiota, suggesting the similarity was due to persistent self-reinoculation with the large-intestine microbiota (FIG. 30, panel A).

Self-reinoculation had differential effects across microbial taxa (FIG. 30, panel C), which could be classified into three main categories depending on the pattern of their change:
1. "Fecal taxa" (e.g., Clostridiales, Bacteroidales, Erysipelotrichales) that either dropped significantly or disappeared (fell below the lower limit of detection [LLOD] of the quantitative sequencing method [1, 17]) in the upper GIT of non-coprophagic mice;
2. "True small-intestine taxa" (e.g., Lactobacillales) that remained relatively stable in the upper GIT in non-coprophagic mice;
3. Taxa that had lower absolute abundance in the cecum (e.g., Bacteroidales, Erysipelotrichales, Betaproteobacteriales) of non-coprophagic (compared with coprophagic) mice.

The results demonstrated that preventing self-reinoculation dramatically reduced the total levels of several prominent taxonomical groups of obligate anaerobes (e.g., Clostridiales, Bacteroidales, Erysipelotrichale) in the upper gastrointestinal microbiota of conventional mice. Despite these differences in taxa, levels of Lactobacillales in the small intestine and cecum, but not in the stomach, remained similar between coprophagic and non-coprophagic animals (FIG. 30, panel C). The physiological significance of the maintained persistent population of Lactobacillales in the upper gastrointestinal tract (e.g., stomach or small intestine) and their overall consistent presence along the entire GIT [158, 159] for the host is not fully understood. However, Lactobacilli colonization in the stomach and small intestine has been shown to promote resistance to colonization by pathogens (reviewed in [160, 161]).

Overall, the composition of the small-intestine microbiota of coprophagic mice was consistent with that previously reported in literature [149]. The upper-GIT microbiota in non-coprophagic mice was dominated by Lactobacilli (FIG. 30, panel C), known to be a prominent microbial taxon in human small-intestine microbiota [162-164]. Importantly, the compositional analysis showed that the single TC-F mouse that had high microbial loads in its stomach and small intestine had a microbial composition in those segments of the GIT similar (i.e., dominated by Lactobacillales) to all other TC-F mice, and very distinct from all coprophagic mice (FIG. 30, panels B,C). The PCA showed that the stomach and mid-small intestine of this mouse clustered with the stomach and mid-small intestine of all other TC-F mice (FIG. 30, panel A).

Example 15: Absolute Quantification of Target Microbiota Indicates that Changes in the Small-Intestine Microbiota Lead to Differences in Inferred Microbial Functional Gene Content Absolute quantification was performed to verify whether the quantitative and qualitative changes in the small-intestine microbiota induced by self-reinoculation result in altered microbial function [7, 165] and an altered metabolite profile, either indirectly, as a result of functional changes in the microbiota, or directly via re-ingestion of fecal metabolites.

To understand how such alterations to microbiota would impact microbial function in the small intestine, experiments were carried out to predict how the absolute abundances of functional microbial genes would be affected. The pipeline for microbial functional inference based on the 16S rRNA marker gene sequences (PICRUSt2) [45, 46] was coupled with the quantitative 16S rRNA gene amplicon sequencing approach [1, 17]. The analysis was focused on microbial functions that would be highly relevant to small-intestine physiology: microbial conversion of host-derived bile acids and microbial modification of xenobiotics.

Figure 31:
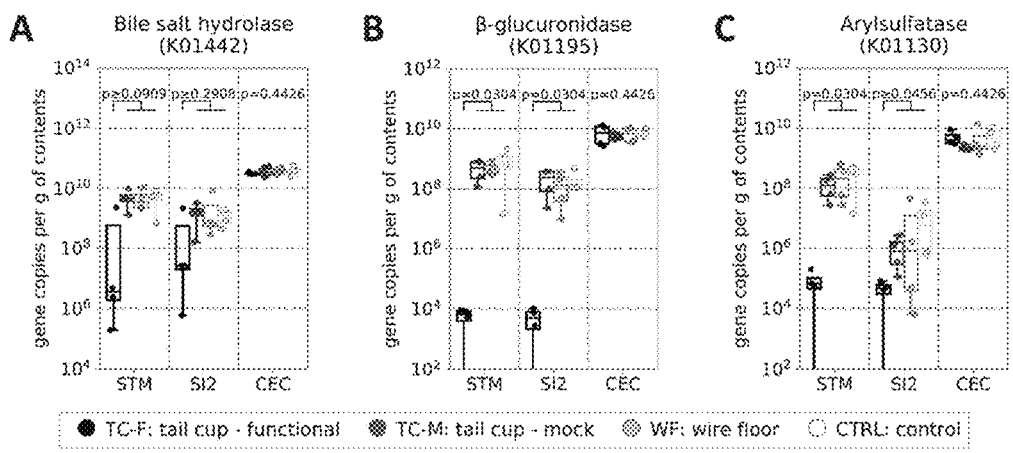
FIG. 31 shows the inference of microbial genes involved in bile-acid and xenobiotic conjugate modification along the GIT of coprophagic and non-coprophagic mice. Inferred absolute abundance of the microbial genes encoding (FIG. 31 Panel A) bile salt hydrolases (cholylglycine hydrolases), (FIG. 31 Panel B) beta-glucuronidases, and (FIG. 31 Panel C) arylsulfatases throughout the GIT (STM=stomach; SI2=middle third of the small intestine (SI) roughly corresponding to the jejunum; CEC=cecum). KEGG orthology numbers are given in parentheses for each enzyme. In all plots, individual data points are overlaid onto box-and-whisker plots; whiskers extend from the quartiles (Q2 and Q3) to the last data point within 1.5× interquartile range (IQR). Multiple comparisons were performed using the Kruskal-Wallis test; pairwise comparisons were performed using the Wilcoxon-Mann-Whitney test with FDR correction. N=4 mice per group.

It was found that the inferred absolute abundances of a number of microbial gene orthologs implicated in enzymatic hydrolysis of conjugated bile acids (bile salt hydrolase, BSH [166-168]) and xenobiotic conjugates (e.g., beta-glucuronidase, arylsulfatase [169, 170]) in the stomach and the small intestine of coprophagic mice were dramatically higher (in some cases by several orders of magnitude) than in non-coprophagic mice (FIG. 31). This difference was not observed in the cecum.

Example 16: Absolute Quantification Indicates that Changes in the Small-Intestine Microbiota Induced by Self-Reinoculation Alter the Bile Acid Profile Bile acids are a prominent class of host-derived compounds with multiple important physiological functions and effects on the host and its gut microbiota [171, 172]. These host-derived molecules are highly amenable to microbial modification in both the small and large intestine [173]. The main microbial bile-acid modifications in the GIT include deconjugation, dehydrogenation, dehydroxylation, and epimerization [172].

Thus, in this example quantitative bile acid profiling along the entire GIT was performed to evaluate the effects of self-reinoculation on bile acid composition.

The small intestine is the segment of the GIT that harbors the highest levels of bile acids (up to 10 mM) and where they function in lipid emulsification and absorption [174-176]. Given these high concentrations of bile acid substrates, we specifically wished to analyze whether the differences observed in small-intestine microbiota (FIGS. 29-30) between coprophagic and non-coprophagic mice would result in pronounced effects on microbial deconjugation of bile acids. Applicant also wished to test whether any differences in bile-acid deconjugation were in agreement with the differences in the absolute BSH gene content we inferred (FIG. 31, panel A) from the absolute microbial abundances (FIG. 30, panel C).

Figure 32:
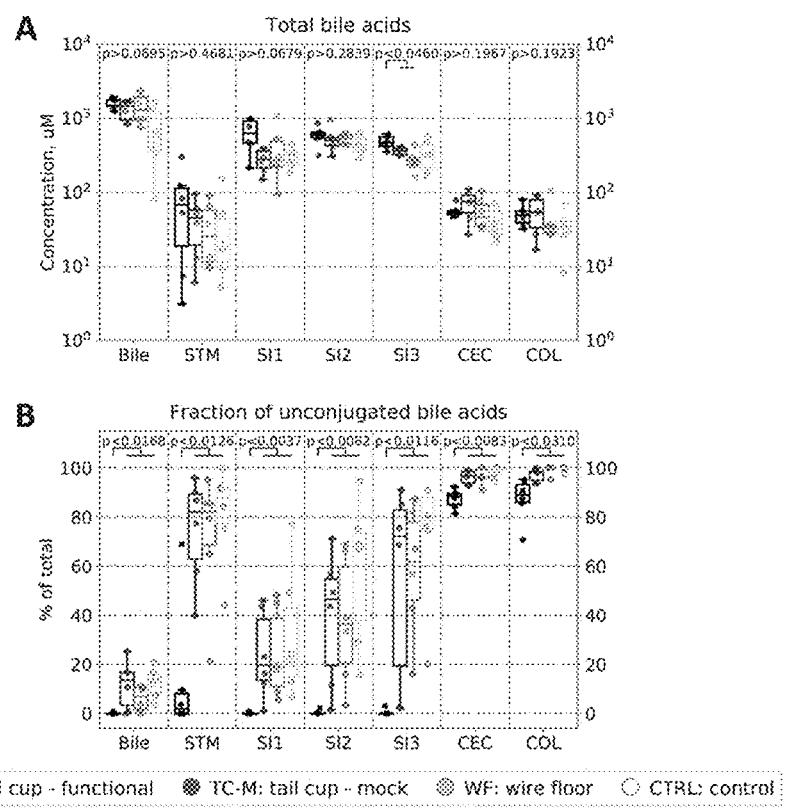
FIG. 32 shows the bile acid profiles in gallbladder bile and in lumenal contents along the entire GIT.

It was first confirmed that in all four experimental groups, total bile acids levels (conjugated and unconjugated; primary and secondary) across all sections of the GIT were highest in the small intestine (FIG. 32, panel A). The levels of conjugated and unconjugated (FIG. 32, panel B) as well as primary (host-synthesized) and secondary (microbe-modified) bile acids (FIG. 37) were then compared between coprophagic and non-coprophagic mice.

Across all sections of the GIT and in bile, non-coprophagic mice (TC-F) had significantly lower levels of unconjugated bile acids compared with coprophagic mice (FIG. 32, panel B). Consistent with the computational inference in FIG. 31, panel A (performed on mid-SI samples only), in all three sections of the small intestine of non-coprophagic mice (TC-F), the levels of unconjugated bile acids were substantially lower than in coprophagic mice. Almost 100% of the total bile acid pool remained in a conjugated form in the small intestine of non-coprophagic mice.

In all groups of coprophagic mice (TC-M, WF, and CTRL) the fraction of unconjugated bile acids gradually increased from the proximal to distal end of the small intestine. Gallbladder bile-acid profiling (FIG. 32, panel B) confirmed that bile acids were secreted into the duodenum predominantly in the conjugated form in all coprophagic mice. This pattern is consistent with the hypothesis that the exposure of bile acids to microbial deconjugation activity increases as they transit down a small intestine with high microbial loads (FIG. 29, panel A) [174].

In the large intestine, non-coprophagic (TC-F) mice carried a smaller fraction of unconjugated bile acids compared with all coprophagic experimental groups (FIG. 32, panel B).

Bile acid deconjugation in the small intestine of coprophagic mice was uniform for all glyco- and tauro-conjugates of all primary and secondary bile acids measured in our study, suggesting a broad-specificity BSH activity was provided by a complex fecal flora in the small intestine of those animals.

Figure 37:
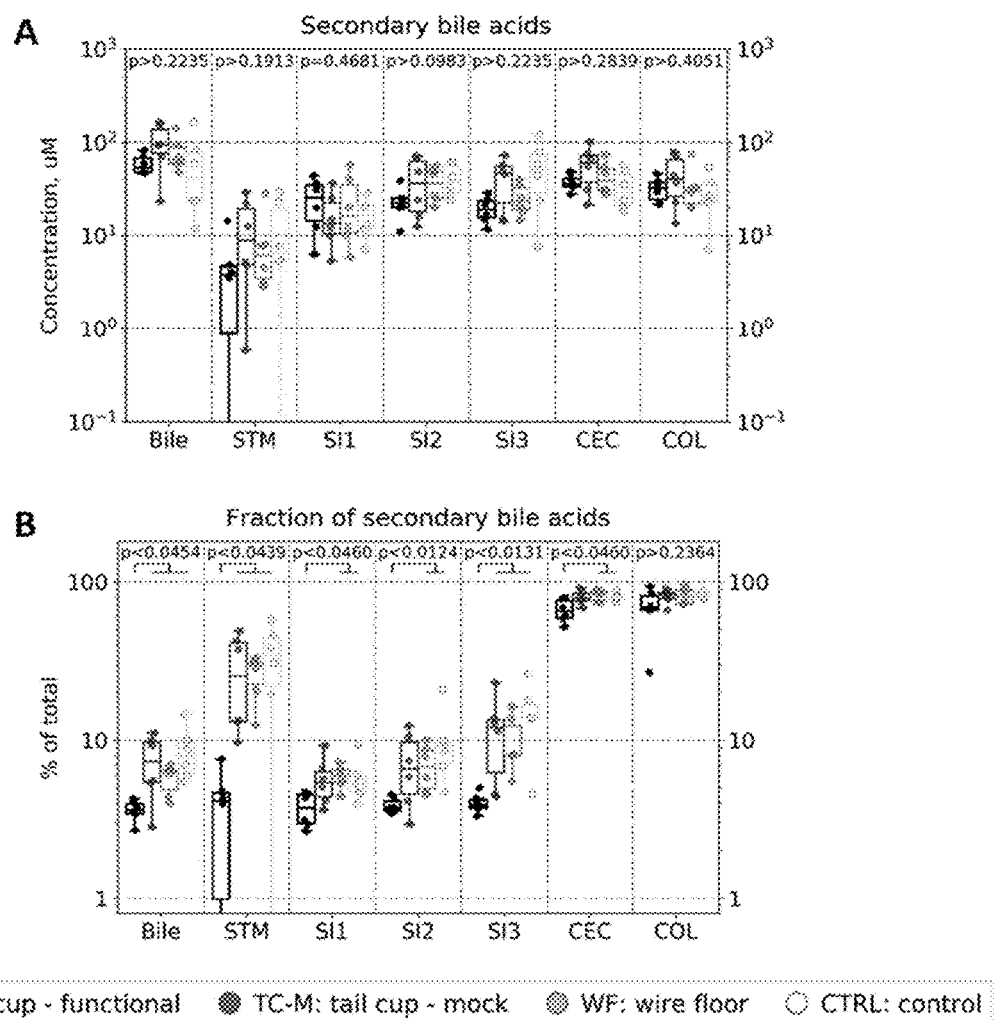
FIG. 37 shows the bile acid profiles in gallbladder bile and in lumenal contents along the entire GIT.
Figure 44:
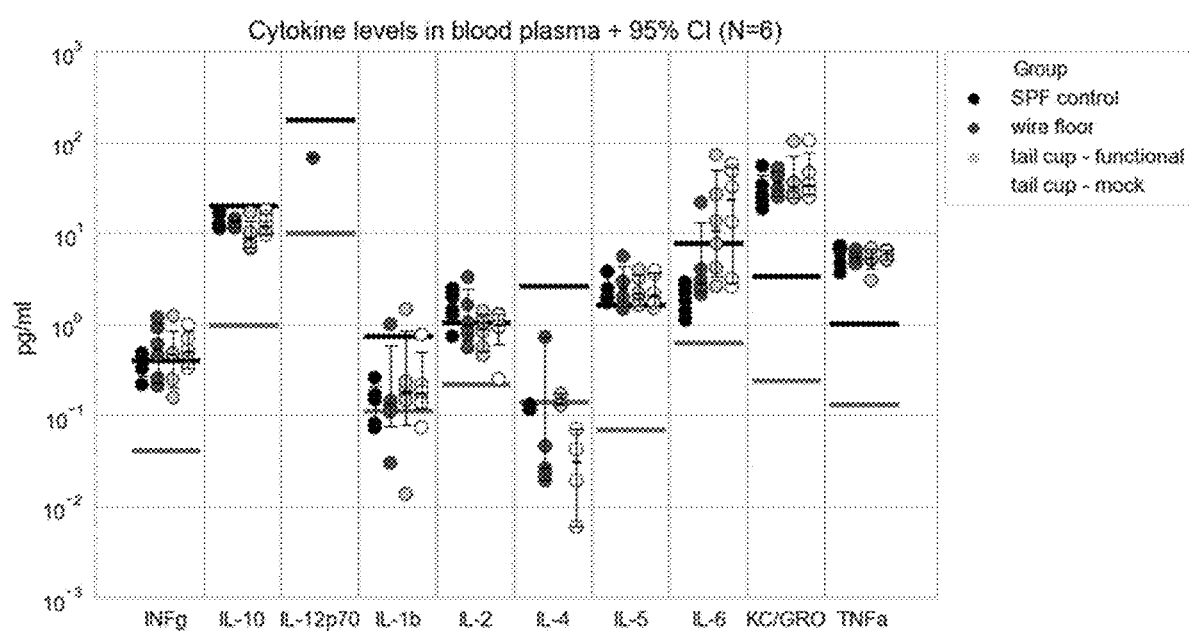
FIG. 44 shows the cytokine levels in blood plasma cross all four groups of animals. The cytokine levels did not demonstrate robust group-dependency. INFg, IL-1b, IL-2, IL-4, IL-6, IL-10, and IL-12p70 in the majority of animals were present at the levels below the lower limit of quantification (LLOQ) (black horizontal line) of the assay. A trend towards higher IL-6 in both groups of mice fitted with either functional or mock tail cups could suggest the stress-related increase of this cytokine.
Figure 45:
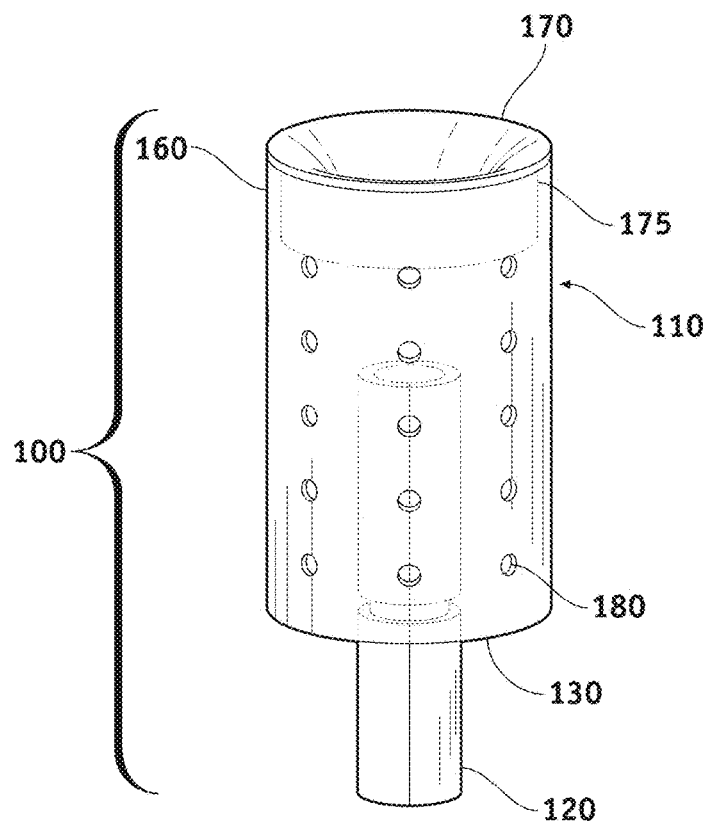
FIGS. 45 to 48 show a schematic representation of a tail-cup device in accordance with some embodiments of the present disclosure.

In gallbladder bile and across all segments of the GIT from the stomach to the cecum, non-coprophagic mice had a statistically significantly lower fraction of total secondary bile acids (conjugated and unconjugated) than coprophagic mice (FIG. 37). This change was uniform for the entire secondary bile acid pool of those analyzed. The only segment of the gut in which the difference in the fraction of secondary bile acids was not statistically significant between coprophagic and non-coprophagic mice was the colon. In fact, the differences in the fractions of total unconjugated and total secondary bile-acids between coprophagic and non-coprophagic mice would have gone largely undetected had we only analyzed colonic contents or stool. These findings further highlight the importance of the comprehensive spatial interrogation of the complex crosstalk between the microbiota and bile acids in the gastrointestinal tract.

Example 17: Absolute Quantification Performed on 16 rRNA Ribonucleotides—Prophetic Samples can be collected from mice and the related RNA extracted.

The total RNA can be extracted from fresh or frozen fecal samples using Qiagen Allprep Powerviral DNA/RNA kit (28000-50; Qiagen) according to the manufacturers protocol.

RNA can then be reverse transcribed into DNA. Briefly, a 20 uL reaction was set up including 10 uL of sample, 0.25 uL of WarmStart RTx (M0380L; New England Biolabs Inc), 9.25 uL of nuclease free water, 0.5 uL of Riboguard RNase inhibitor (RG90910K; Lucigen), 1.25 uL of 10 mM dNTP mix (N0447S; New England Biolabs Inc), 2.5 uL of 10× isothermal amplification buffer (B0537S; New England Biolabs Inc), and 1.25 uL of reverse (UN00R0, '-GGAC-TACHVGGGTWTCTAAT-3' [16, 18]) primer (SEQ ID NO: 26) (Integrated DNA Technologies, San Diego, CA, USA) at the final concentration of 500 nM.

The reverse transcription thermocycling protocol can be set up as follows: Primer annealing at 25° C. for 5 mins, cDNA synthesis at 55° C. for 10 mins, and enzyme heat inactivation at 80° C. for 10 mins.

Assay can be performed on a real-time PCR instrument (CFX96 Real-Time PCR Detection System, Bio-Rad Laboratories).

The output cDNA template from this step then followed the protocol in Example 1 for generation of barcoded amplicon libraries for sequencing.

Example 18: Tail Cup Design to Prevent Self-Reinoculation

Functional tail cups have been shown to reliably prevent the self-reinoculation with fecal flora. However, the tail cup approach has limitations. Tail cups in the current design may not be suitable for female rodents due to anatomical differences leading to urine entering and remaining inside the devices [177]. Animals need to be singly housed to prevent them from gnawing on each other's tail cups and causing device failure or injury. The tail cup approach may be hard to implement in younger and actively growing mice (e.g., before or around weaning). Some mice in the study developed self-inflicted skin lesions from over-grooming at the location where the tail cups come in contact with the body at the animal's hind end. Thus, the approach in its current implementation is limited to 2-3 weeks in adult animals.

Figure 35:
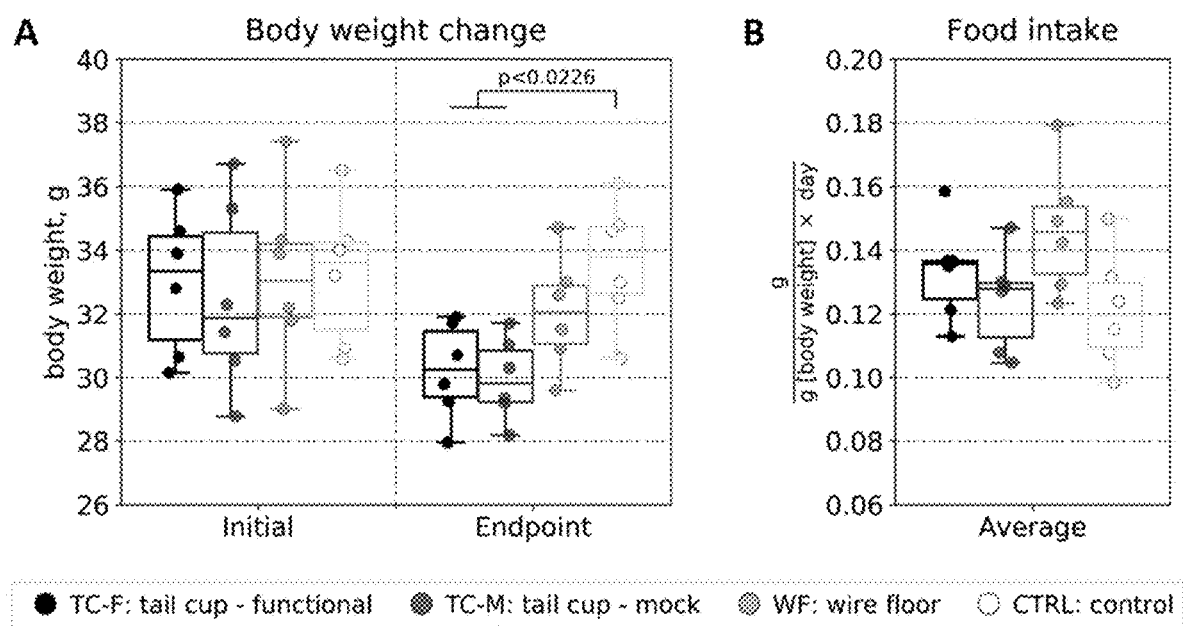
FIG. 35 shows a plot of body weight changing across all groups of mice in relation to food intake over the course of the study.

Applicant's device design reduced the risk of tail injury and necrosis described in previous works [178] and allows for emptying the cups only once every 24 hours to reduce handling stress. Because host stress can affect the microbiota [179] and other physiological parameters, a mock tail-cup group was included. Both TC-F and TC-M mice demonstrated a similar degree of weight loss (FIG. 35, panel A) when compared with the WF and CTRL mice despite similar food intake rates across all four groups (FIG. 35, panel B). Mice fitted with mock tail cups (TC-M) had microbial patterns and bile acids profiles similar to control mice (CTRL), thus the effects we observed in non-coprophagic mice are not attributable to stress.

The current tail cup approach is also implementable in gnotobiotic settings (e.g., flexible film isolators and individually ventilated cages), which can aid studies that involve association of mice with defined microbial communities or with human-derived microbiota.

An additional description is provided with reference to FIGS. 45-48 showing an exemplary a tail cup device (100) for animals such as rodents, the device comprised of a cup (110) for trapping excreted feces and a tail sleeve (120) for mounting of the cup (110) at a tail base of a rodent having a sufficiently long tail, such as mice (including deer mouse, Natal multimammate mouse, vesper mouse, long-tailed pocket mouse, little pocket mouse, canyon mouse, members of the genus harvest mouse) or rats (including cotton rat, obese sand rat, rice rat, white-tailed rat, kangaroo rat, desert woodrat), degu, voles (bank, red-backed vole, meadow vole, mountain vole, tundra vole, prairie vole, woodland/pine vole, Brandt's vole, California vole), gophers (e.g., pocket gophers), mole-rats (e.g., naked mole-rat, Damaraland mole-rat), and moles, the tail sleeve (120) being configured to be applied to the tail of the rodent.

In the illustration of FIGS. 45-48, the cup (110) is a tubular-shaped component configured to trap fecal matter and prevent the rodent from accessing it, with an exemplary length of 2-5 cm and an exemplary diameter of 1-3 cm. While FIGS. 45-48, show a circular or oval cross section by way of example, any other shape, e.g. rectangular, can be devised by the person skilled in the art. Additionally, while the drawings show a generally uniform cross-section of the cup along its length, embodiments are also possible where larger cross-section areas are provided close to one end of the cup (110) and smaller cross-section areas are provided close to the other end of the cup (110).

In the illustration of FIGS. 45-48, the distal end or surface (130) of the tubular cup (110) comprises an orifice (140) operating as a locking opening of the cup (110) to allow passing through of the tail sleeve (120) from the inside to the outside of the cup (110). The orifice (140) may be round, oval or of similar shape with an exemplary 0.5-0.7 cm diameter. In order to allow a proper locking engagement of the tail sleeve (120) when applied to the tail of the rodent and when pressure is not applied to the sides of the cup (110), the diameter (or at least one of the two axes) of the orifice (140) is smaller than the diameter of the tail sleeve (120). While the figures show a central placement of the orifice (140) on the distal surface (130), off-center placements are also possible. Off-center placement of the orifice, for example closer to the dorsal side of the cup, would allow for an increased size (centrally asymmetric on the cross-section and linearly asymmetric on a longitudinal section) cup compartment on the ventral side of the cup where fecal matter may accumulate under gravity when animals spend most of their time in their natural prone position.

In the illustration of FIGS. 45-48, distal surface (130) also includes an unlocking slit (150A-D) for opening of the cup (110) before or after use. Unlocking slit (150A-D) has a narrow diameter when compared with other dimensions of the cup (110), usually less than 1.0 mm. While the unlocking slit includes portions (150A), (150B) across the orifice (140) on the distal surface (130), intersecting the orifice (140) and spanning along a diametral extension of the distal surface (130), it also includes side portions (150C), (150D) extending along opposite side walls of the cup (110). Other embodiments can also be provided (e.g. in case the locking orifice is placed off-center) where the unlocking slit crosses the orifice along a chord extension (for circular devices) of the distal surface. The purpose of the unlocking slit is to install/unlock the tail sleeve (120) in/from the orifice (140) by increasing the gap formed by the orifice (140) through pression (e.g. with fingers, such as thumb on one side and index on the other while holding the cup) alongside portions (150C), (150D), e.g. on pressing points (150CC) and (150DD), corresponding to the ends of their respective side portions. These pressing points can have no specific shape at all and just be located at the straight end of their respective side portions, or can have a shape (e.g. circular with a 1-2 mm diameter) to address deformation stress dissipation concerns upon enlargement of the orifice. If desired, as also shown in the drawings, the pressing points (150CC), (150DD), can be placed on opposite sides of the cup (110) (e.g. 180 degrees apart in case of a cylindrical embodiment) to allow for a stronger hold of the cup (110) while applying pressure, thus providing better structural integrity and responsiveness to the pressing force. The length of side portions (150), (150D) depends on parameters such as cup length, shape, cross section profile, size and material and should be chosen to allow a sufficient increase of the orifice and unlocking slit when unlocking the cup (110) from the tail sleeve (120) upon application on the pressing points (150CC), (150DD) to allow removal of the cup (110) from the rodent and/or related emptying of the cup (110), while not compromising the mechanical integrity of the device, not increasing the risk of the locking mechanism failure, and the cup's purpose to effectively entrap fecal matter. While the figures exemplary show a flat arrangement of the distal surface (130), such surface can also be spherical, conical or differently shaped, if required.

In the illustration of FIGS. 45-48, reference will now be made to the proximal end or surface (160) of the cup (110), the proximal end having a cross sectional dimension sufficiently wide to fit around a posterior end of the rodent more proximal than the anus to ensure falling of the fecal pellets into the cup, but also preferably more distal than the urethral opening and genitals to prevent urine from accessing the cup and from discomfort or damage to the genital area of the animal. While the proximal surface (160) can be shaped as a straight/flat cut as shown in the figures, embodiments are also possible where the proximal surface is carved or shaped to better fit around the rodent's posterior end and better accommodate for the genital anatomy of the rodent, varying between genders.

In the illustration of FIGS. 45-48, a reinforcement and/or protective ring (170) is located along the proximal end (160) and is configured to come in contact with a body (skin) portion close to and/or around the genital area of the rodent, which portion the rodent may be able to reach with its mouth and/or teeth. The reinforcement and/or protective ring (170) is made from an inert (in order not to corrode or leak any chemical compounds) material hard enough to prevent the animal from damaging it by chewing (which would necessitate cup replacement), such as metal (e.g. medical grade stainless steel, titanium and/or suitable metal alloys), ceramic, glass, tough plastic (such as PTFE/Teflon or Kevlar) and/or combinations of the same. Usage of soft materials would likely result in deterioration of the proximal end of the cup due to rodents chewing on it, thus resulting in the proximal edge of the cup becoming jagged or sharp and potentially leading to severe skin damage when the rodent moves around and the cup's edge rubs against the skin.

In the illustration of FIGS. 45-48, the reinforcement and/or protective ring (170) comprises a proximal flange, an internal conical (funnel) or round section and a distal cylindrical part.

The internal section of the reinforcement and/or protective ring (170) fitting around the animal body may have a conical shape to allow for a more effective fecal entrapment inside the cup in cases where the rodent is allowed to freely mode around, frequently resulting in the tail cup and the animal's tail tilting to the sides away from the longitudinal body axis. On the other hand, a round shape of the internal section has the advantage of serving as a joint surface when the animal moves around and the cup rubs against the animal's body/skin. Overall the design of the proximal end of the cup should allow for some degree of freedom/motion (not only axial rotation) relatively to the animal's posterior end, at least partially matching the degree of freedom/motion characteristic for the tail base, in order to minimize or eliminate any inhibition of animal's physical activity/motion.

On the other hand, in the illustration of FIGS. 45-48, the outside diameter of the flange of the reinforcement and/or protective ring (170) is comparable to or larger than the cross-sectional extension (e.g. diameter) of the cup to ensure that the edge of the proximal surface (end) (160) of the cup (110) is not exposed to chewing. To further prevent animals from chewing on the proximal edge of the cup, the reinforcement and/or protective ring (170) may be installed to allow for some gap (e.g. 2-3 mm) between the flared edge of the ring and the edge of the proximal surface (edge) of the cup. If desired, the flared edge of the ring (170) may also be configured to wrap around the edge of the cup. Given that the material of the ring is harder than the material of the cup this provides better protection from the animal's teeth.

Additionally, placement of the reinforcement and/or protective ring (170) at the proximal end of the cup (110) may be adjustable in order to control the snug fit of the cup (110) against the animal's posterior end after installation of the tail sleeve (120).

In its current exemplary implementation, reinforcement and/or protective ring (170) is made by a stainless steel grommet with reduced flange edge diameter and length, performed with a cutter on a lathe to improve size and reduce weight, thus resulting in a straight proximal edge of the cup (110). The person skilled in the art will understand that if the proximal edge is carved more anatomically than the reinforcement and/or protective ring, it will have to be shaped accordingly.

As shown in the illustration of FIGS. 45-48, reinforcement and/or protective ring (170) is preferably coupled (e.g. attached) to cup (110) using a coupling ring (175) (made of e.g. latex or plastic tubing). Presence of the coupling ring (175) also allows adjusting the depth and placement of the reinforcement and/or protective ring (170) inside the cup (110), thus tuning the fit or snugness of the cup (110). Embodiments are also possible where coupling ring (175) is not needed when the cup itself is made such that the reinforcement and/or protective ring (170) can be attached to the cup directly. It should be noted that a simple soldering and/or gluing of the ring would not be preferred, as it would not allow an adjustable arrangement.

Cup (110) may be made from a clear (e.g. transparent, such as polypropylene) material to allow for an easier observation of the device degree of filling with animal excretions. However, an opaque (e.g. non-transparent) material may be preferred in cases where the excretions need to be protected from light, e.g. for further analysis. The material can be, for example, a mesh material with an exemplary mesh size of up to 1 mm.

Cup (110) may also comprise venting perforations or boreholes (180) to allow for the fecal excretions to accelerate the desiccation of trapped fecal excretions and prevent moisture entrapment. Advantageously, drying fecal pellets distribute uniformly within the cup when the animal moves around. If fecal excretions are not allowed to dry, they could potentially stick to the inside surface of the cup and build up around the anus, likely imposing some resistance for further defecation, an important animal welfare consideration. The venting perforations (180) can be of different shape, size, number, and distribution considering that: a) their size should be small enough and their shape (e.g. round) should be designed to prevent the fecal pellets from falling out, especially after drying and/or shrinking. The number of the perforations should be sufficiently large and their distribution should be sufficiently uniform to allow faster fecal matter desiccation.

Reference will now be made to the tail sleeve (120) of the illustration of FIGS. 45-48, which is configured to hold the cup snugly against the posterior end of the animal while at the same time maximizing distributing the opposing force over a larger surface area of the tail skin to reduce the damaging effects of such shear force on the skin and other potential negative effects such as tail strangulation. At the same time the sleeve (if made from a stiffer material) should only cover a fraction of the tail (e.g. less than a half of the total length) to allow for some degree of freedom/motion of the distal part of the tail and not to inhibit the animal's movement.

As shown in FIG. 47, tail sleeve (120) comprises a longitudinally split or open tubular component (210) (having an exemplary length of 2-5 cm, an exemplary inside diameter of ⅛"-comparable to or slightly smaller than the tail outside diameter at the tail base- and an exemplary outside diameter of ¼") and an intermediate locking groove (220) on its outside surface, the latter configured to allow locking of the tail sleeve (120) through the orifice (140) of the cup (110). In particular, the outside diameter of the groove (220) can be smaller than the outside diameter of the tubular component (210) and also slightly smaller than the orifice or locking opening (140) of the cup (110). In order to accommodate for variable tail diameters among animals along the tail length, a longitudinal strip of the wall of the sleeve (e.g. 1-2 mm wide) can be optionally removed to prevent uneven tail compression and to facilitate uniform application of adhesive force as later explained.

In the illustration of FIGS. 45-48, the tubular component can be cylindrically or conically shaped (to accommodate the slightly conical tail shape) and may have various degrees of softness or stiffness, but it should be sufficiently soft to conform to the tail shape upon installation without applying excessive pressure and sufficiently stiff not to overstretch or deform in order to withstand the shear force from the snugly fit cup (110) when locked onto it. As with the cup (110), also the sleeve (120) may be opaque or clear for easier tail health monitoring. In accordance with an embodiment of the disclosure, the tubular component is made from a material devoid of components that upon leaking from the material can be toxic to the animal (e.g., plasticizer-free tubing) as it can come in contact, in some cases, with the tail skin through a layer of curable adhesive or adhesive tape, both of which can potentially aid the extraction of toxic components from the material of the tubular component. Potential alternatives can include surface patterning, e.g. nano- or micro-perforations to provide gecko-like adhesion. More generally, any other means that allows the inside surface of the sleeve to be sufficiently adhesive and/or sticky can be devised by the person skilled in the art.

In the illustration of FIGS. 45-48, while the figures show a tail sleeve made of a tubular component cut along its entire length, other realizations are possible where the cut partially occurs only for a set length starting at the proximal end, in order to accommodate the portion of the tail immediately following the tail base, i.e. the part of the tail that is largest in diameter.

The intermediate locking groove (220) extends perpendicularly to the longitudinal direction of the sleeve (120) along the outside surface of the sleeve (120). As already noted above, the groove allows locking of the tail sleeve (120) through the orifice (140) of the cup (110). If desired, multiple such locking grooves (220) can be provided in a parallel arrangement along the longitudinal extension of the tail sleeve (120) in order to provide for adjustable locking degrees and extensions of the sleeve (120) on the cup (110) thus allowing an easy adjustment of the snugness of the cup fit once the sleeve is installed on the animal's tail.

Alternatively to the one or more locking grooves (220), the tail sleeve can have a tubular component with a variable outside diameter along its length, where the proximal (relatively to the desired locking point/level) portion of the tail sleeve has an outside diameter slightly smaller than the locking opening of the cup, and the distal (relatively to the desired locking point/level) portion of the sleeve has an outside diameter larger than the locking opening of the cup.

Additionally, if desired, the distal edge of the tail sleeve may be tapered along its inside diameter to prevent distal tail skin (at the distal edge of the tail sleeve) from bulging up due to the applied shear force (directed distally) from snug cup fitting and strangulating the distal end of the tail.

If necessary and/or required, the tail sleeve (120) can be secured to the tail skin surface of the animal by an adhesive, such as curable adhesive, curable glue, double-sided adhesive tape, the alternative adhesion means described above. Use of double-sided adhesive tape (opaque or clear for easier tail health monitoring) appears to be preferable as it allows instantaneous tail sleeve installation. In particular, the tape can be pre-applied to the inside surface of the tail sleeve which can be then be almost instantaneously placed onto the animal's tail while the animal is restrained for a very short amount of time (about 5-15 seconds). Additionally, with the double-sided adhesive the tail sleeve and the tail cup can be easily removed and placed back at desired times without causing any skin surface damage.

Advantageously, when mounted, the tail cup (110) may freely rotate along its longitudinal axis in order to ensure that the edges of the locking opening (140) do not press too hard on the tail sleeve (120), do not strangulate the animal's tail and at the same time are not under an excessive shear force or stress due to the snugness of the cup fit.

According to several embodiments, the above described device prevents coprophagy in rodents for a large amount of experimentations, it allows fecal collection in rodents for downstream fecal analyses (no need for animals to be housed on wire floors or metabolic cages) and it allows separation of fecal excretions from urine excretions when either of these need to be collected without cross-contaminating each other with their corresponding components/analytes.

In summary, the description of the present example shows a novel combination of tail cup and tail sleeve together with methods for installing them on an animal such as a rodent, by preventing coprophagy and making the gut microbiome of the rodent more human-like, thus allowing obtainment of a rodent model of the human digestive tract, in particular small intestine.

Example 19: Rodent Model with a "Humanized" Digestive Tract

The upper gastrointestinal tract plays a prominent role in human physiology as the primary site for enzymatic digestion and nutrient absorption, immune sampling, and drug uptake. Alterations to the small-intestine microbiome have been implicated in various human diseases, such as non-alcoholic steatohepatitis and inflammatory bowel conditions. Yet, the physiological and functional roles of the small-intestine microbiota in humans remain poorly characterized because of the complexities associated with its sampling. Rodent models are used extensively in microbiome research and enable the spatial, temporal, compositional, and functional interrogation of the gastrointestinal microbiota and its effects on the host physiology and disease phenotype. Classical, culture-based studies have documented that fecal microbial self-reinoculation (via coprophagy) affects the composition and abundance of microbes in the murine proximal gastrointestinal tract.

This pervasive self-reinoculation behavior could be a particularly relevant study factor when investigating small-intestine microbiota. Modern microbiome studies either do not take self-reinoculation into account, or assume that approaches such as single housing mice or housing on wire mesh floors eliminate it. These assumptions have not been rigorously tested with modern tools. Here, we used quantitative 16S rRNA gene amplicon sequencing, quantitative microbial functional gene content inference, and metabolomic analyses of bile acids to evaluate the effects of self-reinoculation on microbial loads, composition, and function in the murine upper gastrointestinal tract.

In coprophagic mice, continuous self-exposure to the fecal flora had substantial quantitative and qualitative effects on the upper gastrointestinal microbiome. These differences in microbial abundance and community composition were associated with an altered profile of the small-intestine bile acid pool, and, importantly, could not be inferred from analyzing large-intestine or stool samples. Overall, the patterns observed in the small intestine of non-coprophagic mice (reduced total microbial load, low abundance of anaerobic microbiota, and bile acids predominantly in the conjugated form) resemble those typically seen in the human smallintestine.

A combined use of the tail-cup herein described and absolute quantification method herein described, resulted in development of a rodent model of the human digestive tract.

Human microbiota-associated (HMA) mice are broadly used in biomedical research to investigate the causal roles of human microbiomes on the host physiology and disease predisposition andphenotype. According the rodent model herein described can be used in several applications, such as biomedical, pharmaceutical research, and personalized medicine as well as basic research biology and additional applications identifiable by a skilled person.

The non-coprophagic rodent model herein described is more similar to humans both in terms of the microbial loads in the upper gastrointestinal tract (e.g., small intestine) and the microbiota composition (e.g., dominated by Lactobacilli spp.).

In particular, non-coprophagic mice have been provided that have a significantly altered small intestinal bile acid profile and are expected to have other physiological effects (e.g., small-intestine mucosal enzymatic activity and immunity, nutrient and xenobiotics uptake, and others) associated with the more human-like patter of gastrointestinal microbial colonization.

It is expected that non-coprophagic mice herein described can be colonized with patient-derived microbiota as a more human-like human-microbiota-associated to provide a "patient-derived microbiome xenograft" model for various applications as will be understood by a skilled person, such as personalized medicine to investigate in vivo the function of the patient's microbiome, its response to and modification by xenobiotics, screening of compounds for its selective modification, and additional applications identifiable by a skilled person.

Accordingly, a non-coprophagic rodent model is described and related use in methods and systems (e.g. kit of parts) for use in study and investigations of the human digestive tract and in particular of the small intestine.

Exemplary applications where the non-coprophagic rodent model of the disclosure can be used comprise applications using:
  conventional specific-pathogen-free (SPF) mice housed in standard animal laboratory conditions;
  gnotobiotic or germ-free mice housed in specialized conditions such as gnotobiotic chambers or cages designed to maintain their gnotobiotic or germ-free status;
  metabolic cages or any kind of specialized setup designed to monitor animas in real time, monitor behavior, movement, food and fluid consumption, collect urine samples, and or collect fecal samples (e.g., "metabolic cage"), especially when urine and feces have to be collected without cross-contaminating each other with the analytes contained in them; when fecal output or gastrointestinal transit needs to be monitored, and/or combination of the above.

Several applications where the non-coprophagic rodent model of the disclosure can be used can be identified in fields such as, probiotic research, toxicology, pharmacology, pharmacokinetics, and additional fields identifiable by a skilled person.

Non-coprophagic human like rodent models can also be further customized by modification of the rodent gut microbiome as described herein to provide non-coprophagic rodent models having target microbiome characterized by a microbiome profile formed by presence, proportion and total load of target prokaryotes. Exemplary target microbiome can be identified in the following Examples 20-25 related to microbiome of the digestive tract of human beings identified in patients who are undergoing either an oral double balloon endoscopy procedure or an esophagogastroduodenoscopy procedure as part of their clinical care.

Example 20: General Protocols for Profiling Human Small-Intestine Microbiome

The following experimental protocols were carried out to assess the absolute microbial loads in the human duodenum and their potential relationship with factors related to health and disease. The recently developed digital PCR anchored 16S rRNA gene amplicon sequencing method, also referred to as "quantitative sequencing", was used to provide absolute total microbes, absolute taxon abundances and filter out contaminants in samples with low microbial abundance. By capturing the absolute microbial abundances of the human duodenal and oral microbiome, one can better understand the makeup of the human duodenal microbiome, improve the understanding of the underlying community structure of certain diseases such as small intestinal bacterial overgrowth (SIBO) and determine how microbial load and composition correlate with upper GI symptoms.

Study population and design: The REIMAGINE (Revealing the Entire Intestinal Microbiota and its Associations with the Genetic, Immunologic, and Neuroendocrine Ecosystem) study was conceived to explore the relationships between the small-intestine microbial populations and different conditions and diseases[105]. Male and female subjects aged 18-80 years undergoing standard-of-care upper endoscopy (esophagogastroduodenoscopy, EGD) without colon preparation were prospectively recruited. The study protocol was approved by the Institutional Review Board (IRB) at Cedars-Sinai Medical Center, and subjects provided informed written consent prior to participation (IRB Protocol: 00035192). Data presented here represents a retrospective analysis of this prospectively collected information.

Questionnaires: Prior to EGD, all subjects completed a study questionnaire documenting demographic information and family and medical history, including GI disease and bowel symptoms, medication use, use of alcohol and recreational drugs, travel history, and dietary habits and changes. Subjects also reported any known underlying conditions, such as GI diseases and disorders, neurologic disease, hematologic disease, autoimmune disease, kidney disease, heart disease and cancer. All medical information provided by subjects was verified through audits of medical records. All data were de-identified prior to analysis.

Blood collection and analysis: After completing the study questionnaire, fasting blood samples were collected in BD Vacutainer SST tubes (Becton Dickson, Franklin Lakes, NJ, USA). Levels of circulating pro- and anti-inflammatory cytokines and chemokines were analyzed on a Luminex FlexMap 3D (Luminex Corp., Austin, TX, USA) using a bead-based multiplex panel that included: GM-CSF, IFNγ, IL10, IL12P70, IL13, IL1B, IL2, IL4, IL5, IL6, IL8, MCP1 and TNFα (EMD Millipore Corp., Billerica, MA, USA, cat. #HCYTOMAG-60K).

Saliva and small-intestine luminal sample collection: Prior to EGD procedure, saliva was collected in a sterile 5 mL tube. During the EGD procedure, samples of duodenal luminal fluid were procured using a custom-designed sterile aspiration double-lumen catheter (Hobbs Medical, Inc.) [180]. Duodenal aspirates (DA) were collected using a custom-designed sterile inner catheter which was pushed through a sterile bone wax cap only after the endoscopist entered the second portion of the duodenum, in order to reduce contamination from the mouth, esophagus, and stomach. After collection, samples were immediately placed on ice and transferred to the laboratory for further analysis.

Aspirate processing and microbial culture: Prior to microbial culture, an equal volume of sterile 1× dithiothreitol (DTT) prepared with RNase and DNase PCR-grade sterile water was added to each saliva and duodenal aspirate (~1 mL) and the samples were vortexed until fully liquified (~30 sec) as described previously[180]. A 100 µl aliquot of each duodenal sample (DA+DTT) was then serially diluted with 900 µL sterile 1× PBS and plated on MacConkey agar (Becton Dickinson), and on blood agar (Becton Dickinson). Plates were incubated at 37° C. for 16-18 h under aerobic (MacConkey) or anaerobic (blood agar) conditions. Plates without bacterial growth after 18 h were re-incubated for an additional 18 hours. Colony forming units (CFU) were then counted electronically using a Scan 500 (Interscience, Paris, France). Saliva+DTT and the remainder of each DA+DTT were centrifuged at maximum speed (>13000 RPM) for 5 min. The supernatant was removed, and 1 mL of sterile Allprotect reagent (Qiagen, Hilden, Germany) was added to the microbial pellet and then stored at −80° C.

DNA isolation: On the day of the DNA isolation, DA pellets were thawed on ice and processed as described previously[180]. Microbial DNA was isolated using the MagAttract PowerSoil DNA KF Kit (Qiagen) on a KingFisher Duo (Thermo Fisher Scientific, Waltham, MA, USA), and quantified using Qubit dsDNA high sensitivity and Qubit dsDNA BR Assay kits (Invitrogen by Thermo Fisher Scientific) on a Qubit 4 Fluorometer (Invitrogen, Carlsbad, CA, USA).

16S rRNA gene sequencing: Extracted DNA was amplified, barcoded and sequenced as described previously[2, 181, 182]. Briefly, amplification of the variable 4 (V4) region of the 16S rRNA gene was performed in 20 uL duplicate reactions with: 8 uL of 2.5×5Prime Hotstart Mastermix (VWR, Radnor, PA, USA), 1 uL of 20× Evagreen (VWR), 5 uL each of 5 uM forward and reverse primers (519F, barcoded 806R, IDT, CoralVille, IA, USA), 3.5 uL of water, and 3.5 uL of extracted DNA template. A CFX96 RT-PCR machine (Bio-Rad Laboratories, Hercules, CA, USA) was used to monitor amplification reactions and all samples were removed in late exponential phase (~10,000 FRU) to minimize chimera formation and non-specific amplification[113, 114, 181]. Amplification was performed under the following cycling conditions: 94° C. for 3 min, up to 50 cycles of 94° C. for 45 s, 54° C. for 60 s, and 72° C. for 90 s. Several samples were rerun after diluting the template as they showed non-exponential amplification in the undiluted sample, a sign of PCR inhibition. Amplified duplicates were pooled together and quantified with KAPA library quantification kit (Roche, Basel, Switzerland) and then all samples were pooled at equimolar concentrations with up to 96 samples per library. AMPureXP beads (Beckman Coulter, Brea, CA, USA) were used to clean up and concentrate libraries before final library quantification with a High Sensitivity D1000 Tapestation Chip (Agilent, Santa Clara, CA, USA). Illumina MiSeq sequencing was performed with a 2×300 bp reagent kit by Fulgent Genetics (Temple City, CA, USA).

Raw reads were demultiplexed by Fulgent Genetics. Demultiplexed forward and reverse reads were processed with QIIME 2 2020.2[183]. Loading of sequence data was performed with the demux plugin followed by quality filtering and denoising with the dada2 plugin[184]. Dada2 trimming parameters were set to the base pair where the average quality score dropped below thirty. All samples were rarefied to the lowest read depth present in all samples (45,386 reads) to decrease biases from varying sequencing depth between samples[109]. The q2-feature-classifier[185] was then used to assign taxonomy to amplicon sequence variants (ASV) with the Silva[56] 132 99% OTUs references. Resulting read count tables were used for downstream analyses in IPython notebooks (see Data Availability Section).

Absolute abundance: Briefly, the Bio-Rad QX200 droplet dPCR system (Bio-Rad Laboratories) was utilized to measure the 16S concentration in each sample with the following reaction components: 1X QX200 EvaGreen Supermix (Bio-Rad), 500 nM forward primer, and 500 nM reverse primer (519F, 806R) and thermocycling conditions: 95° C. for 5 min, 40 cycles of 95° C. for 30 s, 52° C. for 30 s, and 68° C. for 30 s, followed by a dye stabilization step of 4° C. for 5 min and 90° C. for 5 min. The final concentration of 16S rRNA gene copies in each sample was corrected for dilutions and normalized to the extracted sample volume For each sample, the input-volume-normalized total microbial load from dPCR was multiplied by each amplicon sequence variant's (ASV) relative abundance to determine the absolute abundance of each ASV. The average of all sample volumes for a specific sample type was used for a few samples (11 duodenum, 10 saliva) that were missing the starting volume information.

Poisson quality filtering: Two separate quality-filtering steps based on Poisson statistics were used to determine the statistical confidence in the measured values. First, a 95% confidence interval was calculated from the repeated measures of water blanks. Samples with a total microbial load below the upper bound of this confidence interval were removed from further analysis.

Second, the limit of detection (LOD) in terms of relative abundance was determined for each sample. Sequencing can be divided into two separate Poisson sampling steps. First, an aliquot of sample is taken from the extracted sample and input into the library amplification reaction. The LOD of the library amplification step was determined by multiplying the total microbial load from dPCR by the input volume into the library amplification reaction and then finding the relative abundance corresponding to an input of three copies. Poisson statistics tells us that the likelihood of sampling one or more copies with an average input of three copies is 95%. The second Poisson sampling step in sequencing arises from the number of reads generated from the amplified library. The accuracy of the second Poisson sampling step was previously shown[181] to follow a negative exponential curve, $LOD = 7.115 * \text{read depth}^{-0.115}$, between the total read depth and relative abundance at which 95% confidence of detection is observed. The minimum of the two described LODs (first determined per sample by total load, and second by sequencing depth) was then determined for each sample. For each sample, the abundance of any ASV with a relative abundance below the LOD was set to zero. After filtering, data tables for each taxonomic level were generated.

Data transforms and dimensionality reduction: For PCA, all absolute taxon abundances were log-transformed. To handle zeros, a pseudo-count of 0.1 reads was added to all taxon relative abundances before multiplying by each sample's total microbial load as determined by digital PCR. PCA was performed with the sklearn.decomposition.PCA function in Python. Ranked feature loadings for each taxon on a given principal component were determined by scaling the corresponding eigenvector by the maximum transformed value for that principal component axis.

Statistical analysis and correlations: Group comparisons (e.g., SIBO vs. no SIBO, saliva vs. duodenum) were analyzed using the non-parametric Kruskal-Wallis rank sums tests with Benjamini-Hochberg multiple hypothesis testing correction using SciPy.stats Kruskal function and statsmodels.stats.multitest multipletests function with the fdr_bh option.

Correlation coefficients were either Spearman or Pearson and corresponding P-values for all correlations were determined with scipy.stats.spearmanr or scipy.stats.pearsonr functions. Multiple hypothesis testing was performed for each group of correlations (e.g. taxa co-correlations, cytokine correlations) separately using the Benjamini-Hochberg procedure.

Data Availability: Sequencing data generated during this study are available in the National Center for Biotechnology Information Sequence Read Archive repository under study accession number PRJNA674353. Raw data for each figure and IPython notebooks for data processing and figure generation are available through CaltechDATA: https://data.caltech.edu/records/1701.

Patient enrollment: the microbiome of the duodenum and its potential relationship with health and disease in a cohort of 250 patients enrolled in the REIMAGINE study at Cedars-Sinai Medical Center were studied. All patients undergoing esophagogastroduodenoscopy (EGD) without colonoscopy preparation as standard of care were eligible to enroll, resulting in patients with a wide range of GI conditions. No healthy controls are currently approved to be included in the study due to the risks associated with the EGD procedure. Summary statistics for patient demographic data and selected metadata categories from the enrollment questionnaire are included in Table 3.

Table 3 shows the summary statistics for the patient cohort used in this study. All patients are from the REIMAGINE study.

TABLE 3

Total subjects 250
Duodenal Aspirate 250
Saliva 21

|  |  | Mean (Std Dev) |
| --- | --- | --- |
| Age |  | 56.9 (14.9) |
| Weight (lbs) |  | 169 (50) |

|  | Male | Percent (N) Female |
| --- | --- | --- |
| Gender | 46% (115) | 54% (135) |
| Antibiotic usage | last 6 months | 40% (100) |
|  | Current | 4% (11) |
| PPI usage | PPI | 34% (86) |
|  | H2 blocker | 4% (10) |
|  | Both | 4% (10) |

TABLE 3-continued

Total subjects 250
Duodenal Aspirate 250
Saliva 21

| Any probiotic usage | 20% (49) |
| --- | --- |
| Smokers | 6% (16) |
| Bloating > 40 | 42% (106) |
| Constipation > 40 | 30% (75) |
| Incomplete Evac > 40 | 34% (84) |
| Excess Gas > 40 | 44% (109) |
| Diarrhea > 40 | 31% (77) |

Example 21: A Log-Normal Distribution of the Total Microbial Load of the Duodenum Across Patients with GI Symptoms In this example, the total microbial load from 250 human duodenal aspirates were examined using the recently developed digital PCR anchored 16S rRNA gene amplicon sequencing and quantification method.

Figure 49:
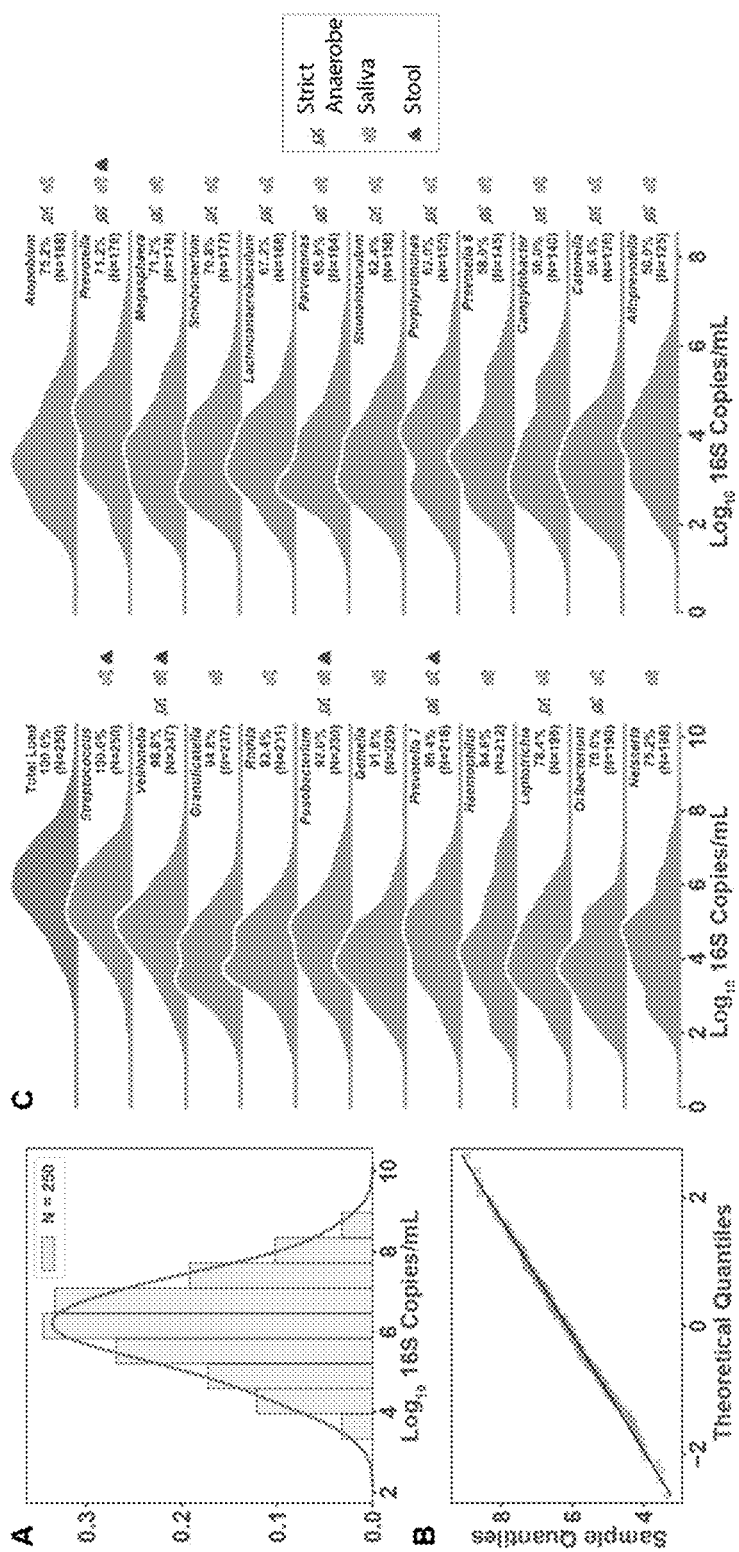
FIG. 49 illustrates in an exemplary embodiment the microbial load distribution across 250 human duodenal aspirate samples.
Figure 50:
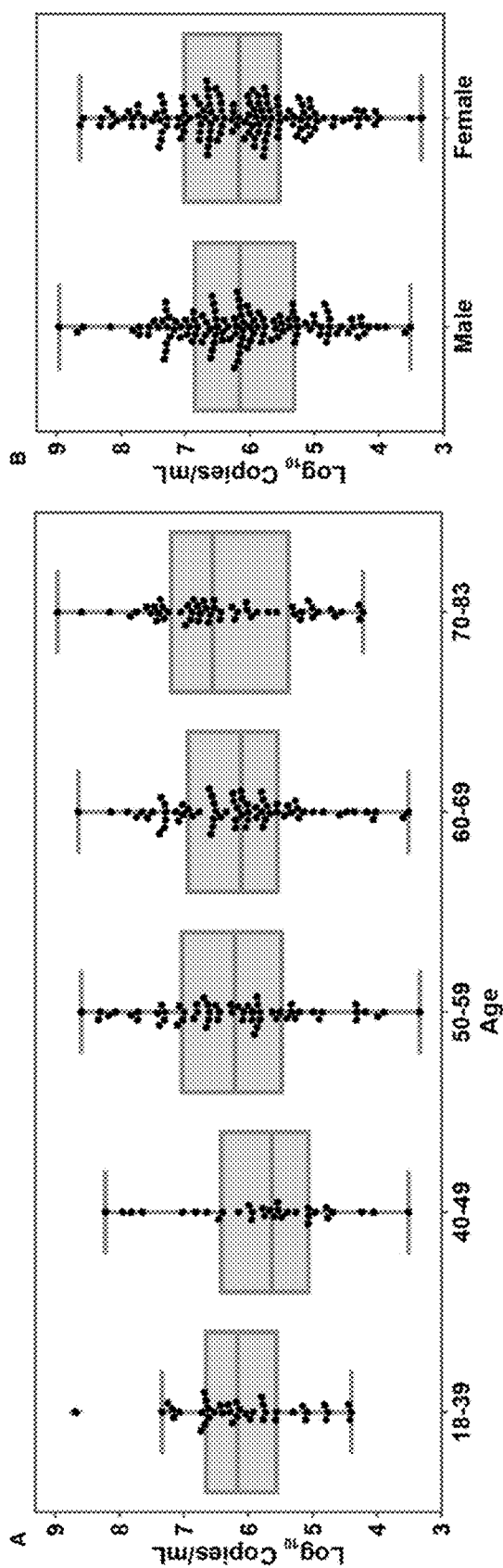
FIG. 50 illustrates in an embodiment the total microbial load breakdown by age (FIG. 50 Panel A) and gender (FIG. 50 Panel B).
Figure 51:
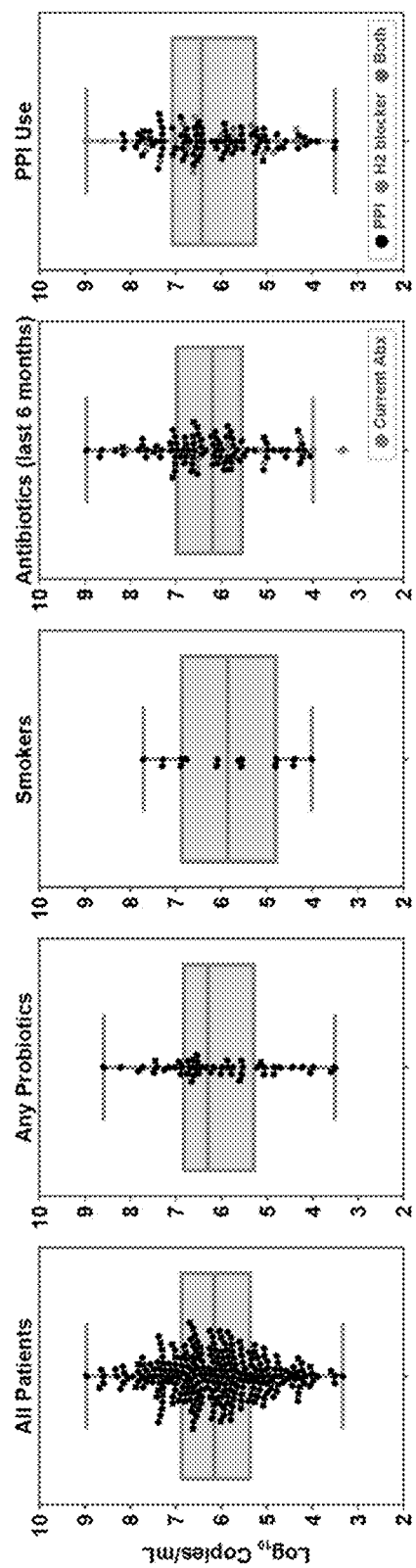
FIG. 51 illustrates in an embodiment the distribution of total microbial load from subpopulations of patients: taking probiotics (N=49), active smokers (N=16), taking antibiotics in the past 6 months (N=100), or taking proton pump inhibitors (PPI, N=106).

The digital PCR-based determination of total microbial load[181, 182] from 250 human duodenal aspirates revealed samples that spanned loads from the detection limit of ~5×10$^3$ rRNA gene copies/mL up to nearly 10$^9$ copies/mL. The overall distribution of total loads was log-normal with mean=6.13 $Log_{10}$ copies/mL and standard deviation=1.12 $Log_{10}$ copies/mL (FIG. 49, panels A, B). A bimodal distribution of total load indicative of potential separation of patients into SIBO and non-SIBO diagnosis was not observed. Neither age nor gender significantly correlated with total microbial load (FIG. 50). Total microbial load also did not correlate with patient reported intake of probiotics supplements or yogurts, smoking, or usage of proton pump inhibitors (FIG. 51). Current antibiotic usage appeared to lower the average total microbial load, but antibiotic usage in the previous six months had no impact (FIG. 51).

Figure 52:
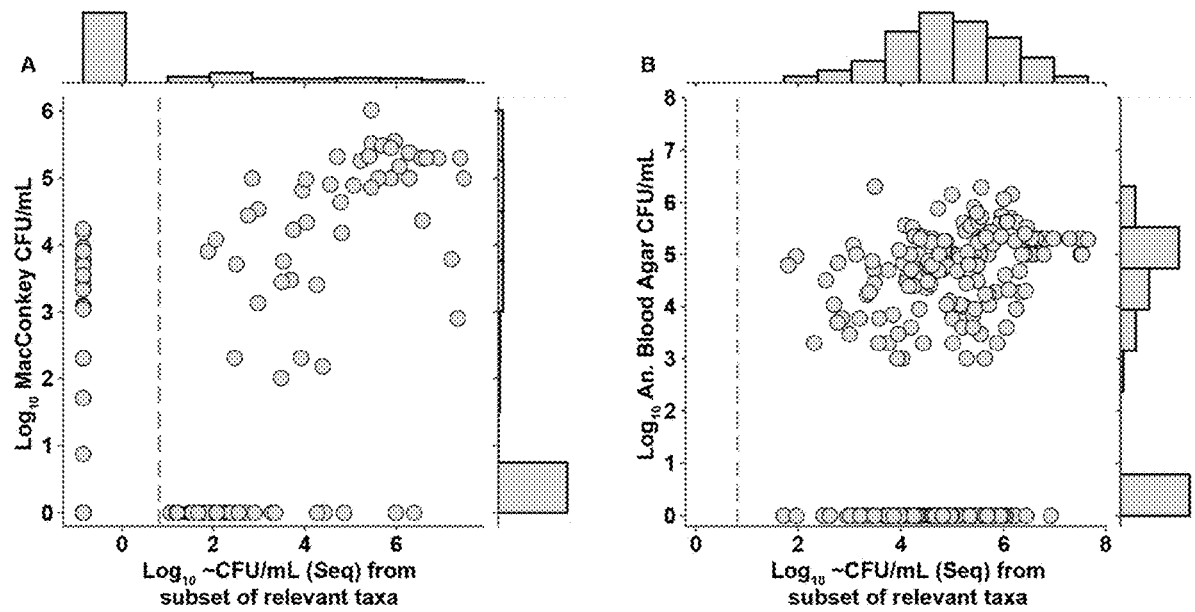
FIG. 52 illustrates in an embodiment the comparison of the culture counts from aerobic (MacConkey agar) and anaerobic (blood agar) plates to the total load of microbes expected to grow on these plates.

Digital PCR anchored 16S rRNA gene amplicon sequencing[181] provided absolute taxon abundances in each sample and a statistical framework for differentiation between real and contaminant taxa (see Example 20). The culture counts from aerobic (MacConkey agar) and anaerobic (blood agar) plates were first compared to the total load of microbes expected to grow on these plates (FIG. 52). For aerobic plating, a bimodal distribution of combined *Escherichia-Shigella, Enterobacteriaceae, Enterococcus*, and *Aeromonas* bacterial load from quantitative sequencing and culture and a high correlation between the two measurements (Spearman, 0.61, P<0.001, N=244) was observed. For anaerobic plating, lower concordance (Spearman, 0.35, P<0.001, N=244) between quantitative sequencing and culture was observed. This discrepancy could reflect the difficulty in culturing many intestinal microbes[186], especially anaerobes that are initially collected and processed in aerobic environments.

Next, the log-transformed absolute-abundance distributions were analyzed for the most prevalent genera in the dataset (FIG. 49, panel C). Prevalence is defined as a taxon's frequency of occurrence in the dataset.

*Streptococcus* was present in all 250 samples and followed an approximately log-normal distribution with a mean load that was approximately half an order of magnitude below that of the mean total microbial load and an equal standard deviation. Other genera showed wide-ranging distributions that deviated from normality. For example, *Porphyromonas* appears bimodal with two local maxima whereas *Haemophilus* exhibits a long tail towards higher microbial loads. The 23 most prevalent genera in this study are also commonly found in the oral microbiota[22]. A subset of these genera (*Streptococcus, Veillonella, Fusobacterium, Prevotella* 7, *Prevotella*) are also commonly found in stool samples, indicating possible survival of these genera throughout the entire GI tract[23]. The majority of prevalent genera are either strict or facultative anaerobes, indicating that parts of the duodenal environment are likely anoxic in this patient population.

Example 22: Direct Transmission of Microbes from Saliva to Duodenum

This example was carried out to investigate whether many of the taxa found in the duodenum originated from the oral cavity.

A subset of 21 patients was analyzed, for whom saliva and duodenum samples collected during the same hospital visit were paired. Digital PCR revealed that the total microbial load in saliva was roughly 2.5 orders of magnitude higher than the total load in the duodenum (Kruskal-Wallis, P<0.001).

Figure 53:
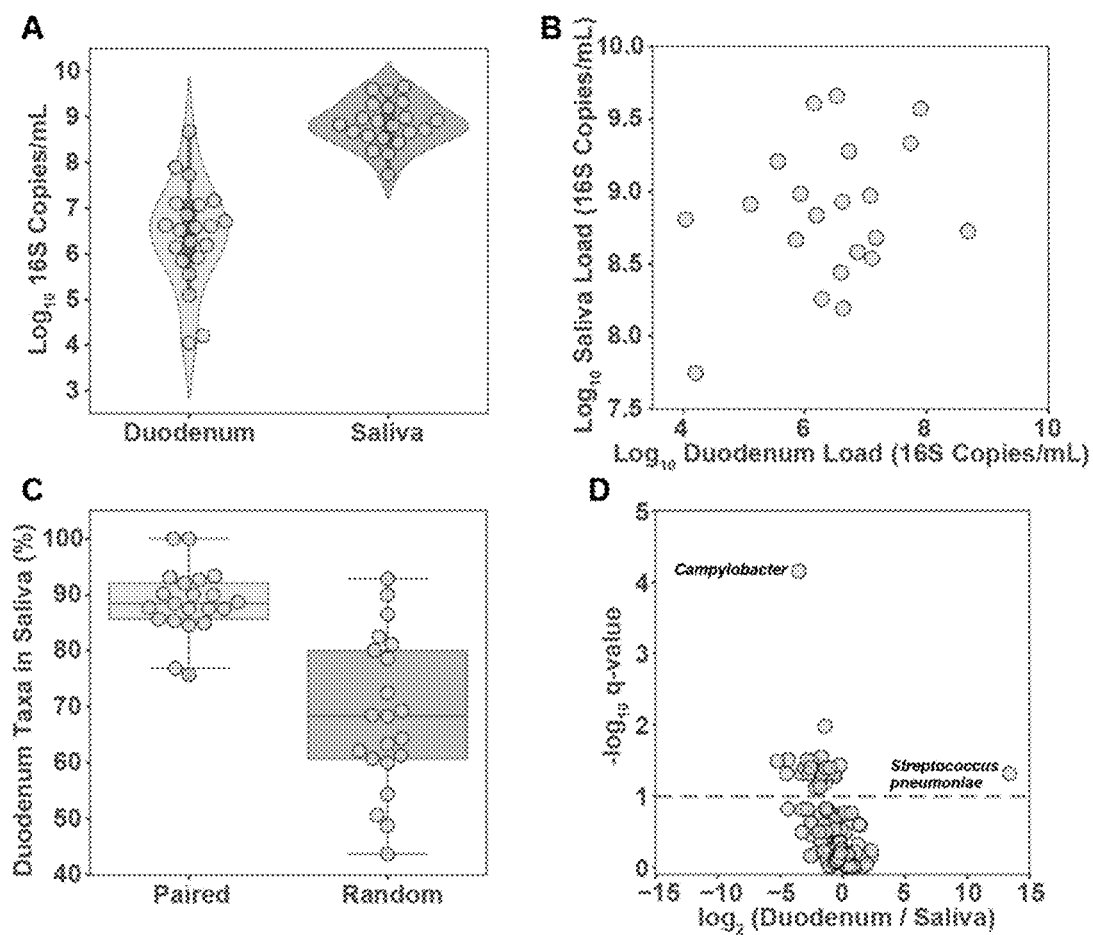
FIG. 53 illustrates in an exemplary embodiment the relationship between saliva and duodenal aspirate microbiomes.

Further, the range in saliva total loads was 3 orders of magnitude smaller than the range in total loads of the duodenum samples (FIG. 53, panel A). No significant correlation was observed between the total microbial loads in paired saliva and duodenum samples (FIG. 53, panel B). In this study, all samples were taken with a custom double-sheathed catheter via endoscope (see Methods) that moves beyond the outer sheath before aspirating duodenal fluid. This custom catheter should limit oral microbiota contamination of the duodenum during the procedure. Additionally, the optimized sample-processing protocol (see Methods) should eliminate extracellular DNA from swallowed dead bacteria.

To evaluate the direct transmission of microbes from saliva to duodenum, the shared taxa were compared between paired (same patient) and randomly paired samples from the same dataset. On average, 89% (±6% S.D.) of the taxa in the duodenum were also found in the paired saliva sample, whereas only 69% (±14% S.D.) were found when the pairs were randomized (FIG. 53, panel C, Kruskal-Wallis, P<0.001), suggesting direct transmission of oral taxa to the duodenum. Genera that were proportionally enriched in either saliva or duodenum samples were investigated. *Campylobacter* was present in 21/21 saliva samples but only 10/21 duodenum samples. The absence of *Campylobacter* in about half of the paired duodenum samples could be the result of *Campylobacter* being sensitive to the antibacterial properties of the stomach and small intestine[187] (FIG. 53, panel D). In contrast, *Streptococcus pneumoniae* was only found in duodenum samples (6/21) (FIG. 53, panel D). These differences in the relative abundance of specific taxa of microbes between paired saliva and duodenum samples also provide evidence against oral contamination in the duodenal samples.

Example 23: Disruptor Taxa Revealed by Taxa Co-Correlations

In this example, the relationships between the top 20 most abundant genera were analyzed. A co-correlation heatmap of these taxa revealed several distinct motifs (FIG. 54, panel A): (1) Taxa whose absolute loads had a high correlation with total load, (2) taxa whose absolute loads had a higher co-correlation with another taxon's absolute load than with total microbial load, (3) taxa with a mutually exclusive relationship with almost all other abundant taxa. Correlation with total load was often an indicator of a prevalent taxon because the variance in total microbial load was larger than the variance in relative abundance. When two taxa have a higher co-correlation with each other than with total load it potentially indicates these taxa share preferred environmental factors or directly cooperate. One group of these co-correlating taxa that included several *Prevotella* species and a species of *Porphyromonas* matches a known shared metabolic niche in the oral cavity[188, 189] (Table 4).

Table 4 shows two groups of taxa (in regular font and bold font) that have stronger co-correlations with another taxon than with total load. Significance values for all correlations and co-correlations were P<0.001.

TABLE 4

| Taxon 1 | Taxon 2 | Co-Correlation | Correlation with Total Load | Difference | Biological Link |
| --- | --- | --- | --- | --- | --- |
| *Alloprevotella* | *Prevotella* | 0.73 | 0.30 | 0.43 | Tertiary plaque biofilm colonizers. |
| *Prevotella* 6 | *Prevotella* 7 | 0.83 | 0.43 | 0.39 | |
| *Porphyromonas* | *Prevotella* | 0.74 | 0.36 | 0.38 | |
| *Prevotella* | *Prevotella* 7 | 0.82 | 0.50 | 0.32 | Metabolize same byproduct of primary colonizers[188, 189]. |
| Megasphaera | Solobacterium | 0.69 | 0.43 | 0.26 | Not Known |
| Solobacterium | Oribacterium | 0.80 | 0.55 | 0.25 | |
| Leptotrichia | Oribacterium | 0.81 | 0.60 | 0.20 | |
| Atopobium | Solobacterium | 0.78 | 0.61 | 0.17 | |

Several genera stood out as having no significant correlation with almost all other abundant taxa: Enterobacteriaceae, *Escherichia-Shigella, Clostridium* sensu stricto 1, and *Lactobacillus* (FIG. 54, panel A). These taxa appeared to disrupt the commonly observed microbial structure (i.e., the prevalent taxa that generally co-correlate with one another) of the duodenal microbiome. This pattern of mutual exclusivity can be represented algorithmically by sorting all taxa by the difference between their maximum abundance and their mean abundance. Practically, this means that these disruptors are relatively rare (i.e., present in a small fraction of samples), but when they are present they usually dominate, excluding other common taxa.

A clustered heatmap of the top 16 taxa as ranked by the difference in their maximum and mean abundances reveals two taxonomic signatures (FIG. 54, panel B). The first signature in the top left of the heatmap contained the mutually-exclusive taxa from the co-correlation heatmap, along with *Enterococcus, Romboutsia, Aeromonas,* and *Bacteroides*. The second signature contained taxa that were generally found in lower abundance, many of which are from the HACEK (*Haemophilus*, Aggregatibacter, Cardiobacterium, Eikenella, Kingella) group of organisms associated with infective endocarditis[187]. However, the second group also clustered with more common taxa in this dataset, such as *Prevotella* and *Fusobacterium*. Thus, all eight of the taxa in the first taxonomic signature were initially labelled as "disruptors" (FIG. 54, panel B, bolded taxa) because their presence appeared to be mutually exclusive with many other common taxa.

Figure 55:
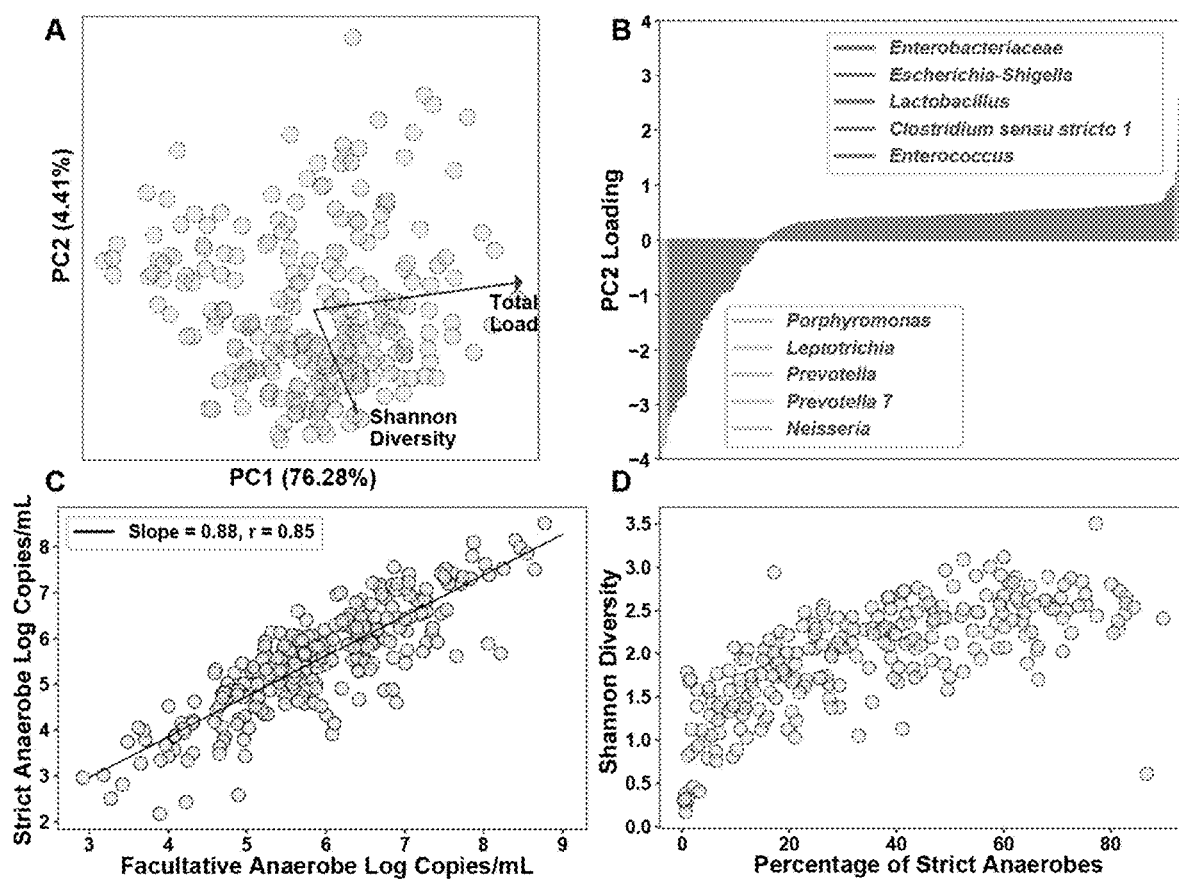
FIG. 55 illustrates in an exemplary embodiment the microbiota diversity controlled by strict anaerobes and disruptor taxa.

Example 24: Aerobic Disruptor Taxa Displace Strict Anaerobes and Decrease Diversity In this example, a principal component analysis (PCA) was performed on the absolute taxon abundances to investigate the drivers of variance in the dataset (FIG. 55, panel A).

Total loads spanned 5 orders of magnitude, accounting for most of the variance. Total load cleanly separated samples along the PC1 axis. The second most explanatory axis, PC2, strongly correlated with the Shannon diversity index of samples (Spearman, 0.74, P<0.001, N=250). Ranked feature loadings for PC2 (FIG. 55, panel B) indicated that many of the disruptor taxa (light grey) are the main drivers of separation in the positive direction of PC2 whereas the five taxa driving most of the separation in the negative direction (light grey) of PC2 consisted of four strict anaerobes (*Porphyromonas, Leptotrichia, Prevotella, Prevotella* 7) and one obligate aerobe (*Neisseria*). It should be noted that many more taxa were strongly associated with the negative direction of PC2 than the positive direction. This separation matches well with the mutual exclusivity seen between the disruptor taxa and other organisms in the co-correlation analysis.

The two disruptor taxa with the highest loads are aerobic pathogens from the Enterobacteriaceae family and the taxa most associated with the negative direction of PC2 were strict anaerobes.

Next, the composition of strict vs facultative anaerobes in each sample was investigated. It was found that a nearly 1:1 correlation between the strict and facultative anaerobe loads across all samples (FIG. 55, panel C). Additionally, the fraction of strict anaerobes in a sample was strongly correlated (Pearson, 0.71, P<0.001, N=250) with Shannon diversity (FIG. 55, panel D), indicating that the disruptor taxa appear to be mutually exclusive with strict anaerobes and the "bloom" of absolute abundance of disruptors decreases Shannon diversity.

Example 25: Absolute Load of Disruptor Taxa Correlates with SIBO and GI Symptoms This example was carried out to determine whether disruptor taxa are associated with disease or GI symptoms.

Figure 56:
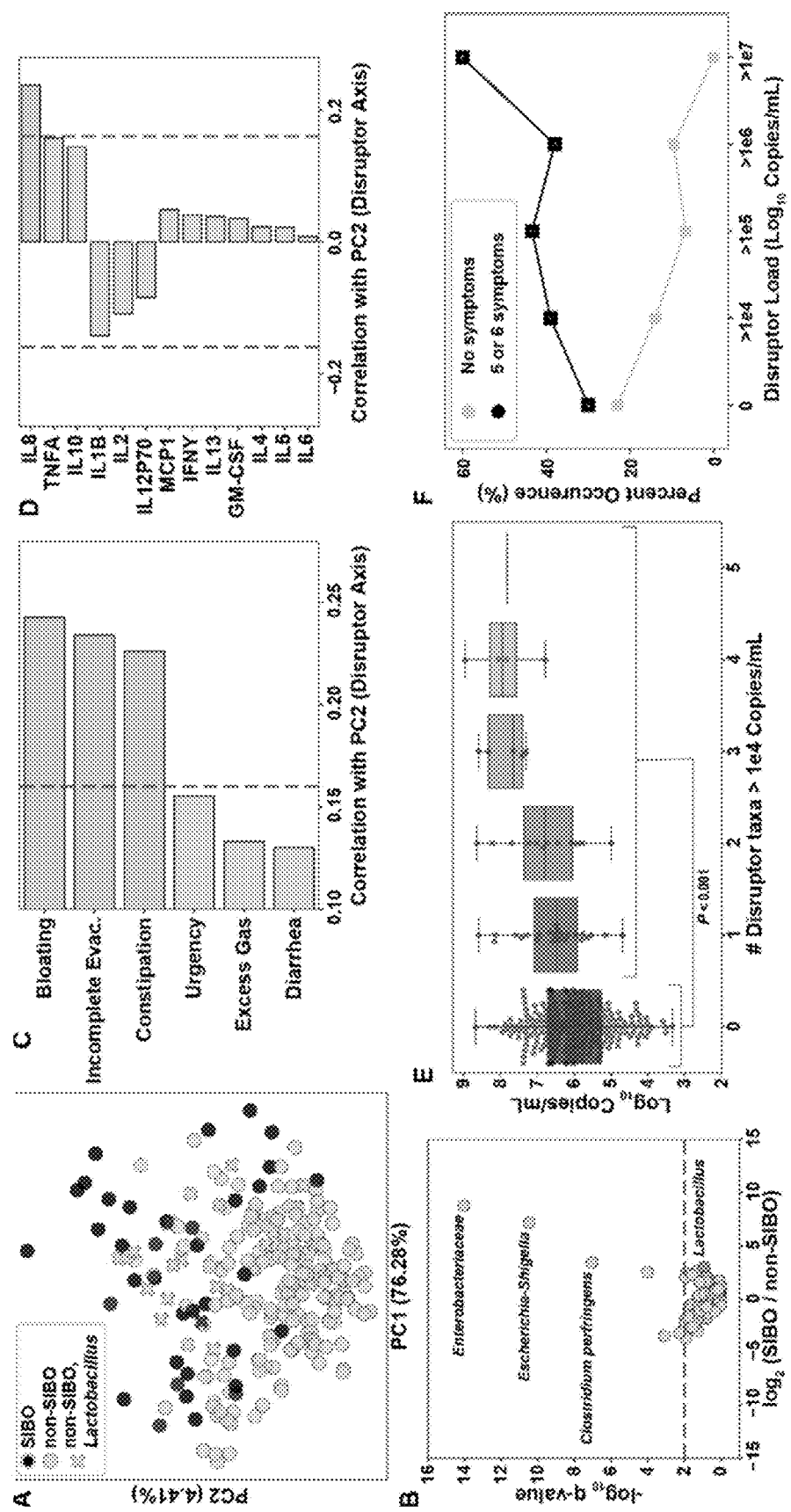
FIG. 56 illustrates in an exemplary embodiment the domination of disruptor species in SIBO samples and their correlation with GI symptoms and the inflammatory cytokine IL8.

Applicant began by looking at patients with and without SIBO (SIBO classification was made based on aerobic culture results, >103 CFU/mL of duodenal aspirate[190]). Coloring the PCA plot by SIBO classification indicates a clear enrichment of patients with SIBO in the positive direction of the disruptor taxa axis (FIG. 56, panel A). Comparing the absolute abundance of species between the SIBO and non-SIBO samples by Kruskal-Wallis showed that the three most significantly different taxa (Enterobacteriaceae, *Escherichia-Shigella, Clostridium perfringens*) were enriched in SIBO samples and were also the three most common disruptor taxa in all samples (FIG. 56, panel B).

Although one cannot be certain of the genera or species represented by the Enterobacteriaceae classification, evidence from previous, published sequencing results from the REIMAGINE study using a different 16S primer set shows that many Enterobacteriaceae in duodenal samples from patients in this study are *Klebsiella* species[191].

*Lactobacillus* abundance was similar in SIBO and non-SIBO samples (FIG. 56, panel B) even though it co-correlated with many of the disruptor taxa (FIG. 54, panel B). Most of the non-SIBO samples that clustered with SIBO samples on the upper part of the PC plot contained *Lactobacillus* (FIG. 56, panel B). *Lactobacillus* does not grow on the aerobic (MacConkey agar) plates used for SIBO classification, which could explain why these samples cluster together by sequencing but are not classified as SIBO by culture.

Figure 57:
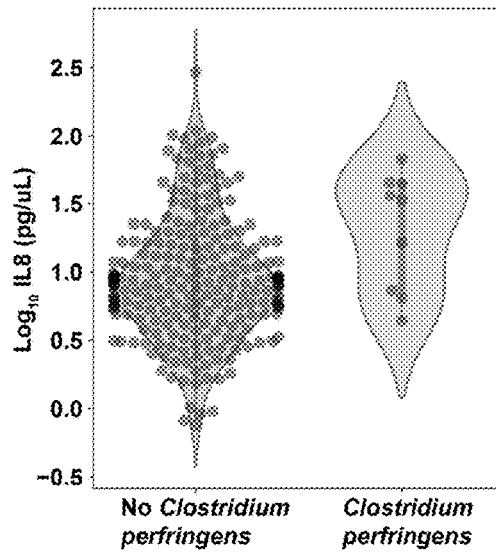
FIG. 57 shows in an embodiment the IL8 levels in samples with and without *Clostridium perfringens*.

Patient-reported GI symptom scores (on a 0-100 scale) were correlated with the disruptor taxa axis (PC2). Bloating, incomplete evacuation, and constipation had the highest correlation with the disruptor taxa axis, whereas correlations between urgency, excess gas, or diarrhea and the disruptor taxa axis were much weaker (FIG. 56, panel C). There was a weak positive correlation between the disruptor taxa axis and serum interleukin 8 (IL8) levels (Spearman, 0.24, P<0.001, N=232), indicating a potential neutrophil-related response (FIG. 56, panel D). However, none of the symptoms or cytokines had a significant correlation with the total load axis (PC1). *C. perfringens* was the single taxa that, when present in patients, coincided with a significant increase (Kruskal-Wallis, P=0.039) in serum IL8 levels (FIG. 57). However, there were only 9/250 samples with *C. perfringens*, limiting our ability to draw conclusions about this relationship.

Figure 58:
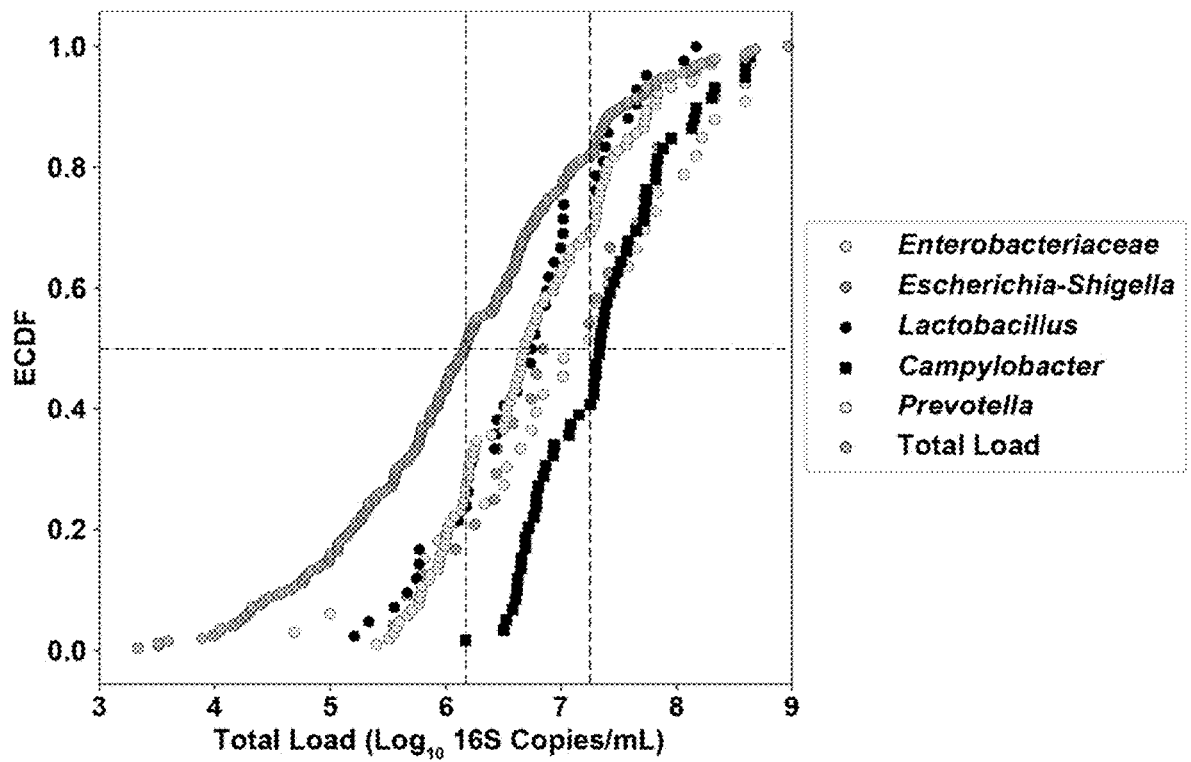
FIG. 58 shows in an embodiment an empiric cumulative distribution function (ECDF) plot demonstrating the enrichment of Enterobacteriaceae (N=33), *Escherichia-Shigella*

In half of the samples containing the two most common disruptor taxa (Enterobacteriaceae, and *Escherichia-Shigella*), the total microbial loads were greater than $10^7$ rRNA gene copies/mL, indicating a clear enrichment of disruptor taxa in samples with higher than average total microbial loads (FIG. 58). *Lactobacillus* did not follow this trend and was found in samples with total microbial loads that were similar to the total loads of samples containing common taxa like *Prevotella* (FIG. 58). Additionally, in patients with high disruptor taxa loads (after excluding *Lactobacillus* load) the presence of *Lactobacillus* at greater than $5 \times 10^4$ copies/mL negatively correlated with bloating symptoms (FIG. 59).

These two facts and the abundance of literature on the potential health benefits of *Lactobacillus*[192, 193] led one to believe *Lactobacillus* likely has a more nuanced relationship with the host than the other taxa classified as disruptors. Thus, *Lactobacillus* was removed from the list of disruptor taxa in the analyses of the association of disruptors with total load (FIG. 56, panel E) and GI symptoms (FIG. 56, panel F). When multiple disruptor taxa were present, there was a significant increase in total microbial load (Kruskal-Wallis, P<0.001; FIG. 56, panel E).

Patient-reported symptom scores are inherently qualitative, so to test whether disruptor taxa loads were correlated with more severe GI symptoms, the 0-100 scores were turned into a binary yes/no variable, representing a severe symptom, by drawing a threshold at the median score reported for each symptom (FIG. 60). The percentage of patients with zero severe symptoms and the percentage of patients with many severe symptoms (people reporting severe symptoms in 5-6 of the 6 symptom categories) as a function of disruptor taxa loads were then calculated. Three observations were made. First, at higher disruptor loads, patients were more likely to have more severe GI symptoms. Second, none of the patients with disruptor loads greater than $10^7$ copies/mL (N=10) had zero symptoms whereas 60% of them had 5 or 6 symptoms. Of the patients without disruptor taxa (N=153), 23% had zero symptoms and 30% had 5 or 6 symptoms. Disruptor loads may also be higher as a function of age, all but one of the individuals with disruptor loads greater than $10^6$ copies/mL (N=23) were older than 50 (FIG. 61). The absolute and relative abundances of disruptor taxa did not correlate (FIG. 62), preventing the clear connection between abundant symptoms and high absolute loads of disruptor taxa from being observed when analyzing only relative abundances.

Example 26: Exemplary Customized Rodent Models

In view of the above, an averaged microbiome profile can be provided which can be used to provide a rodent model of the common small intestinal microbiome presence of *streptococcus, Veillonella, fusobacterium, Prevotella, Neisseria* where each has a relative abundance of greater than 0.1% and the total load is roughly 1e6 copies/mL.

An averaged microbiome profile can also be provided which can be used to provide a rodent model of human SIBO comprising presence of Enterobacteriaceae with a relative abundance greater than 1% and the total load greater than 1e6 copies/mL.

An averaged microbiome profile can also be provided which can be used to provide a rodent model of the common stool microbiome comprising presence of *bacteroides*, lachnospiraceae, ruminococcaceae where each has a relative abundance of greater than 0.1% and the total load is roughly 1e11 copies/mL.

In summary, provided herein are methods and systems and related composition, to provide a rodent model having a target microbiome profile formed by a target presence, a target proportion and/or a target total load of a target prokaryote of a target taxon, based on absolute quantification of the target prokaryote. Further provided are rodents identified and/obtained by the methods herein described and related use in testing methods performed in connection with physiological or pathological conditions in an individual preferably a human individual.

In particular, methods and systems and related composition, to provide a rodent model having a target microbiome profile are performed using methods and systems for absolute quantification of a target 16S rRNA and/or of a target prokaryotic taxon, based on amplifying and sequencing a same 16S rRNA recognition segment in which target 16S rRNA conserved regions flank 16S rRNA variable regions, conserved and variable among a plurality of sample 16S rRNAs and/or of a sample prokaryotic taxon of higher taxonomic rank with respect to the target taxon. In the methods and systems, absolute abundance of the a plurality of sample 16S rRNAs and/or of the sample prokaryotic taxon detected by the amplifying, is multiplied by the relative abundance of the target 16S rRNA and/or of a target prokaryotic taxon detected by the sequencing to provide the absolute quantification in accordance with method and systems of the disclosure.

Provided herein are also a tail-cup and related use to prevent coprophagia in rodent and/or other coprophagic animals. Further provided herein is a non-coprophagic rodent identified and/or obtained by the combined used of the tail-cup and the absolute quantification methods herein described and related use and methods identifiable by a skilled person upon reading of the present disclosure.

The examples set forth above are provided to give those of ordinary skill in the art a complete disclosure and description of how to make and use the embodiments of the compounds, compositions, rodents, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure, including references cited in any one of the Appendices, are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2506-USCIP-Sequence-Listing_ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Bogatyrev, S. R., *Development of Analytical Tools and Animal Models for Studies of Small-Intestine Dysbiosis*. 2020, California Institute of Technology.
2. Bogatyrev, S. R., J. C. Rolando, and R. F. Ismagilov, *Self-reinoculation with fecal flora changes microbiota density and composition leading to an altered bile-acid profile in the mouse small intestine*. Microbiome, 2020. 8(1): p. 19.
3. Callahan, B. J., et al., *DADA2: High-resolution sample inference from Illumina amplicon data*. Nat Methods, 2016. 13(7): p. 581-3.
4. Vandeputte, D., et al., *Quantitative microbiome profiling links gut community variation to microbial load*. Nature, 2017. 551(7681): p. 507-511.
5. Tourlousse, D. M., et al., *Synthetic spike-in standards for high-throughput 16S rRNA gene amplicon sequencing*. Nucleic Acids Research, 2016. 45(4): p. e23-e23.
6. Jian, C., et al., *Quantitative PCR provides a simple and accessible method for quantitative microbiota profiling*. PLoS One, 2020. 15(1): p. e0227285.
7. Contijoch, E. J., et al., *Gut microbiota density influences host physiology and is shaped by host and microbial factors*. Elife, 2019. 8.
8. Olson, C. A., et al., *The Gut Microbiota Mediates the Anti-Seizure Effects of the Ketogenic Diet*. Cell, 2018. 173(7): p. 1728-1741.e13.
9. Klindworth, A., et al., *Evaluation of general 16S ribosomal RNA gene PCR primers for classical and next-generation sequencing-based diversity studies*. Nucleic Acids Res, 2013. 41(1): p. e1.
10. Collado, M. C., et al., *Intestinal integrity and Akkermansia muciniphila, a mucin-degrading member of the intestinal microbiota present in infants, adults, and the elderly*. Applied and environmental microbiology, 2007. 73(23): p. 7767-7770.
11. Rinttilä, T., et al., *Development of an extensive set of 16S rDNA-targeted primers for quantification of pathogenic and indigenous bacteria in faecal samples by real-time PCR*. Journal of Applied Microbiology, 2004. 97(6): p. 1166-1177.
12. Kennedy, N. A., et al., *The impact of different DNA extraction kits and laboratories upon the assessment of human gut microbiota composition by 16S rRNA gene sequencing*. PLoS One, 2014. 9(2): p. e88982.
13. Castillo, M., et al., *Quantification of total bacteria, enterobacteria and lactobacilli populations in pig digesta by real-time PCR*. Veterinary Microbiology, 2006. 114(1): p. 165-170.
14. Nguyen, T. L., et al., *How informative is the mouse for human gut microbiota research?* Dis Model Mech, 2015. 8(1): p. 1-16.
15. Zmora, N., et al., *Personalized Gut Mucosal Colonization Resistance to Empiric Probiotics Is Associated with Unique Host and Microbiome Features*. Cell, 2018.174 (6): p. 1388-1405 e21.
16. Caporaso, J. G., et al., *Ultra-high-throughput microbial community analysis on the Illumina HiSeq and MiSeq platforms*. ISME J, 2012. 6(8): p. 1621-4.
17. Bogatyrev, S. R. and R. F. Ismagilov, *Quantitative microbiome profiling in lumenal and tissue samples with broad coverage and dynamic range via a single-step 16S rRNA gene DNA copy quantification and amplicon barcoding*. bioRxiv, 2020: p. 2020.01.22.914705.
18. Caporaso, J. G., et al., *Global patterns of 16S rRNA diversity at a depth of millions of sequences per sample*. Proc Natl Acad Sci USA, 2011. 108 Suppl 1: p. 4516-22.
19. Aigrain, L., Y. Gu, and M. A. Quail, *Quantitation of next generation sequencing library preparation protocol efficiencies using droplet digital PCR assays—a systematic comparison of DNA library preparation kits for Illumina sequencing*. BMC Genomics, 2016. 17: p. 458.
20. *KAPA Library Quantification Technical Guide v2.19*. 2019.
21. *Illumina Adapter Sequences 1000000002694 v11*. 2019.
22. Atarashi, K., et al., *Ectopic colonization of oral bacteria in the intestine drives TH1 cell induction and inflammation*. Science, 2017. 358(6361): p. 359.
23. Schmidt, T. S. B., et al., *Extensive transmission of microbes along the gastrointestinal tract*. eLife, 2019. 8: p. e42693.
24. Elazhary, M. A., et al., *A simple procedure for the preliminary identification of aerobic gram negative intestinal bacteria with special reference to the Enterobacteriaceae*. Canadian journal of comparative medicine: Revue canadienne de medecine comparee, 1973. 37(1): p. 43-46.
25. Ruoff, K. L., *Miscellaneous Catalase-Negative, Gram-Positive Cocci: Emerging Opportunists*. Journal of Clinical Microbiology, 2002. 40(4): p. 1129.
26. *Approved Lists of Bacterial Names (Amended)*. 1989, Washington (DC): ASM Press.
27. Zhang, Z., et al., *Roles and applications of probiotic Lactobacillus strains*. Applied Microbiology and Biotechnology, 2018. 102(19): p. 8135-8143.
28. Park, J. C. and S.-H. Im, *Of men in mice: the development and application of a humanized gnotobiotic mouse model for microbiome therapeutics*. Experimental & Molecular Medicine, 2020.52(9):p. 1383-1396.
29. Wirtz, S. and M. F. Neurath, *Mouse models of inflammatory bowel disease*. Advanced Drug Delivery Reviews, 2007. 59(11): p. 1073-1083.
30. Lutz, T. A. and S. C. Woods, *Overview of animal models of obesity*. Current protocols in pharmacology, 2012. Chapter 5: p. Unit5.61-Unit5.61.
31. Pizarro, T. T., et al., *SAMP1/YitFc mouse strain: a spontaneous model of Crohn's disease-like ileitis*. Inflammatory bowel diseases, 2011. 17(12): p. 2566-2584.

32. Pearson, J. A., F. S. Wong, and L. Wen, *The importance of the Non Obese Diabetic (NOD) mouse modelin autoimmune diabetes*. Journal of autoimmunity, 2016. 66: p. 76-88.
33. Croy, B. A., et al., *Chapter 13—Mouse Models of Immunodeficiency*, in The Mouse in Biomedical Research (Second Edition), J. G. Fox, et al., Editors. 2007, Academic Press: Burlington. p. 275-289.
34. Waldner, M. J. and M. F. Neurath, *Chemically Induced Mouse Models of Colitis*. Current Protocols in Pharmacology, 2009. 46(1): p. 5.55.1-5.55.15.
35. Yi, M., et al., *Gut microbiome modulates efficacy of immune checkpoint inhibitors*. Journal of Hematology & Oncology, 2018. 11(1): p. 47.
36. Di Gioia, D., et al., *Bifidobacteria: their impact on gut microbiota composition and their applications as probiotics in infants*. Applied Microbiology and Biotechnology, 2014. 98(2): p. 563-577.
37. Gevers, D., et al., *The Treatment-Naive Microbiome in New-Onset Crohn's Disease*. Cell Host & Microbe, 2014. 15(3): p. 382-392.
38. Myers, E. W. and W. Miller, *Optimal alignments in linear space*. Comput Appl Biosci, 1988. 4(1): p. 11-7.
39. Smith, T. F. and M. S. Waterman, *Comparison of biosequences*. Advances in Applied Mathematics, 1981.2(4):p. 482-489.
40. Needleman, S. B. and C. D. Wunsch, *A general method applicable to the search for similarities in the amino acid sequence of two proteins*. J Mol Biol, 1970. 48(3): p. 443-53.
41. Pearson, W. R. and D. J. Lipman, *Improved tools for biological sequence comparison*. Proc Natl Acad Sci USA, 1988. 85(8): p. 2444-8.
42. Karlin, S. and S. F. Altschul, *Methods for assessing the statistical significance of molecular sequence features by using general scoring schemes*. Proc Natl Acad Sci USA, 1990. 87(6): p. 2264-8.
43. Karlin, S. and S. F. Altschul, *Applications and statistics for multiple high-scoring segments in molecular sequences*. Proc Natl Acad Sci USA, 1993. 90(12): p. 5873-7.
44. Bodilis, J., et al., *Variable copy number, intra-genomic heterogeneities and lateral transfers of the 16S rRNA gene in Pseudomonas*. PLoS One, 2012. 7(4): p. e35647.
45. Douglas, G. M., et al., *PICRUSt2: An improved and customizable approach for metagenome inference*. bioRxiv, 2020: p. 672295.
46. Langille, M. G., et al., *Predictive functional profiling of microbial communities using 16S rRNA marker gene sequences*. Nat Biotechnol, 2013. 31(9): p. 814-21.
47. Angly, F. E., et al., *CopyRighter: a rapid tool for improving the accuracy of microbial community profiles through lineage-specific gene copy number correction*. Microbiome, 2014. 2: p. 11.
48. Bowman, J. S. and H. W. Ducklow, *Microbial Communities Can Be Described by Metabolic Structure: A General Framework and Application to a Seasonally Variable, Depth-Stratified Microbial Community from the Coastal West Antarctic Peninsula*. PLoS One, 2015. 10(8): p. e0135868.
49. Stoddard, S. F., et al., *rrnDB: improved tools for interpreting rRNA gene abundance in bacteria and archaea and a new foundation for future development*. Nucleic Acids Res, 2015. 43(Database issue):p. D593-8.
50. Koressaar, T. and M. Remm, *Enhancements and modifications of primer design program Primer3*. Bioinformatics, 2007. 23(10): p. 1289-91.
51. Untergasser, A., et al., *Primer3—new capabilities and interfaces*. Nucleic Acids Res, 2012. 40(15): p. e115.
52. Koressaar, T., et al., *Primer3_masker: integrating masking of template sequence with primer design software*. Bioinformatics, 2018. 34(11): p. 1937-1938.
53. Marshall, O. J., *PerlPrimer: cross-platform, graphical primer design for standard, bisulphite and real-time PCR*. Bioinformatics, 2004. 20(15): p. 2471-2.
54. Ye, J., et al., *Primer-BLAST: a tool to design target-specific primers for polymerase chain reaction*. BMC Bioinformatics, 2012. 13: p. 134.
55. Pruesse, E., et al., *SILVA: a comprehensive online resource for quality checked and aligned ribosomal RNA sequence data compatible with ARB*. Nucleic Acids Res, 2007. 35(21): p. 7188-96.
56. Quast, C., et al., *The SILVA ribosomal RNA gene database project: improved data processing and web-based tools*. Nucleic acids research, 2013. 41(Database issue): p. D590-D596.
57. *The advantage of long reads in 16S rDNA-based microbiome studies*. [cited 2020 Jul. 9, 2020]; Available from: https://nanoporotech.com/resource-centre/advantage-long-reads-16s-rdna-based-microbiome-studies.
58. Shin, J., et al., *Analysis of the mouse gut microbiome using full-length 16S rRNA amplicon sequencing*. Sci Rep, 2016. 6: p. 29681.
59. Nygaard, A. B., et al., *A preliminary study on the potential of Nanopore MinON and Illumina MiSeq 16S rRNA gene sequencing to characterize building-dust microbiomes*. Sci Rep, 2020. 10(1): p. 3209.
60. Sambo, F., et al., *Optimizing PCR primers targeting the bacterial 16S ribosomal RNA gene*. BMC Bioinformatics, 2018. 19(1): p. 343.
61. Lutzoni Lab:16S ribosomal DNA. [cited 2020 Jul. 9, 2020]; Available from: http://lutzonilab.org/16s-ribosomal-dna/.
62. Turner, S., et al., *Investigating deep phylogenetic relationships among cyanobacteria and plastids by small subunit rRNA sequence analysis*. J Eukaryot Microbiol, 1999. 46(4): p. 327-38.
63. Lane, D. J., *16S/23S rRNA sequencing*, in Nucleic acid techniques in bacterial systematics, E. Stackebrandt and M. Goodfellow, Editors. 1991, John Wiley and Sons: New York, NY. p. 115-175.
64. Nubel, U., F. Garcia-Pichel, and G. Muyzer, *PCR primers to amplify 16S rRNA genes from cyanobacteria*. Appl Environ Microbiol, 1997. 63(8): p. 3327-32.
65. Rudi, K., et al., *Strain characterization and classification of oxyphotobacteria in clone cultures on the basis of 16S rRNA sequences from the variable regions V6, V7, and V8*. Appl Environ Microbiol, 1997. 63(7): p. 2593-9.
66. Weisburg, W. G., et al., *16S ribosomal DNA amplification for phylogenetic study*. J Bacteriol, 1991. 173(2): p. 697-703.
67. Hodkinson, B. P. and F. Lutzoni, *A microbiotic survey of lichen-associated bacteria reveals a new lineage from the Rhizobiales*. Symbiosis, 2010. 49(3): p. 163-180.
68. *16S Metagenomic sequencing library preparation: Preparing 16S ribosomal RNA gene amplicons for the Illumina MiSeq system (Illumina Technical Note 15044223 Rev. B)* 2013, Illumina.
69. Gohl, D. M., et al., *Systematic improvement of amplicon marker gene methods for increased accuracy in microbiome studies*. Nat Biotechnol, 2016. 34(9): p. 942-9.
70. Lundberg, D. S., et al., *Practical innovations for high-throughput amplicon sequencing*. Nat Methods, 2013. 10(10): p. 999-1002.

71. Zhou, H. W., et al., *BIPES, a cost-effective high-throughput method for assessing microbial diversity*. ISME J, 2011. 5(4): p. 741-9.
72. Claesson, M. J., et al., *Comparison of two next-generation sequencing technologies for resolving highly complex microbiota composition using tandem variable 16S rRNA gene regions*. Nucleic Acids Res, 2010. 38(22): p. e200.
73. Zymo Research: Quick-16S NGS Library Prep Kit. [cited 2020 Jul. 9, 2020]; Available from: https://www.zymoresearch.com/products/quick-16s-ngs-library-prep-kit.
74. *Zymo Research Quick-16S NGS Library Prep Kit*. p. 21.
75. Korbie, D. J. and J. S. Mattick, *Touchdown PCR for increased specificity and sensitivity in PCR amplification*. Nat Protoc, 2008. 3(9): p. 1452-6.
76. Polz, M. F. and C. M. Cavanaugh, *Bias in template-to-product ratios in multitemplate PCR*. Appl Environ Microbiol, 1998. 64(10): p. 3724-30.
77. Spiess, A. N, C. Feig, and C. Ritz, *Highly accurate sigmoidal fitting of real-time PCR data by introducing a parameter for asymmetry*. BMC Bioinformatics, 2008.9: p. 221.
78. Schloss, P. D., et al., *Introducing mothur: open-source, platform-independent, community-supported software for describing and comparing microbial communities*. Appl Environ Microbiol, 2009. 75(23): p. 7537-41.
79. Caporaso, J. G., et al., *QIIME allows analysis of high-throughput community sequencing data*. Nat Methods, 2010. 7(5): p. 335-6.
80. Bolyen, E., et al., *Reproducible, interactive, scalable and extensible microbiome data science using QIIME 2*. Nat Biotechnol, 2019. 37(8): p. 852-857.
81. Kreutz, J. E., *Theoretical design and analysis of multi-volume digital assays with wide dynamic range validated experimentally with microfluidic digital PCR*. Anal Chem, 2011. 83(21): p. 8158-68.
82. Wrzosek, L., et al., *Transplantation of human microbiota into conventional mice durably reshapes the gut microbiota*. Scientific Reports, 2018. 8(1): p. 6854.
83. Geyer, R. P., B. R. Geyer, and et al., *Growth studies with rats kept under conditions that prevent coprophagy*. J Nutr, 1947. 33(2): p. 129-42.
84. V. Chalam Metta, L. N., B. Connor Johnson, *A Tubular Coprophagy-Preventing Cage for the Rat*. The Journal of Nutrition, 1961. 74(4): p. 473-476.
85. Yoshio KURIHARA, S., Seizi SUKEMORI, Sumimaro ITOH, *Hydrous Feces Induced Coprophagy in Rat*. Japanese Journal of livestock Management, 1997. 32(3): p. 91-98.
86. S. SUKEMORI, S., Y. KURIHARA, S. ITO, *Comparison of Three Types of Equipment for Preventing Coprophagy in Rats*. Japanese Journal of livestock Management, 2000. 36(2): p. 69-75.
87. Saito, K. Y. E. K. Y. T. R., *A simple method for prevention of coprophagy in the mouse*. Laboratory Animals, 1988.
88. and, B. K. A. and A. Softly, *Prevention of coprophagy in the rat. A new method*. British Journal of Nutrition, 1966. 20(3): p. 595-598.
89. Bo, T. B., et al., *Coprophagy prevention alters microbiome, metabolism, neurochemistry, and cognitive behavior in a small mammal*. ISME J, 2020. 14(10): p. 2625-2645.
90. Richard H. Barnes, G. F., Bette McGehee, Ann Brown, *Prevention of Coprophagy in the Rat*. The Journal of Nutrition, 1957. 63(4): p. 489-498.
91. Chubb, D. L. F. J. W. L. G., *A simplified metabolism cage and tail cup for young rats*. Laboratory Animals, 1970.
92. Schaarschmidt, K., et al., *[Improved model of a fecal collection device for the prevention of coprophagia in the rat]*. J Exp Anim Sci, 1991. 34(2): p. 67-71.
93. Smyth, R. E., *Fecal cup for collection of feces in male rats*. Lab Anim Sci, 1979. 29(5): p. 677-8.
94. Ryer, F. H. and D. W.Walker, *An anal cup for rats in metabolic studies involving radioactive materials*. Lab Anim Sci, 1971. 21(6): p. 942-3.
95. Ohta, A., et al., *Prevention of coprophagy modifies magnesium absorption in rats fed with fructo-oligosaccharides*. Br J Nutr, 1996. 75(5): p. 775-84.
96. Neale, R. J., *Coprophagy in iron-deficient rats*. Lab Anim, 1982. 16(2): p. 204-7.
97. Neale, R. J., *Coprophagy in iron-deficient rats: II. 2 novel methods of prevention*. Lab Anim, 1984. 18(2): p. 119-24.
98. Zhang, D., D. G. Hendricks, and A. W. Mahoney, *Effect of coprophagy on bioavailability of iron from plantfoods fed to anemic rats*. Plant Foods Hum Nutr, 1992. 42(2): p. 97-108.
99. Geever, E. F., D. Kan, and S. M. Levenson, *Effect of coprophagy on experimental iron absorption in the rat*. J Nutr, 1969. 98(1): p. 95-8.
100. Fajardo, G. and H. Hornicke, *Problems in estimating the extent of coprophagy in the rat*. Br J Nutr, 1989. 62(3): p. 551-61.
101. Thomas, R. L. and L. J. Roe, *Coprophagy in laboratory animals: a preliminary study to assess potential influences of excreta ingestion on radionuclide retention patterns*. Am Ind Hyg Assoc J, 1974. 35(11): p. 741-7.
102. Calattini, S., et al., *Functional and Biochemical Characterization of Hepatitis C Virus (HCV) Particles Produced in a Humanized Liver Mouse Model*. J Biol Chem, 2015. 290(38): p. 23173-87.
103. Strom, M. G. a. S., *Mice With Human Livers*. Gastroenterology, 2013. 145(6): p. 1209-1214.
104. Zymo Research: ZymoBIOMICS Microbial Community Standards. [cited 2020 Jul. 9, 2020]; Available from: https://www.zymoresearch.com/collections/zymo-biomics-microbial-community-standards..
105. Leite, G. G. S., et al., *Mapping the Segmental Microbiomes in the Human Small Bowel in Comparison with Stool: A REIMAGINE Study*. Digestive Diseases and Sciences, 2020. 65(9): p. 2595-2604.
106. *AVMA Guidelines for the Euthanasia of Animal: 2013 Edition*. 2013.
107. Aitchison, J., *The Statistical Analysis of Compositional Data*. Journal of the Royal Statistical Society: Series B (Methodological), 1982. 44(2): p. 139-160.
108. McMurdie, P. J. and S. Holmes, *Waste Not, Want Not: Why Rarefying Microbiome Data Is Inadmissible*. PLOS Computational Biology, 2014. 10(4): p. e1003531.
109. Weiss, S., et al., *Normalization and microbial differential abundance strategies depend upon data characteristics*. Microbiome, 2017. 5(1): p. 27.
110. Bokulich, N. A., et al., *Optimizing taxonomic classification of marker-gene amplicon sequences with QIIME 2's q2-feature-classifier plugin*. Microbiome, 2018. 6(1): p. 90.
111. Kruskal, W. H. and W. A. Wallis, *Use of Ranks in One-Criterion Variance Analysis*. Journal of the American Statistical Association, 1952. 47(260): p. 583-621.
112. Benjamini, Y. and Y. Hochberg, *Controlling the False Discovery Rate: A Practical and Powerful Approach to Multiple Testing*. Journal of the Royal Statistical Society: Series B (Methodological), 1995. 57(1): p. 289-300.

113. Suzuki, M. T. and S. J. Giovannoni, *Bias caused by template annealing in the amplification of mixtures of 16S rRNA genes by PCR*. Appl Environ Microbiol, 1996. 62(2): p. 625-30.

114. Acinas, S. G., et al., *PCR-induced sequence artifacts and bias: insights from comparison of two 16S rRNA clone libraries constructed from the same sample*. Applied and environmental microbiology, 2005. 71(12): p. 8966-8969.

115. Martino, C., et al., *A Novel Sparse Compositional Technique Reveals Microbial Perturbations*. mSystems, 2019. 4(1): p. e00016-19.

116. Donaldson, G. P., S. M. Lee, and S. K. Mazmanian, *Gut biogeography of the bacterial microbiota*. Nat Rev Microbiol, 2016. 14(1): p. 20-32.

117. Barnes, R. H., et al., *Prevention of coprophagy in the rat*. J Nutr, 1957. 63(4): p. 489-98.

118. Frape, D. L., J. Wilkinson, and L. G. Chubb, *A simplified metabolism cage and tail cup for young rats*. Lab Anim, 1970. 4(1): p. 67-73.

119. Hoff, J., *Methods of blood collection in the mouse*. Lab Animal, 2000. 29(10): p. 47-53.

120. Oblinger, J. L. and J. A. Koburger, *Understanding and Teaching the Most Probable Number Technique1*. Journal of Milk and Food Technology, 1975. 38(9): p. 540-545.

121. Rowe, R., R. Todd, and J. Waide, *Microtechnique for most-probable-number analysis*. Appl Environ Microbiol, 1977. 33(3): p. 675-80.

122. Kuai, L., A. A. Nair, and M. F. Polz, *Rapid and simple method for the most-probable-number estimation of arsenic-reducing bacteria*. Appl Environ Microbiol, 2001. 67(7): p. 3168-73.

123. Chen, C. Y., G. W. Nace, and P. L. Irwin, *A 6×6 drop plate method for simultaneous colony counting and MPN enumeration of Campylobacter jejuni, Listeria monocytogenes, and Escherichia coli*. J Microbiol Methods, 2003. 55(2): p. 475-9.

124. Ozkanca, R., et al., *Resuscitation and quantification of stressed Escherichia coli K12 NCTC8797 in water samples*. Microbiol Res, 2009. 164(2): p. 212-20.

125. Blodgett, R. BAM Appendix 2: Most Probable Number from Serial Dilutions. 2010; Available from: https://www.fda/gov/food/laboratory-methods-food/bam-appendix-2-most-probable-number-serial-dilutions.

126. Taxonomy classifiers for use with q2-feature-classifier. Aug. 6, 2019]; Available from: https://docs.qiime2.org/2019.1/data-resources/#taxonomy-classifiers-for-use-with-q2-feature-classifier.

127. SILVA rRNA database project. Available from: https//www.arb-silva.de/downloas/archive/qiime.

128. Zaiontz, C., *Real Statistics Resource Pack (Release 6.2)*. 2019.

129. Walt, S. v. d., S. C. Colbert, and G. Varoquaux, *The NumPy Array: A Structure for Efficient Numerical Computation*. Computing in Science & Engineering, 2011. 13(2): p. 22-30.

130. McKinney, W. *Data Structures for Statistical Computing in Python*. in *9th Python in Science Conference*.

131. Jones, E., et al., *{SciPy}: Open source scientific tools for {Python}*.

132. Virtanen, P., et al., *SciPy 1.0: fundamental algorithms for scientific computing in Python*. Nat Methods, 2020. 17(3): p. 261-272.

133. Seabold, S. and J. Perktold. *statsmodels: Econometric and statistical modeling with python*. in *9th Python in Science Conference*. 2010.

134. Hunter, J. D., *Matplotlib: A 2D Graphics Environment*. Computing in Science & Engineering, 2007. 9(3): p. 90-95.

135. Waskom, M., et al., *mwaskom/seaborn: v0.9.0 (July 2018)*. 2018.

136. Perez, F. and B. E. Granger, *IPython: A System for Interactive Scientific Computing*. Computing in Science & Engineering, 2007. 9(3): p. 21-29.

137. Kluyver, T., et al. *Jupyter Notebooks—a publishing format for reproducible computational workflows*. in *20th International Conference on Electronic Publishing*. 2016.

138. Anaconda, *Anaconda Software Distribution. Version 4.7.11*. 2019.

139. Davis, N. M., et al., *Simple statistical identification and removal of contaminant sequences in marker-gene and metagenomics data*. Microbiome, 2018. 6(1): p. 226.

140. Gloor, G. B., et al., *It's all relative: analyzing microbiome data as compositions*. Ann Epidemiol, 2016. 26(5): p. 322-9.

141. Lovell, D., et al., *Proportionality: a valid alternative to correlation for relative data*. PLoS Comput Biol, 2015. 11(3): p. e1004075.

142. Pedregosa, F., et al., *Scikit-learn: Machine Learning in Python*. Journal of machine learning research, 2012.12:p. 2825-2830.

143. van den Berg, R. A., et al., *Centering, scaling, and transformations: improving the biological information content of metabolomics data*. BMC Genomics, 2006. 7: p. 142.

144. Narushima, S., et al., *Deoxycholic acid formation in gnotobiotic mice associated with human intestinal bacteria*. Lipids, 2006. 41(9): p. 835-43.

145. Narushima, S., et al., *Absence of cecal secondary bile acids in gnotobiotic mice associated with two human intestinal bacteria with the ability to dehydroxylate bile acids in vitro*. Microbiol Immunol, 1999. 43(9): p. 893-7.

146. Chikai, T., H. Nakao, and K. Uchida, *Deconjugation of bile acids by human intestinal bacteria implanted in germ-free rats*. Lipids, 1987. 22(9): p. 669-71.

147. Smith, H. W., *Observations on the Flora of the Alimentary Tract of Animals and Factors Affecting Its Composition*. J Pathol Bacteriol, 1965. 89: p. 95-122.

148. Syed, S. A., G. D. Abrams, and R. Freter, *Efficiency of various intestinal bacteria in assuming normal functions of enteric flora after association with germ-free mice*. Infect Immun, 1970. 2(4): p. 376-86.

149. Gu, S., et al., *Bacterial community mapping of the mouse gastrointestinal tract*. PLoS One, 2013. 8(10): p. e74957.

150. Suzuki, T. A. and M. W. Nachman, *Spatial Heterogeneity of Gut Microbial Composition along the Gastrointestinal Tract in Natural Populations of House Mice*. PLoS One, 2016. 11(9): p. e0163720.

151. Ericsson, A. C., et al., *The influence of caging, bedding, and diet on the composition of the microbiota in different regions of the mouse gut*. Sci Rep, 2018. 8(1): p. 4065.

152. Ebino, K. Y., *Studies on coprophagy in experimental animals*. Jikken Dobutsu, 1993. 42(1): p. 1-9.

153. Takahashi, K. W., et al., *Strain Difference in Coprophagous Behavior in Laboratory Mice (Mus musculus)*. Zoological Science, 1985. 2(2): p. p 249-255.

154. Roscoe, M. H., *Spontaneous Cures in Rats reared upon a Diet devoid of Vitamin B and Antineuritic Vitamin*. J Hyg (Lond), 1927. 27(1): p. 103-7.

155. Barnes, R. H. and G. Fiala, *Effects of the prevention of coprophagy in the rat. I. Growth studies*. J Nutr, 1958. 64(4): p. 533-40.

156. Barnes, R. H., *Nutritional implications of coprophagy*. Nutr Rev, 1962. 20: p. 289-91.
157. Hörnicke, H. and G. Björnhag, *Coprophagy and related strategies for digesta utilization*, in Digestive Physiology and Metabolism in Ruminants: Proceedings of the 5th International Symposium on Ruminant Physiology, held at Clermont—Ferrand, on 3rd-7th September, 1979, Y. Ruckebusch and P. Thivend, Editors. 1980, Springer Netherlands: Dordrecht. p. 707-730.
158. Hugenholtz, F. and W. M. de Vos, *Mouse models for human intestinal microbiota research: a critical evaluation*. Cell Mol Life Sci, 2018. 75(1): p. 149-160.
159. Tannock, G. W., *The Lactic Microflora of Pigs, Mice and Rats*, in The Lactic Acid Bacteria Volume 1: The Lactic Acid Bacteria in Health and Disease, B. J. B. Wood, Editor. 1992, Springer US: Boston, MA. p. 21-48.
160. Wang, Z. K. and Y. S. Yang, *Upper gastrointestinal microbiota and digestive diseases*. World J Gastroenterol, 2013. 19(10): p. 1541-50.
161. Lievin-Le Moal, V. and A. L. Servin, *Anti-Infective Activities of Lactobacillus Strains in the Human Intestinal Microbiota: From Probiotics to Gastrointestinal Anti-Infectious Biotherapeutic Agents*. Clin Microbiol Rev, 2014. 27(2): p. 167-99.
162. Saffouri, G. B., et al., *Small intestinal microbial dysbiosis underlies symptoms associated with functional gastrointestinal disorders*. Nat Commun, 2019. 10(1): p. 2012.
163. Seekatz, A. M., et al., *Spatial and Temporal Analysis of the Stomach and Small-Intestinal Microbiota in Fasted Healthy Humans*. mSphere, 2019. 4(2).
164. Vuik, F., et al., *Composition of the mucosa-associated microbiota along the entire gastrointestinal tract of human individuals*. United European Gastroenterol J, 2019. 7(7): p. 897-907.
165. Xu, Z., et al., *Which is more important for classifying microbial communities: who's there or what they can do?* ISME J, 2014. 8(12): p. 2357-9.
166. Foley, M. H., et al., *Bile salt hydrolases: Gatekeepers of bile acid metabolism and host-microbiome crosstalk in the gastrointestinal tract*. PLoS Pathog, 2019. 15(3): p. e1007581.
167. Dong, Z. and B. H. Lee, *Bile salt hydrolases: Structure and function, substrate preference, and inhibitor development*. Protein Sci, 2018. 27(10): p. 1742-1754.
168. Joyce, S. A., et al., *Bacterial bile salt hydrolase in host metabolism: Potential for influencing gastrointestinal microbe-host crosstalk*. Gut Microbes, 2014. 5(5): p. 669-74.
169. *Role of the Gut Flora in Toxicity and Cancer.* 1988: Academic Press. 528.
170. Klaassen, C. D. and J. Y. Cui, *Review: Mechanisms of How the Intestinal Microbiota Alters the Effects of Drugs and Bile Acids*. Drug Metab Dispos, 2015. 43(10): p. 1505-21.
171. Schneider, K. M., S. Albers, and C. Trautwein, *Role of bile acids in the gut-liver axis*. J Hepatol, 2018. 68(5): p. 1083-1085.
172. Wahlstrom, A., et al., *Intestinal Crosstalk between Bile Acids and Microbiota and Its Impact on Host Metabolism*. Cell Metab, 2016. 24(1): p. 41-50.
173. Ridlon, J. M. and J. S. Bajaj, *The human gut sterolbiome: bile acid-microbiome endocrine aspects and therapeutics*. Acta Pharm Sin B, 2015. 5(2): p. 99-105.
174. Northfield, T. C. and I. McColl, *Postprandial concentrations of free and conjugated bile acids down the length of the normal human small intestine*. Gut, 1973. 14(7): p. 513-8.
175. Tso, P., et al., *Acute inhibition of intestinal lipid transport by Pluronic L-81 in the rat*. Am J Physiol, 1981. 241(6): p. G487-97.
176. Phan, C. T. and P. Tso, *Intestinal lipid absorption and transport*. Front Biosci, 2001. 6: p. D299-319.
177. Metta, V. C., L. Nash, and B. C. Johnson, *A Tubular Coprophagy—Preventing Cage for the Rat*. The Journal of Nutrition, 1961. 74(4): p. 473-476.
178. Ebino, K. Y., et al., *A simple method for prevention of coprophagy in the mouse*. Lab Anim, 1988. 22(1): p. 1-4.
179. Franklin, C. L. and A. C. Ericsson, *Microbiota and reproducibility of rodent models*. Lab Anim (NY), 2017. 46(4): p. 114-122.
180. Leite, G. G. S., et al., *Optimizing microbiome sequencing for small intestinal aspirates: validation of novel techniques through the REIMAGINE study*. BMC Microbiology, 2019. 19(1): p. 239.
181. Barlow, J. T., S. R. Bogatyrev, and R. F. Ismagilov, *A quantitative sequencing framework for absolute abundance measurements of mucosal and lumenal microbial communities*. Nature Communications, 2020. 11(1): p. 2590.
182. Bogatyrev, S. R. and R. F. Ismagilov, *Quantitative microbiome profiling in lumenal and tissue samples with broad coverage and dynamic range via a single-step 16S rRNA gene DNA copy quantification and amplicon barcoding*. bioRxiv, 2020: p. 10.1101/2020.01.22.914705v1.
183. Bolyen, E., et al., *QIIME 2: Reproducible, interactive, scalable, and extensible microbiome data science*. PeerJ Preprints, 2018. 6: p. e27295v2.
184. Callahan, B. J., et al., *DADA2: High-resolution sample inference from Illumina amplicon data*. Nature Methods, 2016. 13: p. 581.
185. Bokulich, N. A., et al., *Optimizing taxonomic classification of marker-gene amplicon sequences with QIIME 2's q2-feature-classifier plugin*. Microbiome, 2018. 6(1): p. 90-90.
186. Lagkouvardos, I., J. Overmann, and T. Clavel, *Cultured microbes represent a substantial fraction of the human and mouse gut microbiota*. Gut Microbes, 2017. 8(5): p. 493-503.
187. Ma, R., et al., *Investigation of the effects of pH and bile on the growth of oral Campylobacter concisus strains isolated from patients with inflammatory bowel disease and controls*. Journal of Medical Microbiology, 2015. 64(4): p. 438-445.
188. Marcotte, H. and M. C. Lavoie, *Oral microbial ecology and the role of salivary immunoglobulin A*. Microbiology and molecular biology reviews: MMBR, 1998. 62(1): p. 71-109.
189. Hojo, K., et al., *Bacterial Interactions in Dental Biofilm Development*. Journal of Dental Research, 2009. 88(11): p. 982-990.
190. Pimentel, M., et al., *ACG Clinical Guideline: Small Intestinal Bacterial Overgrowth*. Official journal of the American College of Gastroenterology|ACG, 2020. 115 (2).
191. Leite, G., et al., *The duodenal microbiome is altered in small intestinal bacterial overgrowth*. PLOS ONE, 2020. 15(7): p. e0234906.
192. Mu, Q., V. J. Tavella, and X. M. Luo, *Role of Lactobacillus reuteri in Human Health and Diseases*. Frontiers in Microbiology, 2018. 9(757).
193. Heeney, D. D., M. G. Gareau, and M. L. Marco, *Intestinal Lactobacillus in health and disease, a driver or just along for the ride?* Current Opinion in Biotechnology, 2018. 49: p. 140-147.

The invention claimed is:

1. A method to provide a rodent model having a target microbiome profile formed by a target presence, a target proportion and/or a target total load of a target prokaryote of a target taxon, the target taxon having a taxonomic rank lower than a sample taxon in a same taxonomic hierarchy, the method comprising providing a rodent having a rodent microbiome;
obtaining a sample of the rodent comprising the rodent microbiome to provide a rodent sample;
quantifying absolute abundance of the target prokaryotes in the rodent sample, to obtain a rodent detected presence, a rodent detected proportion and/or a rodent detected total load of the target prokaryotes in the rodent, each target prokaryote being of a target taxon having a taxonomic rank lower than a sample taxon in a same taxonomic hierarchy;
comparing the rodent detected presence, the rodent detected proportion of and/or the rodent detected total load of the target prokaryotes with the target presence, the target proportion and/or the target total load of the target prokaryotes in the target microbiome profile,
wherein quantifying in the modified sample absolute abundance of the target prokaryotes is performed by
amplifying a 16S rRNA recognition segment comprising a 16S rRNA variable region specific for the target taxon flanked by target 16S rRNA conserved regions specific for the sample taxon, by performing amplification of nucleic acids extracted from the sample with primers comprising a primer target sequence specific for the target 16S rRNA conserved regions to quantitatively detect an absolute abundance of prokaryotes of the sample taxon in the sample and to provide an amplified 16S rRNA recognition segment,
sequencing the amplified 16S rRNA recognition segment with primers comprising the primer target sequence specific for the target 16S rRNA conserved region and the 16S rRNA variable regions to detect a relative abundance of the prokaryotes of the target taxon with respect to the prokaryotes of the sample taxon in the sample, and
multiplying the relative abundance of the prokaryotes of the target taxon in the sample times absolute abundance of the prokaryotes of the sample taxon in the sample to quantify the absolute abundance of the prokaryotes of the target taxon in the sample,
and wherein
the detected presence of the target prokaryote in the rodent is provided by the detected relative abundance and/or absolute abundance wherein presence is detected when the relative abundance is greater than a threshold,
the detected proportion is provided by the relative abundance of the target prokaryote and/or by the quantified absolute abundance in combination with the detected relative abundance providing the detected proportion of the target prokaryote in the rodent, and
the total load of the target prokaryote is provided by detected absolute abundance of the target prokaryote of the target taxa and/or the detected absolute abundance of prokaryotes of the sample taxon.

2. The method of claim 1, further comprising
modifying the rodent microbiome by introducing, enriching and/or depleting prokaryotes in the rodent microbiome to provide the rodent microbiome with the target prokaryotes with the target presence, the target proportion, and/or the target total load;
obtaining a sample of the rodent comprising the rodent microbiome following the modifying to obtain a rodent modified sample;
quantifying absolute abundance of the target prokaryotes in the rodent modified sample, to obtain a detected rodent modified presence, a detected rodent modified proportion and/or a detected rodent modified total load of the target prokaryotes in the rodent, each target prokaryote being of a target taxon having a taxonomic rank lower than a sample taxon in a same taxonomic hierarchy; and
comparing the detected rodent modified presence, the detected rodent modified proportion and/or the detected rodent modified total load of the target prokaryotes with the target presence, the target proportion and/or the target total load of the target prokaryotes in the target microbiome profile.

3. The method of claim 2, further comprising
repeating
the modifying,
the obtaining to provide a rodent modified sample,
the quantifying absolute abundance of the target prokaryotes in the rodent modified sample, and
the comparing,
until the detected rodent modified presence, the detected rodent modified proportion and/or the detected rodent modified total load of the target prokaryote is substantially the same as the target presence, the target proportion and/or the target total load of the target prokaryotes, to obtain the rodent model having the target microbiome profile.

4. The method of claim 2, wherein the modifying comprises preventing coprophagia of the rodent.

5. The method of claim 1, wherein the microbiome is a microbiome of the gastrointestinal tract of a human individual.

6. The method of claim 1, wherein the target microbiome is associated with a physiological or pathological condition of a human individual.

7. The method of claim 1, wherein the target prokaryote comprises a *Lactobacillus* and *Bifidobacterium* strain.

8. The method of claim 1, wherein the target microbiome is associated with a pathological condition of a human individual and wherein, the target prokaryote comprises at least one Proteobacteria prokaryotes selected from *Escherichia, Serratia, Campylobacter, Enterococcus, Klebsiella, Pseudomonas, Staphylococcus, Salmonella* and *Yersinia* prokaryotes.

9. The method of claim 1, wherein the target microbiome is associated with a pathological condition of a human individual and wherein, the target prokaryote comprises *Clostridium difficile* prokaryote.

10. The method of claim 1, wherein the target microbiome is associated with a pathological condition of the immune system and/or gastrointestinal tract of the human individual.

11. The method of claim 1, wherein the target 16S rRNAs conserved regions have a homology of at least 90% among the 16S rRNAs of prokaryotes of the sample taxon.

12. The method of claim 1, wherein the target 16S rRNAs conserved regions range from 15 to 25 nucleotides.

13. The method of claim 1, wherein the 16S rRNA variable region comprises at least one region having a signature sequence unique to the 16S rRNAs of prokaryotes of the target taxon.

14. The method of claim 1, wherein the primer target sequence has at least 90% homology with the target 16S rRNAs conserved regions.

15. The method of claim 1, wherein the 16S rRNA is a 16S rRNA gene.

16. The method of claim 1, wherein the amplifying is performed by
amplifying a first portion of the at least two portions of the sample to quantitatively detect an absolute abundance of the plurality of sample 16S rRNAs in the sample, and amplifying a second portion of the sample to provide an amplified 16S rRNA recognition segment.

17. The method of claim 16, wherein the amplifying the first portion of the sample is performed by digital amplification of the 16S rRNA recognition segment, to quantitatively detect an absolute abundance of the plurality of sample 16S rRNA in the sample and performing real-time PCR to provide an amplified 16S rRNA recognition segment.

18. The method of claim 17, wherein the digital amplification is performed by digital PCR.

19. The method of claim 1, wherein the amplifying is performed by real-time qPCR.

20. The method of claim 19, wherein the amplifying is performed with primers further comprising a barcode, adapter, linker, pad and/or frameshifting sequence for next generation sequencing.

21. The method of claim 20, wherein the sequencing and the amplifying are performed on a same sample or portion thereof to quantitatively detect an absolute abundance of the plurality of sample 16S rRNA and to provide an amplified 16S rRNA recognition segment from the same sample or portion thereof.

22. The method of claim 19, wherein sequencing the amplified 16S rRNA recognition segment is performed by amplicon sequencing.

23. The method of claim 19, wherein the sequencing is performed by next generation sequencing with primers further comprising a barcode, adapter, linker, pad and/or frameshifting sequence.

24. The method of claim 23, wherein the primers used in sequencing the amplified 16S rRNA recognition segment further comprise an indexing primer for multiplexing/combining amplicons from multiple samples for simultaneous next generation sequencing.

25. The method of claim 19, wherein the primers comprise a forward primer comprising a primer target sequence of SEQ ID NO: 25 and a reverse primer comprising a primer target sequence of SEQ ID NO: 26.

\* \* \* \* \*

SEQUENCE LISTING

<160> NUMBER OF SEQ ID NOS: 81

<210> SEQ ID NO 1
<211> LENGTH: 19
<212> TYPE: DNA
<213> ORGANISM: artificial sequence
<220> FEATURE:
<223> OTHER INFORMATION: synthetic polynucleotide

<400> SEQUENCE: 1
gtgccagcag ccgcggtaa                                                19

<210> SEQ ID NO 2
<211> LENGTH: 19
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (9)..(9)
<223> OTHER INFORMATION: M is A or C

<400> SEQUENCE: 2
gtgccagcmg ccgcggtaa                                                19

<210> SEQ ID NO 3
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: M is A or C

<400> SEQUENCE: 3
cagcmgccgc ggtaa                                                    15

<210> SEQ ID NO 4
<211> LENGTH: 19
<212> TYPE: DNA
<213> ORGANISM: artificial sequence
<220> FEATURE:
<223> OTHER INFORMATION: synthetic polynucleotide

<400> SEQUENCE: 4
gtgccagcca ccgcggtca                                                19

<210> SEQ ID NO 5
<211> LENGTH: 19
<212> TYPE: DNA
<213> ORGANISM: artificial sequence
<220> FEATURE:
<223> OTHER INFORMATION: synthetic polynucleotide

<400> SEQUENCE: 5
gtgccagcca ccgcggtca                                                19

<210> SEQ ID NO 6
<211> LENGTH: 20
<212> TYPE: DNA
<213> ORGANISM: artificial sequence
<220> FEATURE:
<223> OTHER INFORMATION: synthetic polynucleotide

<400> SEQUENCE: 6

```
cagcacgtga aggtggggac                                                  20

<210> SEQ ID NO 7
<211> LENGTH: 20
<212> TYPE: DNA
<213> ORGANISM: artificial sequence
<220> FEATURE:
<223> OTHER INFORMATION: synthetic polynucleotide

<400> SEQUENCE: 7
ggtgtcggct taagtgccat                                                  20

<210> SEQ ID NO 8
<211> LENGTH: 19
<212> TYPE: DNA
<213> ORGANISM: artificial sequence
<220> FEATURE:
<223> OTHER INFORMATION: synthetic polynucleotide

<400> SEQUENCE: 8
cggtacctga ctaagaagc                                                   19

<210> SEQ ID NO 9
<211> LENGTH: 21
<212> TYPE: DNA
<213> ORGANISM: artificial sequence
<220> FEATURE:
<223> OTHER INFORMATION: synthetic polynucleotide

<400> SEQUENCE: 9
gcagcagtag ggaatcttcc a                                                21

<210> SEQ ID NO 10
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: M is A or C

<400> SEQUENCE: 10
cagcmgccgc ggtaa                                                       15

<210> SEQ ID NO 11
<211> LENGTH: 20
<212> TYPE: DNA
<213> ORGANISM: artificial sequence
<220> FEATURE:
<223> OTHER INFORMATION: synthetic polynucleotide

<400> SEQUENCE: 11
ccttgcggtt ggcttcagat                                                  20

<210> SEQ ID NO 12
<211> LENGTH: 18
<212> TYPE: DNA
<213> ORGANISM: artificial sequences
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: Y is C or T
```

```
<400> SEQUENCE: 12
cggaygtaag ggccgtgc                                                 18

<210> SEQ ID NO 13
<211> LENGTH: 19
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (6)..(6)
<223> OTHER INFORMATION: Y is C or T

<400> SEQUENCE: 13
agtttyattc ttgcgaacg                                                19

<210> SEQ ID NO 14
<211> LENGTH: 17
<212> TYPE: DNA
<213> ORGANISM: artificial sequence
<220> FEATURE:
<223> OTHER INFORMATION: synthetic polynucleotide

<400> SEQUENCE: 14
caccgctaca catggag                                                  17

<210> SEQ ID NO 15
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: H is A or C or T
<220> FEATURE:
<221> NAME/KEY: misc_feature
<222> LOCATION: (9)..(9)
<223> OTHER INFORMATION: V is A or C or G
<220> FEATURE:
<221> NAME/KEY: misc_feature
<222> LOCATION: (14)..(14)
<223> OTHER INFORMATION: W is A or T

<400> SEQUENCE: 15
ggactachvg ggtwtctaat                                               20

<210> SEQ ID NO 16
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: M is A or C

<400> SEQUENCE: 16
cagcmgccgc ggtaa                                                    15

<210> SEQ ID NO 17
<211> LENGTH: 20
<212> TYPE: DNA
<213> ORGANISM: artificial sequence
<220> FEATURE:
<223> OTHER INFORMATION: synthetic polynucleotide
```

```
<220> FEATURE:
<221> NAME/KEY: misc_feature
<222> LOCATION: (8)..(8)
<223> OTHER INFORMATION: H is A or C or T
<220> FEATURE:
<221> NAME/KEY: misc_feature
<222> LOCATION: (9)..(9)
<223> OTHER INFORMATION: V is A or C or G
<220> FEATURE:
<221> NAME/KEY: misc_feature
<222> LOCATION: (14)..(14)
<223> OTHER INFORMATION: W is A or T

<400> SEQUENCE: 17
ggactachvg ggtwtctaat                                               20

<210> SEQ ID NO 18
<211> LENGTH: 56
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (46)..(46)
<223> OTHER INFORMATION: M is A or C

<400> SEQUENCE: 18
aatgatacgg cgaccaccga gatctacact atggtaattg tcagcmgccg cggtaa       56

<210> SEQ ID NO 19
<211> LENGTH: 68
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (25)..(25)
<223> OTHER INFORMATION: N is A or C or G or T
<220> FEATURE:
<221> NAME/KEY: misc_feature
<222> LOCATION: (26)..(26)
<223> OTHER INFORMATION: N is A or C or G or T
<220> FEATURE:
<221> NAME/KEY: misc_feature
<222> LOCATION: (27)..(27)
<223> OTHER INFORMATION: N is A or C or G or T
<220> FEATURE:
<221> NAME/KEY: misc_feature
<222> LOCATION: (28)..(28)
<223> OTHER INFORMATION: N is A or C or G or T
<220> FEATURE:
<221> NAME/KEY: misc_feature
<222> LOCATION: (29)..(29)
<223> OTHER INFORMATION: N is A or C or G or T
<220> FEATURE:
<221> NAME/KEY: misc_feature
<222> LOCATION: (30)..(30)
<223> OTHER INFORMATION: N is A or C or G or T
<220> FEATURE:
<221> NAME/KEY: misc_feature
<222> LOCATION: (31)..(31)
<223> OTHER INFORMATION: N is A or C or G or T
<220> FEATURE:
<221> NAME/KEY: misc_feature
<222> LOCATION: (32)..(32)
<223> OTHER INFORMATION: N is A or C or G or T
<220> FEATURE:
<221> NAME/KEY: misc_feature
<222> LOCATION: (33)..(33)
<223> OTHER INFORMATION: N is A or C or G or T
<220> FEATURE:
<221> NAME/KEY: misc_feature
<222> LOCATION: (34)..(34)
```

```
<223> OTHER INFORMATION: N is A or C or G or T
<220> FEATURE:
<221> NAME/KEY: misc_feature
<222> LOCATION: (35)..(35)
<223> OTHER INFORMATION: N is A or C or G or T
<220> FEATURE:
<221> NAME/KEY: misc_feature
<222> LOCATION: (36)..(36)
<223> OTHER INFORMATION: N is A or C or G or T
<220> FEATURE:
<221> NAME/KEY: misc_feature
<222> LOCATION: (56)..(56)
<223> OTHER INFORMATION: H is A or C or T
<220> FEATURE:
<221> NAME/KEY: misc_feature
<222> LOCATION: (57)..(57)
<223> OTHER INFORMATION: V is A or C or G
<220> FEATURE:
<221> NAME/KEY: misc_feature
<222> LOCATION: (62)..(62)
<223> OTHER INFORMATION: W is A or T

<400> SEQUENCE: 19
caagcagaag acggcatacg agatnnnnnn nnnnnnagtc agtcagccgg actachvggg     60 twtctaat                                                              68

<210> SEQ ID NO 20
<211> LENGTH: 20
<212> TYPE: DNA
<213> ORGANISM: artificial sequence
<220> FEATURE:
<223> OTHER INFORMATION: synthetic polynucleotide

<400> SEQUENCE: 20
aatgatacgg cgaccaccga                                                 20

<210> SEQ ID NO 21
<211> LENGTH: 21
<212> TYPE: DNA
<213> ORGANISM: artificial sequence
<220> FEATURE:
<223> OTHER INFORMATION: synthetic polynucleotide

<400> SEQUENCE: 21
caagcagaag acggcatacg a                                               21

<210> SEQ ID NO 22
<211> LENGTH: 27
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (17)..(17)
<223> OTHER INFORMATION: M is A or C

<400> SEQUENCE: 22
tatggtaatt gtcagcmgcc gcggtaa                                         27

<210> SEQ ID NO 23
<211> LENGTH: 32
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (20)..(20)
<223> OTHER INFORMATION: H is A or C or T
```

```
<220> FEATURE:
<221> NAME/KEY: misc_feature
<222> LOCATION: (21)..(21)
<223> OTHER INFORMATION: V is A or C or G
<220> FEATURE:
<221> NAME/KEY: misc_feature
<222> LOCATION: (26)..(26)
<223> OTHER INFORMATION: W is A or T

<400> SEQUENCE: 23
agtcagtcag ccggactach vgggtwtcta at                             32

<210> SEQ ID NO 24
<211> LENGTH: 32
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (7)..(7)
<223> OTHER INFORMATION: W is A or T
<220> FEATURE:
<221> NAME/KEY: misc_feature
<222> LOCATION: (12)..(12)
<223> OTHER INFORMATION: B is C or G or T
<220> FEATURE:
<221> NAME/KEY: misc_feature
<222> LOCATION: (13)..(13)
<223> OTHER INFORMATION: D is A or G or T

<400> SEQUENCE: 24
attagawacc cbdgtagtcc ggctgactga ct                             32

<210> SEQ ID NO 25
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: M is A or C

<400> SEQUENCE: 25
cagcmgccgc ggtaa                                                15

<210> SEQ ID NO 26
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: H is A or C or T
<220> FEATURE:
<221> NAME/KEY: misc_feature
<222> LOCATION: (9)..(9)
<223> OTHER INFORMATION: V is A or C or G
<220> FEATURE:
<221> NAME/KEY: misc_feature
<222> LOCATION: (14)..(14)
<223> OTHER INFORMATION: W is A or T

<400> SEQUENCE: 26
ggactachvg ggtwtctaat                                           20

<210> SEQ ID NO 27
```

```
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: H is A or C or T
<220> FEATURE:
<221> NAME/KEY: misc_feature
<222> LOCATION: (9)..(9)
<223> OTHER INFORMATION: V is A or C or G
<220> FEATURE:
<221> NAME/KEY: misc_feature
<222> LOCATION: (14)..(14)
<223> OTHER INFORMATION: W is A or T

<400> SEQUENCE: 27
ggactachvg ggtwtctaat                                           20

<210> SEQ ID NO 28
<211> LENGTH: 20
<212> TYPE: DNA
<213> ORGANISM: artificial sequence
<220> FEATURE:
<223> OTHER INFORMATION: synthetic polynucleotide

<400> SEQUENCE: 28
agagtttgat cctggctcag                                           20

<210> SEQ ID NO 29
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (12)..(12)
<223> OTHER INFORMATION: M is A or C

<400> SEQUENCE: 29
agagtttgat cmtggctcag                                           20

<210> SEQ ID NO 30
<211> LENGTH: 22
<212> TYPE: DNA
<213> ORGANISM: artificial sequence
<220> FEATURE:
<223> OTHER INFORMATION: synthetic polynucleotide

<400> SEQUENCE: 30
cggacgggtg agtaacgcgt ga                                        22

<210> SEQ ID NO 31
<211> LENGTH: 22
<212> TYPE: DNA
<213> ORGANISM: artificial sequence
<220> FEATURE:
<223> OTHER INFORMATION: synthetic polynucleotide

<400> SEQUENCE: 31
ccagactcct acgggaggca gc                                        22

<210> SEQ ID NO 32
<211> LENGTH: 19
<212> TYPE: DNA
<213> ORGANISM: artificial sequence
```

<220> FEATURE:
<223> OTHER INFORMATION: synthetic polynucleotide

<400> SEQUENCE: 32
ctcctacggg aggcagcag                                              19

<210> SEQ ID NO 33
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: Y is C or T

<400> SEQUENCE: 33
ggggaatytt ccgcaatggg                                             20

<210> SEQ ID NO 34
<211> LENGTH: 19
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (9)..(9)
<223> OTHER INFORMATION: M is A or C

<400> SEQUENCE: 34
gtgccagcmg ccgcggtaa                                              19

<210> SEQ ID NO 35
<211> LENGTH: 19
<212> TYPE: DNA
<213> ORGANISM: artificial sequence
<220> FEATURE:
<223> OTHER INFORMATION: synthetic polynucleotide

<400> SEQUENCE: 35
gtgccagcag ccgcggtaa                                              19

<210> SEQ ID NO 36
<211> LENGTH: 16
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (2)..(2)
<223> OTHER INFORMATION: R is G or A
<220> FEATURE:
<221> NAME/KEY: misc_feature
<222> LOCATION: (13)..(13)
<223> OTHER INFORMATION: R is G or A
<220> FEATURE:
<221> NAME/KEY: misc_feature
<222> LOCATION: (15)..(15)
<223> OTHER INFORMATION: R is G or A

<400> SEQUENCE: 36
crcctgggga gtrcrg                                                 16

<210> SEQ ID NO 37
<211> LENGTH: 16
<212> TYPE: DNA

```
<213> ORGANISM: artificial sequence
<220> FEATURE:
<223> OTHER INFORMATION: synthetic polynucleotide

<400> SEQUENCE: 37
caacgagcgc aaccct                                                          16

<210> SEQ ID NO 38
<211> LENGTH: 18
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (13)..(13)
<223> OTHER INFORMATION: Y is C or T
<220> FEATURE:
<221> NAME/KEY: misc_feature
<222> LOCATION: (16)..(16)
<223> OTHER INFORMATION: W is A or T

<400> SEQUENCE: 38
gggctacaca cgygcwac                                                        18

<210> SEQ ID NO 39
<211> LENGTH: 18
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (2)..(2)
<223> OTHER INFORMATION: W is A or T
<220> FEATURE:
<221> NAME/KEY: misc_feature
<222> LOCATION: (14)..(14)
<223> OTHER INFORMATION: K is G or T

<400> SEQUENCE: 39
gwattaccgc ggckgctg                                                        18

<210> SEQ ID NO 40
<211> LENGTH: 25
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (7)..(7)
<223> OTHER INFORMATION: W is A or T
<220> FEATURE:
<221> NAME/KEY: misc_feature
<222> LOCATION: (23)..(23)
<223> OTHER INFORMATION: W is A or T

<400> SEQUENCE: 40
gactacwggg gtatctaatc ccwtt                                                25

<210> SEQ ID NO 41
<211> LENGTH: 23
<212> TYPE: DNA
<213> ORGANISM: artificial sequence
<220> FEATURE:
<223> OTHER INFORMATION: synthetic polynucleotide

<400> SEQUENCE: 41
cttgtgcggg ccccogtcaa ttc                                                  23
```

```
<210> SEQ ID NO 42
<211> LENGTH: 23
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (9)..(9)
<223> OTHER INFORMATION: N is Inosine
<220> FEATURE:
<221> NAME/KEY: misc_feature
<222> LOCATION: (19)..(19)
<223> OTHER INFORMATION: Y is C or T
<220> FEATURE:
<221> NAME/KEY: misc_feature
<222> LOCATION: (21)..(21)
<223> OTHER INFORMATION: R is G or A
<220> FEATURE:
<221> NAME/KEY: misc_feature
<222> LOCATION: (22)..(22)
<223> OTHER INFORMATION: Y is C or T

<400> SEQUENCE: 42
gtcaattcnt ttgagtttya ryc                                           23

<210> SEQ ID NO 43
<211> LENGTH: 25
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (13)..(13)
<223> OTHER INFORMATION: N is Inosine
<220> FEATURE:
<221> NAME/KEY: misc_feature
<222> LOCATION: (23)..(23)
<223> OTHER INFORMATION: Y is C or T
<220> FEATURE:
<221> NAME/KEY: misc_feature
<222> LOCATION: (25)..(25)
<223> OTHER INFORMATION: R is G or A

<400> SEQUENCE: 43
ccccgtcaat tcntttgagt ttyar                                         25

<210> SEQ ID NO 44
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (11)..(11)
<223> OTHER INFORMATION: M is A or C
<220> FEATURE:
<221> NAME/KEY: misc_feature
<222> LOCATION: (15)..(15)
<223> OTHER INFORMATION: R is G or A

<400> SEQUENCE: 44
ccgtcaattc mtttragttt                                               20

<210> SEQ ID NO 45
<211> LENGTH: 16
<212> TYPE: DNA
<213> ORGANISM: artificial sequence
<220> FEATURE:
```

<223> OTHER INFORMATION: synthetic polynucleotide

<400> SEQUENCE: 45
agggttgcgc tcgttg                                                          16

<210> SEQ ID NO 46
<211> LENGTH: 16
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (16)..(16)
<223> OTHER INFORMATION: M is A or C

<400> SEQUENCE: 46
gayttgacgt catccm                                                          16

<210> SEQ ID NO 47
<211> LENGTH: 16
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: Y is C or T

<400> SEQUENCE: 47
gayttgacgt catcca                                                          16

<210> SEQ ID NO 48
<211> LENGTH: 21
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (14)..(14)
<223> OTHER INFORMATION: R is G or A
<220> FEATURE:
<221> NAME/KEY: misc_feature
<222> LOCATION: (17)..(17)
<223> OTHER INFORMATION: Y is C or T
<220> FEATURE:
<221> NAME/KEY: misc_feature
<222> LOCATION: (19)..(19)
<223> OTHER INFORMATION: R is G or A

<400> SEQUENCE: 48
cggtgtgtac aagrccygrg a                                                    21

<210> SEQ ID NO 49
<211> LENGTH: 25
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (18)..(18)
<223> OTHER INFORMATION: R is G or A
<220> FEATURE:
<221> NAME/KEY: misc_feature

```
<222> LOCATION: (21)..(21)
<223> OTHER INFORMATION: Y is C or T
<220> FEATURE:
<221> NAME/KEY: misc_feature
<222> LOCATION: (23)..(23)
<223> OTHER INFORMATION: R is G or A

<400> SEQUENCE: 49
cgggcggtgt gtacaagrcc ygrga                                        25

<210> SEQ ID NO 50
<211> LENGTH: 17
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (15)..(15)
<223> OTHER INFORMATION: R is G or A

<400> SEQUENCE: 50
gacgggcggt gtgtrca                                                 17

<210> SEQ ID NO 51
<211> LENGTH: 19
<212> TYPE: DNA
<213> ORGANISM: artificial sequence
<220> FEATURE:
<223> OTHER INFORMATION: synthetic polynucleotide

<400> SEQUENCE: 51
ggttaccttg ttacgactt                                               19

<210> SEQ ID NO 52
<211> LENGTH: 15
<212> TYPE: DNA
<213> ORGANISM: artificial sequence
<220> FEATURE:
<223> OTHER INFORMATION: synthetic polynucleotide

<400> SEQUENCE: 52
accttgttac gactt                                                   15

<210> SEQ ID NO 53
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: M is A or C

<400> SEQUENCE: 53
cagcmgccgc ggtaa                                                   15

<210> SEQ ID NO 54
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: H is A or C or T
<220> FEATURE:
```

```
<221> NAME/KEY: misc_feature
<222> LOCATION: (9)..(9)
<223> OTHER INFORMATION: V is A or C or G
<220> FEATURE:
<221> NAME/KEY: misc_feature
<222> LOCATION: (14)..(14)
<223> OTHER INFORMATION: W is A or T

<400> SEQUENCE: 54
ggactachvg ggtwtctaat                                                    20

<210> SEQ ID NO 55
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: M is A or C

<400> SEQUENCE: 55
cagcmgccgc ggtaa                                                         15

<210> SEQ ID NO 56
<211> LENGTH: 15
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (5)..(5)
<223> OTHER INFORMATION: N is A or C or G or T

<400> SEQUENCE: 56
cagcngccgc ggtaa                                                         15

<210> SEQ ID NO 57
<211> LENGTH: 14
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: M is A or C

<400> SEQUENCE: 57
agcmgccgcg gtaa                                                          14

<210> SEQ ID NO 58
<211> LENGTH: 14
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: N is A or C or G or T

<400> SEQUENCE: 58
agcngccgcg gtaa                                                          14

<210> SEQ ID NO 59
<211> LENGTH: 14
```

```
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: Y is C or T
<220> FEATURE:
<221> NAME/KEY: misc_feature
<222> LOCATION: (9)..(9)
<223> OTHER INFORMATION: M is A or C

<400> SEQUENCE: 59
gtgycagcmg ccgc                                              14

<210> SEQ ID NO 60
<211> LENGTH: 14
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: N is A or C or G or T
<220> FEATURE:
<221> NAME/KEY: misc_feature
<222> LOCATION: (9)..(9)
<223> OTHER INFORMATION: N is A or C or G or T

<400> SEQUENCE: 60
gtgncagcng ccgc                                              14

<210> SEQ ID NO 61
<211> LENGTH: 13
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: Y is C or T
<220> FEATURE:
<221> NAME/KEY: misc_feature
<222> LOCATION: (9)..(9)
<223> OTHER INFORMATION: M is A or C

<400> SEQUENCE: 61
gtgycagcmg ccg                                               13

<210> SEQ ID NO 62
<211> LENGTH: 13
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: N is A or C or G or T
<220> FEATURE:
<221> NAME/KEY: misc_feature
<222> LOCATION: (9)..(9)
<223> OTHER INFORMATION: N is A or C or G or T

<400> SEQUENCE: 62
gtgncagcng ccg                                               13

<210> SEQ ID NO 63
```

```
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: Y is C or T
<220> FEATURE:
<221> NAME/KEY: misc_feature
<222> LOCATION: (9)..(9)
<223> OTHER INFORMATION: M is A or C

<400> SEQUENCE: 63
gtgycagcmg cc                                                           12

<210> SEQ ID NO 64
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: N is A or C or G or T
<220> FEATURE:
<221> NAME/KEY: misc_feature
<222> LOCATION: (9)..(9)
<223> OTHER INFORMATION: N is A or C or G or T

<400> SEQUENCE: 64
gtgncagcng cc                                                           12

<210> SEQ ID NO 65
<211> LENGTH: 13
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: M is A or C

<400> SEQUENCE: 65
gcmgccgcgg taa                                                          13

<210> SEQ ID NO 66
<211> LENGTH: 13
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: N is A or C or G or T

<400> SEQUENCE: 66
gcngccgcgg taa                                                          13

<210> SEQ ID NO 67
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
```

```
<222> LOCATION: (2)..(2)
<223> OTHER INFORMATION: M is A or C

<400> SEQUENCE: 67
cmgccgcggt aa                                                              12

<210> SEQ ID NO 68
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (2)..(2)
<223> OTHER INFORMATION: N is A or C or G or T

<400> SEQUENCE: 68
cngccgcggt aa                                                              12

<210> SEQ ID NO 69
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: M is A or C

<400> SEQUENCE: 69
gcmgccgcgg ta                                                              12

<210> SEQ ID NO 70
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: N is A or C or G or T

<400> SEQUENCE: 70
gcngccgcgg ta                                                              12

<210> SEQ ID NO 71
<211> LENGTH: 13
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (4)..(4)
<223> OTHER INFORMATION: M is A or C

<400> SEQUENCE: 71
agcmgccgcg gta                                                             13

<210> SEQ ID NO 72
<211> LENGTH: 13
<212> TYPE: DNA
<213> ORGANISM: artificial sequence
<220> FEATURE:
<223> OTHER INFORMATION: synthetic polynucleotide
<220> FEATURE:
```

<221> NAME/KEY: misc_feature
<222> LOCATION: (4)..(4)
<223> OTHER INFORMATION: N is A or C or G or T

<400> SEQUENCE: 72
agcngccgcg gta                                                              13

<210> SEQ ID NO 73
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: H is A or C or T
<220> FEATURE:
<221> NAME/KEY: misc_feature
<222> LOCATION: (9)..(9)
<223> OTHER INFORMATION: V is A or C or G
<220> FEATURE:
<221> NAME/KEY: misc_feature
<222> LOCATION: (14)..(14)
<223> OTHER INFORMATION: W is A or T

<400> SEQUENCE: 73
ggactachvg ggtwtctaat                                                       20

<210> SEQ ID NO 74
<211> LENGTH: 20
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (8)..(8)
<223> OTHER INFORMATION: N is A or C or G or T
<220> FEATURE:
<221> NAME/KEY: misc_feature
<222> LOCATION: (9)..(9)
<223> OTHER INFORMATION: N is A or C or G or T
<220> FEATURE:
<221> NAME/KEY: misc_feature
<222> LOCATION: (14)..(14)
<223> OTHER INFORMATION: N is A or C or G or T

<400> SEQUENCE: 74
ggactacnng ggtntctaat                                                       20

<210> SEQ ID NO 75
<211> LENGTH: 56
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (46)..(46)
<223> OTHER INFORMATION: M is A or C

<400> SEQUENCE: 75
aatgatacgg cgaccaccga gatctacact atggtaattg tcagcmgccg cggtaa              56

<210> SEQ ID NO 76
<211> LENGTH: 68
<212> TYPE: DNA
<213> ORGANISM: artificial sequence
<220> FEATURE:
<223> OTHER INFORMATION: synthetic polynucleotide -continued

```
<220> FEATURE:
<221> NAME/KEY: misc_feature
<222> LOCATION: (25)..(25)
<223> OTHER INFORMATION: N is A or C or G or T
<220> FEATURE:
<221> NAME/KEY: misc_feature
<222> LOCATION: (26)..(26)
<223> OTHER INFORMATION: N is A or C or G or T
<220> FEATURE:
<221> NAME/KEY: misc_feature
<222> LOCATION: (27)..(27)
<223> OTHER INFORMATION: N is A or C or G or T
<220> FEATURE:
<221> NAME/KEY: misc_feature
<222> LOCATION: (28)..(28)
<223> OTHER INFORMATION: N is A or C or G or T
<220> FEATURE:
<221> NAME/KEY: misc_feature
<222> LOCATION: (29)..(29)
<223> OTHER INFORMATION: N is A or C or G or T
<220> FEATURE:
<221> NAME/KEY: misc_feature
<222> LOCATION: (30)..(30)
<223> OTHER INFORMATION: N is A or C or G or T
<220> FEATURE:
<221> NAME/KEY: misc_feature
<222> LOCATION: (31)..(31)
<223> OTHER INFORMATION: N is A or C or G or T
<220> FEATURE:
<221> NAME/KEY: misc_feature
<222> LOCATION: (32)..(32)
<223> OTHER INFORMATION: N is A or C or G or T
<220> FEATURE:
<221> NAME/KEY: misc_feature
<222> LOCATION: (33)..(33)
<223> OTHER INFORMATION: N is A or C or G or T
<220> FEATURE:
<221> NAME/KEY: misc_feature
<222> LOCATION: (34)..(34)
<223> OTHER INFORMATION: N is A or C or G or T
<220> FEATURE:
<221> NAME/KEY: misc_feature
<222> LOCATION: (35)..(35)
<223> OTHER INFORMATION: N is A or C or G or T
<220> FEATURE:
<221> NAME/KEY: misc_feature
<222> LOCATION: (36)..(36)
<223> OTHER INFORMATION: N is A or C or G or T
<220> FEATURE:
<221> NAME/KEY: misc_feature
<222> LOCATION: (56)..(56)
<223> OTHER INFORMATION: H is A or C or T
<220> FEATURE:
<221> NAME/KEY: misc_feature
<222> LOCATION: (57)..(57)
<223> OTHER INFORMATION: V is A or C or G
<220> FEATURE:
<221> NAME/KEY: misc_feature
<222> LOCATION: (62)..(62)
<223> OTHER INFORMATION: W is A or T

<400> SEQUENCE: 76
caagcagaag acggcatacg agatnnnnnn nnnnnnagtc agtcagccgg actachvggg      60 twtctaat                                                              68

<210> SEQ ID NO 77
<211> LENGTH: 20
<212> TYPE: DNA
<213> ORGANISM: artificial sequence
<220> FEATURE:
<223> OTHER INFORMATION: synthetic polynucleotide

<400> SEQUENCE: 77
aatgatacgg cgaccaccga                                                 20
```

```
<210> SEQ ID NO 78
<211> LENGTH: 21
<212> TYPE: DNA
<213> ORGANISM: artificial sequence
<220> FEATURE:
<223> OTHER INFORMATION: synthetic polynucleotide

<400> SEQUENCE: 78
caagcagaag acggcatacg a                                              21

<210> SEQ ID NO 79
<211> LENGTH: 27
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (17)..(17)
<223> OTHER INFORMATION: M is A or C

<400> SEQUENCE: 79
tatggtaatt gtcagcmgcc gcggtaa                                        27

<210> SEQ ID NO 80
<211> LENGTH: 32
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (20)..(20)
<223> OTHER INFORMATION: H is A or C or T
<220> FEATURE:
<221> NAME/KEY: misc_feature
<222> LOCATION: (21)..(21)
<223> OTHER INFORMATION: V is A or C or G
<220> FEATURE:
<221> NAME/KEY: misc_feature
<222> LOCATION: (26)..(26)
<223> OTHER INFORMATION: W is A or T

<400> SEQUENCE: 80
agtcagtcag ccggactach vgggtwtcta at                                  32

<210> SEQ ID NO 81
<211> LENGTH: 32
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (7)..(7)
<223> OTHER INFORMATION: W is A or T
<220> FEATURE:
<221> NAME/KEY: misc_feature
<222> LOCATION: (12)..(12)
<223> OTHER INFORMATION: B is C or G or T
<220> FEATURE:
<221> NAME/KEY: misc_feature
<222> LOCATION: (13)..(13)
<223> OTHER INFORMATION: D is A or G or T

<400> SEQUENCE: 81
attagawacc cbdgtagtcc ggctgactga ct                                  32
```